(12) United States Patent
Narayanan et al.

(10) Patent No.: US 10,654,809 B2
(45) Date of Patent: May 19, 2020

(54) SELECTIVE ANDROGEN RECEPTOR DEGRADER (SARD) LIGANDS AND METHODS OF USE THEREOF

(71) Applicant: University of Tennessee Research Foundation, Knoxville, TN (US)

(72) Inventors: Ramesh Narayanan, Cordova, TN (US); Duane D. Miller, Collierville, TN (US); Thamarai Ponnusamy, Memphis, TN (US); Dong-Jin Hwang, Arlington, TN (US); Yali He, Germantown, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 0 days.

(21) Appl. No.: 15/923,668

(22) Filed: Mar. 16, 2018

(65) Prior Publication Data
US 2018/0273487 A1    Sep. 27, 2018

Related U.S. Application Data

(63) Continuation-in-part of application No. 15/620,761, filed on Jun. 12, 2017.
(Continued)

(51) Int. Cl.
| C07D 231/16 | (2006.01) |
| C07D 207/34 | (2006.01) |
| C07D 233/68 | (2006.01) |
| C07D 207/06 | (2006.01) |
| C07D 295/15 | (2006.01) |
| C07D 249/08 | (2006.01) |
| C07D 213/84 | (2006.01) |
| C07D 239/74 | (2006.01) |
| C07D 401/12 | (2006.01) |
| C07D 249/04 | (2006.01) |
| C07D 209/08 | (2006.01) |
| C07C 317/46 | (2006.01) |

(Continued)

(52) U.S. Cl.
CPC .......... *C07D 231/16* (2013.01); *A61K 9/0014* (2013.01); *A61K 31/277* (2013.01); *A61K 31/40* (2013.01); *A61K 31/415* (2013.01); *A61K 31/4164* (2013.01); *A61K 31/4192* (2013.01); *A61K 31/4196* (2013.01); *A61K 31/44* (2013.01); *A61K 31/4439* (2013.01); *A61K 31/517* (2013.01); *A61K 31/5375* (2013.01); *A61K 45/06* (2013.01); *C07C 255/60* (2013.01); *C07C 317/46* (2013.01); *C07D 207/06* (2013.01); *C07D 207/34* (2013.01); *C07D 209/08* (2013.01); *C07D 213/84* (2013.01); *C07D 233/68* (2013.01); *C07D 239/74* (2013.01); *C07D 249/04* (2013.01); *C07D 249/08* (2013.01); *C07D 295/15* (2013.01); *C07D 401/12* (2013.01)

(58) Field of Classification Search
CPC .. A61K 31/40; A61K 31/415; A61K 31/4164; A61K 31/4196; A61K 31/4439; A61K 31/5375; A61K 31/277; A61K 31/4192; A61K 31/44; A61K 31/517; A61K 31/41; A61K 31/655; A61K 45/06; A61K 9/0014; A61P 35/00; C07C 255/60; C07C 317/46; C07D 207/06; C07D 207/34; C07D 209/08; C07D 213/84; C07D 231/16; C07D 23/68; C07D 239/74; C07D 249/04; C07D 249/08; C07D 295/15; C07D 401/12
See application file for complete search history.

(56) References Cited

U.S. PATENT DOCUMENTS

| 5,480,656 A | 1/1996 | Okada et al. |
| 5,575,987 A | 11/1996 | Kamei et al. |

(Continued)

FOREIGN PATENT DOCUMENTS

| CN | 1597662 A | | 3/2005 | |
| CN | 2015-10631654 | * | 9/2016 | ............. A61K 45/06 |

(Continued)

OTHER PUBLICATIONS

Wen, et al, Targeting fatty acid synthase with ASC-J9 suppresses proliferation and invasion of prostate cancer cells, Molecular Carcinogenesis, 55(12), 2278-2290 (2016). (Year: 2016).*

(Continued)

*Primary Examiner* — Erich A Leeser
(74) *Attorney, Agent, or Firm* — Mark S. Cohen; Pearl Cohen; Zedek Latzer Baratz LLP

(57) ABSTRACT

This invention is directed to pyrrole, pyrazole, imidazole, triazole, and morpholine based selective androgen receptor degrader (SARD) compounds including heterocyclic anilide rings and their synthetic precursors, R-isomers, and non-hydroxylated and/or non-chiral propanamides, and pharmaceutical compositions and uses thereof in treating prostate cancer, advanced prostate cancer, castration resistant prostate cancer, triple negative breast cancer, other cancers expressing the androgen receptor, androgenic alopecia or other hyperandrogenic dermal diseases, Kennedy's disease, amyotrophic lateral sclerosis (ALS), abdominal aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

38 Claims, 44 Drawing Sheets

Related U.S. Application Data

(60) Provisional application No. 62/482,036, filed on Apr. 5, 2017, provisional application No. 62/455,397, filed on Feb. 6, 2017, provisional application No. 62/348,474, filed on Jun. 10, 2016.

(51) Int. Cl.

| | | |
|---|---|---|
| *C07C 255/60* | (2006.01) | |
| *A61K 31/4192* | (2006.01) | |
| *A61K 9/00* | (2006.01) | |
| *A61K 45/06* | (2006.01) | |
| *A61K 31/40* | (2006.01) | |
| *A61K 31/4164* | (2006.01) | |
| *A61K 31/5375* | (2006.01) | |
| *A61K 31/4196* | (2006.01) | |
| *A61K 31/44* | (2006.01) | |
| *A61K 31/517* | (2006.01) | |
| *A61K 31/277* | (2006.01) | |
| *A61K 31/4439* | (2006.01) | |
| *A61K 31/415* | (2006.01) | |

(56) References Cited

U.S. PATENT DOCUMENTS

| | | |
|---|---|---|
| 5,631,020 A | 5/1997 | Okada et al. |
| 5,643,607 A | 7/1997 | Okada et al. |
| 5,716,640 A | 2/1998 | Kamei et al. |
| 5,814,342 A | 9/1998 | Okada et al. |
| 6,036,976 A | 3/2000 | Takechi et al. |
| 7,022,870 B2 | 4/2006 | Dalton et al. |
| 7,118,552 B2 | 10/2006 | Shaw et al. |
| 7,220,247 B2 | 5/2007 | Shaw et al. |
| 7,500,964 B2 | 3/2009 | Shaw et al. |
| 7,741,371 B2 | 6/2010 | Dalton et al. |
| 8,735,440 B2 | 5/2014 | McKnight et al. |
| 9,550,742 B2 | 1/2017 | Marugan et al. |
| 10,314,797 B2 | 6/2019 | Narayanan et al. |
| 2005/0101657 A1 | 5/2005 | Furuya et al. |
| 2006/0142387 A1 | 6/2006 | Cadilla et al. |
| 2006/0173037 A1 | 8/2006 | Schlienger et al. |
| 2006/0241180 A1 | 10/2006 | Dalton et al. |
| 2007/0049629 A1 | 3/2007 | Scanlan et al. |
| 2007/0123512 A1 | 5/2007 | Ratilainen |
| 2007/0123563 A1 | 5/2007 | Dalton et al. |
| 2007/0173546 A1 | 7/2007 | Dalton et al. |
| 2007/0265290 A1 | 11/2007 | Dalton et al. |
| 2008/0293766 A1 | 11/2008 | Diamond et al. |
| 2009/0042844 A1 | 2/2009 | Labrie et al. |
| 2009/0060873 A1 | 3/2009 | Sporn et al. |
| 2009/0142323 A1 | 6/2009 | Quarles et al. |
| 2010/0227846 A1 | 9/2010 | Ito et al. |
| 2011/0028719 A1 | 2/2011 | Slon-Usakiewicz |
| 2014/0018433 A1 | 1/2014 | Dalton et al. |
| 2014/0094474 A1 | 4/2014 | Törmäkängas et al. |
| 2015/0331777 A1 | 11/2015 | Lvin |
| 2017/0029370 A1 | 2/2017 | Narayanan et al. |
| 2017/0095446 A1 | 4/2017 | Narayanan et al. |
| 2017/0166526 A1 | 6/2017 | Narayanan et al. |
| 2018/0118663 A1 | 5/2018 | Narayanan et al. |
| 2018/0271849 A1 | 9/2018 | Ge et al. |
| 2018/0273487 A1 | 9/2018 | Narayanan et al. |
| 2018/0360805 A1 | 12/2018 | Narayanan et al. |

FOREIGN PATENT DOCUMENTS

| | | | |
|---|---|---|---|
| EP | | 100172 A1 | 2/2004 |
| EP | | 2159049 A1 | 3/2010 |
| WO | WO 2002/016310 A1 | | 2/2002 |
| WO | WO 2002/046164 A1 | | 6/2002 |
| WO | WO 2003/106401 A1 | | 12/2003 |
| WO | WO 2005/000794 A1 | | 1/2005 |
| WO | WO 2005/120477 A2 | | 12/2005 |
| WO | WO 2007/005887 A2 | | 1/2007 |
| WO | WO 2007/126988 A2 | | 11/2007 |
| WO | WO 2008/011072 A2 | | 1/2008 |
| WO | WO 2008/124000 A2 | | 10/2008 |
| WO | WO 2009/010480 A1 | | 1/2009 |
| WO | WO 2009/069736 A1 | | 6/2009 |
| WO | WO 2009/082437 A2 | | 7/2009 |
| WO | WO 2012/007644 A1 | | 1/2012 |
| WO | WO 2014/113260 A1 | | 7/2014 |
| WO | WO 2015/042297 A1 | | 3/2015 |

OTHER PUBLICATIONS

Aggarwal et al. "Androgens affect muscle, motor neuron, and survival in a mouse model of SOD1-related amyotrophic lateral sclerosis". Neurobiology of aging. Aug. 1, 2014;35(8):1929-38.

Antonarakis et al. "Clinical significance of androgen receptor splice variant-7 mRNA detection in circulating tumor cells of men with metastatic castration-resistant prostate cancer treated with first-and second-line abiraterone and enzalutamide" Journal of Clinical Oncology. Apr. 6, 2017;35(19):2149-56.

Baniahmad A. "Inhibition of the androgen receptor by antiandrogens in spinobulbar muscle atrophy" Journal of Molecular Neuroscience. Mar. 1, 2016:58(3):343-7.

Bryce et al. "Androgen receptor splice variant 7 in castration-resistant prostate cancer: Clinical considerations" International Journal of Urology. Aug. 1, 2016;23(8):646-53.

Cochrane et al. "Role of the androgen receptor in breast cancer and preclinical analysis of enzalutamide" Breast Cancer Research, Feb. 2014;16(1):R7.

Davis et al. "Pharmacologic blockade and genetic deletion of androgen receptor attenuates aortic aneurysm formation" Journal of vascular surgery. Jun. 1, 2016;63(6):1602-12.

Galbiati et al. "The anabolic/androgenic steroid nandrolone exacerbates gene expression modifications induced by mutant SOD1 in muscles of mice models of amyotrophic lateral sclerosis". Pharmacological research. Feb. 1, 2012;65(2):221-30.

Hsieh et al. "Androgen receptor trinucleotide polymorphism in leiomyoma" Journal of assisted reproduction and genetics. Dec. 1, 2004;21(12):4537.

International Search Report for PCT Application No. PCT/US2017/37063 dated Sep. 15, 2017.

Joseph et al. "A clinically relevant androgen receptor mutation confers resistance to second-generation antiandrogens enzalutamide and ARN-509" Cancer discovery. Sep. 1, 2013;3(9):1020-9.

Kanda et al. "Androgen receptor signaling in hepatocellular carcinoma and pancreatic cancers" World Journal of Gastroenterology; WJG. Jul. 28, 2014;20(28):9229.

Kawahara et al. "ELK1 is up-regulated by androgen in bladder cancer cells and promotes tumor progression" Oncotarget. Oct. 6, 2015;6(30):29860.

Lieberman et al. "Peripheral androgen receptor gene suppression rescues disease in mouse models of spinal and bulbar muscular atrophy" Cell reports. May 8, 2014;7(3):774-84.

Lieberman et al., editors. Pharrnaceuticai Dosage Forms: Tablets: 1980. Marcel Dekker; 1980.

Locati et al. "Clinical activity of androgen deprivation therapy in patients with metastatic/relapsed androgen receptor-positive salivary gland cancers" Head & neck. May 1, 2016;38(5):724-31.

McBeth et al. "Involvement of the androgen and glucocorticoid receptors in bladder cancer" International journal of endocrinciogy, 2015;2015.

Miller et al. "Phase III, randomized, placebo-controlled study of once-daily oral zibotentan (ZD4054) in patients with non-metastatic castration-resistant prostate cancer" Prostate cancer and prostatic diseases. Jun. 2013;16(2):187.

PUBMED, CID 20221988, Dec. 5, 2007, pp. 1-11; retrieved from the Internet <URL: https://pubchem.ncbi.nm.nih.gov/compound/20221988; p. 3, formula.

Remington et al. "Remington's pharmaceutical sciences", 1553-1593, current edition.

Remond et al. "Handbook of Pharmaceutical Excipients" American Pharmaceutical Association.

(56) References Cited

OTHER PUBLICATIONS

Renier et al. "Antiandrogen flutamide protects male mice from androgen-dependent toxicity in three models of spinal bulbar muscular atrophy" Endocrinology. Jul. 1, 2014;155(7):2624-34.

Rosa et al. "Polymorphisms of CYP17A1, CYP19, and androgen in Brazilian women with uterine leiomyomas" Clinical chemistry and laboratory medicine. Jun. 1, 2008;46(6):814-23.

Sun et al. "Castration resistance in human prostate cancer is conferred by a frequently occurring androgen receptor splice variant" The Journal of clinical investigation. Aug. 2, 2010;120(8):2715-30.

Andersen et al. "Regression of castrate-recurrent prostate cancer by a small-molecule inhibitor of the amino-terminus domain of the androgen receptor" Cancer cell. Jun. 15, 2010;17(6):535-46.

Antonarakis et al. "AR-V7 and resistance to enzalutamide and abiraterone in prostate cancer" New England Journal of Medicine. Sep. 11, 2014;371(11):1028-38.

Aradi et al. "DFTB+, a sparse matrix-based implementation of the DFTB method" The Journal of Physical Chemistry A. Jul. 5, 2007;111(26):5678-84.

Attard et al. "Selective inhibition of CYP17 with abiraterone acetate is highly active in the treatment of castration-resistant prostate cancer" Journal of clinical oncology. May 26, 2009;27(23):3742-8.

Baek et al. "Ligand-specific allosteric regulation of coactivator functions of androgen receptor in prostate cancer cells" Proceedings of the National Academy of Sciences of the United States of America. Feb. 28, 2006;103(9):3100-5.

Berrevoets et al. "Effects of antiandrogens on transformation and transcription activation of wild-type and mutated (LNCaP) androgen receptors" The Journal of steroid biochemistry and molecular biology. Dec. 31, 1993;46(6):731-6.

Bohl et al. "Structural basis for antagonism and resistance of bicalutamide in prostate cancer" Proceedings of the National Academy of Sciences. Apr. 26, 2005;102(17):6201-6.

Bohl et al. "A ligand-based approach to identify quantitative structure-activity relationships for the androgen receptor" Journal of medicinal chemistry. Jul. 15, 2004;47(15):3765.

Bohl et al. "Structural basis for accommodation of nonsteroidal ligands in the androgen receptor" Journal of Biological Chemistry. Nov. 11, 2005;280(45):37747-54.

Bratenko et al. "Polyfunctional pyrazoles. 3.* Synthesis of 3-(3-aryl-4-formyl-1-pyrazolyl) propionic acids and their amides" Chemistry of Heterocyclic Compounds. Oct. 1, 2004;40(10):1279-82.

Claessens et al. "Diverse roles of androgen receptor (AR) domains in AR-mediated signaling" Nuclear receptor signaling. Jun. 27, 2008;6:e008.

Clegg et al. "ARN-509: a novel antiandrogen for prostate cancer treatment" Cancer research. Mar. 15, 2012;72(6):1494-503.

Dalvit et al. "Identification of compounds with binding affinity to proteins via magnetization transfer from bulk water" Journal of biomolecular NMR. Sep. 1, 2000:18(1):65-8.

Danquah et al. "Combination therapy of antiandrogen and XIAP inhibitor for treating advanced prostate cancer" Pharmaceutical research. Aug. 1, 2012;29(8):2079-91.

Database Caplus Chemical Abstracts Serivce; Database Accession No. 2005:14358; Abstract of WO 2005000794, published Jan. 6, 2005.

Dehm et al. "Alternatively spliced androgen receptor variants" Endocrine-related cancer. Oct. 1, 2011;18(5):R183-96.

Dehm et al. "Splicing of a novel androgen receptor exon generates a constitutively active androgen receptor that mediates prostate cancer therapy resistance" Cancer research. Jul. 1, 2008;68(13):5469-77.

De Bono et al. "Abraterone and increased survival in metastatic prostate cancer" New England Journal of Medicine. May 26, 2011;364(21):1995-2005.

Dias et al. "NMR approaches in structure-based lead discovery: recent developments and new frontiers for targeting multi-protein complexes" Progress in biophysics and molecular biology. Nov. 1, 2014;116(2-3)101-12.

Duke III, Charles B., et al. "Synthesis and biological studies of androgen receptor ligands: Towards mutation-resistant nonsteroidal antagonism." Abstracts of Papers of the American Chemical Society. vol. 240.

Elstner et al. "Sett-consistent-charge density-functional tight-binding method for simulations of complex materials properties" Physical Review B. Sep. 15, 1998;58(11):7260.

Epps et al. "Determination of the affinity of drugs toward serum albumin by measurement of the quenching of the intrinsic tryptophan fluorescence of the protein" Journal of pharmacy and pharmacology. Jan. 1999;51(1):41-8.

Gal et al. "Efficient isothermal titration calorimetry technique identifies direct interaction of small molecule inhibitors with the target protein," Combinatorial chemistry & high throughput screening. Jan. 1, 2016;19(1):4-13.

Hara et al. "Novel mutations of androgen receptor: a possible mechanism of bicalutamide withdrawal syndrome" Cancer research. Jan. 1, 2003;63(1):149-53.

Hu et al. "Distinct transcriptional programs mediated by the ligand-dependent full-length androgen: receptor and its splice variants in castration-resistant prostate cancer" Cancer research, Jul. 15, 2012;72(14):3457-62.

Hwang et al. "Arylisothiocyanato selective androgen receptor modulators (SARMs) for prostate cancer" Bioorganic & medicinal chemistry. Oct. 1, 2006;14(19):5525-38.

Jin et al. "Synthesis and biological evaluation of 1-substituted-3(5)-(6-methylpyridin-2-yl)-4-(quinoline-6-yl)pyrazoles as transforming growth factor-$\beta$ type 1 receptor kinase inhibitors". Bioorganic & Med. Chem. (2011) 19: 2633-2640.

Jin et al. "Synthesis and biological evaluation of 1-substituted-3(5)-(6-methylpyridin-2-yl)-4-(quinoxalin-6-yl)pyrazoles as transforming growth factor-$\beta$ type 1 receptor kinase inhbitors". European J. of Med. Chem. (2011) 46: 3917-3925.

Kim et al. "Ribosomal proteins as unrevealed caretakers for cellular stress and genomic instability" Oncotarget. Feb. 1, 2014;5(4):860-71.

Klotz L. "Maximal androgen blockade for advanced prostate cancer" Best Practice & Research Clinical Endocrinology & Metabolism. Apr. 30, 2008;22(2):331-40.

Lallous et al. "Functional analysis of androgen receptor mutations that confer anti-androgen resistance identified in circulating cell-free DNA from prostate cancer patients" Genome biology, Dec. 2016;17(1):10.

La Spada et al. "Androgen receptor gene mutations in linked spinal and bulbar muscular atrophy" Nature. Jul. 1991;352(6330):77.

Li et al. "Androgen receptor splice variants mediate enzalutamide resistance in castration resistant prostate cancer cell lines" Cancer research. 2013 Jan 15:73(2):483-9.

Li et al. "On the physical origin of blue-shifted hydrogen bonds" Journal of the American Chemical Society. Aug. 14, 2002;124(32):9639-47.

Maclean et al. "Spinal and bulbar muscular atrophy: androgen receptor dysfunction caused by a trinucleotide repeat expansion" Journal of the neurological sciences. Feb. 29, 1996;135(2):149-57.

Marhefka et al. "Homology modeling using multiple molecular dynamics simulations and docking studies of the human androgen receptor ligand binding domain bound to testosterone and nonsteroidal ligands" Journal of medicinal chemistry, May 24, 2001:44(11):1729-40.

Marhefka et al. "Design, synthesis, and biological characterization of metabolically stable selective androgen receptor modulators" Journal of medicinal chemistry. Feb. 12, 2004;47(4):993.

McGinley et al. "Circumventing anti-androgen resistance by molecular design" Journal of the American Chemical Society. Apr. 4, 2007;129(13):3822-3.

Miller Irreversible Nonsteroida SARMs for Prostate Cancer at http://grantome.com/grant/NIH/R01-DK065227-20, 2003.

Mitsiades N. "A road map to comprehensive androgen receptor axis targeting for castration-resistant prostate cancer" Cancer research. Aug. 1, 2013:73(15):4599-605.

Monge et al. "Unfaithfulness and promiscuity of a mutant androgen receptor in a hormone-refractory prostate cancer" Cellular and molecular life sciences. Feb. 1, 2006;63(4):487-97.

(56) References Cited

OTHER PUBLICATIONS

Nagata et al. "Preparation and reactions of cyclic α-monocarbonyl azo-compounds: 1-pyrazolin-3-one derivatives" Journal of the Chemical Society C: Organic. 1970(4):540-50.
Narayanan et al "Selective androgen receptor modulators (SARMs) negatively regulate triple-negative breast cancer growth and epithelial: mesenchymal stem cell signaling" PloS one. Jul. 29, 2014;9(7):e103202.
Narayanan et al. "Biological synthesis of metal nanoparticles by microbes" advances in colloid and interface science. Apr. 22, 2010;156(1-2):1-3.
Nazareth et al. "Activation of the human androgen receptor through a protein kinase A signaling pathway" Journal of Biological Chemistry. Aug. 16, 1996;271(33):19900-7.
Nyquist et al. "TALEN-engineered AR gene rearrangements reveal endocrine uncoupling of androgen receptor in prostate cancer" Proceedings of the National Academy of Sciences. Oct. 22, 2013;110(43):17492-7.
Office Action dated Jul. 5, 2019 issued in corresponding U.S. Appl. No. 15/981,892.
Rawel et al. "Determining the binding affinities of phenolic compounds to proteins by quenching of the intrinsic tryptophan fluorescence" Molecular nutrition & food research. Aug. 2006;50(8):705-13.
Rygula et al. "Raman spectroscopy of proteins: a review" Journal of Raman Spectroscopy. Aug. 2013;44(8):1061-76.
Sadar MD. "Androgen-independent induction of prostate-specific antigen gene expression via cross-talk between the androgen receptor and protein kinase a signal transduction pathways" Journal of Biological Chemistry. Mar. 19, 1999;274(12):7777-83.
Sadar et al. "Ligand-independent activation of the androgen receptor by the differentiation agent butyrate in human prostate cancer cells" Cancer research. Oct. 15, 2000;60(20):5825-31.
Sartor et al. "Androgen receptor variant-7: an important predictive biomarker in castrate resistant prostate cancer" Asian journal of andrology. May 2015;17(3):439.
Scher et al. "Increased survival with enzalutamide in prostate cancer after chemotherapy" New England Journal of Medicine. Sep. 27, 2012;367(13):1187-97.
Shortridge et al. "Estimating protein-ligand binding affinity using high-throughput screening by NMR" Journal of combinatorial chemistry. Oct. 3, 2008;10(5):948-58.
Sieber PR. "Treatment of bicalutamide-induced breast events" Expert review of anticancer therapy. Dec. 1, 2007;7(12):1773-9.
Siegel et al. "Cancer statistics" CA Cancer. J. Clin. 2014;64:9-29.
Tan et al. "Dehydroepiandrosterone activates mutant androgen receptors expressed in the androgen-dependent human prostate cancer xenograft CWR22 and LNCaP cells" Molecular endocrinology. Apr. 1, 1997;11(4):450-9.
Tran et al. "Development of a second-generation antiandrogen for treatment of advanced prostate cancer" Science. May 8, 2009;324(5928):787-90.
Ueda et al. Ligand-independent activation of the androgen receptor by interleukin-6 and the role of steroid receptor coactivator-1 in prostate cancer cells: Journal of Biological Chemistry. Oct. 11, 2002;277(41):38087-94.
Wang et al. "Small molecule inhibition of the steroid receptor coactivators, SRC-3 and SRC-1" Molecular endocrinology. Dec. 1, 2011;25(12):2041-53.
Wang et al. "Effects of hydrogen bond and solvent polarity on the C=O stretching of bis (2 thienyl) ketone in solution" The Journal of chemical physics. Mar. 28, 2012;136(12):03B614.
Watson et al. "Constitutively active androgen receptor splice variants expressed in castration resistant prostate cancer require full-length androgen receptor" Proceedings of the national academy of sciences. Sep. 28, 2010;107(39):16759-65.
Weiner LP. "Possible role of androgen receptors in amyotrophic lateral sclerosis: a hypothesis" Archives of neurology. Mar. 1, 1980;37(3):129-31.
Wen et al. "LHRH-conjugated micelles for targeted delivery of antiandrogen to treat advanced prostate cancer" Pharmaceutical research. Oct. 1, 2014;31(10):2784-95.
Wen et al. "Targeting fatty acid synthase with ASC-J9 suppresses proliferation and invasion of prostate cancer cells" Molecular carcinogenesis. Dec. 2016;55(12):2278-90.
West AR. "Solid state chemistry and its applications" John Wiley & Sons; 1988; pp. 358, 365.
Xu et al. "hSSB1 binds and protects p21 from ubiquitin-mediated degradation and positively correlates with p21 in human hepatocellular carcinomas" Oncogene. May 12, 2011;30(19):2219-29.
Yamashita et al. "ASC-J9 suppresses castration-resistant prostate cancer growth through degradation of full-length and splice variant androgen receptors" Neoplasia. Jan. 1, 2012;14(1):74IN9-83IN12.
Yepuru et al. "Steroidogenic enzyme AKR1C3 is a novel androgen receptor-selective coactivator that promotes prostate cancer growth" Clinical Cancer Research. Oct. 15, 2013;19(20):5613-25.
Yoshida et al. "Antiandrogen bicalutarnide promotes tumor growth in a novel androgen-dependent prostate cancer xenograft model derived from a bicalutamide-treated patient" Cancer Research. Nov. 1, 2005;65(21):9611-6.
Zhou et al. "Study of the impact of the T877A mutation on ligand-induced helix-12 positioning of the androgen receptor resulted in design and synthesis of novel antiandrogens" Proteins: Structure, Function, and Bioinformatics. Feb. 15, 2010;78(3):623-37.

\* cited by examiner

Figure 2A: Antagonist Mode Transactivation for SARDs 11 and 1002
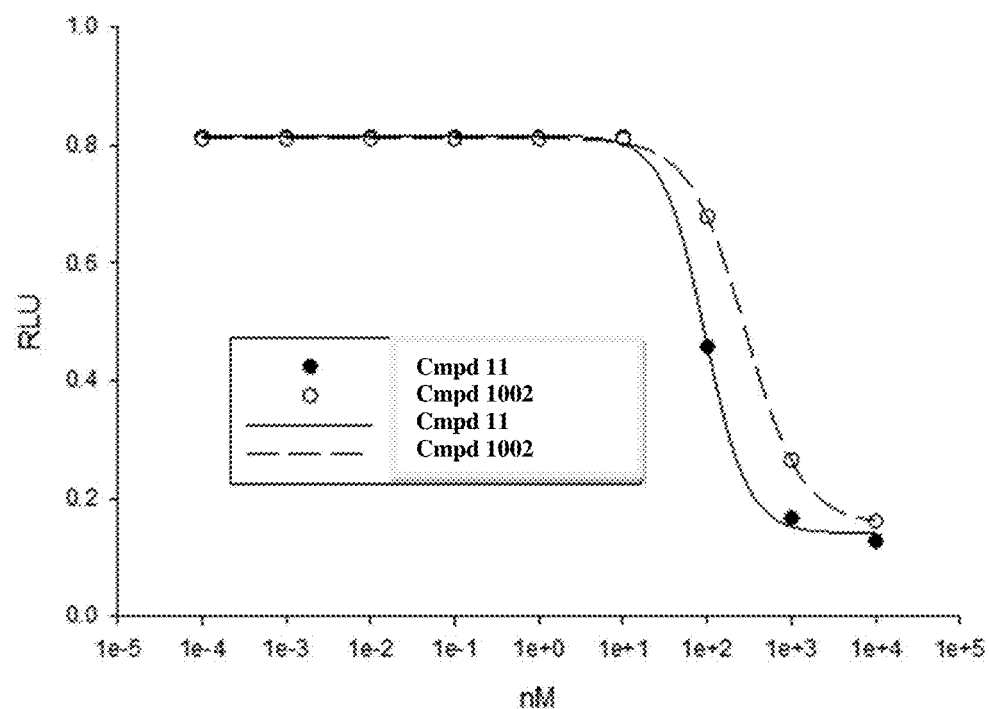

Figure 2B: SARD Activity Retained for *R*-isomers of 11 (11R (*R*-isomer)) and 1002 (1020)
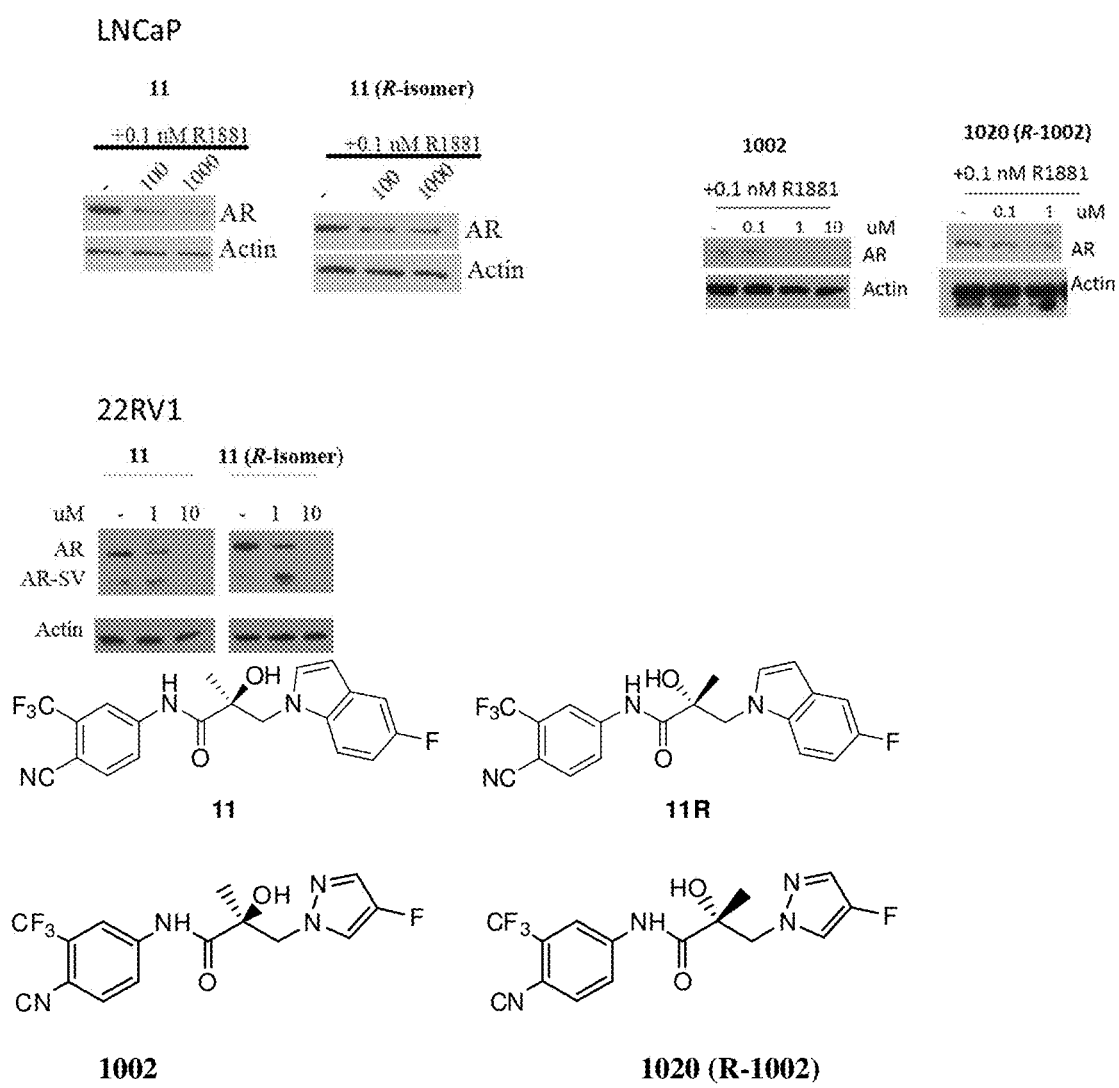

Figure 6A: Transactivation of 1006
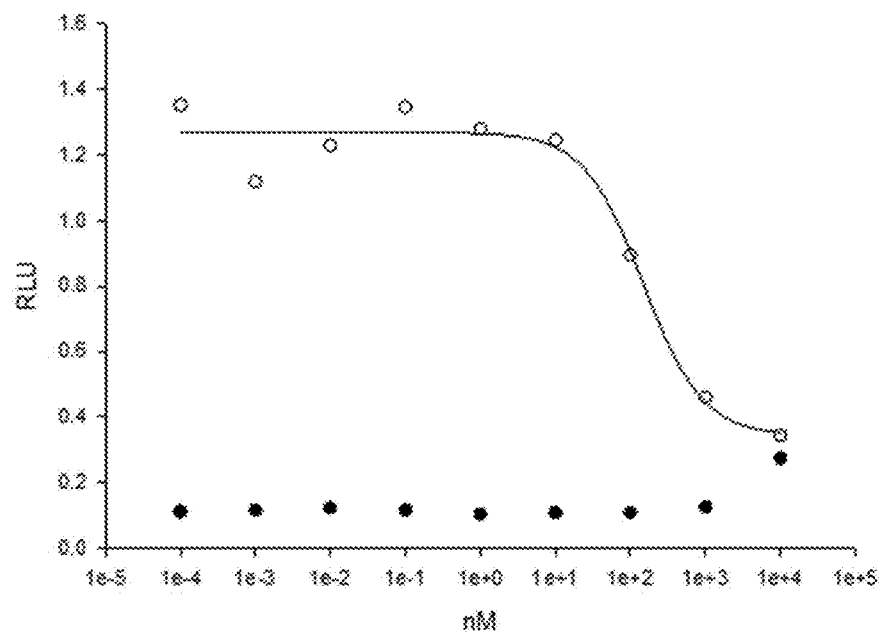
Figure 6B:
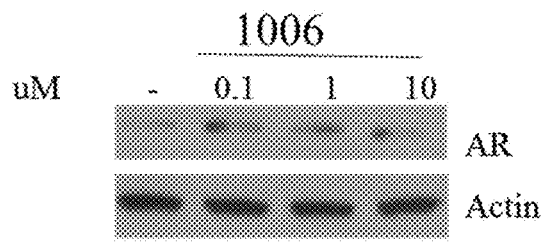

Compound 17

Figure 14: Phase I and Phase I&II Metabolism of 1002 in Mouse Liver Microsomes (MLM)

Phase I (MLM)

| Time | Anal/IS | % remaining |
|---|---|---|
| 0 | 0.242 | 100% |
| 5 | 0.245 | 101% |
| 10 | 0.216 | 90% |
| 30 | 0.139 | 58% |
| 60 | 0.079 | 33% |

Half-life (min) 36.53
Clearance 1.89

Phase II (MLM)

| Time | Anal/IS | % remaining |
|---|---|---|
| 0 | 0.221 | 100% |
| 5 | 0.195 | 88% |
| 10 | 0.240 | 109% |
| 30 | 0.176 | 80% |
| 60 | 0.125 | 57% |

Half-life (min) 77.96
Clearance 0.88

Figure 15A: Phase I Metabolism of 1002 in MLM (single experiment).
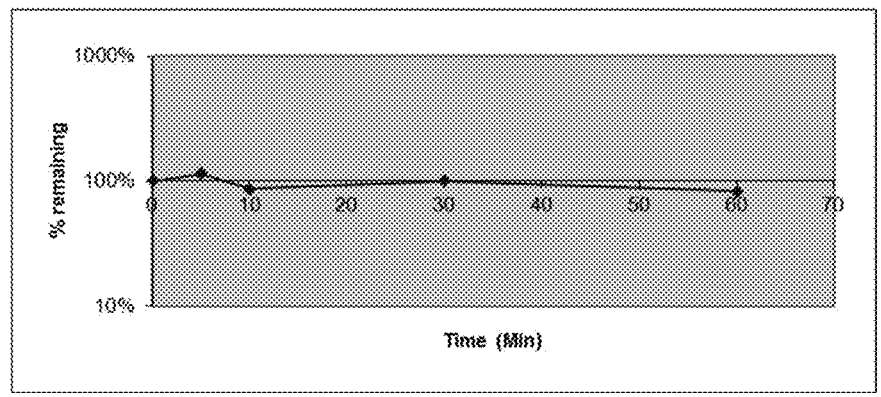
| Time | Anal/IS | % remaining |
|------|---------|-------------|
| 0    | 1.291   | 100%        |
| 5    | 1.484   | 115%        |
| 10   | 1.126   | 87%         |
| 30   | 1.294   | 100%        |
| 60   | 1.079   | 84%         |
Figure 15B: Phase I & II Metabolism of 1002 in MLM (Single Experiment).
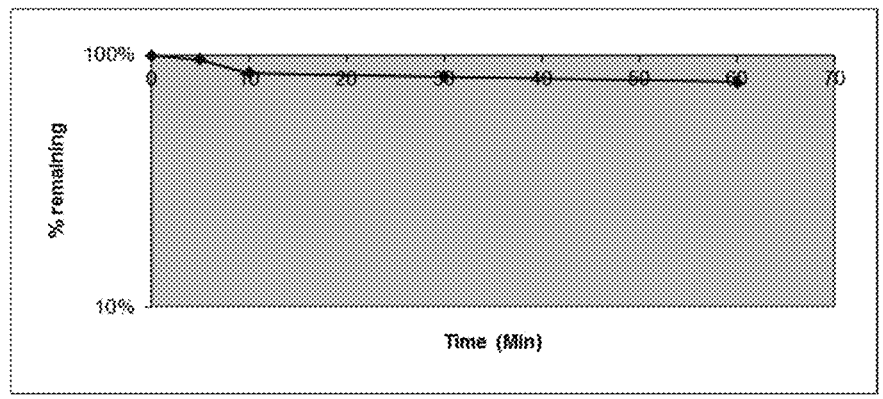
| Time | Anal/IS | % remaining |
|------|---------|-------------|
| 0    | 1.332   | 100%        |
| 5    | 1.277   | 96%         |
| 10   | 1.132   | 85%         |
| 30   | 1.094   | 82%         |
| 60   | 1.045   | 78%         |

Figure 16A: Phase I Metabolism of 1002 in Human Liver Microsomes (HLM) (single experiment)
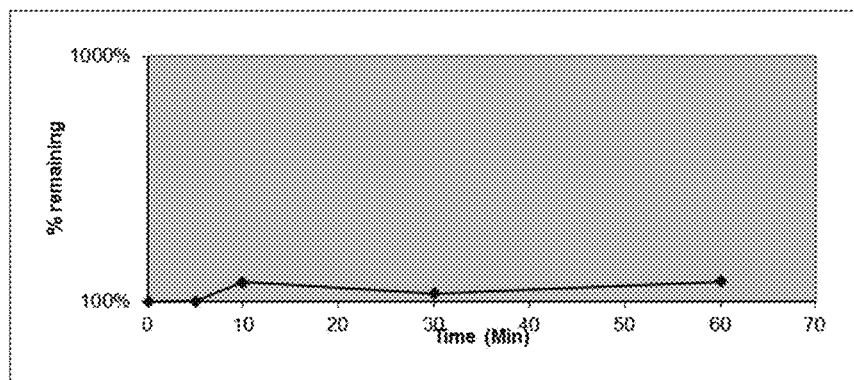
| Time | Anal/IS | % remaining |
|---|---|---|
| 0 | 2.074 | 100% |
| 5 | 2.089 | 101% |
| 10 | 2.488 | 120% |
| 30 | 2.238 | 108% |
| 60 | 2.510 | 121% |
Figure 16B: Phase I & II Metabolism of 1002 in Human Liver Microsomes (HLM) (single experiment)
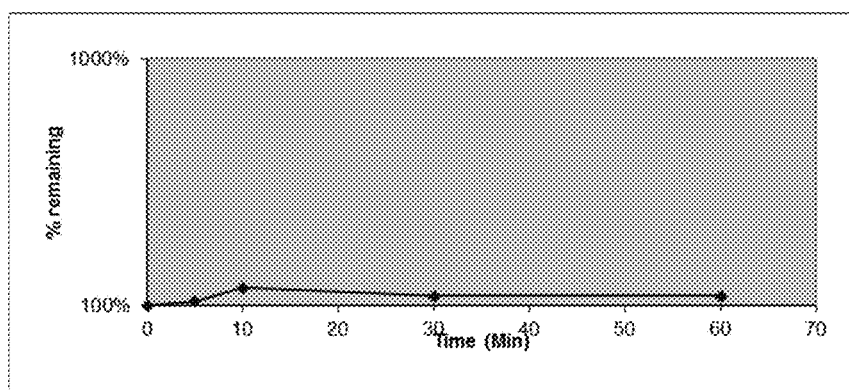
| Time | Anal/IS | % remaining |
|---|---|---|
| 0 | 2.256 | 100% |
| 5 | 2.349 | 104% |
| 10 | 2.664 | 118% |
| 30 | 2.473 | 110% |
| 60 | 2.467 | 109% |

Figure 17: Phase I Metabolism of 1001 in MLM.
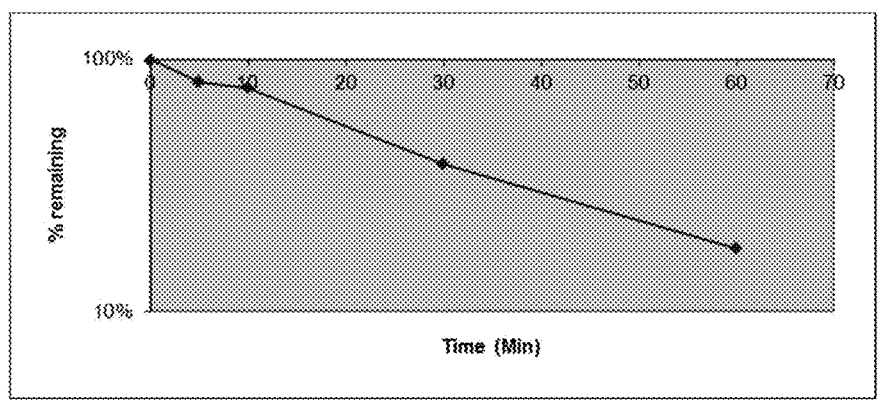
| Time | Anal/IS | % remaining |
|------|---------|-------------|
| 0    | 4.543   | 100%        |
| 5    | 3.694   | 81%         |
| 10   | 3.500   | 77%         |
| 30   | 1.751   | 39%         |
| 60   | 0.810   | 18%         |

Figure 18A: Effect of 1002 on Seminal Vesicles Weight (normalized to body weight) in Intact Mice
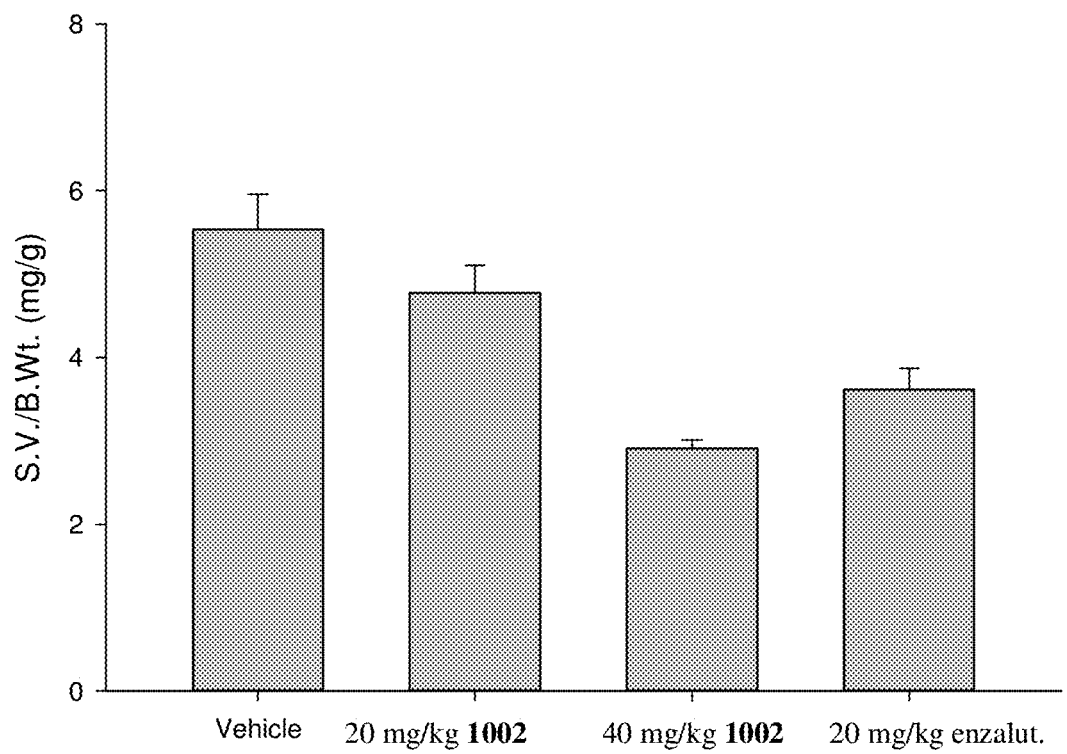
Figure 18B: Effect of 1002 on Seminal Vesicles Weight in Castrated Mice
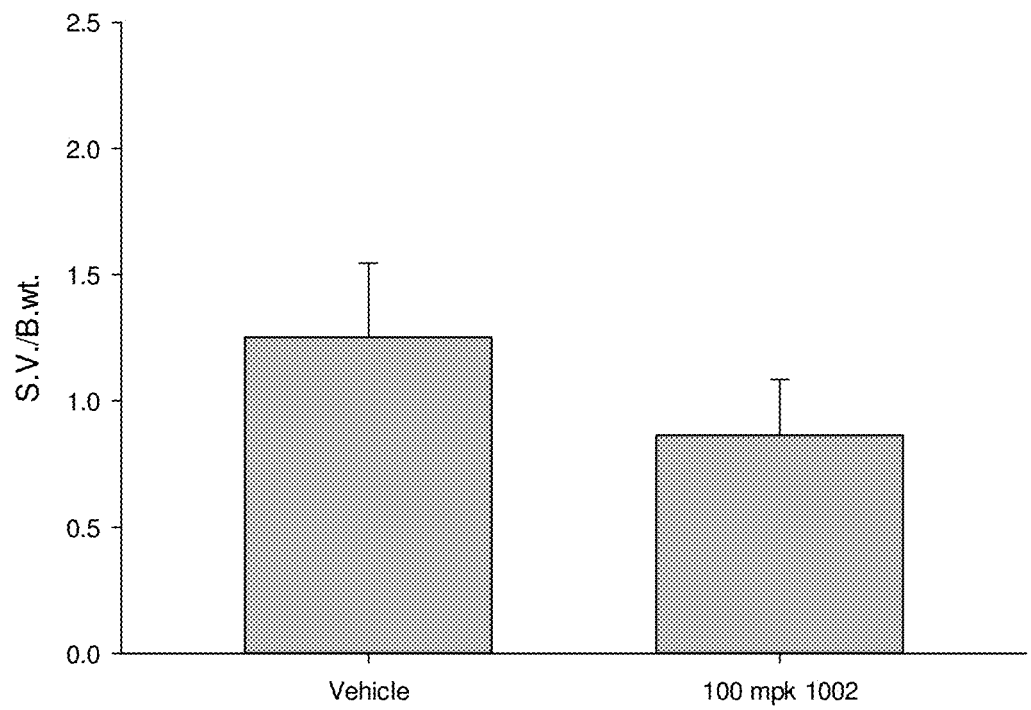

Figure 20A: Full Length AR Degradation Assays
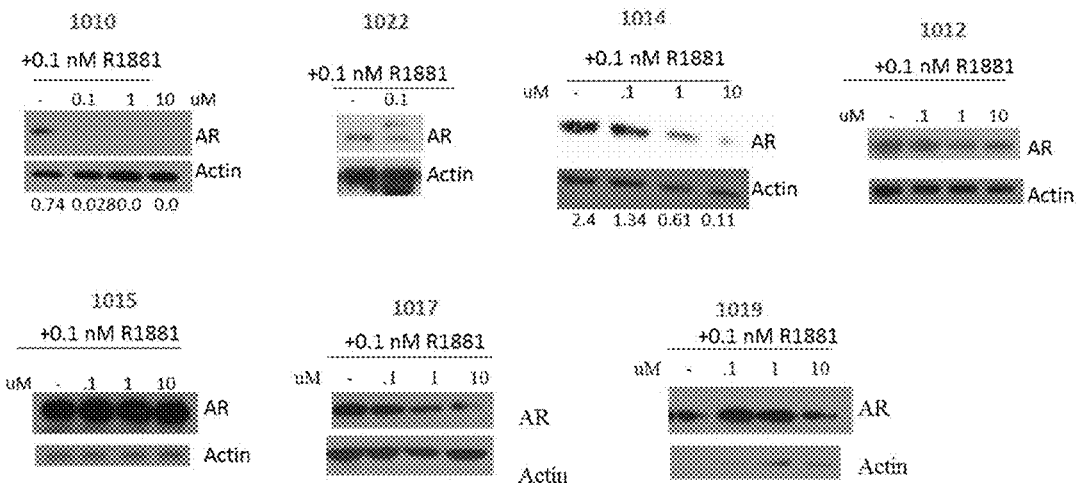
Figure 20B: Splice Variant AR Degradation Assays
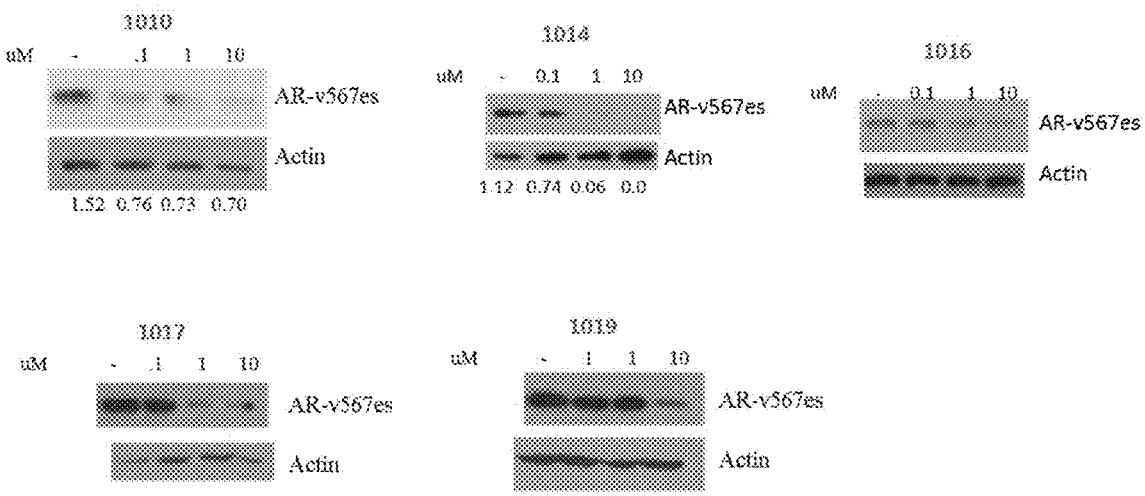

Figure 21A: Anti-tumor Efficacy for 1002 in HBrt 1071 Triple Negative Breast Cancer (TNBC) Patient-Derived Xenograft (PDX)
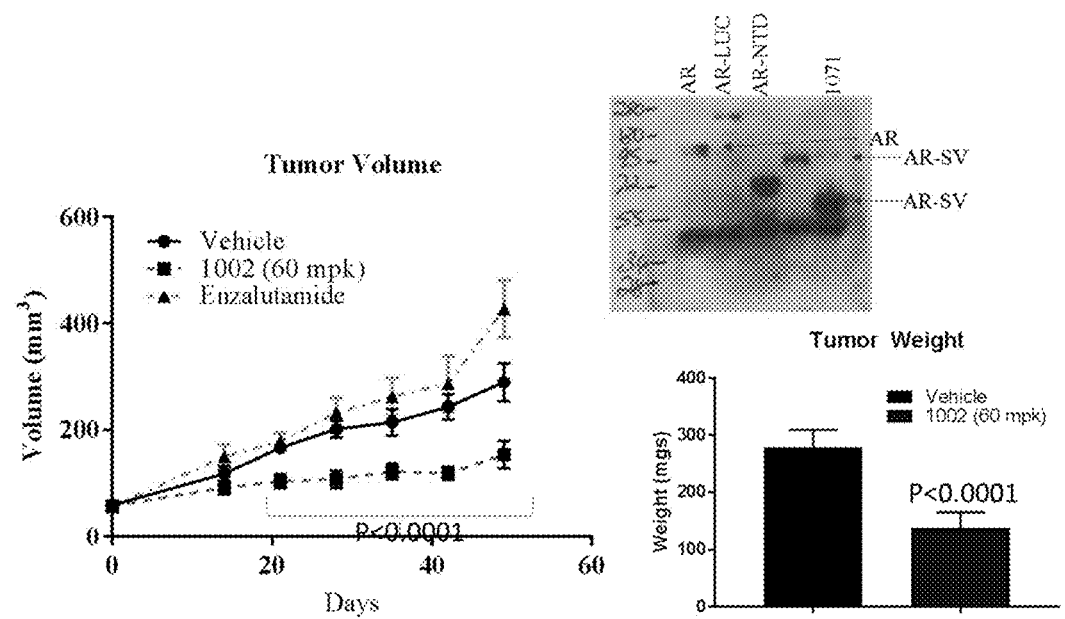

Figure 21B:
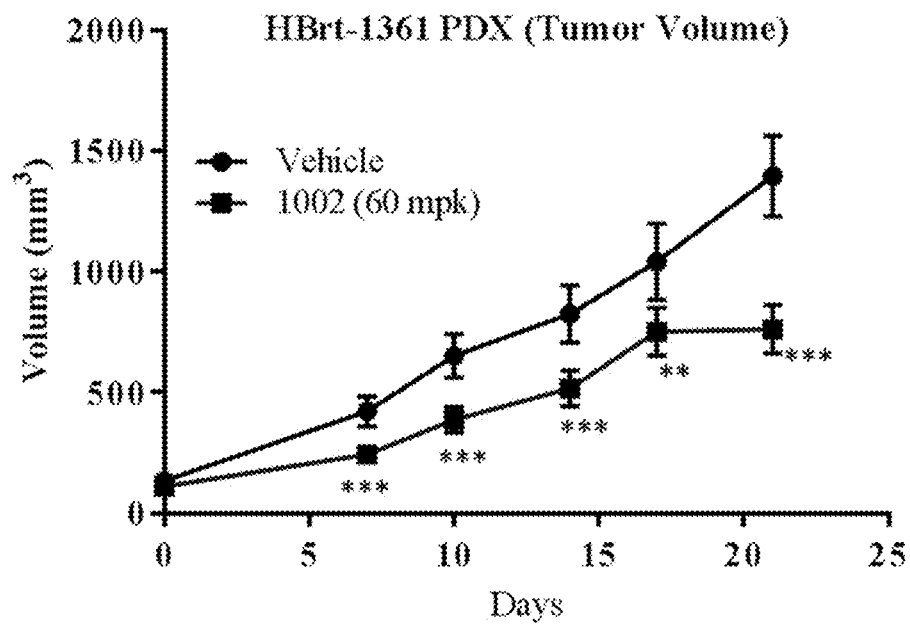
** p<0.01
*** p<0.001
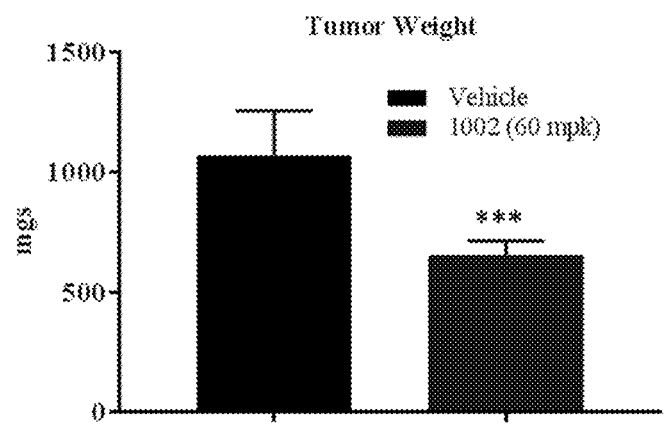

Figure 22: SARDs Bind to AF-1 Region of the N-Terminal Domain (NTD) of the Androgen Receptor
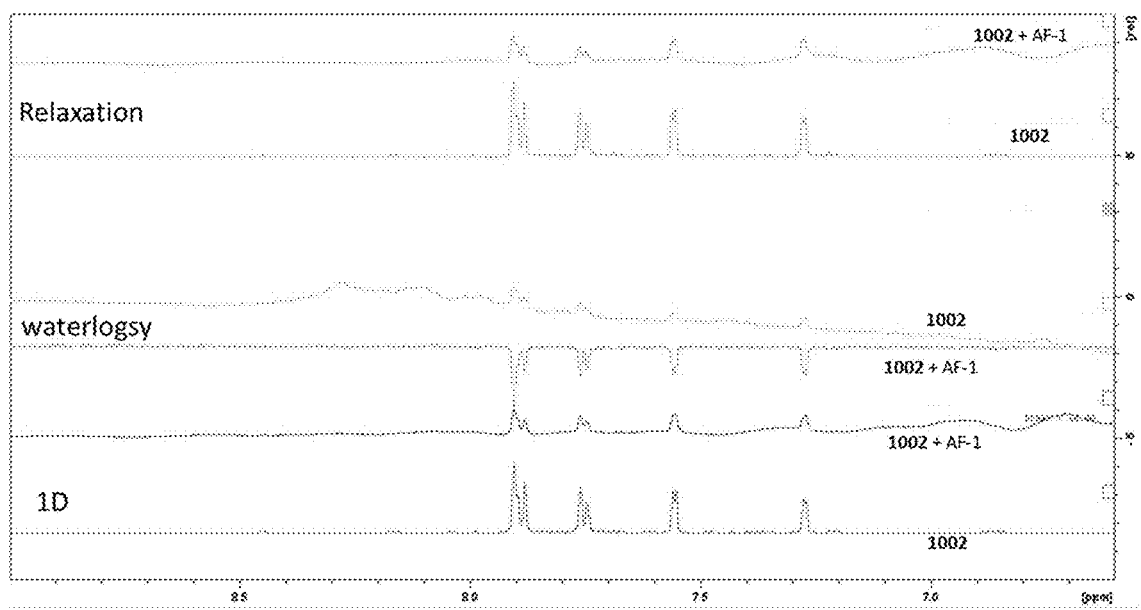

Figure 23: LNCaP-Enzalutamide Resistant (LNCaP-EnzR) Cells MR49F Growth Assay
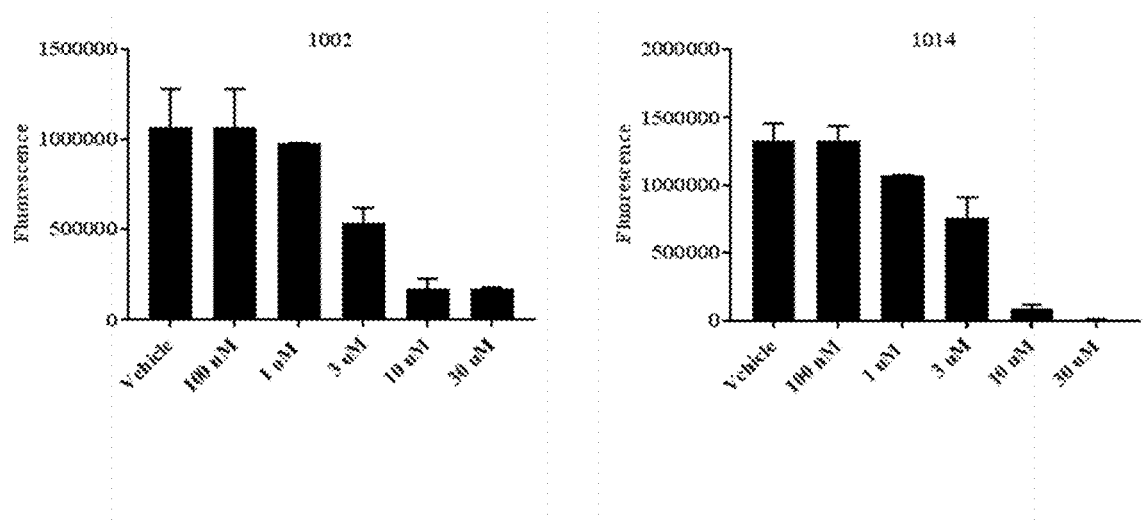

Figure 24: Serum and tumor levels of 1014 and Other SARDSs in a 22RV1 Xenograft Experiment
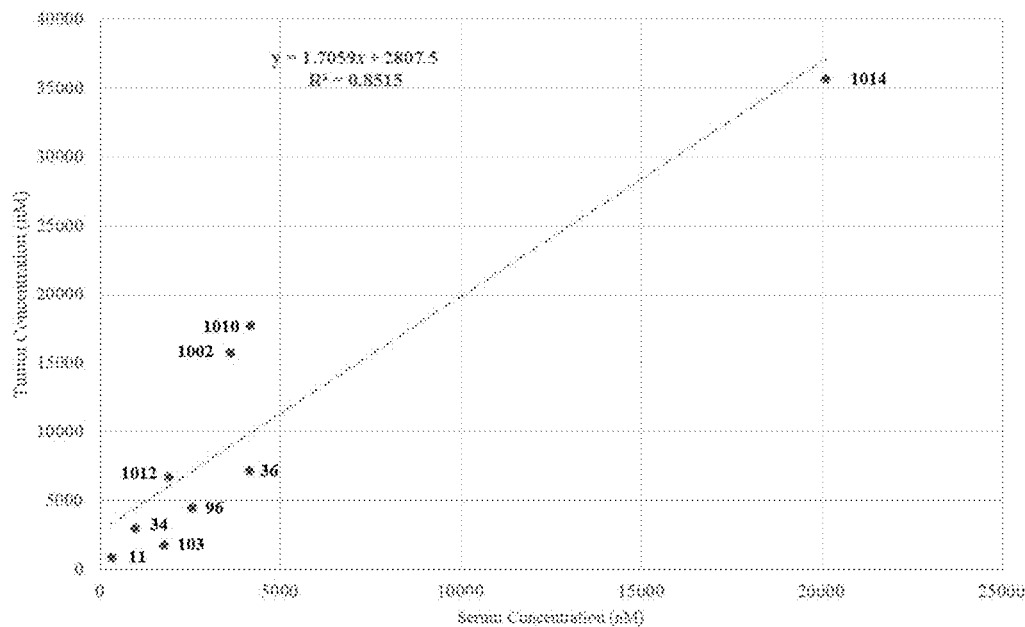
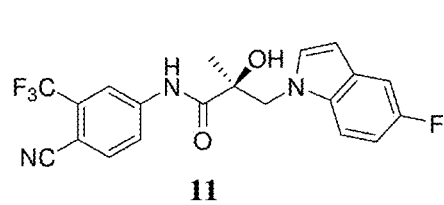
11
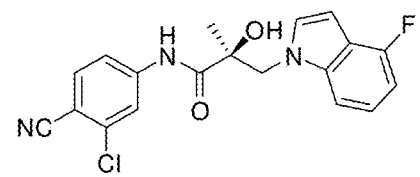
36
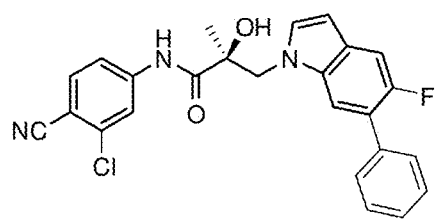
34
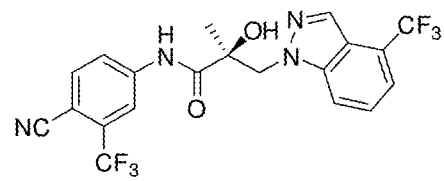
96
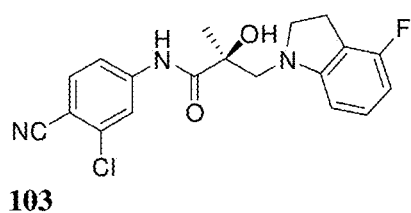
103

Figure 25: Hershberger Assay
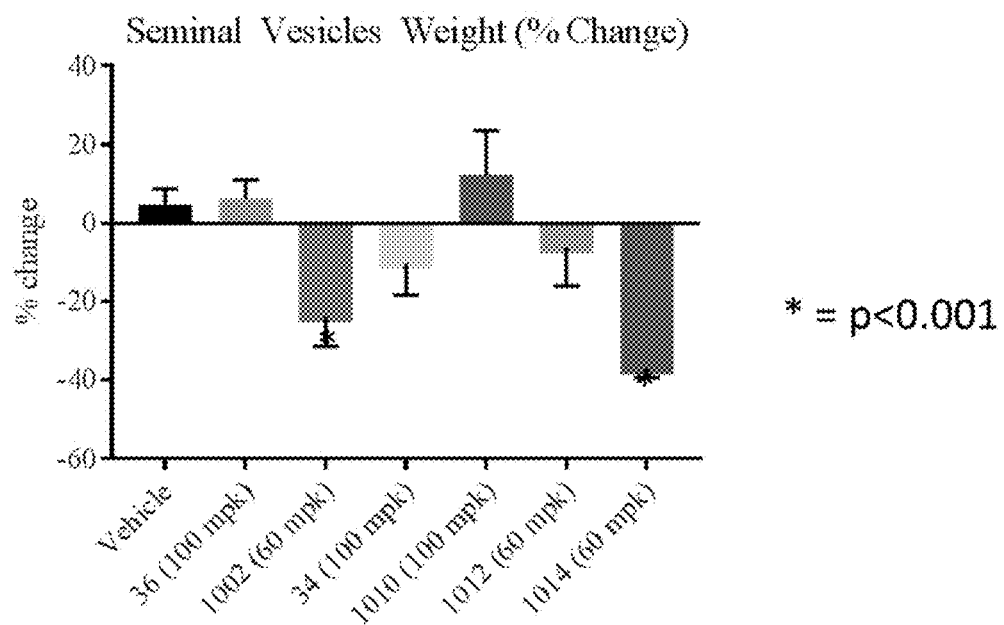
$* = p<0.001$
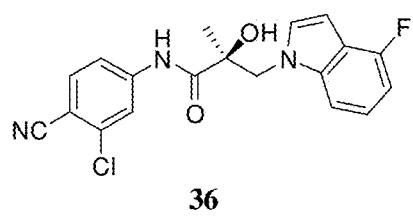
36
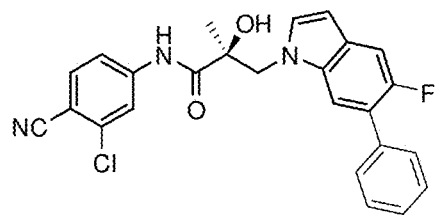
34

Figure 26
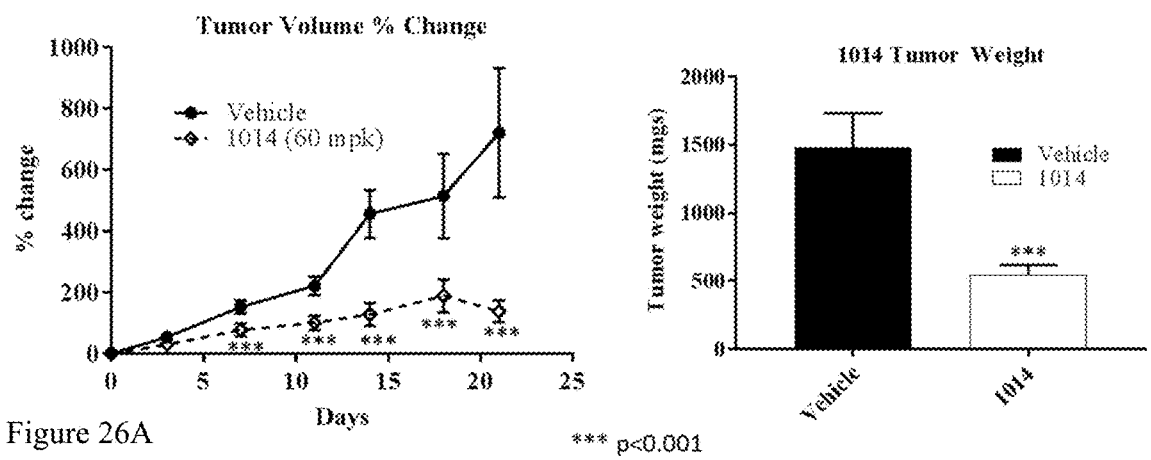
Figure 26A
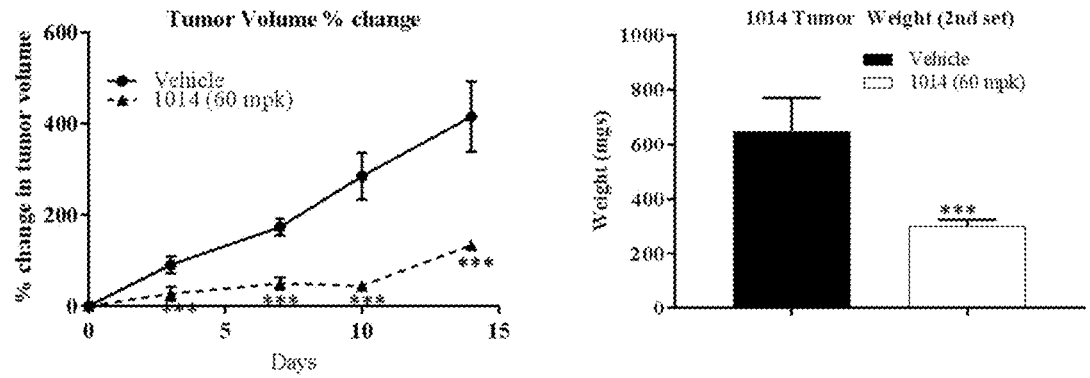
Figure 26B

Figure 27
Figure 27A
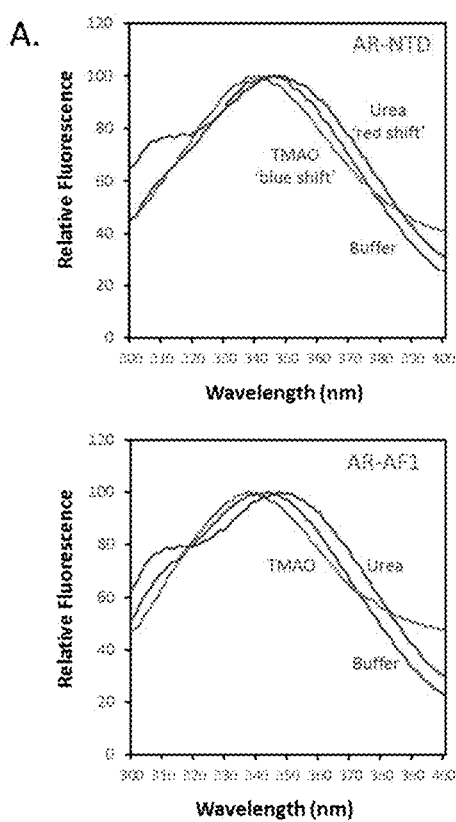
Figure 27B
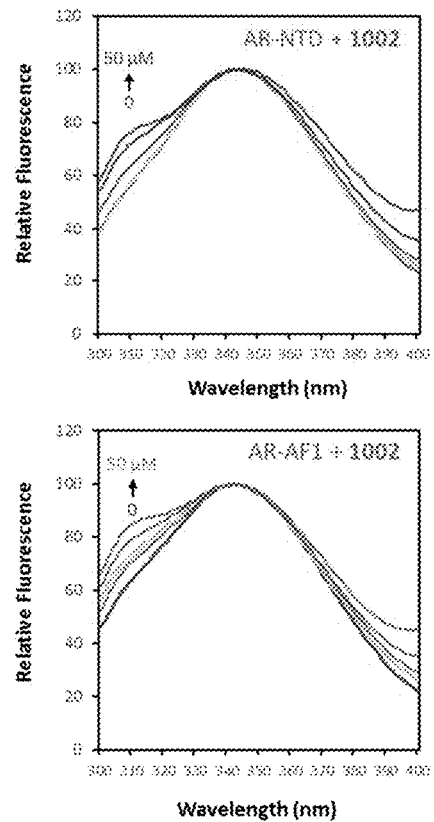

Figure 27
Figure 27C
Figure 27D
C.
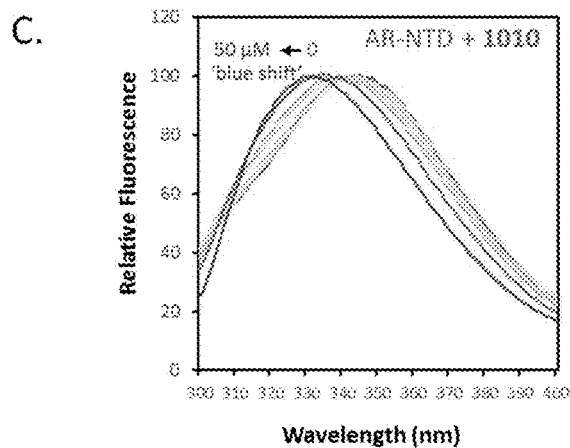
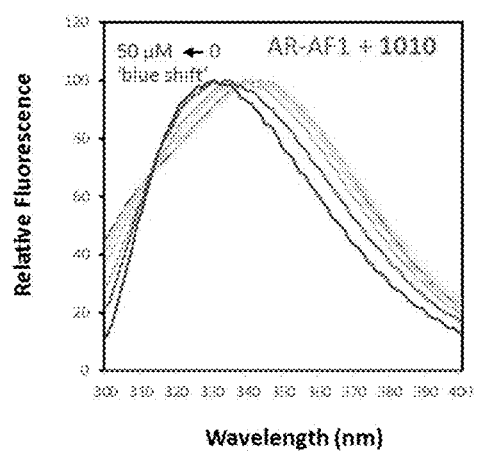
D.
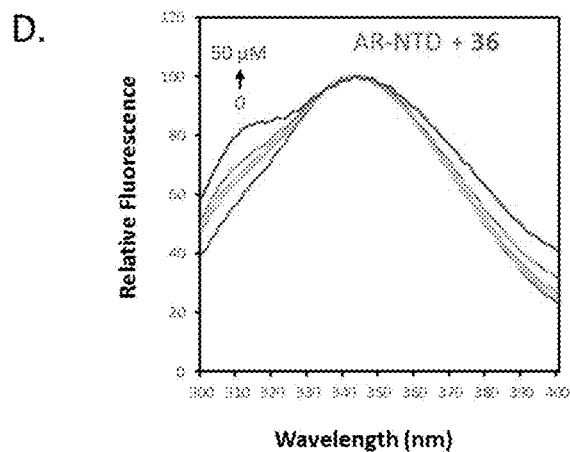
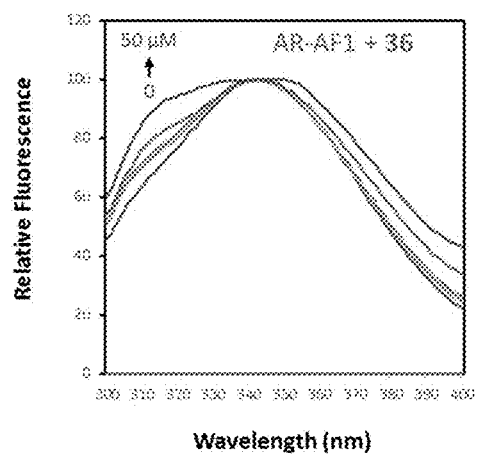
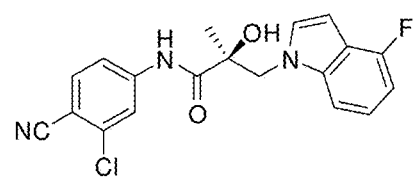
36

Figure 28A: Full Length AR Degradation Assays
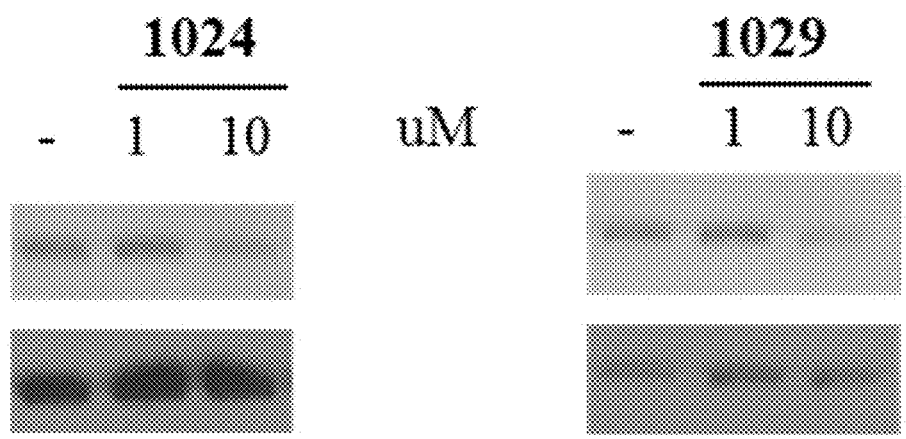
Figure 28B: Splice Variant (22RV1 cells) AR Degradation Assays
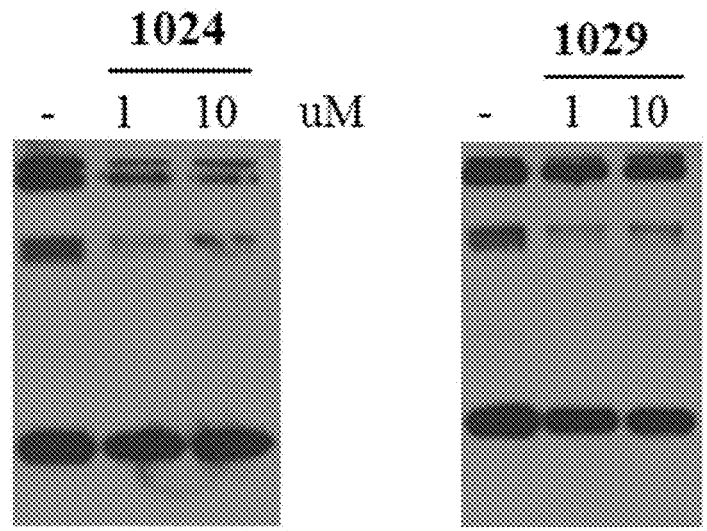

Figure 28C: Full Length AR Degradation Assays
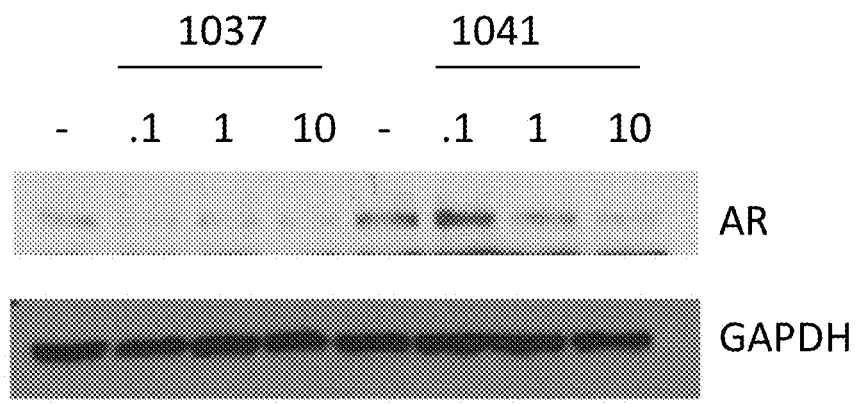
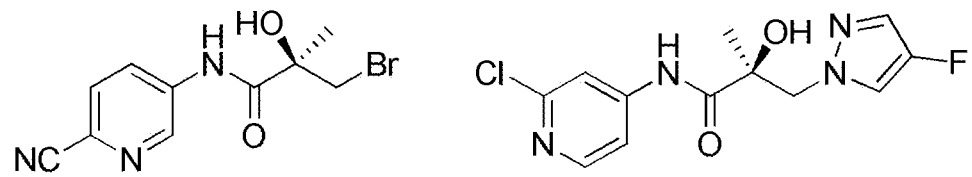
Figure 28D: Full Length AR Degradation Assays
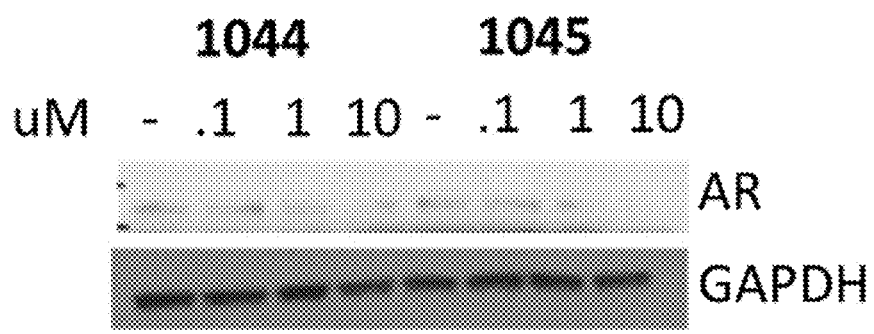
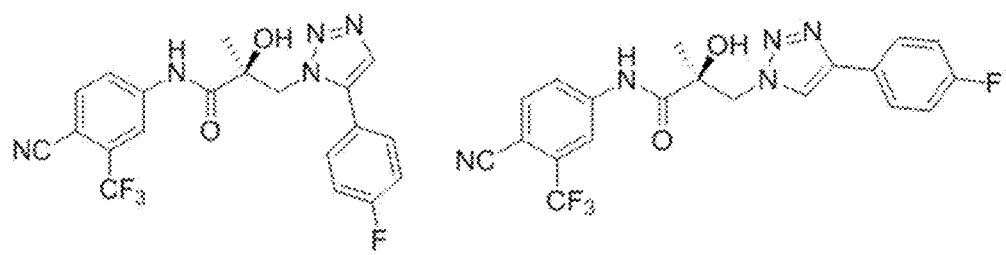

Compound 11

Compound 1002

Figure 32
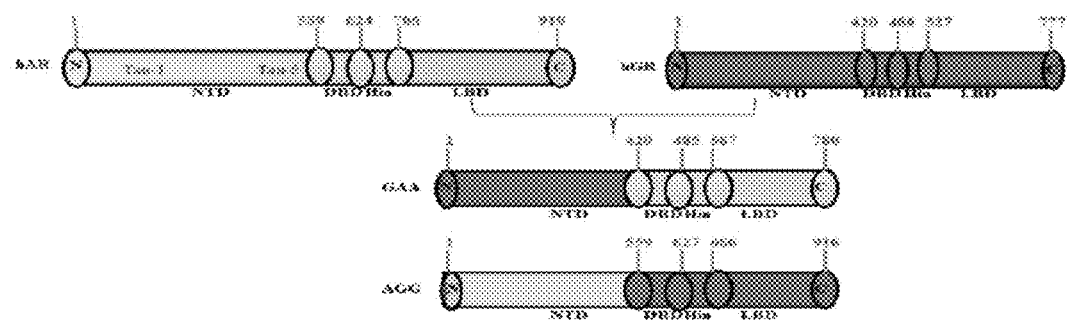
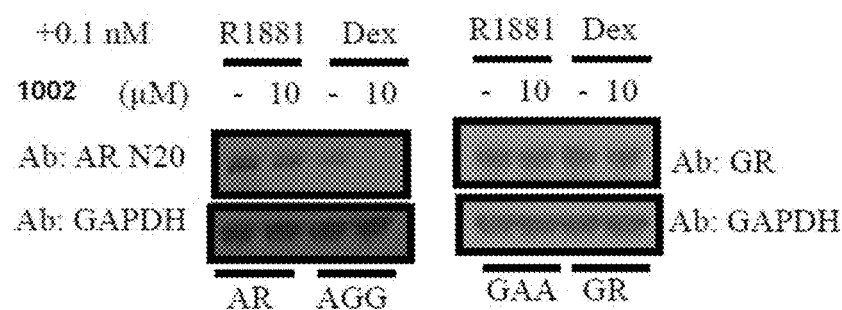

SELECTIVE ANDROGEN RECEPTOR DEGRADER (SARD) LIGANDS AND METHODS OF USE THEREOF

CROSS REFERENCE TO RELATED APPLICATIONS

This application is a Continuation-in-Part application of U.S. patent application Ser. No. 15/620,761, filed on Jun. 12, 2017, which claims the benefit of U.S. Provisional Ser. No. 62/348,474, filed on Jun. 10, 2016, U.S. Provisional Ser. No. 62/455,397, filed on Feb. 6, 2017 and U.S. Provisional Ser. No. 62/482,036 filed on Apr. 5, 2017, which are all incorporated in their entirety herein by reference.

FIELD OF THE INVENTION

This invention is directed to pyrrole, pyrazole, imidazole, triazole, and morpholine based selective androgen receptor degrader (SARD) compounds including heterocyclic anilide rings and their synthetic precursors, R-isomers, and non-hydroxylated and/or non-chiral propanamides, and pharmaceutical compositions and uses thereof in treating prostate cancer, advanced prostate cancer, castration resistant prostate cancer, triple negative breast cancer, other cancers expressing the androgen receptor, androgenic alopecia or other hyperandrogenic dermal diseases, Kennedy's disease, amyotrophic lateral sclerosis (ALS), abdominal aortic aneurysm (AAA), and uterine fibroids, and to methods for reducing the levels of androgen receptor-full length (AR-FL) including pathogenic or resistance mutations, AR-splice variants (AR-SV), and pathogenic polyglutamine (polyQ) polymorphisms of AR in a subject.

BACKGROUND OF THE INVENTION

Prostate cancer (PCa) is one of the most frequently diagnosed noncutaneous cancers among men in the US and is the second most common cause of cancer deaths with more than 200,000 new cases and over 30,000 deaths each year in the United States. PCa therapeutics market is growing at an annual rate of 15-20% globally.

Androgen-deprivation therapy (ADT) is the standard of treatment for advanced PCa. Patients with advanced prostate cancer undergo ADT, either by luteinizing hormone releasing hormone (LHRH) agonists, LHRH antagonists or by bilateral orchiectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with CRPC have a median survival of 12-18 months. Though castration-resistant, CRPC is still dependent on the androgen receptor (AR) signaling axis for continued growth. The primary reason for CRPC re-emergence is re-activation of AR by alternate mechanisms such as: 1) intracrine androgen synthesis, 2) AR splice variants (AR-SV), e.g., that lack ligand binding domain (LBD), 3) AR-LBD mutations with potential to resist AR antagonists (i.e., mutants that are not sensitive to inhibition by AR antagonists, and in some cases AR antagonists act as agonists of the AR bearing these LBD mutations), and 4) amplifications of the AR gene within the tumor. A critical barrier to progress in treating CRPC is that AR signaling inhibitors such as enzalutamide, bicalutamide, and abiraterone, acting through the LBD, fail to inhibit growth driven by the N-terminal domain (NTD)-dependent constitutively active AR-SV such as AR-V7, the most prominent AR-SV. Recent high-impact clinical trials with enzalutamide and abiraterone in CRPC patients demonstrated that just 13.9% of AR-V7-positive patients among 202 patients starting treatment with enzalutamide (Xtandi) or abiraterone acetate (Zytiga) had PSA responses to either of the treatments (Antonarakis E S, Lu C, Luber B, et al. *J. Clin. Oncol.* 2017 Apr. 6. doi: 10.1200/JCO.2016.70.1961), indicating the requirement for next generation AR antagonists that target AR-SVs. In addition, a significant number of CRPC patients are becoming refractory to abiraterone or enzalutamide, emphasizing the need for next generation AR antagonists.

Current evidences demonstrate that CRPC growth is dependent on constitutively active AR including AR-SV's that lack the LBD such as AR-V7 and therefore cannot be inhibited by conventional antagonists. AR inhibition and degradation through binding to a domain that is distinct from the AR LBD provides alternate strategies to manage CRPC.

Molecules that degrade the AR prevent any inadvertent AR activation through growth factors or signaling pathways, or promiscuous ligand-dependent activation. In addition, molecules that inhibit the constitutive activation of AR-SVs are extremely important to provide extended benefit to CRPC patients.

Currently only a few chemotypes are known to degrade AR which include the SARDs ARN-509, AZD-3514, and ASC-J9. However, these molecules degrade AR indirectly at much higher concentrations than their binding coefficient and they fail to degrade the AR-SVs that have become in recent years the primary reason for resurgence of treatment-resistant CRPC.

This invention describes novel AR antagonists with unique pharmacology that strongly (high potency and efficacy) and selectively bind AR (better than known antagonists in some cases; bind to LBD and/or NTD), antagonize AR, and degrade AR full length (AR-FL) and AR-SV. Selective androgen receptor degrader (SARD) compounds possess dual degradation and AR-SV inhibitory functions and hence are distinct from any available CRPC therapeutics. These novel selective androgen receptor degrader (SARD) compounds inhibit the growth of PCa cells and tumors that are dependent on AR-FL and AR-SV for proliferation.

SARDs have the potential to evolve as new therapeutics to treat CRPCs that are untreatable with any other antagonists. This unique property of degrading AR-SV has extremely important health consequences for prostate cancer. Till date only one series of synthetic molecules (EPI-001, EPI-506, etc.) and some marine natural products such as the sinkotamides and glycerol ether Naphetenone B, are reported to bind to AR-NTD and inhibit AR function and PCa cell growth, albeit at lower affinity and inability to degrade the receptor. The SARDs reported herein also bind to AR-NTD and inhibit NTD-driven (e.g., ligand independent) AR activity.

The positive correlation between AR and PCa and the lack of a fail-safe AR antagonist, emphasizes the need for molecules that inhibit AR function through novel or alternate mechanisms and/or binding sites, and that can elicit antagonistic activities within an altered cellular environment.

Although traditional antiandrogens such as enzalutamide, bicalutamide and flutamide and androgen deprivation therapies (ADT) were approved for use in prostate cancer, there is significant evidence that antiandrogens could also be used in a variety of other hormone dependent and hormone independent cancers. For example, antiandrogens have been tested in breast cancer (enzalutamide; Breast Cancer Res. (2014) 16(1): R7), non-small cell lung cancer (shRNAi AR), renal cell carcinoma (ASC-J9), partial androgen insensitivity syndrome (PAIS) associated malignancies such as gonadal tumors and seminoma, advanced pancreatic cancer (*World J. Gastroenterology* 20(29), 9229), cancer of the ovary, fallopian tubes, or peritoneum, cancer of the salivary gland (Head and Neck (2016) 38, 724-731; ADT was tested in AR-expressing recurrent/metastatic salivary gland cancers and was confirmed to have benefit on progression free survival and overall survival endpoints), bladder cancer (*Oncotarget* 6(30), 29860-29876); *Int J. Endocrinol* (2015), Article ID 384860), pancreatic cancer, lymphoma (including mantle cell), and hepatocellular carcinoma. Use of a more potent antiandrogen such as a SARD in these cancers may more efficaciously treat the progression of these and other cancers. Other cancers may also benefit from SARD treatment such as breast cancer (e.g., triple negative breast cancer (TNBC)), testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer.

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, enzalutamide and other LBD-directed traditional AR antagonists would not be able to antagonize AR-SVs in these TNBC's. However, SARDs of this invention which are capable of destroying AR-SVs (see Table 1 and Example 5) through a binding site in the NTD of AR (see Example 9) would be able to antagonize AR including AR-SV observed in TNBC patient derived xenograpfts and provide an anti-tumor effect, as shown in Example 8.

Traditional antiandrogens such as bicalutamide and flutamide were approved for use in prostate cancer. Subsequent studies have demonstrated the utility of antiandrogens (e.g., flutamide, spironolactone, cyproterone acetate, finasteride and chlormadinone acetate) in androgen-dependent dermatological conditions such as androgenic alopecia (male pattern baldness), acne vulgaris, and hirsutism (e.g., in female facial hair). Prepubertal castration prevents sebum production and androgenic alopecia but this can be reversed by use of testosterone, suggesting its androgen-dependence.

The AR gene has a polymorphism of glutamine repeats (polyQ) within exon 1 which when shortened may augment AR transactivation (i.e., hyperandrogenism). It has been found that shortened polyQ polymorphisms are more common in people with alopecia, hirsutism, and acne. Classic antiandrogens are undesirable for these purposes because they are ineffective through dermal dosing and their long-term systemic use raises the risks of untoward sexual effects such as gynecomastia and impotence. Further, similar to CPRC discussed above, inhibition of ligand-dependent AR activity alone may not be sufficient as AR can be activated by various cellular factors other than the endogeneous androgens testosterone (T) and dihydrotestosterone (DHT), such as growth factors, kinases, co-activator overexpression and/or promiscuous activation by other hormones (e.g., estrogens or glucocorticoids). Consequently, blocking the binding of T and DHT to AR with a classical antiandrogen may not be sufficient to have the desired efficacy.

An emerging concept is the topical application of a SARD to destroy the AR locally to the affected areas of the skin or other tissue without exerting any systemic antiandrogenism. For this use, a SARD that does not penetrate the skin or is rapidly metabolized would be preferable.

Supporting this approach is the observation that cutaneous wound healing has been demonstrated to be suppressed by androgens. Castration of mice accelerates cutaneous wound healing while attenuating the inflammation in the wounds. The negative correlation between androgen levels and cutaneous healing and inflammation, in part, explains another mechanism by which high levels of endogenous androgens exacerbate hyperandrogenic dermatological conditions. Further, it provides a rationale for the treatment of wounds such as diabetic ulcers or even trauma, or skin disorders with an inflammatory component such as acne or psoriasis, with a topical SARD.

Androgenic alopecia occurs in ~50% of Caucasian males by midlife and up to 90% by 80 years old. Minoxidil (a topical vasodilator) and finasteride (a systemic 5alpha reductase type II inhibitor) are FDA approved for alopecia but require 4-12 months of treatment to produce a therapeutic effect and only arrest hair loss in most with mild to moderate hair regrowth in 30-60%. Since currently available treatments have slow and limited efficacy that varies widely between individuals, and produce unwanted sexual side effects, it is important to find a novel approach to treat androgenic alopecia and other hyperandrogenic dermatologic diseases.

Amyotrophic lateral sclerosis (ALS) is a fatal neurodegenerative disease characterized by selective loss of upper and lower motor neurons and skeletal muscle atrophy. Epidemiologic and experimental evidence suggest the involvement of androgens in ALS pathogenesis ("Anabolic/androgenic steroid nandrolone exacerbates gene expression modifications induced by mutant SOD1 in muscles of mice models of amyotrophic lateral sclerosis." Galbiati M, Onesto E, Zito A, Crippa V, Rusmini P, Mariotti R, Bentivoglio M, Bendotti C, Poletti A. *Pharmacol. Res.* 2012, 65(2), 221-230), but the mechanism through which androgens modify the ALS phenotype is unknown. A transgenic animal model of ALS demonstrated improved survival upon surgical castration (i.e., androgen ablation). Treatment of these castrated animals with the androgen agonist nandrolone decanoate worsened disease manifestations. Castration reduces the AR level, which may be the reason for extended survival. The survival benefit is reversed by androgen agonist ("Androgens affect muscle, motor neuron, and survival in a mouse model of SOD1-related amyotrophic lateral sclerosis."

Aggarwal T, Polanco M J, Scaramuzzino C, Rocchi A, Milioto C, Emionite L, Ognio E, Sambataro F, Galbiati M, Poletti A, Pennuto M. *Neurobiol. Aging.* 2014 35(8), 1929-1938). Notably, stimulation with nandrolone decanoate promoted the recruitment of endogenous androgen receptor into biochemical complexes that were insoluble in sodium dodecyl sulfate, a finding consistent with protein aggregation. Overall, these results shed light on the role of androgens as modifiers of ALS pathogenesis via dysregulation of androgen receptor homeostasis. Antiandrogens should block the effects of nandrolone undecanoate or endogeneous androgens and reverse the toxicities due to AR aggregation. Further, an antiandrogen that can block action of LBD-dependent AR agonists and concomitantly lower AR protein levels, such as the SARDs of this invention, would be therapeutic in ALS. Riluzole is an available drug for ALS treatment, however, it only provides short-term effects. There is an urgent need for drugs that extend the survival of ALS patients.

Androgen receptor action promotes uterine proliferation. Hyperandrogenicity of the short polyQ A R has been associated with increased leiomyoma or uterine fibroids. (Hsieh Y Y, Chang C C, Tsai F J, Lin C C, Yeh L S, Peng C T. *J. Assist. Reprod. Genet.* 2004, 21(12), 453-457). A separate study of Brazilian women found that shorter and longer [CAG](n) repeat alleles of A R were exclusive to the leiomyoma group in their study (Rosa F E, Canevari Rde A, Ambrosio E P, Ramos Cirilo P D, Pontes A, Rainho C A, Rogatto S R. *Clin. Chem. Lab. Med.* 2008, 46(6), 814-823). Similarly, in Asian Indian women long polyQ AR was associated with endometriosis and leiomyoma and can be regarded as high-risk markers. SARDs could be used in women with uterine fibroids, especially those expressing shorter and longer [CAG](n) repeat alleles, to treat existing uterine fibroids, prevent worsening of fibroids and/or ameliorate carcinogenicity associated with fibroids.

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated porcine pancreatic elastase (0.35 U/mL) induced AAA by 84.2% and 91.5% compared to vehicle (121%). Further AR −/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

X-linked spinal-bulbar atrophy (SBMA—also known as Kennedy's disease) is a muscular atrophy that arises from a defect in the androgen receptor gene on the X chromosome. Proximal limb and bulbar muscle weakness results in physical limitations including dependence on a wheelchair in some cases. The mutation results in a protracted polyglutamine tract added to the N-terminal domain of the androgen receptor (polyQ AR). Binding and activation of this lengthened polyQ AR by endogenous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Support of use antiandrogen comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). Currently there are no disease-modifying treatments but rather only symptom directed treatments. Efforts to target the polyQ AR of Kennedy's disease as the proximal mediator of toxicity by harnessing cellular machinery to promote its degradation, i.e., through the use of a SARD, hold promise for therapeutic intervention. Selective androgen receptor degraders such as those reported herein bind to and degrade all androgen receptors tested (full length, splice variant, antiandrogen resistance mutants, etc.) so degradation of polyQ AR polymorphism is also expected, indicating that they are promising leads for treatment of SBMA.

Here we describe, inter alia, pyrrole, pyrazole, triazole, imidazole, and morpholine based selective androgen receptor degrader (SARD) compounds that may bind to the LBD and/or an alternate binding and degradation domain (BDD) located in the NTD, antagonize AR, and degrade AR thereby blocking ligand-dependent and ligand-independent AR activities. This novel mechanism produces improved efficacy when dosed systemically (e.g., for prostate cancer) or topically (e.g., dermatological diseases).

SUMMARY OF THE INVENTION

One embodiment of the invention encompasses a selective androgen receptor degrader (SARD) compound represented by the structure of formula I:

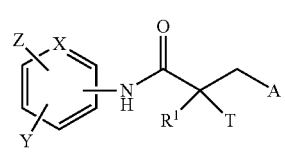

wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;

A is $R^2$ or $R^3$;

$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

$R^3$ is $NHR^2$, halide, $N_3$, $OR^4$, $CF_3$, $COR^4$, COCl, $COCOR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4SO_3H$, $SO_2NH_2$, $SO_2NH(R^4)$, $SO_2N(R^4)_2$, $NH_2$, $NH(R^4)$, $N(R^4)_2$, CO(N-heterocycle), $C(O)(C_1-C_{10})$alkyl, $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its optical isomer, isomer, pharmaceutically acceptable salt, pharmaceutical product, polymorph, hydrate or any combination thereof;

wherein if A is Br or I, $R^1$ is $CH_3$, and T is OH, then X is N or the aniline ring forms a fused heterocyclic ring.

In another embodiment, this invention is directed to a SARD compound represented by the structure of formula IA:

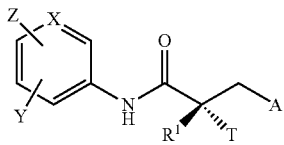

wherein

T is H, OH, OR, OCOR, $CH_3$, —$NHCOCH_3$, or NHCOR;

$R^1$ is H, $CH_3$, $CH_2F$, $CHF_2$, $CF_3$, $CH_2CH_3$, or $CF_2CF_3$;

or T and $R^1$ form a 3-8 carbocyclic or heterocyclic ring;

Y is H, $CF_3$, F, I, Br, Cl, CN, or $C(R)_3$;

Z is H, $NO_2$, CN, halide COOH, COR, NHCOR, CONHR, or Y and Z form a 5 to 8 membered fused ring;

X is CH or N;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;

A is $R^2$ or $R^3$;

$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

$R^3$ is, $NHR^2$, halide, $N_3$, $OR^4$, $CF_3$, $COR^4$, COCl, $COCOR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4SO_3H$, $SO_2NH_2$, $SO_2NH(R^4)$, $SO_2N(R^4)_2$, $NH_2$, $NH(R^4)$, $N(R^4)_2$, CO(N-heterocycle), $C(O)(C_1-C_{10})$alkyl, $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof;

wherein if A is Br or I, $R^1$ is $CH_3$, and T is OH, then X is N or the aniline ring forms a fused heterocyclic ring.

In another embodiment, this invention is directed to a SARD compound represented by the structure of formula IB:

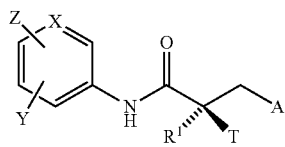

wherein

T is H, OH, OR, OCOR, $CH_3$, —$NHCOCH_3$, or NHCOR;

$R^1$ is H, $CH_3$, $CH_2F$, $CHF_2$, $CF_3$, $CH_2CH_3$, or $CF_2CF_3$;

or T and $R^1$ form a 3-8 carbocyclic or heterocyclic ring;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

X is CH or N;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;

A is $R^2$ or $R^3$;

$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;

$R^3$ is $NHR^2$, halide, $N_3$, $OR^4$, $CF_3$, $COR^4$, COCl, $COCOR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof;

wherein if A is Br or I, $R^1$ is $CH_3$, and T is OH, then X is N or the aniline ring forms a fused heterocyclic ring.

The invention encompasses a SARD compound represented by the structure of formula II:

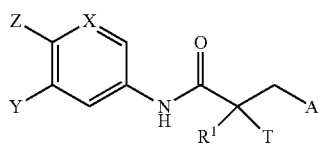

wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
R$^3$ is NHR$^2$, halide, N$_3$, OR$^4$, CF$_3$, COR$^4$, COCl, COO-COR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer, isomer, pharmaceutically acceptable salt, pharmaceutical product, polymorph, hydrate or any combination thereof;
wherein if A is Br or I, R$^1$ is CH$_3$, and T is OH, then X is N or the aniline ring forms a fused heterocyclic ring.

In another embodiment, this invention is directed to a SARD compound represented by the structure of formula IIA:

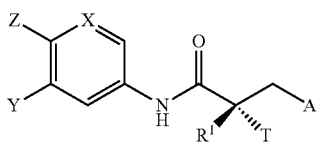

wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
R$^3$ is NHR$^2$, halide, N$_3$, OR$^4$, CF$_3$, COR$^4$, COCl, COO-COR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SR$^4$, SO$_2$R$^4$, SOR$^4$SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
or its isomer, pharmaceutically acceptable salt, pharmaceutical product, polymorph, hydrate or any combination thereof;
wherein if A is Br or I, R$^1$ is CH$_3$, and T is OH, then X is N or the aniline ring forms a fused heterocyclic ring.

In another embodiment, this invention is directed to a SARD compound represented by the structure of formula IIB:

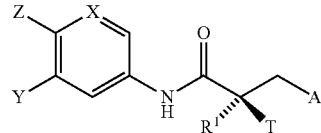

wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;

$R^3$ is $NHR^2$, halide, $N_3$, $OR^4$, $CF_3$, $COR^4$, $COCl$, $COOCOR^4$, $COOR^4$, $OCOR^4$, $OCONHR^4$, $NHCOOR^4$, $NHCONHR^4$, $OCOOR^4$, $CN$, $CONH_2$, $CONH(R^4)$, $CON(R^4)_2$, $SR^4$, $SO_2R^4$, $SOR^4SO_3H$, $SO_2NH_2$, $SO_2NH(R^4)$, $SO_2N(R^4)_2$, $NH_2$, $NH(R^4)$, $N(R^4)_2$, $CO(N\text{-heterocycle})$, $NO_2$, cyanate, isocyanate, thiocyanate, isothiocyanate, mesylate, tosylate, triflate, $PO(OH)_2$ or $OPO(OH)_2$; and $R^4$ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof;

wherein if A is Br or I, $R^1$ is $CH_3$, and T is OH, then X is N or the aniline ring forms a fused heterocyclic ring.

In another embodiment, the invention encompasses a selective androgen receptor degrader compound represented by the structure of formula VII:

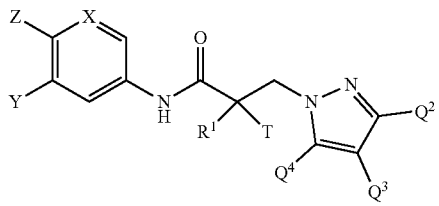

VII wherein

X is CH or N;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^2$, $Q^3$, or $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR; or its optical isomer, isomer, pharmaceutically acceptable salt, pharmaceutical product, polymorph, hydrate or any combination thereof.

In another embodiment, the invention encompasses a selective androgen receptor degrader compound represented by the structure of formula VIIA:

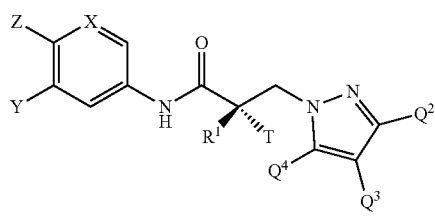

VIIA wherein

X is CH or N;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH; and $Q^2$, $Q^3$, or $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR; or its isomer, pharmaceutically acceptable salt, pharmaceutical product, polymorph, hydrate or any combination thereof.

In another embodiment, the invention encompasses a selective androgen receptor degrader compound represented by the structure of formula VIIB:

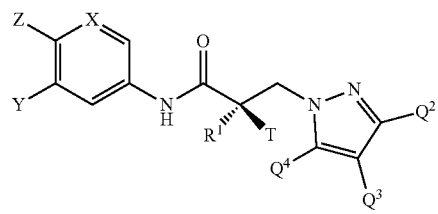

VIIB wherein

X is CH or N;

Y is H, $CF_3$, F, I, Br, Cl, CN, or $C(R)_3$;

Z is H, $NO_2$, CN, halide, COOH, COR, NHCOR, CONHR, or Y and Z form a 5 to 8 membered fused ring;

$R^1$ is H, $CH_3$, $CH_2F$, $CHF_2$, $CF_3$, $CH_2CH_3$, or $CF_2CF_3$;

T is H, OH, OR, OCOR, $CH_3$, —$NHCOCH_3$, or NHCOR;

or T and $R^1$ form a 3-8 carbocyclic or heterocyclic ring;

R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;

and $Q^2$, $Q^3$, or $Q^4$ are each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR; or its isomer, pharmaceutically acceptable salt, pharmaceutical product, polymorph, hydrate or any combination thereof.

Yet another embodiment of the invention encompasses the SARD compound represented by the structure of any one of the following compounds:

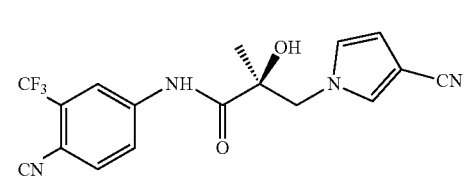
1001
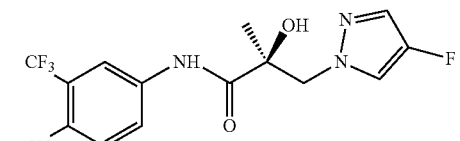
1002
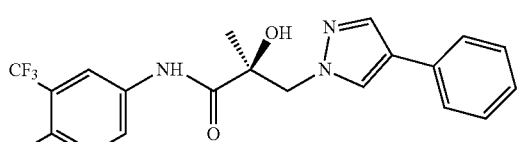
1003
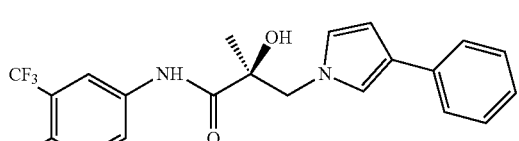
1004
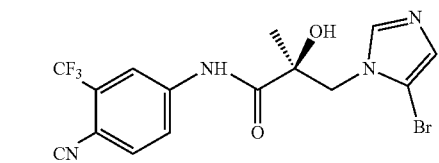
1005
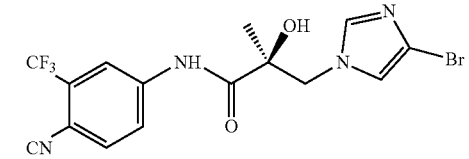
1006
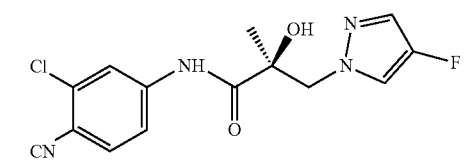
1007
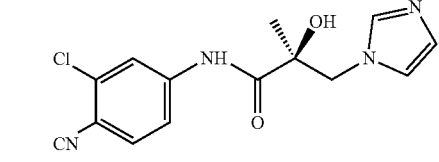
1008
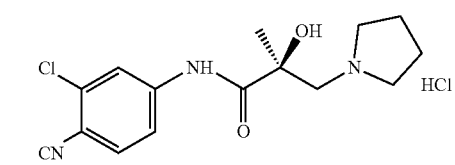
1009
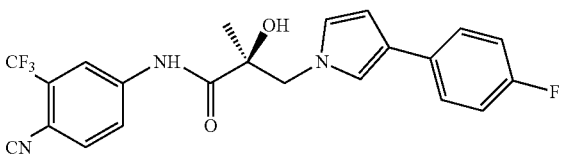
1010
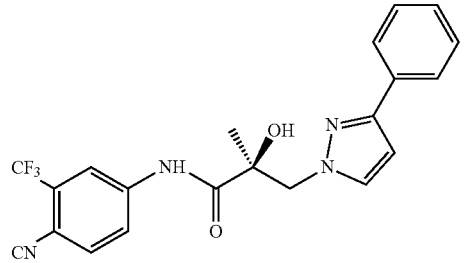
1011
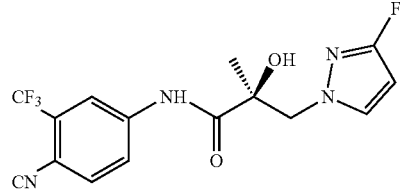
1012
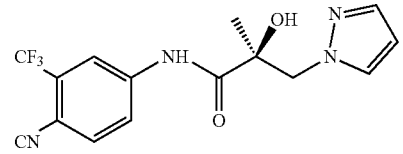
1013
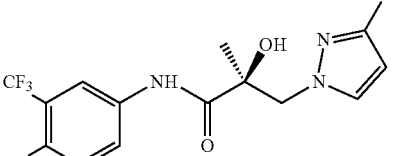
1014
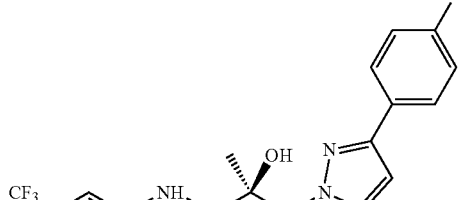
1015
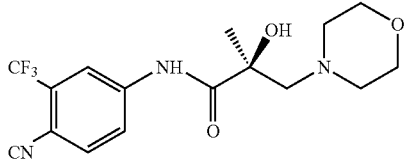
1016

| | |
|---|---|
| 1017 | 1026 |
| 1018 | 1027 |
| 1019 | 1028 |
| 1020 | 1029 |
| 1021 | 1030 |
| 1022 | 1031 |
| 1023 | 1032 |
| 1024 | 1033 |
| 1025 | |

-continued

1034
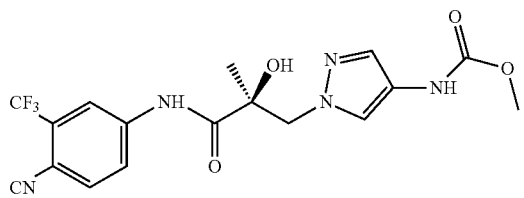

1035
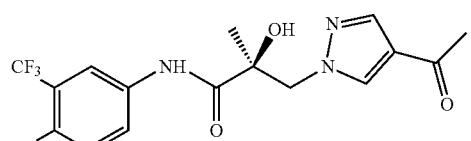

1036
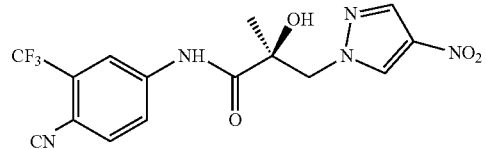

1037
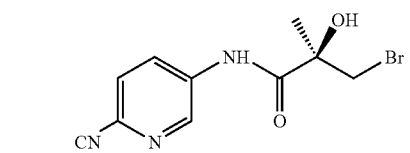

1038
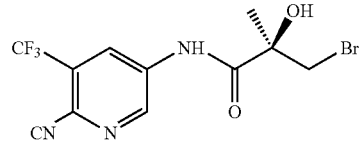

1039
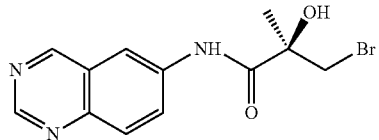

1040
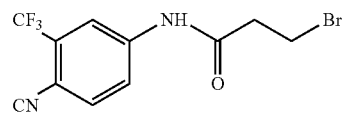

1041
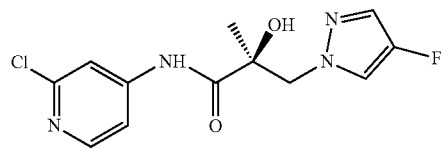

1042
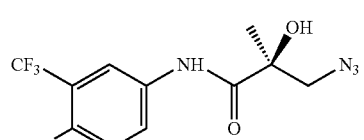

1043
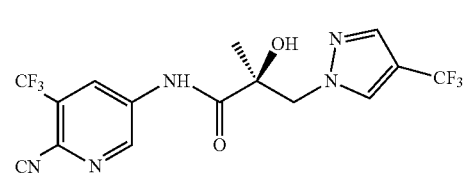

-continued

1044
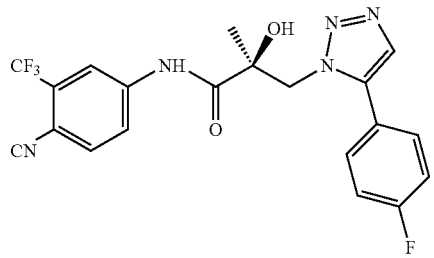

1045
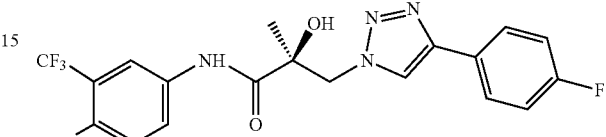

1046
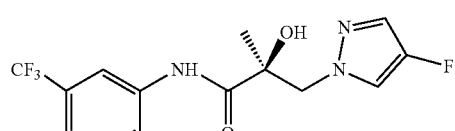

1047
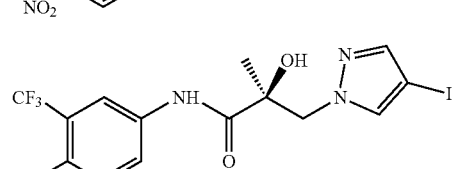

1048
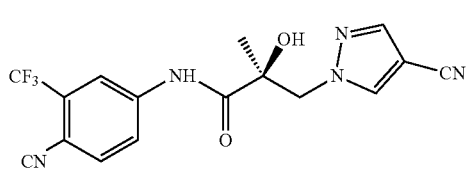

1049
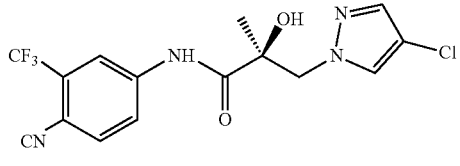

One embodiment of the invention encompasses the SARD compound having at least one of the following properties: binds to the AR through an alternate binding and degradation domain (BDD), e.g. in the NTD; binds to the AR through the AR ligand binding domain (LBD); exhibits AR-splice variant (AR-SV) degradation activity; exhibits AR-full length (AR-FL) degradation activity including pathogenic mutations thereof; exhibits AR-SV inhibitory activity (i.e., is an AR-SV antagonist); exhibits AR-FL inhibitory activity (i.e., is an AR-FL antagonist) including pathogenic mutations thereof; possesses dual AR-SV degradation and AR-SV inhibitory functions; and/or dual AR-FL degradation and AR-FL inhibitory functions.

Another embodiment of the invention encompasses pharmaceutical compositions comprising a SARD compound according to this invention, or its isomer, pharmaceutically acceptable salt, pharmaceutical product, polymorph, hydrate or any combination thereof, and a pharmaceutically acceptable carrier. The pharmaceutical composition may be formulated for topical use. The topical pharmaceutical composition may be a solution, lotion, salve, cream, ointment, liposome, spray, gel, foam, roller stick, cleansing soaps or bars, emulsion, mousse, aerosol, or shampoo.

The invention encompasses a method of treating prostate cancer (PCa) or increasing survival in a male subject in need of treatment comprising administering to the subject a therapeutically effective amount of a compound defined by formulas I-VII, IA-ID, IIA, IIB, VIIA, or VIIB or any of compounds 1001-1049. The prostate cancer includes, but is not limited to, advanced prostate cancer, castration resistant prostate cancer (CRPC), metastatic CRPC (mCRPC), non-metastatic CRPC (nmCRPC), high-risk nmCRPC or any combination thereof. Another embodiment of the invention encompasses the method further comprising administering androgen deprivation therapy. Alternatively, the method may treat a prostate or other cancer that is resistant to treatment with known androgen receptor antagonist(s) or ADT. In another embodiment, the method may treat enzalutamide resistant prostate cancer. In another embodiment, the method may treat abiraterone resistant prostate cancer. Yet another embodiment of the invention encompasses a method of treating prostate or other AR antagonist resistant cancer with a SARD compound of the invention wherein the androgen receptor antagonist(s) is at least one of enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, or spironolactone.

Yet another embodiment of the invention encompasses a method of treating prostate or other cancers using a SARD compound of the invention wherein the other cancers are selected from breast cancer such as triple negative breast cancer (TNBC), testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer. In another embodiment, the breast cancer is triple negative breast cancer (TNBC).

The invention encompasses a method of reducing the levels of AR-splice variants in a subject comprising administering to the subject a therapeutically effective amount of a compound of this invention, or its isomer, pharmaceutically acceptable salt, pharmaceutical product, polymorph, hydrate or any combination thereof. The method may comprise further reducing the levels of AR-full length in the subject.

Another embodiment of the invention encompasses a method of treating Kennedy's disease in a subject comprising administering to the subject a compound of formulas I-VII, IA-ID, IIA, IIB, VIIA, or VIIB or a compound of another formula of the invention.

Yet another embodiment of the invention encompasses a method of: (a) treating acne in a subject, e.g., acne vulgaris; (b) decreasing sebum production in a subject, e.g., treats sehorrhea, seborrheic dermatitis, or acne; (c) treating hirsutism in a subject, e.g., female facial hair; (d) treating alopecia in a subject, e.g., androgenic alopecia, alopecia areata, alopecia secondary to chemotherapy, alopecia secondary to radiation therapy, alopecia induced by scarring, or alopecia induced by stress; (e) treating a hormonal condition in female, e.g., precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, or vaginal dryness; (f) treating sexual perversion, hypersexuality, or paraphilias in a subject; (g) treating androgen psychosis in a subject; (h) treating virilization in a subject; (i) treating complete or partial androgen insensitivity syndrome in a subject; (j) increasing or modulating ovulation in an animal; (k) treating of cancer in a subject; or any combination thereof, by administering a compound of this invention or a pharmaceutical composition thereof.

One embodiment of the invention encompasses methods of reducing the levels of polyglutamine (polyQ) AR polymorphs in a subject comprising administering a compound according to this invention. The method may inhibit, degrade, or both the function of the polyglutamine (polyQ) AR polymorphs (polyQ-AR). The polyQ-AR may be a short polyQ polymorph or a long polyQ polymorph. When the polyQ-AR is a short polyQ polymorph, the method further treats dermal disease. When the polyQ-AR is a long polyQ polymorph, the method further treats Kennedy's disease.

Another embodiment of the invention encompasses methods of treating amyotrophic lateral sclerosis (ALS) in a subject by administering a therapeutically effective amount of the compound of the invention, or its isomer, pharmaceutically acceptable salt, pharmaceutical product, polymorph, hydrate or any combination thereof; or a pharmaceutical composition thereof.

Another embodiment of the invention encompasses methods of treating abdominal aortic aneurysm (AAA) in a subject by administering a therapeutically effective amount of the compound of the invention, or its isomer, pharmaceutically acceptable salt, pharmaceutical product, polymorph, hydrate or any combination thereof; or a pharmaceutical composition thereof.

Yet another embodiment of the invention encompasses methods of treating uterine fibroids in a subject by administering a therapeutically effective amount of the compound of this invention, or its isomer, pharmaceutically acceptable salt, pharmaceutical product, polymorph, hydrate or any combination thereof; or a pharmaceutical composition thereof.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

FIG. 1A plotted the results with RLU reported on the y-axis and SARD concentration on the x-axis, where the antagonist mode was reported in closed dots. A curve was fitted to the closed dots. FIG. 1B illustrates the Western blot of the androgen receptor degradation assay with AD1 cells and the results were reported in Table 1, under SARD Activity: Full Length % Inhibition. FIG. 1C illustrates the Western blot of the androgen receptor degradation splice variant assay with D567es cells. (The results in 22RV1 cells were reported in Table 1, under 'SARD Activity: S.V. % Inhibition'.)

FIG. 2A and FIG. 2B: The transactivation results for 11 (an indole) and 1002 (a pyrazole of this invention) were reported based on measured luciferase light emissions and reported as relative light unit intensity (RLU). FIG. 2A plotted the results with RLU reported on the y-axis and SARD concentration on the x-axis, where the antagonist mode was reported for 11 and 1002. Compound 11 is represented in closed dots and solid line and 1002 is represented in open dots and dashed line. A curve was fitted to the open and closed dots for 1002 and 11, respectively. FIG. 2B illustrates the Western blots of an AR degradation assay with AD1 cells (Full Length AR) and a splice variant assay with 22RV1 cells for 11, 11R (R-isomer of 11), 1002, and 1020 (R-isomer of 1002). The results were reported in Table 1 in columns labeled 'SARD Activity: Full Length % Inhibition' and 'SARD Activity: S.V. % Inhibition', respectively. In short, the R-isomer of indole and pyrazole SARDs retained SARD activity, in contrast to LBD-dependent inhibitors.

FIG. 3A plotted the results with RLU reported on the y-axis and SARD concentration on the x-axis, where the agonist mode was reported in closed dots and the antagonist mode was reported in open dots. A curve was fitted to the open dots. FIG. 3B illustrates the Western blot of the full length androgen receptor degradation assay and the results were reported in Table 1, under SARD Activity: Full Length % Inhibition.

FIG. 4A plotted the results with RLU reported on the y-axis and SARD concentration on the x-axis, where the agonist mode was reported in closed dots and antagonist mode was reported in open dots. A curve was fitted to the open dots. FIG. 4B illustrates the Western blot of the full length androgen receptor degradation assay and the results were reported in Table 1, under SARD Activity: Full Length % Inhibition. The numbers under the Western blot indicate the ratio of AR to actin in each lane.

FIG. 5A plotted the results with RLU reported on the y-axis and SARD concentration on the x-axis, where the agonist mode was reported in closed dots and antagonist mode was reported in open. A curve was fitted to the open dots. FIG. 5B illustrates the Western blot of the full length androgen receptor degradation assay and the results were reported in Table 1, under SARD Activity: Full Length % Inhibition.

FIG. 6A and FIG. 6B: The transactivation result of 1006 was reported based on measured luciferase light emissions and reported as relative light unit intensity (RLU). FIG. 6A plotted the results with RLU reported on the y-axis and SARD concentration on the x-axis, where the agonist mode was reported in closed dots and antagonist mode was reported in open dots. A curve was fitted to the open dots. FIG. 6B illustrates the Western blot of the full length androgen receptor degradation assay and the results were reported in Table 1, under SARD Activity: Full Length % Inhibition.

FIG. 8 plotted the results with RLU reported on the y-axis and SARD concentration on the x-axis, where the antagonist mode was reported in closed dots. A curve was fitted to the closed dots.

FIG. 9 plotted the results with RLU reported on the y-axis and SARD concentration on the x-axis, where the antagonist mode was reported in closed dots. A curve was fitted to the closed dots.

FIG. 10 plotted the results with RLU reported on the y-axis and SARD concentration on the x-axis, where the antagonist mode was reported in closed dots. A curve was fitted to the closed dots.

FIG. 11 plotted the results with RLU reported on the y-axis and SARD concentration on the x-axis, where the antagonist mode was reported in closed dots. A curve was fitted to the closed dots.

FIG. 12 plotted the results with RLU reported on the y-axis and SARD concentration on the x-axis, where the antagonist mode was reported in closed dots. A curve was fitted to the closed dots.

FIG. 13A plotted the results with RLU reported on the y-axis and SARD concentration on the x-axis, where the antagonist mode was reported in closed dots. A curve was fitted to the closed dots. FIG. 13B illustrates the Western blot of the full length androgen receptor degradation assay and the results were reported in Table 1, under SARD Activity: Full Length % Inhibition. FIG. 13C illustrates the Western blot of the androgen receptor degradation splice variant assay with 22RV1 cells and the results were reported in Table 1, under SARD Activity: S.V. % Inhibition.

FIG. 14: FIG. 14 illustrates the phase I and phase I & II data as a raw data table for the determination of metabolic stability for 1002 in mouse liver microsomes (MLM) and the $T_{1/2}$ (half-life in minutes) and $CL_{int}$ (clearance in μL/min/mg protein) values calculated therefrom.

FIG. 15A and FIG. 15B: FIG. 15A reports phase I data as a raw data table and graphed data for one experiment for 1002 in mouse liver microsomes (MLM). FIG. 15B reports phase I & II data as a raw data table and graphed data for one experiment for 1002 in mouse liver microsomes (MLM). Value for $T_{1/2}$ was 224 min. $CL_{int}$ was 3.12 μL/min/mg.

FIG. 16A and FIG. 16B: FIG. 16A reports phase I data for human liver microsomes (HLM). FIG. 16B reports phase I & II data as a raw data table and graphed data for one experiment for 1002 in human liver microsomes (HLM). For this experiment, the calculated value for $T_{1/2}$ was infinity and $CL_{int}$ was 0. Suggesting greater stability for 1002 in HLM than MLM.

FIG. 17: FIG. 17 reports phase I data as a raw data table and graphed data for one experiment for 1001 in mouse liver microsomes (MLM). Value for $T_{1/2}$ was 23.5 min and $CL_{int}$ was 29.5 μL/min/mg. Results depict relatively poor stability for 1001, but still an improvement compared to 11.

FIG. 18A and FIG. 18B: Hershberger method (mice): Male mice (20-25 grams body weight; n=5-7/group) were either left intact (FIG. 18A) or castrated (FIG. 18B) and treated as indicated in the figures for 13 days. Treatment of castrated mice was initiated 3 days after castration. Mice were sacrificed on day 14 after treatment initiation and seminal vesicles were removed and weighed. Seminal vesicles weights were either represented as is or were normalized to body weight and represented.

FIG. 19A reports weights organs in intact Sprague Dawley rats with body weights of 165-180 grams treated daily with vehicle, 40 mg/kg 1002, 60 mg/kg 1002, or 20 mg/kg enzalutamide orally. After 13 days of treatment, the rats were sacrificed and the weights of prostate, seminal vesicles, and levator ani were measured. FIG. 19B reports the same data as a % decrease from vehicle. Bottom right pane illustrates intact vs. castrated % organ weights for vehicle treated rats.

FIG. 20A and FIG. 20B: Degradation of full length and splice variant (AR-v567ES) androgen receptors (in vitro) for 1010, 1012, 1014, 1015, 1016, 1017, 1019 and 1022: FIG. 20A illustrates for each compound the Western blot of the full length androgen receptor degradation assay. The results were reported in Table 1, under SARD Activity: Full Length % Inhibition. FIG. 20B illustrates the Western blot of the androgen receptor degradation splice variant assay with D567es.

FIG. 21A and FIG. 21B: Anti-tumor efficacy for 1002 in triple negative breast cancer (TNBC) patient-derived xenograft (PDX) is presented in HBrt 1071 triple negative breast cancer (FIG. 21A) and in HBrt 1361 triple negative breast cancer (FIG. 21B).

FIG. 22: depicts binding of 1002 to AF-1 region of the N-terminal domain (NTD) of the androgen receptor. 1D and waterLogsy NMR experiments demonstrate that 1002 bandwidth are broadened in the presence of a peptide derived from the AF-1 region of the NTD. Moreover, relaxation and waterLogsy demonstrate that the tumbling rate in solution for 1002 is slowed upon addition of AF-1, strongly suggestive of 1002 binding to AF-1 region as its targeted protein interaction.

FIG. 23: depicts a LNCaP-enzalutamide resistant (LNCaP-EnzR) cells MR49F growth assay using 1002 and 1014. 1002 and 1014 inhibit the growth of LNCaP-EnzR cells in the low micromolar range.

FIG. 24: depicts the serum and tumor levels of 11, 34, 36, 96, 103, 1002, 1010, 1012, and 1014 achieved in a 22RV1 xenograft experiment.

FIG. 25: depicts reductions in seminal vesicles weights (% change) for animals treated with 34, 36, 1002, 1010, 1012, and 1014 in a Hershberger assay.

FIGS. 26A-B: depicts tumor growth inhibition of LNCaP-enzalutamide-resistant (LNCaP-EnzR) xenografts treated with 1014 at 60 mg/kg administered orally. Two different experiments (Experiment 1 in FIG. 26A and Experiment 2 in FIG. 26B) are shown.

FIGS. 27A-27D: depict steady state fluorescence studies demonstrating interactions between SARDs 1002, 1010, and 36 (indole), and N-terminal fragments of the AR such AR-NTD (amino acids 1-559) and AR-AF1 (amino acids 141-486). FIG. 27A depicts the perturbation of the fluorescent signal of AR-NTD and AR-AF1 in the presence of urea (denaturant), TMAO (folding stabilizer), and buffer, but no SARD. FIGS. 27B-27D depict the perturbations of AR-NTD and AR-AF1 fluorescence associated with the titrations of 1002 (FIG. 27B), 1010 (FIG. 27C), and 36 (FIG. 27D), respectively.

FIGS. 28A-28D: depicts degradation of full length and/or splice variant (22RV1) androgen receptors (in vitro) for 1024 (FIG. 28A), 1029 (FIG. 28B), 1037 and 1041 (FIG. 28C), and 1044-1045 (FIG. 28D). FIGS. 28A, 28C, and 28D illustrate the Western blots of the full length androgen receptor degradation assay. The results were reported in Table 1, under SARD Activity: Full Length % Inhibition. FIG. 28B illustrates the Western blots of the androgen receptor degradation splice variant assay with 22RV1 cells which are represented in Table 1 in the column labeled 'SARD Activity: S.V. % Inhibition'.

(FIG. 29A) Enzalutamide inhibited F876L AR at doses more potent than wildtype AR but was a weaker antagonist of W741L AR (FIG. 29B). However, when the assay was run in agonist mode (FIG. 29C), enzalutamide, at higher doses acted as an agonist of F876L AR. This is characteristic of agonist switch mutations in which AR antagonists of wildtype AR become AR agonists in due to the AR mutation. By comparison, SARDs like 1002 possess no intrinsic transcriptional agonist activity on wildtype AR or F876L AR, suggesting that tumors possessing agonist switch mutations can be inhibited by SARDs of this invention. Similarly, W741L is an agonist switch mutation conferring resistance to bicalutamide, which is inhibited by SARDs.

FIGS. 30A-30E: SARDs degrade the AR, AR-SV, and AR-F876L (MR49F), but not PR and ER (see ZR-75-1 cells). FIG. 30A: LNCaP (compound 11); FIG. 30B: LNCaP (compound 1002); FIG. 30C: ZR-75-1 (compound 1002); FIG. 30D: LNCaP-AR-V7 (compounds 11 and 1002); and FIG. 30E: MR49F (compound 1002). LNCaP cells possess the T877A mutation which confers resistance to flutamide (or hydroxyflutamide, the active metabolite) which demonstrates that SARDs will degrade an agonist switch mutant AR. Likewise, the F876L AR mutation confers resistance to enzalutamide and abiraterone and FIG. 30E demonstrates the ability to degrade this mutant. Cumulatively, this is good evidence that agonist switch mutations to current anti-androgens can be overcome with the SARDs of this invention.

FIG. 31A: compounds 11 and 1002; and FIG. 31B: compound 1002 and bortezomib. The FIG. 31A shows an immunoblot in which a fusion portion with AR connected to hemagglutinin (HA) is expressed in cells. Then the cells are treated with the indicated SARDs or untreated, the AR complex is immunoprecipitated with anti-HA, and run on a Western blot and visualized with anti-ubiquitin antibody (anti-Ub). In the untreated lane, there is no observed ubiquitination of AR, whereas there is various degrees of ubiquitination of AR in the SARD (11 and 1002) treated lanes which are apparent as a smear of AR molecular weights extending up from the fusion protein molecular weight. This indicated that the SARDs induced the ubiquitination of AR. Relative AR levels are shown under each lane (10% input:AR). FIG. 31B indicates that 1002 degrades AR at 10 micromolar in the presence of 50 micromolar cycloheximide. Further, bortezomib, a protease inhibitor, does not induce AR expression at 1, 5 and 10 micromolar. However, co-treatment of cells with 1002 and 1, 5 and 10 micromolar resulted in a dose responsive reversal of the SARD activity of 1002. Reversal of SARD activity by a proteasome inhibitor indicates that the 1002 and other SARDs of this invention work by a proteasome-dependent protein degradation pathway.

FIG. 32: SARDs require AR-NTD containing constructs (e.g. AR or AGG chimera) to degrade the AR whereas SARDs were unable to degrade GR-NTD containing constructs (GR and GAA chimera).

FIG. 34A: FKBP5 expression in LNCaP cells; FIG. 34B: Growth inhibition of LNCaP cells; FIG. 34C: FKBP5 expression in enzalutamide resistant (EnzR)LNCaP cells; and FIG. 34D: Growth inhibition in LNCaP-EnzR cells. 1002 inhibited the AR-dependent gene FKBP5 in either LNCaP and LNCaP-EnzR cells demonstrating the ability to inhibit the AR-axis in either CRPC's such as LNCaP (T877A) or enzalutamide resistant prostate cancers, and, correspondingly, to also inhibit cell growth in these AR-dependent cell lines whereas enzalutamide was unable to significantly inhibit FKBP5 or growth in the LNCaP-EnzR cell line.

Figure 1A:
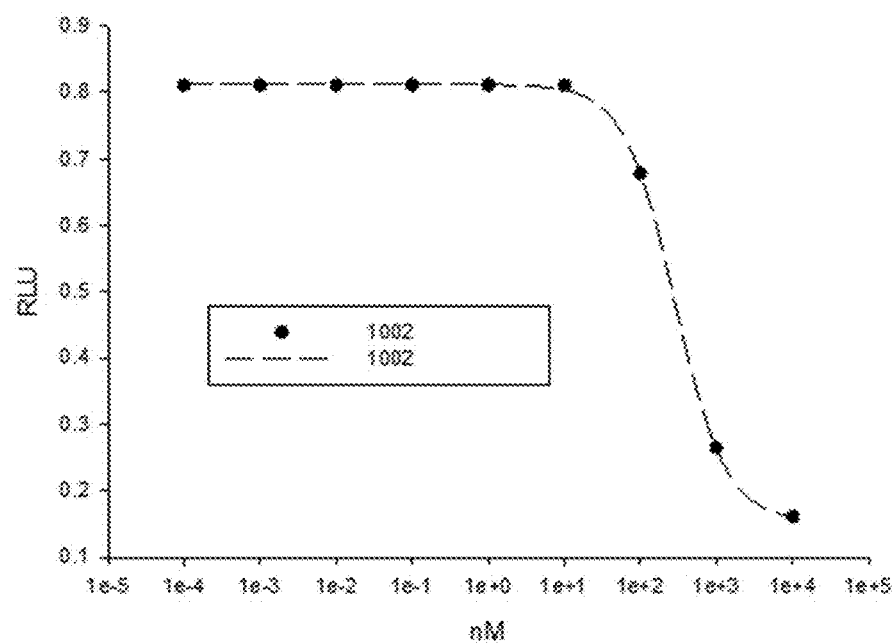
FIGS. 1A-1C: The transactivation result of 1002 was reported based on measured luciferase light emissions and reported as relative light unit intensity (RLU).

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Androgens act in cells by binding to the AR, a member of the steroid receptor superfamily of transcription factors. As the growth and maintenance of prostate cancer (PCa) is largely controlled by circulating androgens, treatment of PCa heavily relies on therapies that target AR. Treatment with AR antagonists such as enzalutamide, bicalutamide or hydroxyflutamide to disrupt receptor activation has been successfully used in the past to reduce PCa growth. All currently available AR antagonists competitively bind AR and recruit corepressors such as NCoR and SMRT to repress transcription of target genes. However, altered intracellular signaling, AR mutations, and increased expression of coactivators lead to functional impairment of antagonists or even transformation of antagonists into agonists. Studies have demonstrated that mutation of W741 and T877 within AR converts bicalutamide and hydroxyflutamide, respectively, to agonists. Similarly, increased intracellular cytokines recruit coactivators instead of corepressors to AR-responsive promoters subsequently converting bicalutamide to an agonist. Similarly, mutations that have been linked to enzalutamide resistance include F876, H874, T877, and di-mutants T877/S888, T877/D890, F876/T877 (i.e., MR49 cells), and H874/T877 (Genome Biol. (2016) 17:10 (doi: 10.1186/s13059-015-0864-1)). Abiraterone resistance mutations include L702H mutations which results in activation of the AR by glucocorticoids such as prednisone, causing resistance to abiraterone because abiraterone is usually prescribed in combination with prednisone. If resistance develops to enzalutamide then often the patient is refractory to abiraterone also and vice versa; or the duration of response is very short. This situation highlights the need for a definitive androgen ablation therapy to prevent AR reactivation in advanced prostate cancers.

Despite initial response to androgen deprivation therapy (ADT), PCa disease progression is inevitable and the cancer emerges as castration-resistant prostate cancer (CRPC). The primary reason for castration resistant prostate cancer (CRPC) re-emergence is re-activation of androgen receptor (AR) by alternate mechanisms such as:
  (a) intracrine androgen synthesis;
  (b) expression of AR splice variants (AR-SV), e.g., that lack ligand binding domain (LBD);
  (c) AR-LBD mutations with potential to resist antagonists;
  (d) hyper-sensitization of AR to low androgen levels, e.g., due to AR gene amplification or AR mutation;
  (e) amplification of the AR gene within the tumor; and
  (f) over expression of coactivators and/or altered intracellular signal transduction.

The invention encompasses novel selective androgen receptor degrader (SARD) compounds encompassed by formula I, which inhibit the growth of prostate cancer (PCa) cells and tumors that are dependent on AR full length (AR-FL) including pathogenic and resistance mutations and wildtype, and/or AR splice variants (AR-SV) for proliferation.

As used herein, unless otherwise defined, a "selective androgen receptor degrader" (SARD) compound is an androgen receptor antagonist capable of inhibiting the growth of PCa cells and tumors that are dependent on AR-full length (AR-FL) and/or AR splice variants (AR-SV) for proliferation. The SARD compound may not bind to ligand binding domain (LBD). Alternatively, a "selective androgen receptor degrader" (SARD) compound is an androgen receptor antagonist capable of causing degradation of a variety of pathogenic mutant variant AR's and wildtype AR and hence are capable of exerting anti-androgenism is a wide variety of pathogenic altered cellular environments found in the disease states embodied in this invention. In one embodiment, the SARD is orally active. In another embodiment, the SARD is applied topically to the site of action.

The SARD compound may bind to the N-terminal domain (NTD) of the AR; to an alternate binding and degradation domain (BDD) of the AR; to both the AR ligand binding domain (LBD) and to an alternate binding and degradation domain (BDD); or to both the N-terminal domain (NTD) and to the ligand binding domain (LBD) of the AR. In one embodiment, the BDD may be located in the NTD. In one embodiment, the BDD is located in the AF-1 region of the NTD. Alternatively, the SARD compound may be capable of: inhibiting growth driven by the N-terminal domain (NTD)-dependent constitutively active AR-SV; or inhibiting the AR through binding to a domain that is distinct from the AR LBD. Also, the SARD compound may be a strong (i.e., highly potent and highly efficacious) selective androgen receptor antagonist, which antagonizes the AR stronger than other known AR antagonists (e.g., enzalutamide, bicalutamide and abiraterone).

The SARD compound may be a selective androgen receptor antagonist, which targets AR-SVs, which cannot be inhibited by conventional antagonists. The SARD compound may exhibit any one of several activities including, but not limited to: AR-SV degradation activity; AR-FL degradation activity; AR-SV inhibitory activity (i.e., is an AR-SV antagonist); AR-FL inhibitory activity (i.e., is an AR-FL antagonist); inhibition of the constitutive activation of AR-SVs; or inhibition of the constitutive activation of AR-FLs. Alternatively, the SARD compound may possess dual AR-SV degradation and AR-SV inhibitory functions, and/or dual AR-FL degradation and AR-FL inhibitory functions; or alternatively possess all four of these activities.

The SARD compound may also degrade AR-FL and AR-SV. The SARD compound may degrade the AR through binding to a domain that is distinct from the AR LBD. The SARD compound may possess dual degradation and AR-SV inhibitory functions that are distinct from any available CRPC therapeutics. The SARD compound may inhibit the re-activation of the AR by alternate mechanisms such as: intracrine androgen synthesis, expression of AR-SV that lack ligand binding domain (LBD) and AR-LBD mutations with potential to resist antagonists, or inhibit re-activated androgen receptors present in pathogenic altered cellular environments.

Examples of AR-splice variants include, but are not limited to, AR-V7 and ARv567es (a.k.a. AR-V12; S. Sun, et al. Castration resistance in human prostate cancer is conferred by a frequently occurring androgen receptor splice variant. *J Clin Invest*. (2010) 120(8), 2715-2730). Nonlimiting examples of AR mutations conferring antiandrogen resistance are: W741L, T877A, and F876L (J. D. Joseph et al. A clinically relevant androgen receptor mutation confers resistance to second-generation antiandrogens enzalutamide and ARN-509. *Cancer Discov*. (2013) 3(9), 1020-1029) mutations. Many other LBD resistance conferring mutations are known in the art and will continue to be discovered. AR-V7 is a splice variant of AR that lacks the LBD (A. H. Bryce & E. S. Antonarakis. Androgen receptor splice variant 7 in castration-resistant prostate cancer: Clinical considerations. *Int J Urol*. (2016 Jun. 3) 23(8), 646-53. doi: 10.1111/iju.13134). It is constitutively active and has been demonstrated to be responsible for aggressive PCa and resistance to endocrine therapy.

The invention encompasses novel selective androgen receptor degrader (SARD) compounds of formulas I-VII, IA-ID, IIA, IIB, VIIA, or VIIB which bind to the AR through an alternate binding and degradation domain (BDD), e.g., the NTD or AF-1. The SARDs may further bind the AR ligand binding domain (LBD).

The SARD compounds may be used in treating CRPC that cannot be treated with any other antagonist. The SARD compounds may treat CRPC by degrading AR-SVs. The SARD compounds may maintain their antagonistic activity in AR mutants that normally convert AR antagonists to agonists. For instance, the SARD compounds maintain their antagonistic activity to AR mutants W741L, T877A, and F876L (J. D. Joseph et al. A clinically relevant androgen receptor mutation confers resistance to second-generation antiandrogens enzalutamide and ARN-509. *Cancer Discov*. (2013) 3(9), 1020-1029). Alternatively, the SARD compounds elicit antagonistic activity within an altered cellular environment in which LBD-targeted agents are not effective or in which NTD-dependent AR activity is constitutively active.

Selective Androgen Receptor Degrader (SARD) Compounds

The invention encompasses selective androgen receptor degrader (SARD) compounds represented by the structure of formula I:

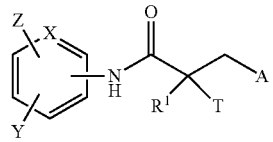

I wherein
T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer, isomer, pharmaceutically acceptable salt, pharmaceutical product, polymorph, hydrate or any combination thereof;
wherein if A is Br or I, $R^1$ is $CH_3$, and T is OH, then X is N or the aniline ring forms a fused heterocyclic ring.

In various embodiments, the SARD compound of formula I has a chiral carbon. In other embodiments, the SARD compound of formula I is a racemic mixture. In other embodiments, the SARD compound of formula I is an (S) isomer. In other embodiments, the SARD compound of formula I is an (R) isomer.

The invention encompasses selective androgen receptor degrader (SARD) compounds represented by the structure of formula IA:

IA

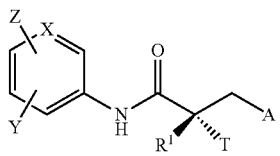

wherein

T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its isomer, pharmaceutically acceptable salt, pharmaceutical product, polymorph, hydrate or any combination thereof;
wherein if A is Br or I, $R^1$ is $CH_3$, and T is OH, then X is N or the aniline ring forms a fused heterocyclic ring.

The invention encompasses selective androgen receptor degrader (SARD) compounds represented by the structure of formula IB:

IB

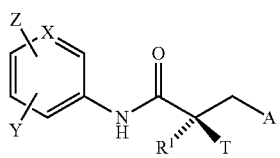

wherein

T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
A is $R^2$ or $R^3$;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
$R^3$ is $NHR^2$, halide, $N_3$, $OR^4$, $CF_3$, $COR^4$, COCl, COO-$COR^4$, $COOR^4$, $OCOR^4$, $OCONHR^4$, $NHCOOR^4$, $NHCONHR^4$, $OCOOR^4$, CN, $CONH_2$, $CONH(R^4)$, $CON(R^4)_2$, $SR^4$, $SO_2R^4$, $SOR^4SO_3H$, $SO_2NH_2$, $SO_2NH(R^4)$, $SO_2N(R^4)_2$, $NH_2$, $NH(R^4)$, $N(R^4)_2$, CO(N-heterocycle), $NO_2$, cyanate, isocyanate, thiocyanate, isothiocyanate, mesylate, tosylate, triflate, $PO(OH)_2$ or $OPO(OH)_2$; and
$R^4$ is H, alkyl, haloalkyl, cycloalkyl, aryl or heteroaryl, wherein said alkyl, haloalkyl, cycloalkyl, aryl or heteroaryl groups are optionally substituted;
or its isomer, pharmaceutically acceptable salt, pharmaceutical product, polymorph, hydrate or any combination thereof;
wherein if A is Br or I, $R^1$ is $CH_3$, and T is OH, then X is N or the aniline ring forms a fused heterocyclic ring.

The invention encompasses selective androgen receptor degrader (SARD) compounds represented by the structure of formula IC:

IC

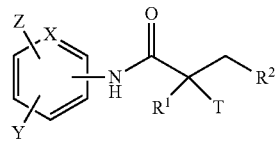

wherein

T is H, OH, OR, OCOR, $CH_3$, —$NHCOCH_3$, or NHCOR;
$R^1$ is H, $CH_3$, $CH_2F$, $CHF_2$, $CF_3$, $CH_2CH_3$, or $CF_2CF_3$;
or T and $R^1$ form a 3-8 carbocyclic or heterocyclic ring;
Y is H, $CF_3$, F, I, Br, Cl, CN, or $C(R)_3$;
Z is H, $NO_2$, CN, halide, COOH, COR, NHCOR, CONHR,
or Y and Z form a 5 to 8 membered fused ring;
X is CH or N;
R is H, alkyl, alkenyl, haloalkyl, alcohol, $CH_2CH_2OH$, $CF_3$, $CH_2Cl$, $CH_2CH_2Cl$, aryl, F, Cl, Br, I, or OH;
$R^2$ is a five or six-membered saturated or unsaturated ring having at least one nitrogen atom and 0, 1, or 2 double bonds, optionally substituted with at least one of $Q^1$, $Q^2$, $Q^3$, or $Q^4$, each independently selected from hydrogen, keto, substituted or unsubstituted linear or branched alkyl, substituted or unsubstituted cycloalkyl, substituted or unsubstituted heterocycloalkyl, haloalkyl, $CF_3$, substituted or unsubstituted aryl, substituted or unsubstituted phenyl, F, Cl, Br, I, CN, $NO_2$, hydroxyl, alkoxy, OR, arylalkyl, NCS, maleimide, NHCOOR, $N(R)_2$, NHCOR, CONHR, COOR or COR;
or its optical isomer, isomer, pharmaceutically acceptable salt, pharmaceutical product, polymorph, hydrate or any combination thereof.

The invention encompasses selective androgen receptor degrader (SARD) compounds represented by the structure of formula ID:

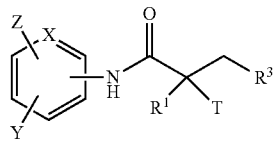

wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
R$^3$ is NHR$^2$, halide, N$_3$, OR$^4$, CF$_3$, COR$^4$, COCl, COO-COR$^4$, COOR$^4$, OCOR$^4$, OCONHR$^4$, NHCOOR$^4$, NHCONHR$^4$, OCOOR$^4$, CN, CONH$_2$, CONH(R$^4$), CON (R$^4$)$_2$, SR$^4$, SO$_2$R$^4$, SOR$^4$SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$H, is alkyl, haloalkyl, cycloalkyl, aryl or heteroaryl, wherein said alkyl, haloalkyl, cycloalkyl, aryl or heteroaryl groups are optionally substituted;
or its optical isomer, isomer, pharmaceutically acceptable salt, pharmaceutical product, polymorph, hydrate or any combination thereof;
wherein if R$^3$ is Br or I, R$^1$ is CH$_3$, and T is OH, then X is N or the aniline ring forms a fused heterocyclic ring.

The invention encompasses a SARD compound represented by the structure of formula II:

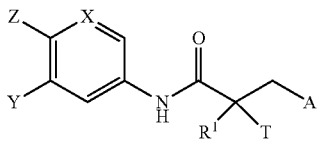

wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
R$^3$ is NHR$^2$, halide, N$_3$, OR$^4$, CF$_3$, COR$^4$, COCl, COO-COR$^4$, COOR$^4$, OCOR$^4$, OCONHR$^4$, NHCOOR$^4$, NHCONHR$^4$, OCOOR$^4$, CN, CONH$_2$, CONH(R$^4$), CON (R$^4$)$_2$, SR$^4$, SO$_2$R$^4$, SOR$^4$SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer, isomer, pharmaceutically acceptable salt, pharmaceutical product, polymorph, hydrate or any combination thereof;
wherein if A is Br or I, R$^1$ is CH$_3$, and T is OH, then X is N or the aniline ring forms a fused heterocyclic ring.

In various embodiments, the SARD compound of formula II has a chiral carbon. In other embodiments, the SARD compound of formula II is a racemic mixture. In other embodiments, the SARD compound of formula II is an (S) isomer. In other embodiments, the SARD compound of formula II is an (R) isomer.

The invention encompasses a SARD compound represented by the structure of formula IIA:

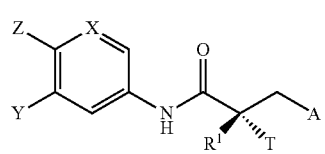

wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a pyrrole, pyrroline, pyrrolidine, pyrazole, pyrazoline, pyrazolidine, triazole, imidazole, imidazoline, imidazolidine, or morpholine ring, said ring optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR;
R$^3$ is NHR$^2$, halide, N$_3$, OR$^4$, CF$_3$, COR$^4$, COCl, COO-COR$^4$, COOR$^4$, OCOR$^4$, OCONHR$^4$, NHCOOR$^4$, NHCONHR$^4$, OCOOR$^4$, CN, CONH$_2$, CONH(R$^4$), CON (R$^4$)$_2$, SR$^4$, SO$_2$R$^4$, SOR$^4$SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO₂, cyanate, isocyanate, thiocyanate, isothiocyanate, mesylate, tosylate, triflate, PO(OH)₂ or OPO(OH)₂; and R⁴ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof;

wherein if A is Br or I, R¹ is CH₃, and T is OH, then X is N or the aniline ring forms a fused heterocyclic ring.

The invention encompasses a SARD compound represented by the structure of formula IIB:

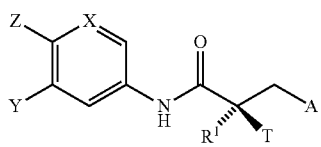

IIB wherein

R¹ is H, CH₃, CH₂F, CHF₂, CF₃, CH₂CH₃, or CF₂CF₃;

or T and R¹ form a 3-8 carbocyclic or heterocyclic ring;

T is H, OH, OR, OCOR, CH₃, —NHCOCH₃, or NHCOR;

Y is H, CF₃, F, I, Br, Cl, CN, or C(R)₃;

Z is H, NO₂, CN, halide, COOH, COR, NHCOR, CONHR, or Y and Z form a 5 to 8 membered fused ring;

X is CH or N;

R is H, alkyl, alkenyl, haloalkyl, alcohol, CH₂CH₂OH, CF₃, CH₂Cl, CH₂CH₂Cl, aryl, F, Cl, Br, I, or OH;

A is R² or R³;

R² a pyrrole, pyrroline, pyrrolidine, pyrazole, pyrazoline, pyrazolidine, triazole, imidazole, imidazoline, imidazolidine, or morpholine ring, said ring optionally substituted with at least one of Q¹, Q², Q³, or Q⁴, each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR;

R³ is NHR², halide, N₃, OR⁴, CF₃, COR⁴, COCl, COOCOR⁴, COOR⁴, OCOR⁴, OCONHR⁴, NHCOOR⁴, NHCONHR⁴, OCOOR⁴, CN, CONH₂, CONH(R⁴), CON(R⁴)₂, SR⁴, SO₂R⁴, SOR⁴SO₃H, SO₂NH₂, SO₂NH(R⁴), SO₂N(R⁴)₂, NH₂, NH(R⁴), N(R⁴)₂, CO(N-heterocycle), NO₂, cyanate, isocyanate, thiocyanate, isothiocyanate, mesylate, tosylate, triflate, PO(OH)₂ or OPO(OH)₂; and R⁴ is H, alkyl, haloalkyl, cycloalkyl, aryl or heteroaryl, wherein said alkyl, haloalkyl, cycloalkyl, aryl or heteroaryl groups are optionally substituted;

or its isomer, pharmaceutically acceptable salt, pharmaceutical product, polymorph, hydrate or any combination thereof;

wherein if A is Br or I, R¹ is CH₃, and T is OH, then X is N or the aniline ring forms a fused heterocyclic ring.

The invention encompasses a SARD compound represented by the structure of formula III:

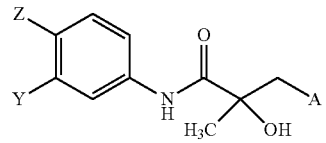

III wherein

Y is H, CF₃, F, I, Br, Cl, CN, or C(R)₃;

Z is H, NO₂, CN, halide, COOH, COR, NHCOR, CONHR, or Y and Z form a 5 to 8 membered fused ring;

R is H, alkyl, alkenyl, haloalkyl, alcohol, CH₂CH₂OH, CF₃, CH₂Cl, CH₂CH₂Cl, aryl, F, Cl, Br, I, or OH;

A is R² or R³;

R² is a pyrrole, pyrroline, pyrrolidine, pyrazole, pyrazoline, pyrazolidine, triazole, imidazole, imidazoline, imidazolidine, or morpholine ring, said ring optionally substituted with at least one of Q¹, Q², Q³, or Q⁴, each independently selected from hydrogen, keto, substituted or unsubstituted linear or branched alkyl, substituted or unsubstituted cycloalkyl, substituted or unsubstituted heterocycloalkyl, haloalkyl, CF₃, substituted or unsubstituted aryl, substituted or unsubstituted phenyl, F, Cl, Br, I, CN, NO₂, hydroxyl, alkoxy, OR, arylalkyl, NCS, maleimide, NHCOOR, N(R)₂, NHCOR, CONHR, COOR or COR;

R³ is NHR², halide, N₃, OR⁴, CF₃, COR⁴, COCl, COOCOR⁴, COOR⁴, OCOR⁴, OCONHR⁴, NHCOOR⁴, NHCONHR⁴, OCOOR⁴, CN, CONH₂, CONH(R⁴), CON(R⁴)₂, SR⁴, SO₂R⁴, SOR⁴SO₃H, SO₂NH₂, SO₂NH(R⁴), SO₂N(R⁴)₂, NH₂, NH(R⁴), N(R⁴)₂, CO(N-heterocycle), NO₂, cyanate, isocyanate, thiocyanate, isothiocyanate, mesylate, tosylate, triflate, PO(OH)₂ or OPO(OH)₂; and R⁴ is H, alkyl, haloalkyl, cycloalkyl, aryl or heteroaryl, wherein said alkyl, haloalkyl, cycloalkyl, aryl or heteroaryl groups are optionally substituted;

or its optical isomer, isomer, pharmaceutically acceptable salt, pharmaceutical product, polymorph, hydrate or any combination thereof;

wherein if A is Br or I, then the aniline ring forms a fused heterocyclic ring.

In various embodiments, the SARD compound of formula III has a chiral carbon. In other embodiments, the SARD compound of formula III is a racemic mixture. In other embodiments, the SARD compound of formula III is an (S) isomer. In other embodiments, the SARD compound of formula III is an (R) isomer.

The invention encompasses a selective androgen receptor degrader compound represented by the structure of formula IV:

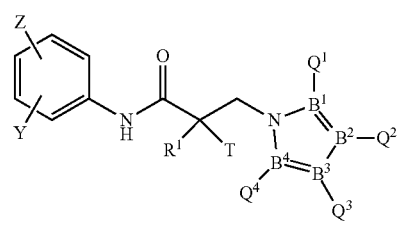

IV wherein

B¹, B², B³, and B⁴ are each independently carbon or nitrogen;

Y is H, CF$_3$, F, I, Br, Cl, CN, or C(R)$_3$;
Z is H, NO$_2$, CN, halide, COOH, COR, NHCOR, CONHR,
  or Y and Z form a 5 to 8 membered fused ring;
  R$^1$ is H, CH$_3$, CH$_2$F, CHF$_2$, CF$_3$, CH$_2$CH$_3$, or CF$_2$CF$_3$;
  T is H, OH, OR, OCOR, CH$_3$, —NHCOCH$_3$, or NHCOR;
  or T and R$^1$ form a 3-8 carbocyclic or heterocyclic ring;
  R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
  Q$^1$, Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; wherein if B$^1$, B$^2$, B$^3$, or B$^4$ is nitrogen then Q$^1$, Q$^2$, Q$^3$, or Q$^4$, respectively, is nothing; or its optical isomer, isomer, pharmaceutically acceptable salt, pharmaceutical product, polymorph, hydrate or any combination thereof.

In various embodiments, the SARD compound of formula IV has a chiral carbon. In other embodiments, the SARD compound of formula IV is a racemic mixture. In other embodiments, the SARD compound of formula IV is an (S) isomer. In other embodiments, the SARD compound of formula IV is an (R) isomer.

The invention encompasses a selective androgen receptor degrader compound represented by the structure of formula V:

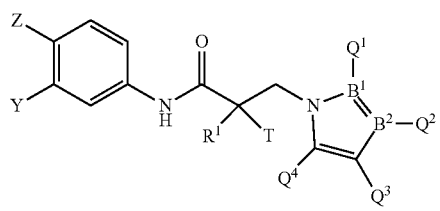

V wherein
  B$^1$ and B$^2$ are each independently carbon or nitrogen;
  Y is H, CF$_3$, F, I, Br, Cl, CN, or C(R)$_3$;
  Z is H, NO$_2$, CN, halide, COOH, COR, NHCOR, CONHR,
  or Y and Z form a 5 to 8 membered fused ring;
  R$^1$ is H, CH$_3$, CH$_2$F, CHF$_2$, CF$_3$, CH$_2$CH$_3$, or CF$_2$CF$_3$;
  T is H, OH, OR, OCOR, CH$_3$, —NHCOCH$_3$, or NHCOR;
  or T and R$^1$ form a 3-8 carbocyclic or heterocyclic ring;
  R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
  Q$^1$, Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; wherein if B$^1$ or B$^2$ is nitrogen then Q$^1$ or Q$^2$, respectively, is nothing; or its optical isomer, isomer, pharmaceutically acceptable salt, pharmaceutical product, polymorph, hydrate or any combination thereof.

In various embodiments, the SARD compound of formula V has a chiral carbon. In other embodiments, the SARD compound of formula V is a racemic mixture. In other embodiments, the SARD compound of formula V is an (S) isomer. In other embodiments, the SARD compound of formula V is an (R) isomer.

The invention encompasses a selective androgen receptor degrader compound represented by the structure of formula VI:

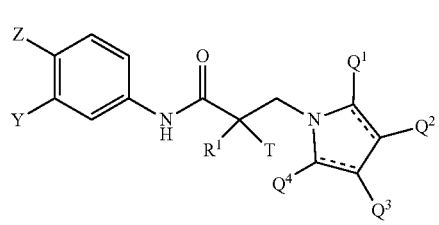

VI wherein
  ⚌ is a single or double bond;
  Y is H, CF$_3$, F, I, Br, Cl, CN, or C(R)$_3$;
  Z is H, NO$_2$, CN, halide, COOH, COR, NHCOR, CONHR,
  or Y and Z form a 5 to 8 membered fused ring;
  R$^1$ is H, CH$_3$, CH$_2$F, CHF$_2$, CF$_3$, CH$_2$CH$_3$, or CF$_2$CF$_3$;
  T is H, OH, OR, OCOR, CH$_3$, —NHCOCH$_3$, or NHCOR;
  or T and R$^1$ form a 3-8 carbocyclic or heterocyclic ring;
  R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and
  Q$^1$, Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its optical isomer, isomer, pharmaceutically acceptable salt, pharmaceutical product, polymorph, hydrate or any combination thereof.

In various embodiments, the SARD compound of formula VI has a chiral carbon. In other embodiments, the SARD compound of formula VI is a racemic mixture. In other embodiments, the SARD compound of formula VI is an (S) isomer. In other embodiments, the SARD compound of formula VI is an (R) isomer.

The invention encompasses a selective androgen receptor degrader compound represented by the structure of formula VII:

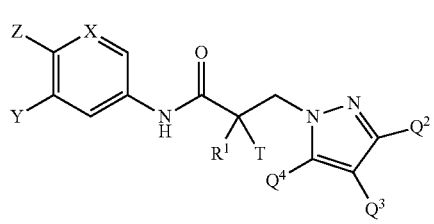

VII wherein
  X is CH or N;
  Y is H, CF$_3$, F, I, Br, Cl, CN, or C(R)$_3$;
  Z is H, NO$_2$, CN, halide, COOH, COR, NHCOR, CONHR,
  or Y and Z form a 5 to 8 membered fused ring;
  R$^1$ is H, CH$_3$, CH$_2$F, CHF$_2$, CF$_3$, CH$_2$CH$_3$, or CF$_2$CF$_3$;

T is H, OH, OR, OCOR, CH$_3$, —NHCOCH$_3$, or NHCOR;

or T and R$^1$ form a 3-8 carbocyclic or heterocyclic ring;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its optical isomer, isomer, pharmaceutically acceptable salt, pharmaceutical product, polymorph, hydrate or any combination thereof.

In various embodiments, the SARD compound of formula VII has a chiral carbon. In other embodiments, the SARD compound of formula VII is a racemic mixture. In other embodiments, the SARD compound of formula VII is an (S) isomer. In other embodiments, the SARD compound of formula VII is an (R) isomer.

The invention encompasses a selective androgen receptor degrader compound represented by the structure of formula VIIA:

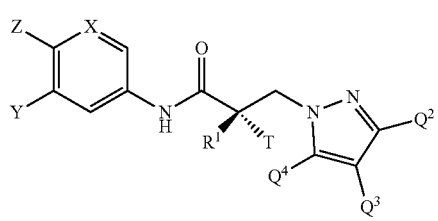

VIIA wherein

X is CH or N;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

R$^1$ is H, CH$_3$, CH$_2$F, CHF$_2$, CF$_3$, CH$_2$CH$_3$, or CF$_2$CF$_3$;

T is H, OH, OR, OCOR, CH$_3$, —NHCOCH$_3$, or NHCOR;

or T and R$^1$ form a 3-8 carbocyclic or heterocyclic ring;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

The invention encompasses a selective androgen receptor degrader compound represented by the structure of formula VIIB:

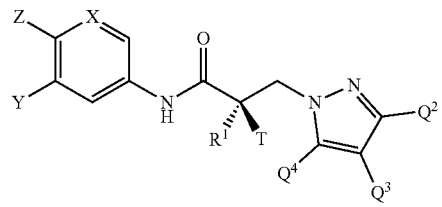

VIIB wherein

X is CH or N;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

R$^1$ is H, CH$_3$, CH$_2$F, CHF$_2$, CF$_3$, CH$_2$CH$_3$, or CF$_2$CF$_3$;

T is H, OH, OR, OCOR, CH$_3$, —NHCOCH$_3$, or NHCOR;

or T and R$^1$ form a 3-8 carbocyclic or heterocyclic ring;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH; and Q$^2$, Q$^3$, or Q$^4$ are each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, arylalkyl, NCS, maleimide, NHCOOR, N(R)$_2$, NHCOR, CONHR, COOR or COR; or its isomer, pharmaceutically acceptable salt, pharmaceutical product, polymorph, hydrate or any combination thereof.

In one embodiment, A of formula I-III, IA, IB, IIA, and IIB and R$^2$ of formula IC is a five or six-membered saturated or unsaturated ring having at least one nitrogen atom. In another embodiment, A is a substituted or unsubstituted pyrrole, pyrroline, pyrrolidine, pyrazole, pyrazoline, pyrazolidine, imidazole, imidazoline, imidazolidine, triazole, tetrazole, pyridine, morpholine, or other heterocyclic ring. Each represents a separate embodiment of this invention. In another embodiment, A is a five or six-membered heterocyclic ring. In another embodiment, a nitrogen atom of the five or six membered saturated or unsaturated ring is attached to the backbone structure of the molecule. In another embodiment, a carbon atom of the five or six membered saturated or unsaturated ring is attached to the backbone structure of the molecule.

In one embodiment, A of formula I-III, IA, IB, IIA, and IIB and R$^3$ of formula ID is NHR$^2$, halide, N$_3$, OR$^4$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH (R$^4$), CON(R$^4$)$_2$, SR$^4$, SO$_2$R$^4$, SOR$^4$SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), NO$_2$, cyanate, isocyanate, thiocyanate, isothiocyanate, mesylate, tosylate, triflate, PO(OH)$_2$ or OPO(OH)$_2$; wherein R$^4$ is H, alkyl, haloalkyl, cycloalkyl, aryl or heteroaryl, wherein said alkyl, haloalkyl, cycloalkyl, aryl or heteroaryl groups are optionally substituted.

In one embodiment, A of formula I-III, IA, IB, IIA, and IIB and R$^3$ of formula ID is NHR$^2$. In one embodiment, A of formula I-III, IA, IB, IIA, and IIB and R$^3$ of formula ID is halide. In one embodiment, A of formula I-III, IA, IB, IIA, and IIB and R$^3$ of formula ID is F. In one embodiment, A of formula I-III, IA, IB, IIA, and IIB and R$^3$ of formula ID is Br. In one embodiment, A of formula I-III, IA, IB, IIA, and IIB and R$^3$ of formula ID is Cl. In one embodiment, A of formula I-III, IA, IB, IIA, and IIB and $R^3$ of formula ID is I. In one embodiment, A of formula I-III, IA, IB, IIA, and IIB and $R^3$ of formula ID is $N_3$. In one embodiment, A of formula I-III, IA, IB, IIA, and IIB and $R^3$ of formula ID is $OR^4$. In one embodiment, A of formula I-III, IA, IB, IIA, and IIB and $R^3$ of formula ID is $CF_3$. In one embodiment, A of formula I-III, IA, IB, IIA, and IIB and $R^3$ of formula ID is $COR^4$. In one embodiment, A of formula I-III, IA, IB, IIA, and IIB and $R^3$ of formula ID is COCl. In one embodiment, A of formula I-III, IA, IB, IIA, and IIB and $R^3$ of formula ID is $COOCOR^4$. In one embodiment, A of formula I-III, IA, IB, IIA, and IIB and $R^3$ of formula ID is $COOR^4$. In one embodiment, A of formula I-III, IA, IB, IIA, and IIB and $R^3$ of formula ID is $OCOR^4$. In one embodiment, A of formula I-III, IA, IB, IIA, and IIB and $R^3$ of formula ID is $OCONHR^4$. In one embodiment, A of formula I-III, IA, IB, IIA, and IIB and $R^3$ of formula ID is $NHCOOR^4$. In one embodiment, A of formula I-III, IA, IB, IIA, and IIB and $R^3$ of formula ID is $NHCONHR^4$. In one embodiment, A of formula I-III, IA, IB, IIA, and IIB and $R^3$ of formula ID is $OCOOR^4$. In one embodiment, A of formula I-III, IA, IB, IIA, and IIB and $R^3$ of formula ID is CN. In one embodiment, A of formula I-III, IA, IB, IIA, and IIB and $R^3$ of formula ID is $CON(R^4)_2$. In one embodiment, A of formula I-III, IA, IB, IIA, and IIB and $R^3$ of formula ID is $SR^4$. In one embodiment, A of formula I-III, IA, IB, IIA, and IIB and $R^3$ of formula ID is $SO_2R^4$. In one embodiment, A of formula I-III, IA, IB, IIA, and IIB and $R^3$ of formula ID is $SOR^4$. In one embodiment, A of formula I-III, IA, IB, IIA, and IIB and $R^3$ of formula ID is $SO_3H$. In one embodiment, A of formula I-III, IA, IB, IIA, and IIB and $R^3$ of formula ID is $SO_2NH_2$. In one embodiment, A of formula I-III, IA, IB, IIA, and IIB and $R^3$ of formula ID is $SO_2NH(R^4)$. In one embodiment, A of formula I-III, IA, IB, IIA, and IIB and $R^3$ of formula ID is $SO_2N(R^4)_2$. In one embodiment, A of formula I-III, IA, IB, IIA, and IIB and $R^3$ of formula ID is $NH_2$. In one embodiment, A of formula I-III, IA, IB, IIA, and IIB and $R^3$ of formula ID is $NH(R^4)$. In one embodiment, A of formula I-III, IA, IB, IIA, and IIB and $R^3$ of formula ID is $N(R^4)_2$. In one embodiment, A of formula I-III, IA, IB, IIA, and IIB and $R^3$ of formula ID is $CONH_2$. In one embodiment, A of formula I-III, IA, IB, IIA, and IIB and $R^3$ of formula ID is $CONH(R^4)$. In one embodiment, A of formula I-III, IA, IB, IIA, and IIB and $R^3$ of formula ID is CO(N-heterocycle). In one embodiment, A of formula I-III, IA, IB, IIA, and IIB and $R^3$ of formula ID is $NO_2$. In one embodiment, A of formula I-III, IA, IB, IIA, and IIB and $R^3$ of formula ID is cyanate. In one embodiment, A of formula I-III, IA, IB, IIA, and IIB and $R^3$ of formula ID is isocyanate. In one embodiment, A of formula I-III, IA, IB, IIA, and IIB and $R^3$ of formula ID is thiocyanate. In one embodiment, A of formula I-III, IA, IB, IIA, and IIB and $R^3$ of formula ID is isothiocyanate. In one embodiment, A of formula I-III, IA, IB, IIA, and IIB and $R^3$ of formula ID is mesylate. In one embodiment, A of formula I-III, IA, IB, IIA, and IIB and $R^3$ of formula ID is tosylate. In one embodiment, A of formula I-III, IA, IB, IIA, and IIB and $R^3$ of formula ID is triflate. In one embodiment, A of formula I-III, IA, IB, IIA, and IIB and $R^3$ of formula ID is $PO(OH)_2$. In one embodiment, A of formula I-III, IA, IB, IIA, and IIB and $R^3$ of formula ID is $OPO(OH)_2$.

In one embodiment $R^4$ is H, alkyl, haloalkyl, cycloalkyl, aryl or heteroaryl, wherein said alkyl, haloalkyl, cycloalkyl, aryl or heteroaryl groups are optionally substituted. Each represents a separate embodiment of this invention. In other embodiment, $R^4$ is H. In other embodiments, $R^4$ is alkyl. In other embodiments, the alkyl is methyl, ethyl, propyl, iso-propyl, butyl, t-butyl, pentyl, neopentyl, iso-pentyl, hexyl, or heptyl, each represents a separate embodiment of this invention. In other embodiments, $R^4$ is haloalkyl In another embodiment, the haloalkyl is $CF_3$, $CF_2CF_3$, iodomethyl, bromomethyl, bromoethyl, bromopropyl, each represents a separate embodiment of the invention. In other embodiments, $R^4$ is cycloalkyl. In other embodiments the cycloalkyl is cyclobutyl, cyclopentyl, cyclohexyl. In various embodiments, the alkyl, haloalkyl, cycloalkyl, aryl or heteroaryl of $R^4$ are further substituted by one or more groups selected from: halide, CN, $CO_2H$, OH, SH, $NH_2$, $NO_2$, $CO_2$—($C_1$-$C_6$ alkyl) or O—($C_1$-$C_6$ alkyl); each represents a separate embodiment of this invention.

In a particular embodiment of formulas I-VI, IA-IC, IIA, or IIB, $Q^1$ is hydrogen. In a particular embodiment of formulas I-VI, IA-IC, IIA, or IIB, $Q^1$ is CN. In a particular embodiment of formulas I-VI, IA-IC, IIA, or IIB, $Q^1$ is F. In a particular embodiment of formulas I-VI, IA-IC, IIA, or IIB, $Q^1$ is NCS. In a particular embodiment of formulas I-VI, IA-IC, IIA, or IIB, $Q^1$ is maleimide. In a particular embodiment of formulas I-VI, IA-IC, IIA, or IIB, $Q^1$ is NHCOOR. In a particular embodiment of formulas I-VI, IA-IC, IIA, or IIB, $Q^1$ is $N(R)_2$. In a particular embodiment of formulas I-VI, IA-IC, IIA, or IIB, $Q^1$ is CONHR. In a particular embodiment of formulas I-VI, IA-IC, IIA, or IIB, $Q^1$ is NHCOR. In a particular embodiment of formulas I-VI, IA-IC, IIA, or IIB, $Q^1$ is Cl. In a particular embodiment of formulas I-VI, IA-IC, IIA, or IIB, $Q^1$ is Br. In a particular embodiment of formulas I-VI, IA-IC, IIA, or IIB, $Q^1$ is I. In a particular embodiment of formulas I-VI, IA-IC, IIA, or IIB, $Q^1$ is $NO_2$. In a particular embodiment of formulas I-VI, IA-IC, IIA, or IIB, $Q^1$ is phenyl. In a particular embodiment of formulas I-VI, IA-IC, IIA, or IIB, $Q^1$ is 4-fluorophenyl. In a particular embodiment of formulas I-VI, IA-IC, IIA, or IIB, $Q^1$ is $CF_3$. In a particular embodiment of formulas I-VI, IA-IC, IIA, or IIB, $Q^1$ is substituted or unsubstituted alkyl. In a particular embodiment of formulas I-VI, IA-IC, IIA, or IIB, $Q^1$ is substituted or unsubstituted cycloalkyl. In a particular embodiment of formulas I-VI, IA-IC, IIA, or IIB, $Q^1$ is substituted or unsubstituted heterocycloalkyl. In a particular embodiment of formulas I-VI, IA-IC, IIA, or IIB, $Q^1$ is haloalkyl. In a particular embodiment of formulas I-VI, IA-IC, IIA, or IIB, $Q^1$ is substituted or unsubstituted aryl. In a particular embodiment of formulas I-VI, IA-IC, IIA, or IIB, $Q^1$ is hydroxyl. In a particular embodiment of formulas I-VI, IA-IC, IIA, or IIB, $Q^1$ is alkoxy. In a particular embodiment of formulas I-VI, IA-IC, IIA, or IIB, $Q^1$ is OR. In a particular embodiment of formulas I-VI, IA-IC, IIA, or IIB, $Q^1$ is arylalkyl. In a particular embodiment of formulas I-VI, IA-IC, IIA, or IIB, $Q^1$ is amine. In a particular embodiment of formulas I-VI, IA-IC, IIA, or IIB, $Q^1$ is amide. In a particular embodiment of formulas I-VI, IA-IC, IIA, and IIB, $Q^1$ is COOR. In a particular embodiment of formulas I-VI, IA-IC, IIA, or IIB, $Q^1$ is COR. In a particular embodiment of formulas I-VI, IA-IC, IIA, or IIB, $Q^1$ is keto.

In a particular embodiment of formulas I-VII, IA-IC, IIA, IIB, VIIA, or VIIB, $Q^2$ is CN. In a particular embodiment of formulas I-VII, IA-IC, IIA, IIB, VIIA, or VIIB, $Q^2$ is hydrogen. In a particular embodiment of formulas I-VII, IA-IC, IIA, IIB, VIIA, or VIIB, $Q^2$ is keto. In a particular embodiment of formulas I-VII, IA-IC, IIA, IIB, VIIA, or VIIB, $Q^2$ is NCS. In a particular embodiment of formulas I-VII, IA-IC, IIA, IIB, VIIA, or VIIB, $Q^2$ is maleimide. In a particular embodiment of formulas I-VII, IA-IC, IIA, IIB, VIIA, or VIIB, $Q^2$ is NHCOOR. In a particular embodiment of formulas I-VII, IA-IC, IIA, IIB, VIIA, or VIIB, $Q^2$ is $N(R)_2$. In a particular embodiment of formulas I-VII, IA-IC, IIA, IIB, VIIA, or VIIB, $Q^2$ is CONHR. In a particular embodiment of formulas I-VII, IA-IC, IIA, IIB, VIIA, or VIIB, $Q^2$ is NHCOR. In a particular embodiment of formulas I-VII, IA-IC, IIA, IIB, VIIA, or VIIB, $Q^2$ is F. In a particular embodiment of formulas I-VII, IA-IC, IIA, IIB, VIIA, or VIIB, $Q^2$ is Cl. In a particular embodiment of formulas I-VII, IA-IC, IIA, IIB, VIIA, or VIIB, $Q^2$ is Br. In a particular embodiment of formulas I-VII, IA-IC, IIA, IIB, VIIA, or VIIB, $Q^2$ is I. In a particular embodiment of formulas I-VII, IA-IC, IIA, IIB, VIIA, or VIIB, $Q^2$ is $NO_2$. In a particular embodiment of formulas I-VII, IA-IC, IIA, IIB, VIIA, or VIIB, $Q^2$ is phenyl. In a particular embodiment of formulas I-VII, IA-IC, IIA, IIB, VIIA, or VIIB, $Q^2$ is 4-fluorophenyl. In a particular embodiment of formulas I-VII, IA-IC, IIA, IIB, VIIA, or VIIB, $Q^2$ is $CF_3$. In a particular embodiment of formulas I-VII, IA-IC, IIA, IIB, VIIA, or VIIB, $Q^2$ is substituted or unsubstituted alkyl. In a particular embodiment of formulas I-VII, IA-IC, IIA, IIB, VIIA, or VIIB, $Q^2$ is substituted or unsubstituted cycloalkyl. In a particular embodiment of formulas I-VII, IA-IC, IIA, IIB, VIIA, or VIIB, $Q^2$ is substituted or unsubstituted heterocycloalkyl. In a particular embodiment of formulas I-VII, IA-IC, IIA, IIB, VIIA, or VIIB, $Q^2$ is haloalkyl. In a particular embodiment of formulas I-VII, IA-IC, IIA, IIB, VIIA, or VIIB, $Q^2$ is substituted or unsubstituted aryl. In a particular embodiment of formulas I-VII, IA-IC, IIA, IIB, VIIA, or VIIB, $Q^2$ is hydroxyl. In a particular embodiment of formulas I-VII, IA-IC, IIA, IIB, VIIA, or VIIB, $Q^2$ is alkoxy. In a particular embodiment of formulas I-VII, IA-IC, IIA, IIB, VIIA, or VIIB, $Q^2$ is OR. In a particular embodiment of formulas I-VII, IA-IC, IIA, IIB, VIIA, or VIIB, $Q^2$ is arylalkyl. In a particular embodiment of formulas I-VII, IA-IC, IIA, IIB, VIIA, or VIIB, $Q^2$ is amine. In a particular embodiment of formulas I-VII, IA-IC, IIA, IIB, VIIA, or VIIB, $Q^2$ is amide. In a particular embodiment of formulas I-VII, IA-IC, IIA, IIB, VIIA, or VIIB, $Q^2$ is COOR. In a particular embodiment of formulas I-VII, IA-IC, IIA, IIB, VIIA, or VIIB, $Q^2$ is COR.

In a particular embodiment of formulas I-VII, IA-IC, IIA, IIB, VIIA, or VIIB, $Q^3$ is CN. In a particular embodiment of formulas I-VII, IA-IC, IIA, IIB, VIIA, or VIIB, $Q^3$ is F. In a particular embodiment of formulas I-VII, IA-IC, IIA, IIB, VIIA, or VIIB, $Q^3$ is NCS. In a particular embodiment of formulas I-VII, IA-IC, IIA, IIB, VIIA, or VIIB, $Q^3$ is maleimide. In a particular embodiment of formulas I-VII, IA-IC, IIA, IIB, VIIA, or VIIB, $Q^3$ is NHCOOR. In a particular embodiment of formulas I-VII, IA-IC, IIA, IIB, VIIA, or VIIB, $Q^3$ is $N(R)_2$. In a particular embodiment of formulas I-VII, IA-IC, IIA, IIB, VIIA, or VIIB, $Q^3$ is CONHR. In a particular embodiment of formulas I-VII, IA-IC, IIA, IIB, VIIA, or VIIB, $Q^3$, is NHCOR. In a particular embodiment of formulas I-VII, IA-IC, IIA, IIB, VIIA, or VIIB, $Q^3$ is hydrogen. In a particular embodiment of formulas I-VII, IA-IC, IIA, IIB, VIIA, or VIIB, $Q^3$ is keto. In a particular embodiment of formulas I-VII, IA-IC, IIA, IIB, VIIA, or VIIB, $Q^3$ is Cl. In a particular embodiment of formulas I-VII, IA-IC, IIA, IIB, VIIA, or VIIB, $Q^3$ is Br. In a particular embodiment of formulas I-VII, IA-IC, IIA, IIB, VIIA, or VIIB, $Q^3$ is I. In a particular embodiment of formulas I-VII, IA-IC, IIA, IIB, VIIA, or VIIB, $Q^3$ is $NO_2$. In a particular embodiment of formulas I-VII, IA-IC, IIA, IIB, VIIA, or VIIB, $Q^3$ is phenyl. In a particular embodiment of formulas I-VII, IA-IC, IIA, IIB, VIIA, or VIIB, $Q^3$ is 4-fluorophenyl. In a particular embodiment of formulas I-VII, IA-IC, IIA, IIB, VIIA, or VIIB, $Q^3$ is $CF_3$. In a particular embodiment of formulas I-VII, IA-IC, IIA, IIB, VIIA, or VIIB, $Q^3$ is substituted or unsubstituted alkyl. In a particular embodiment of formulas I-VII, IA-IC, IIA, IIB, VIIA, or VIIB, $Q^3$ is substituted or unsubstituted cycloalkyl. In a particular embodiment of formulas I-VII, IA-IC, IIA, IIB, VIIA, or VIIB, $Q^3$ is substituted or unsubstituted heterocycloalkyl. In a particular embodiment of formulas I-VII, IA-IC, IIA, IIB, VIIA, or VIIB, $Q^3$ is haloalkyl. In a particular embodiment of formulas I-VII, IA-IC, IIA, IIB, VIIA, or VIIB, $Q^3$ is substituted or unsubstituted aryl. In a particular embodiment of formulas I-VII, IA-IC, IIA, IIB, VIIA, or VIIB, $Q^3$ is hydroxyl. In a particular embodiment of formulas I-VII, IA-IC, IIA, IIB, VIIA, or VIIB, $Q^3$ is alkoxy. In a particular embodiment of formulas I-VII, IA-IC, IIA, IIB, VIIA, or VIIB, $Q^3$ is OR. In a particular embodiment of formulas I-VII, IA-IC, IIA, IIB, VIIA, or VIIB, $Q^3$ is arylalkyl. In a particular embodiment of formulas I-VII, IA-IC, IIA, IIB, VIIA, or VIIB, $Q^3$ is amine. In a particular embodiment of formulas I-VII, IA-IC, IIA, IIB, VIIA, or VIIB, $Q^3$ is amide. In a particular embodiment of formulas I-VII, IA-IC, IIA, IIB, VIIA, or VIIB, $Q^3$ is COOR. In a particular embodiment of formulas I-VII, IA-IC, IIA, IIB, VIIA, or VIIB, $Q^3$ is COR.

In a particular embodiment of formulas I-VII, IA-IC, IIB, VIIA, or VIIB, $Q^4$ is CN. In a particular embodiment of formulas I-VII, IA-IC, IIA, IIB, VIIA, or VIIB, $Q^4$ is F. In a particular embodiment of formulas I-VII, IA-IC, IIA, IIB, VIIA, or VIIB, $Q^4$ is NCS. In a particular embodiment of formulas I-VII, IA-IC, IIA, IIB, VIIA, or VIIB, $Q^4$ is maleimide. In a particular embodiment of formulas I-VII, IA-IC, IIA, IIB, VIIA, or VIIB, $Q^4$ is NHCOOR. In a particular embodiment of formulas I-VII, IA-IC, IIA, IIB, VIIA, or VIIB, $Q^4$ is $N(R)_2$. In a particular embodiment of formulas I-VII, IA-IC, IIA, IIB, VIIA, or VIIB, $Q^4$ is CONHR. In a particular embodiment of formulas I-VII, IA-IC, IIA, IIB, VIIA, or VIIB, $Q^4$, is NHCOR. In a particular embodiment of formulas I-VII, IA-IC, IIA, IIB, VIIA, or VIIB, $Q^4$ is hydrogen. In a particular embodiment of formulas I-VII, IA-IC, IIA, IIB, VIIA, or VIIB, $Q^4$ is keto. In a particular embodiment of formulas I-VII, IA-IC, IIA, IIB, VIIA, or VIIB, $Q^4$ is Cl. In a particular embodiment of formulas I-VII, IA-IC, IIA, IIB, VIIA, or VIIB, $Q^4$ is Br. In a particular embodiment of formulas I-VII, IA-IC, IIA, IIB, VIIA, or VIIB, $Q^4$ is I. In a particular embodiment of formulas I-VII, IA-IC, IIA, IIB, VIIA, or VIIB, $Q^4$ is $NO_2$. In a particular embodiment of formulas I-VII, IA-IC, IIA, IIB, VIIA, or VIIB, $Q^4$ is phenyl. In a particular embodiment of formulas I-VII, IA-IC, IIA, IIB, VIIA, or VIIB, $Q^4$ is 4-fluorophenyl. In a particular embodiment of formulas I-VII, IA-IC, IIA, IIB, VIIA, or VIIB, $Q^4$ is $CF_3$. In a particular embodiment of formulas I-VII, IA-IC, IIA, IIB, VIIA, or VIIB, $Q^4$ is substituted or unsubstituted alkyl. In a particular embodiment of formulas I-VII, IA-IC, IIA, IIB, VIIA, or VIIB, $Q^4$ is substituted or unsubstituted cycloalkyl. In a particular embodiment of formulas I-VII, IA-IC IIA, IIB, VIIA, or VIIB, $Q^4$ is substituted or unsubstituted heterocycloalkyl. In a particular embodiment of formulas I-VII, IA-IC, IIA, IIB, VIIA, or VIIB, $Q^4$ is haloalkyl. In a particular embodiment of formulas I-VII, IA-IC, IIA, IIB, VIIA, or VIIB, $Q^4$ is substituted or unsubstituted aryl. In a particular embodiment of formulas I-VII, IA-IC, IIA, IIB, VIIA, or VIIB, $Q^4$ is hydroxyl. In a particular embodiment of formulas I-VII, IA-IC, IIA, IIB, VIIA, or VIIB, $Q^4$ is alkoxy. In a particular embodiment of formulas I-VII, IA-IC, IIA, IIB, VIIA, or VIIB, $Q^4$ is OR. In a particular embodiment of formulas I-VII, IA-IC, IIA, IIB, VIIA, or VIIB, $Q^4$ is arylalkyl. In a particular embodiment of formulas I-VII, IA-IC, IIA, IIB, VIIA, or VIIB, $Q^4$ is amine. In a particular embodiment of formulas I-VII, IA-IC, IIA, IIB, VIIA, or VIIB, $Q^3$ is amide. In a particular embodiment of formulas I-VII, IA-IC, IIA, IIB, VIIA, or VIIB, $Q^4$ is COOR. In a particular embodiment of formulas I-VII, IA-IC, IIA, IIB, VIIA, or VIIB, $Q^4$ is COR. In a particular embodiment of formulas I, IA, IB, IC, ID, II, IIA, IIB, VII, VIIA, or VIIB, X is CH. In a particular embodiment of formulas I, IA, IB, IC, ID, II, IIA, IIB, VII, VIIA, or VIIB, X is N.

In some embodiments, wherein if A or $R^3$ is Br or I, $R^1$ is $CH_3$, and T is OH, then X is N or the aniline ring forms a fused heterocyclic ring.

In a particular embodiment of formulas I-VII, IA, IB, IC, ID, IIA, IIB, VIIA, or VIIB, Y is H. In a particular embodiment of formulas I-VII, IA, IB, IC, ID, IIA, IIB, VIIA, or VIIB, Y is $CF_3$. In a particular embodiment of formulas I-VII, IA, IB, IC, ID, IIA, IIB, VIIA, or VIIB, Y is F. In a particular embodiment of formulas I-VII, IA, IB, IC, ID, IIA, IIB, VIIA, or VIIB, Y is I. In a particular embodiment of formulas I-VII, IA, IB, IC, ID, IIA, IIB, VIIA, or VIIB, Y is Br. In a particular embodiment of formulas I-VII, IA, IB, IC, ID, IIA, IIB, VIIA, or VIIB, Y is Cl. In a particular embodiment of formulas I-VII, IA, IB, IC, ID, IIA, IIB, VIIA, or VIIB, Y is CN. In a particular embodiment of formulas I-VII, IA, IB, IC, ID, IIA, IIB, VIIA, or VIIB, Y is $C(R)_3$.

In a particular embodiment of formulas I-VII, IA, IB, IC, ID, IIA, IIB, VIIA, or VIIB, Z is H. In a particular embodiment of formulas I-VII, IA, IB, IC, ID, IIA, IIB, VIIA, or VIIB, Z is $NO_2$. In a particular embodiment of formulas I-VII, IA, IB, IC, ID, IIA, IIB, VIIA, or VIIB, Z is CN. In a particular embodiment of formulas I-VII, IA, IB, IC, ID, IIA, IIB, VIIA, or VIIB, Z is a halide. In a particular embodiment of formulas I-VII, IA, IB, IC, ID, IIA, IIB, VIIA, or VIIB, Z is F. In a particular embodiment of formulas I-VII, IA, IB, IC, ID, IIA, IIB, VIIA, or VIIB, Z is Cl. In a particular embodiment of formulas I-VII, IA, IB, IC, ID, IIA, IIB, VIIA, or VIIB, Z is Br. In a particular embodiment of formulas I-VII, IA, IB, IC, ID, IIA, IIB, VIIA, or VIIB, Z is I. In a particular embodiment of formulas I-VII, IA, IB, IC, ID, IIA, IIB, VIIA, or VIIB, Z is COOH. In a particular embodiment of formulas I-VII, IA, IB, I IC, ID, IA, IIB, VIIA, or VIIB, Z is COR. In a particular embodiment of formulas I-VII, IA, IB, IC, ID, IIA, IIB, VIIA, or VIIB, Z is NHCOR. In a particular embodiment of formulas I-VII, IA, IB, IC, ID, IIA, IIB, VIIA, or VIIB, Z is CONHR.

In a particular embodiment of formulas I-VII, IA, IB, IC, ID, IIA, IIB, VIIA, or VIIB, Y and Z forms a fused ring with the phenyl. In other embodiments, the fused ring with the phenyl is a 5 to 8 membered ring. In other embodiments, the fused ring with the phenyl is a 5 or 6 membered ring. In other embodiments, the ring is a carbocyclic or heterocyclic. In other embodiments, Y and Z form together with the phenyl to form a naphthyl, quinolinyl, benzimidazolyl, indazolyl, indolyl, isoindolyl, indenyl, or quinazolinyl. In a particular embodiment, Y and Z form together with the phenyl to form a quinazolin-6-yl ring system.

In a particular embodiment of formulas I, II, IV, V, VI, VII, IA, IB, IC, ID, IIA, IIB, VIIA, or VIIB, $R^1$ is H. In a particular embodiment of formulas I, II, IV, V, VI, VII, IA, IB, IC, ID, IIA, IIB, VIIA, or VIIB, $R^1$ is $CH_3$. In a particular embodiment of formulas I, II, IV, V, VI, VII, IA, IB, IIA, IIB, IC, ID, VIIA, or VIIB, $R^1$ is $CH_2F$. In a particular embodiment of formulas I, II, IV, V, VI, VII, IA, IB, IC, ID, IIA, IIB, VIIA, or VIIB, $R^1$ is $CHF_2$. In a particular embodiment of formulas I, II, IV, V, VI, VII, IA, IB, IC, ID, IIA, IIB, VIIA, or VIIB, $R_1$ is $CF_3$. In a particular embodiment of formulas I, II, IV, V, VI, VII, IA, IB, IC, ID, IIA, IIB, VIIA, or VIIB, $R^1$ is $CH_2CH_3$. In a particular embodiment of formulas I, II, IV, V, VI, VII, IA, IB, IC, ID, IIA, IIB, VIIA, or VIIB, $R^1$ is $CF_2CF_3$.

In a particular embodiment of formulas I, II, IV, V, VI, VII, IA, IB, IC, ID, IIA, IIB, VIIA, or VIIB, T is H. In a particular embodiment of formulas I, II, IV, V, VI, VII, IA, IB, IC, ID, IIA, IIB, VIIA, or VIIB, T is OH. In a particular embodiment of formulas I, II, IV, V, VI, VII, IA, IB, IC, ID, IIA, IIB, VIIA, or VIIB, T is OR. In a particular embodiment of formulas I, II, IV, V, VI, VII, IA, IB, IC, ID, IIA, IIB, VIIA, or VIIB, T is OCOR In a particular embodiment of formulas I, II, IV, V, VI, VII, IA, IB, IC, ID, IIA, IIB, VIIA, or VIIB, T is $CH_3$. In a particular embodiment of formulas I, II, IV, V, VI, VII, IA, IB, IC, ID, IIA, IIB, VIIA, or VIIB, T is —$NHCOCH_3$. In a particular embodiment of formulas I, II, IV, V, VI, VII, IA, IB, IC, ID, IIA, IIB, VIIA, or VIIB, T is NHCOR.

In a particular embodiment of formulas I, II, IV, V, VI, VII, IA, IB, IC, ID, IIA, IIB, VIIA, or VIIB, T and $R^1$ form a 3-8 carbocyclic or heterocyclic ring. In other embodiments, T and $R^1$ form a 3, 4, 5, 6, 7, or 8 membered carbocyclic or heterocyclic ring. Each represents a separate embodiment of this invention. In some embodiments T and $R^1$ form a carbocyclic ring such as cyclopropyl, cyclobutyl, cyclopentyl, cyclohexyl, etc. In some embodiments T and $R^1$ form a heterocyclic ring such as piperidine, pyridine, furan, thiphene, pyrrole, pyrazole, pyrimidine, etc.

In a particular embodiment of formulas I-VII, IA, IB, IC, ID, IIA, IIB, VIIA, or VIIB, R is H. In a particular embodiment of formulas I-VII, IA, IB, IC, ID, IIA, IIB, VIIA, or VIIB, R is alkyl. In a particular embodiment of formulas I-VII, IA, IB, IC, ID, IIA, IIB, VIIA, or VIIB, R is alkenyl. In a particular embodiment of formulas I-VII, IA, IB, IC, ID, IIA, IIB, VIIA, or VIIB, R is haloalkyl. In a particular embodiment of formulas I-VII, IA, IB, IC, ID, IIA, IIB, VIIA, or VIIB, R is alcohol. In a particular embodiment of formulas I-VII, IA, IB, IC, ID, IIA, IIB, VIIA, or VIIB, R is $CH_2CH_2OH$. In a particular embodiment of formulas I-VII, IA, IB, IC, ID, IIA, IIB, VIIA, or VIIB, R is $CF_3$. In a particular embodiment of formulas I-VII, IA, IB, IC, ID, IIA, IIB, VIIA, or VIIB, R is $CH_2Cl$. In a particular embodiment of formulas I-VII, IA, IB, IC, ID, IIA, IIB, VIIA, or VIIB, R is $CH_2CH_2Cl$. In a particular embodiment of formulas I-VII, IA, IB, IC, ID, IIA, IIB, VIIA, or VIIB, R is aryl. In a particular embodiment of formulas I-VII, IA, IB, IC, ID, IIA, IIB, VIIA, or VIIB, R is F. In a particular embodiment of formulas I-VII, IA, IB, IC, ID, IIA, IIB, VIIA, or VIIB, R is Cl. In a particular embodiment of formulas I-VII, IA, IB, IC, ID, IIA, IIB, VIIA, or VIIB, R is Br. In a particular embodiment of formulas I-VII, IA, IB, IC, ID, IIA, IIB, VIIA, or VIIB, R is I. In a particular embodiment of formulas I-VII, IA, IB, IC, ID, IIA, IIB, VIIA, or VIIB, R is OH.

In a particular embodiment of formula IV, $Q^1$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^1$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^1$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula IV, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VII, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIA, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIB, $Q^2$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula IV, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VII, $Q^3$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula IV, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula V, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VI, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VII, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIA, $Q^4$ is H, CN, $CF_3$, phenyl, 4-fluorophenyl, F, Br, Cl, I, COMe, NHCOOMe, NHCOMe or $NHCOOC(CH_3)_3$.

In a particular embodiment of formula VIIB, $Q^4$ is H, CN, $CF_3$, phenyl, 4-fluorophenyl, F, Br, Cl, I, COMe, NHCOOMe, NHCOMe or $NHCOOC(CH_3)_3$.

The invention encompasses a selective androgen receptor degrader (SARD) compound selected from any one of the following structures:

1001
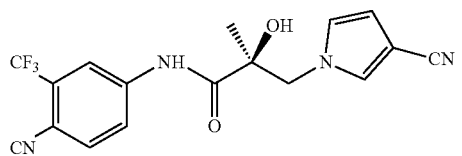

1002
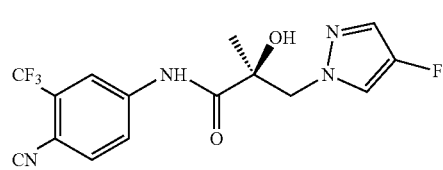

1003
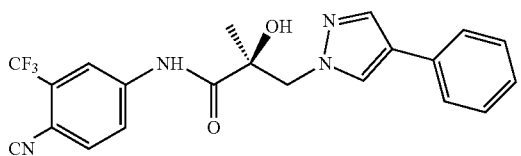

1004
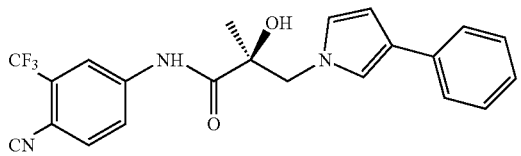

1005
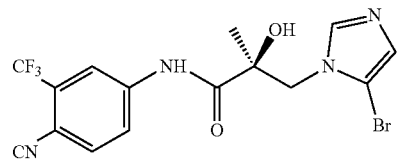

1006
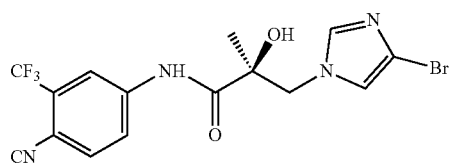

1007
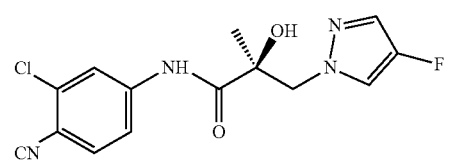

1008
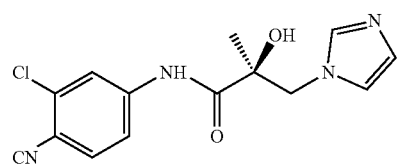

1009
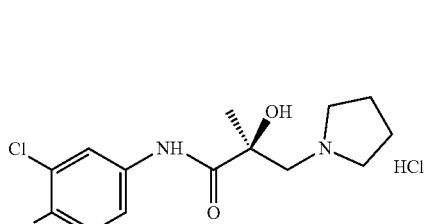

1010
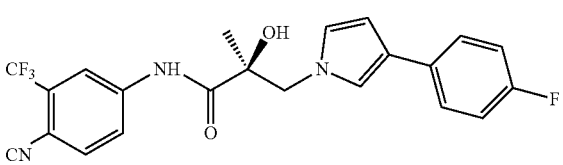

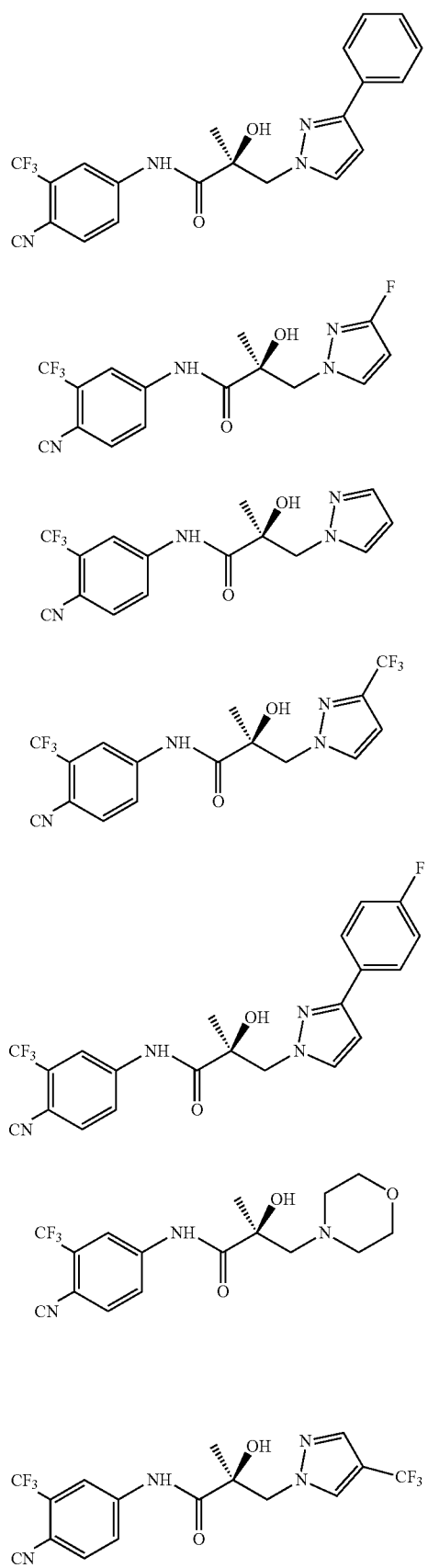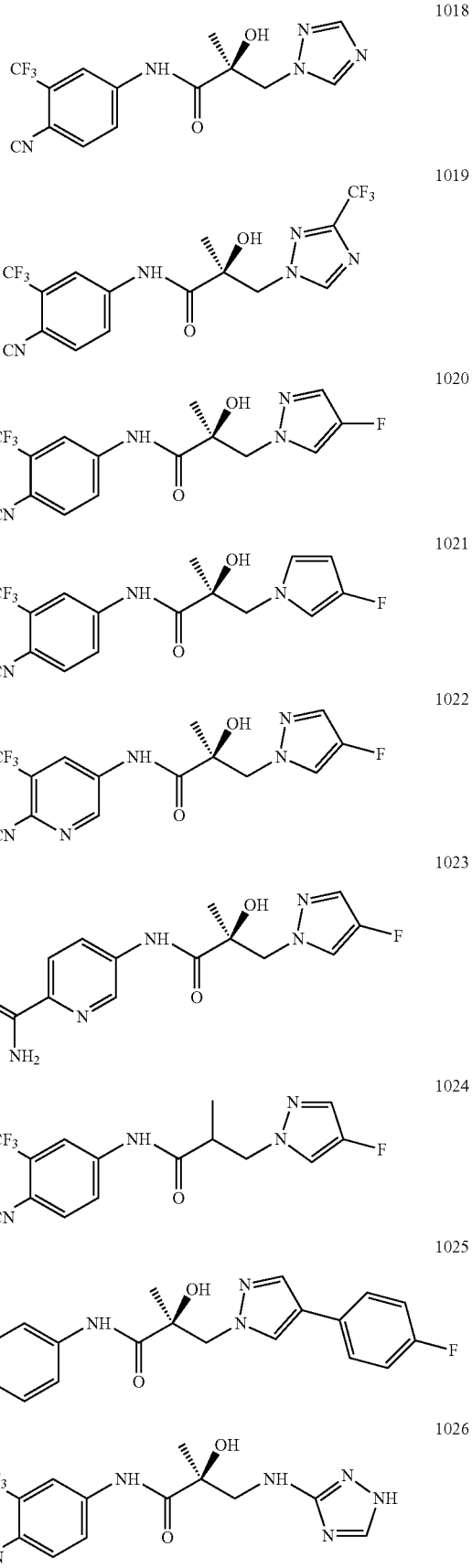

-continued
1027
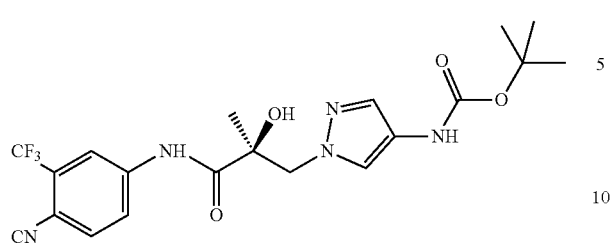
1028
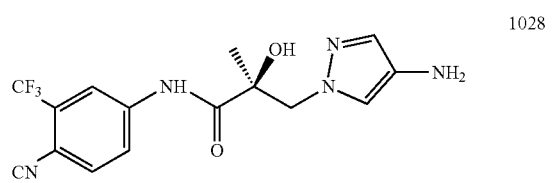
1029
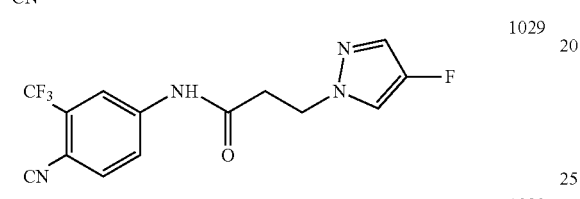
1030
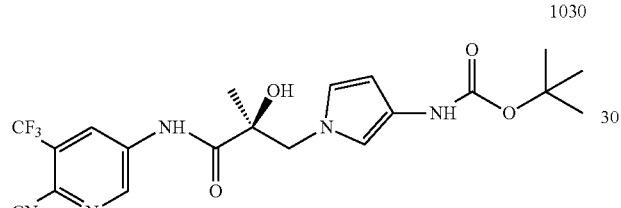
1031
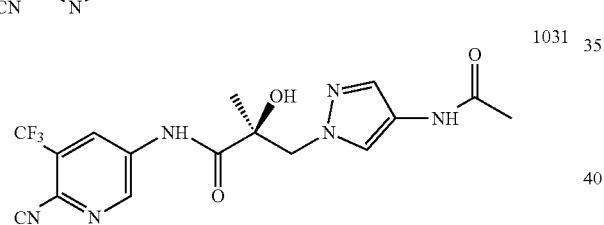
1032
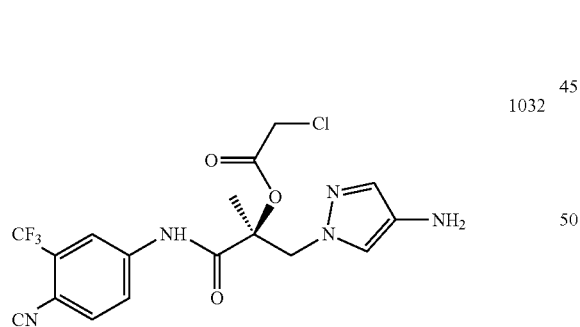
1033
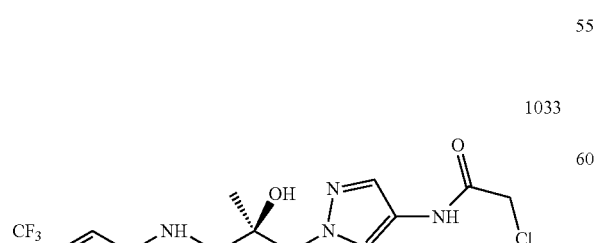
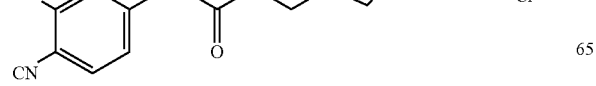
-continued
1034
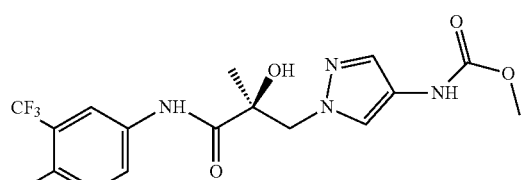
1035
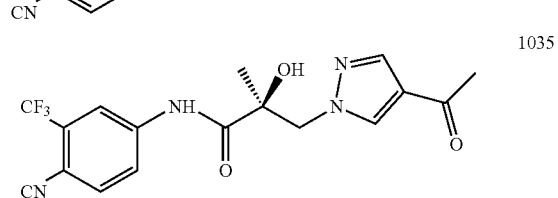
1036
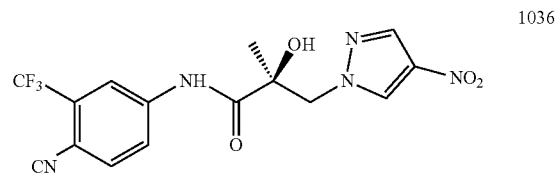
1037
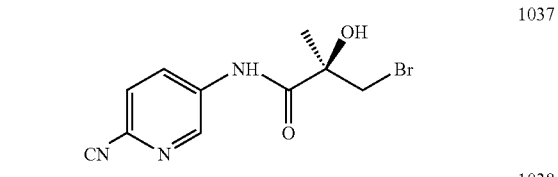
1038
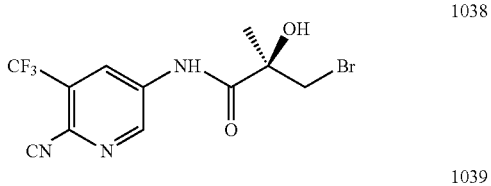
1039
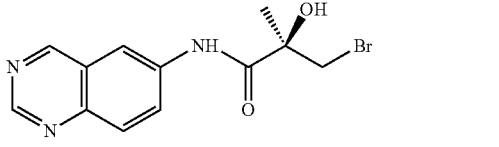
1040
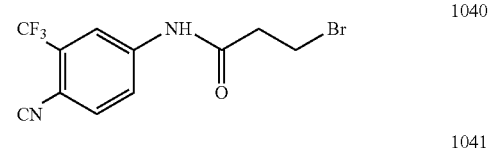
1041
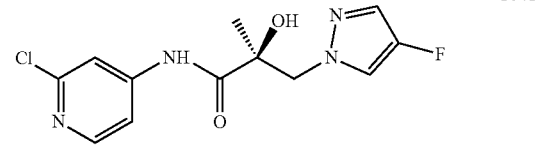
1042
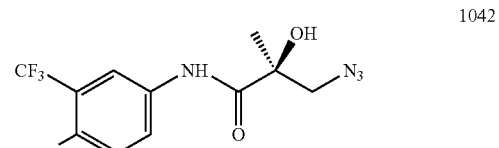
1043
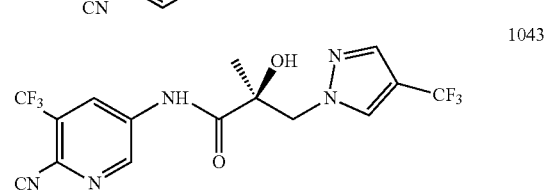

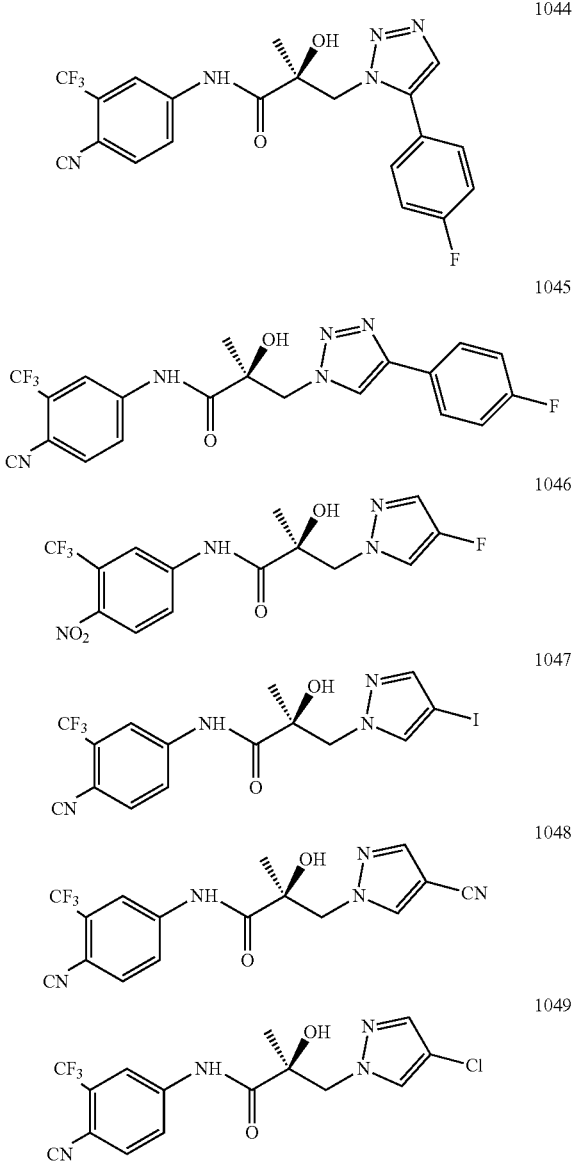

As used herein, the term "heterocycle" or "heterocyclic ring" group refers to a ring structure comprising in addition to carbon atoms, at least one atom of sulfur, oxygen, nitrogen or any combination thereof, as part of the ring. The heterocycle may be a 3-12 membered ring; 4-8 membered ring; a 5-7 membered ring; or a 6 membered ring. Preferably, the heterocycle is a 5 to 6 membered ring. Typical examples of heterocycles include, but are not limited to, piperidine, pyridine, furan, thiophene, pyrrole, pyrrolidine, pyrazole, pyrazine, piperazine or pyrimidine. Examples of $C_5$-$C_8$ heterocyclic rings include pyran, dihydropyran, tetrahydropyran, dihydropyrrole, tetrahydropyrrole, pyrazine, dihydropyrazine, tetrahydropyrazine, pyrimidine, dihydropyrimidine, tetrahydropyrimidone, pyrazole, dihydropyrazole, tetrahydropyrazole, triazole, tetrazole, piperidine, piperazine, pyridine, dihydropyridine, tetrahydropyridine, morpholine, thiomorpholine, furan, dihydrofuran, tetrahydrofuran, thiophene, dihydrothiophene, tetrahydrothiophene, thiazole, imidazole, isoxazole, and the like. The heterocycle ring may be fused to another saturated or unsaturated cycloalkyl or a saturated or unsaturated heterocyclic ring. When the heterocycle ring is substituted, the substituents include at least one of halogen, haloalkyl, hydroxyl, alkoxy, carbonyl, amido, alkylamido, dialkylamido, cyano, nitro, $CO_2H$, amino, alkylamino, dialkylamino, carboxyl, thiol, or thioalkyl.

The term "aniline ring system" refers to the conserved ring represented to the left of the structures in this document which is substituted by X, Y, and/or Z.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes and ($C_3$-$C_7$) cycloalkenyl groups, such as cyclopropenyl, cyclobutenyl, cyclopentenyl, cyclohexenyl, and cycloheptenyl, and unsaturated cyclic and bicyclic terpenes. Examples of $C_5$-$C_8$ carbocyclic include cyclopentane, cyclopentene, cyclohexane, and cyclohexene rings. A cycloalkyl group can be unsubstituted or substituted by at least one substituent. Preferably, the cycloalkyl group is a monocyclic ring or bicyclic ring.

The term "alkyl" refers to a saturated aliphatic hydrocarbon, including straight-chained and branched-chained. Typically, the alkyl group has 1-12 carbons, 1-7 carbons, 1-6 carbons, or 1-4 carbon atoms. A branched alkyl is an alkyl substituted by alkyl side chains of 1 to 5 carbons. The branched alkyl may have an alkyl substituted by a $C_1$-$C_5$ haloalkyl. Additionally, the alkyl group may be substituted by at least one of halogen, haloalkyl, hydroxyl, alkoxy carbonyl, amido, alkylamido, dialkylamido, nitro, CN, amino, alkylamino, dialkylamino, carboxyl, thio or thioalkyl.

An "arylalkyl" group refers to an alkyl bound to an aryl, wherein alkyl and aryl are as defined herein. An example of an arylalkyl group is a benzyl group.

An "alkenyl" group refers to an unsaturated hydrocarbon, including straight chain and branched chain having one or more double bonds. The alkenyl group may have 2-12 carbons, preferably the alkenyl group has 2-6 carbons or 2-4 carbons. Examples of alkenyl groups include, but are not limited to, ethenyl, propenyl, butenyl, cyclohexenyl, etc. The alkenyl group may be substituted by at least one halogen, hydroxy, alkoxy carbonyl, amido, alkylamido, dialkylamido, nitro, amino, alkylamino, dialkylamino, carboxyl, thio, or thioalkyl.

As used herein the term "aryl" group refers to an aromatic group having at least one carbocyclic aromatic group or heterocyclic aromatic group, which may be unsubstituted or substituted. When present, substituents include, but are not limited to, at least one halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. The aryl group may be a 4-12 membered ring, preferably the aryl group is a 4-8 membered ring. Also the aryl group may be a 6 or 5 membered ring.

The term "heteroaryl" refers to an aromatic group having at least one heterocyclic aromatic ring. In one embodiment, the heteroaryl comprises at least one heteroatom such as sulfur, oxygen, nitrogen, silicon, phosphorous or any combination thereof, as part of the ring. In another embodiment, the heteroaryl may be unsubstituted or substituted by one or more groups selected from halogen, aryl, heteroaryl, cyano, haloalkyl, hydroxy, alkoxy carbonyl, amido, alkylamido, dialkylamido, nitro, amino, alkylamino, dialkylamino, carboxy or thio or thioalkyl. Nonlimiting examples of heteroaryl rings are pyranyl, pyrrolyl, pyrazinyl, pyrimidinyl, pyrazolyl, pyridinyl, furanyl, thiophenyl, thiazolyl, indolyl, imidazolyl, isoxazolyl, and the like. In one embodiment, the heteroaryl group is a 5-12 membered ring. In one embodiment, the heteroaryl group is a five membered ring. In one embodiment, the heteroaryl group is a six membered ring. In another embodiment, the heteroaryl group is a 5-8 membered ring. In another embodiment, the heteroaryl group comprises of 1-4 fused rings. In one embodiment, the heteroaryl group is 1,2,3-triazole. In one embodiment the heteroaryl is a pyridyl. In one embodiment the heteroaryl is a bipyridyl. In one embodiment the heteroaryl is a terpyridyl.

As used herein, the term "haloalkyl" group refers to an alkyl group that is substituted by one or more halogen atoms, e.g. by F, Cl, Br or I.

A "hydroxyl" group refers to an OH group. It is understood by a person skilled in the art that when T, $Q^1$, $Q^2$, $Q^3$, or $Q^4$, in the compounds of the present invention is OR, then R is not OH.

The term "halogen" or "halo" or "halide" refers to a halogen; F, Cl, Br or I.

In one embodiment, this invention provides the compounds and/or its use and/or, its derivative, optical isomer, isomer, metabolite, pharmaceutically acceptable salt, pharmaceutical product, hydrate, N-oxide, prodrug, polymorph, crystal or combinations thereof.

In one embodiment, the methods of this invention make use of "pharmaceutically acceptable salts" of the compounds, which may be produced, by reaction of a compound of this invention with an acid or base.

The compounds of the invention may be converted into pharmaceutically acceptable salts. A pharmaceutically acceptable salt may be produced by reaction of a compound with an acid or base.

Suitable pharmaceutically acceptable salts of amines may be prepared from an inorganic acid or from an organic acid. Examples of inorganic salts of amines include, but are not limited to, bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphates, sulfates, sulfamates, sulfanilates, sulfonic acids (alkylsulfonates, arylsulfonates, halogen substituted alkylsulfonates, halogen substituted arylsulfonates), sulfonates, or thiocyanates.

Examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates. Examples of inorganic salts of carboxylic acids or phenols may be selected from ammonium, alkali metals, and alkaline earth metals. Alkali metals include, but are not limited to, lithium, sodium, potassium, or cesium. Alkaline earth metals include, but are not limited to, calcium, magnesium, aluminium; zinc, barium, cholines, or quaternary ammoniums. Examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolines, piperazines, procaine, tris(hydroxymethyl)methylamines, triethylamines, triethanolamines, trimethylamines, tromethamines and ureas.

In various embodiments, the pharmaceutically acceptable salts of the compounds of this invention include: HCl salt, oxalic acid salt, L-(+)-tartaric acid salt, HBr salt and succinic acid salt. Each represents a separate embodiment of this invention.

Salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

The methods of the invention may use an uncharged compound or a pharmaceutically acceptable salt of the compound. In particular, the methods use pharmaceutically acceptable salts of compounds of formulas I-VII, IA, IB, IC, ID, IIA, IIB, VIIA, or VIIB. The pharmaceutically acceptable salt may be an amine salt or a salt of a phenol of the compounds of formulas I-VII, IA, IB, IC, ID, IIA, IIB, VIIA, or VIIB.

In one embodiment, the methods of this invention make use of a free base, free acid, non charged or non-complexed compounds of formulas I-VII, IA, IB, IC, ID, IIA, IIB, VIIA, or VIIB, and/or its isomer, pharmaceutical product, hydrate, polymorph, or combinations thereof.

In one embodiment, the methods of this invention make use of an optical isomer of a compound of formulas I-VII, IA, IB, IC, ID, IIA, IIB, VIIA, or VIIB. In one embodiment, the methods of this invention make use of an isomer of a compound of formulas I-VII, IA, IB, IC, ID, IIA, IIB, VIIA, or VIIB. In one embodiment, the methods of this invention make use of a pharmaceutical product of a compound of formulas I-VII, IA, IB, IC, ID, IIA, IIB, VIIA, or VIIB. In one embodiment, the methods of this invention make use of a hydrate of a compound of formulas I-VII, IA, IB, IC, ID, IIA, IIB, VIIA, or VIIB. In one embodiment, the methods of this invention make use of a polymorph of a compound of formulas I-VII, IA, IB, IC, ID, IIA, IIB, VIIA, or VIIB. In one embodiment, the methods of this invention make use of a metabolite of a compound of formulas I-VII, IA, IB, IC, ID, IIA, IIB, VIIA, or VIIB. In another embodiment, the methods of this invention make use of a composition comprising a compound of formulas I-VII, IA, IB, IC, ID, IIA, IIB, VIIA, or VIIB, as described herein, or, in another embodiment, a combination of isomer, metabolite, pharmaceutical product, hydrate, polymorph of a compound of formulas I-VII, IA, IB, IC, ID, IIA, IIB, VIIA, or VIIB.

As used herein, the term "isomer" includes, but is not limited to, optical isomers, structural isomers, or conformational isomers.

The term "isomer" is meant to encompass optical isomers of the SARD compound. It will be appreciated by those skilled in the art that the SARDs of the present invention contain at least one chiral center. Accordingly, the compounds may exist as optically-active (such as an (R) isomer or (S) isomer) or racemic forms. Optically active compounds may exist as enantiomerically enriched mixtures. Some compounds may also exhibit polymorphism. It is to be understood that the present invention encompasses any racemic, optically active, polymorphic, or stereroisomeric form, or mixtures thereof. Thus, the invention may encompass SARD compounds as pure (R)-isomers or as pure (S)-isomers. It is known in the art how to prepare optically active forms. For example, by resolution of the racemic form by recrystallization techniques, by synthesis from optically active starting materials, by chiral synthesis, or by chromatographic separation using a chiral stationary phase.

Compounds of the invention may be hydrates of the compounds. As used herein, the term "hydrate" includes, but is not limited to, hemihydrate, monohydrate, dihydrate, or trihydrate. The invention also includes use of N-oxides of the amino substituents of the compounds described herein.

This invention provides, in other embodiments, use of metabolites of the compounds as herein described. In one embodiment, "metabolite" means any substance produced from another substance by metabolism or a metabolic process.

In one embodiment, the compounds of this invention are prepared according to Example 1.
Biological Activity of Selective Androgen Receptor Degraders A method of treating prostate cancer (PCa) or increasing the survival of a male subject suffering from prostate cancer comprising administering to the subject a therapeutically effective amount of a compound or its pharmaceutically acceptable salt, represented by a compound of formula I:

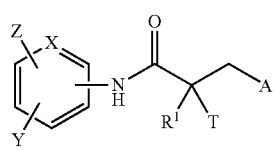

wherein
T is H, OH, OR, OCOR, CH$_3$, —NHCOCH$_3$, or NHCOR;
R$^1$ is H, CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
ZH, is NO$_2$, CN, halide, COOH, COR, NHCOR, CONHR, or Y and Z form a 5 to 8 membered ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a five-membered saturated or unsaturated ring having at least one nitrogen atom and 0, 1, or 2 double bonds, optionally substituted with at least one of Q$^1$, Q$^2$, Q$^3$, or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, benzyl, NCS, maleimide, NHCOOR, N(R)$_2$, NHCOR, CONHR, COOR or COR;
R$^3$ is NHR$^2$, halide, N$_3$, OR$^4$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH2, CONH(R$^4$), CON(R$^4$)$_2$, SR$^4$, SO$_2$R$^4$, SOR$^4$SO$_3$H, SO$_2$NH$_2$, SO$_2$NH(R$^4$), SO$_2$N(R$^4$)$_2$, NH$_2$, NH(R$^4$), N(R$^4$)$_2$, CO(N-heterocycle), C(O)(C$_1$-C$_{10}$)alkyl, NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
or its optical isomer, isomer, pharmaceutically acceptable salt, pharmaceutical product, polymorph, hydrate or any combination thereof.

In another embodiment, if A is Br or I, R$^1$ is CH$_3$, and T is OH, then X is N or the aniline ring forms a fused heterocyclic ring.

A method of treating prostate cancer (PCa) or increasing the survival of a male subject suffering from prostate cancer comprising administering to the subject a therapeutically effective amount of a compound or its pharmaceutically acceptable salt, or isomer, represented by a compound of formulas I-VII, IA-ID, IIA, IIB, VIIA, or VIIB.

The prostate cancer may be advanced prostate cancer, refractory prostate cancer, castration resistant prostate cancer (CRPC), metastatic CRPC (mCRPC), non-metastatic CRPC (nmCRPC), high-risk nmCRPC or any combination thereof.

The prostate cancer may depend on AR-FL and/or AR-SV for proliferation. The prostate or other cancer may be resistant to treatment with an androgen receptor antagonist. The prostate or other cancer may be resistant to treatment with enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, spironolactone, or any combination thereof. The method may also reduce the levels of AR, AR-FL, AR-FL with antiandrogen resistance-conferring AR-LBD mutations, AR-SV, gene-amplified AR, or any combination thereof.

In one embodiment, this invention provides a method of treating enzalutamide resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating abiraterone resistant prostate cancer comprising administering to the subject a therapeutically effective amount of a compound of this invention, or its optical isomer, isomer, pharmaceutically acceptable salt, pharmaceutical product, polymorph, hydrate or any combination thereof.

In one embodiment, this invention provides a method of treating triple negative breast cancer (TNBC) comprising administering to the subject a therapeutically effective amount of a compound of this invention, or its optical isomer, isomer, pharmaceutically acceptable salt, pharmaceutical product, polymorph, hydrate or any combination thereof.

The method may further comprise a second therapy such as androgen deprivation therapy (ADT) or LHRH agonist or antagonist. LHRH agonists include, but are not limited to, leuprolide acetate.

The invention encompasses a method of treating or inhibiting the progression of prostate cancer (PCa) or increasing the survival of a male subject suffering from prostate cancer comprising administering to the subject a therapeutically effective amount of a SARD compound or pharmaceutically acceptable salt, wherein the compound is at least one of compounds 1001 to 1049.

The invention encompasses a method of treating or inhibiting the progression of refractory prostate cancer (PCa) or increasing the survival of a male subject suffering from refractory prostate cancer comprising administering to the subject a therapeutically effective amount of a SARD compound or pharmaceutically acceptable salt, wherein the compound is represented by a compound of formulas I-VII, IA, IB, IC, ID, IIA, IIB, VIIA, or VIIB, or the compound is at least one of compounds 1001 to 1049.

The invention encompasses a method of treating or increasing the survival of a male subject suffering from castration resistant prostate cancer (CRPC) comprising administering to the subject a therapeutically effective amount of a SARD wherein the compound is represented by a compound of formulas I-VII, IA, IB, IC, ID, IIA, IIB, VIIA, or VIIB, or at least one of compounds 1001 to 1049.

The method may further comprise administering androgen deprivation therapy to the subject.

The invention encompasses a method of treating or inhibiting the progression of enzalutamide resistant prostate cancer (PCa) or increasing the survival of a male subject suffering from enzalutamide resistant prostate cancer comprising administering to the subject a therapeutically effective amount of a SARD compound or pharmaceutically acceptable salt, wherein the compound is represented by a compound of formulas I-VII, IA, IB, IC, ID, IIA, IIB, VIIA, or VIIB, or the compound is at least one of compounds 1001 to 1049.

The method may further comprise administering androgen deprivation therapy to the subject.

The invention encompasses a method of treating or inhibiting the progression of triple negative breast cancer (TNBC) or increasing the survival of a female subject suffering from triple negative breast cancer comprising administering to the subject a therapeutically effective amount of a SARD compound or pharmaceutically acceptable salt, wherein the compound is represented by a compound of formulas I-VII, IA, IB, IC, ID, IIA, IIB, VIIA, or VIIB, or the compound is at least one of compounds 1001 to 1049.

As used herein, the term "increase the survival" refers to a lengthening of time when describing the survival of a subject. Thus in this context, the compounds of the invention may be used to increase the survival of men with advanced prostate cancer, refractory prostate cancer, castration resistant prostate cancer (CRPC); metastatic CRPC (mCRPC); non-metastatic CRPC (nmCRPC); or high-risk nmCRPC; or women with TNBC.

Alternatively, as used herein, the terms "increase", "increasing", or "increased" may be used interchangeably and refer to an entity becoming progressively greater (as in size, amount, number, or intensity), wherein for example the entity is sex hormone-binding globulin (SHBG) or prostate-specific antigen (PSA).

The compounds and compositions of the invention may be used for increasing metastasis-free survival (MFS) in a subject suffering from non-metastatic prostate cancer. The non-metastatic prostate cancer may be non-metastatic advanced prostate cancer, non-metastatic CRPC (nmCRPC), or high-risk nmCRPC.

The SARD compounds described herein may be used to provide a dual action. For example, the SARD compounds may treat prostate cancer and prevent metastasis. The prostate cancer may be refractory prostate cancer; advanced prostate cancer; castration resistant prostate cancer (CRPC); metastatic CRPC (mCRPC); non-metastatic CRPC (nmCRPC); or high-risk nmCRPC.

The SARD compounds described herein may be used to provide a dual action. For example, the SARD compounds may treat TNBC and prevent metastasis.

Men with advanced prostate cancer who are at high risk for progression to castration resistant prostate cancer (CRPC) are men on ADT with serum total testosterone concentrations greater than 20 ng/dL or men with advanced prostate cancer who at the time of starting ADT had either (1) confirmed Gleason pattern 4 or 5 prostate cancer, (2) metastatic prostate cancer, (3) a PSA doubling time <3 months, (4) a PSA≥20 ng/mL, or (5) a PSA relapse in <3 years after definitive local therapy (radical prostatectomy or radiation therapy).

Normal levels of prostate specific antigen (PSA) are dependent on several factors, such as age and the size of a male subject's prostate, among others. PSA levels in the range between 2.5-10 ng/mL are considered "borderline high" while levels above 10 ng/mL are considered "high." A rate change or "PSA velocity" greater than 0.75/year is considered high. PSA levels may increase despite ongoing ADT or a history of ADT, surgical castration or despite treatment with antiandrogens and/or LHRH agonist.

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. "Phase III, randomized, placebo-controlled study of once-daily oral zibotentan (ZD4054) in patients with non-metastatic castration-resistant prostate cancer," *Prostate Canc Prost Dis*. February; 16:187-192). This relatively rapid progression of their disease underscores the importance of novel therapies for these individuals.

The methods of the invention may treat subjects with PSA levels greater than 8 ng/mL where the subject suffers from high-risk nmCRPC. The patient population includes subjects suffering from nmCRPC where PSA doubles in less than 8 months or less than 10 months. The method may also treat patient populations where the total serum testosterone levels are greater than 20 ng/mL in a subject suffering from high-risk nmCRPC. In one case, the serum free testosterone levels are greater than those observed in an orchiectomized male in a subject suffering from high-risk nmCRPC.

The pharmaceutical compositions of the invention may further comprise at least one LHRH agonist or antagonist, antiandrogen, anti-programmed death receptor 1 (anti-PD-1) drug or anti-PD-L1 drug. LHRH agonists include, but are not limited to, leuprolide acetate (Lupron®) (U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). LHRH antagonists include, but are not limited to, degarelix or abarelix. Antiandrogens include, but are not limited to, bicalutamide, flutamide, finasteride, dutasteride, enzalutamide, nilutamide, chlormadinone, abiraterone, or any combination thereof. Anti-PD-1 drugs include, but are not limited to, AMP-224, nivolumab, pembrolizumab, pidilizumab, and AMP-554. Anti-PD-L1 drugs include, but are not limited to, BMS-936559, atezolizumab, durvalumab, avelumab, and MPDL3280A. Anti-CTLA-4 drugs include, but are not limited to, ipilimumab and tremelimumab.

Treatment of prostate cancer, advanced prostate cancer, CRPC, mCRPC and/or nmCRPC may result in clinically meaningful improvement in prostate cancer related symptoms, function and/or survival. Clinically meaningful improvement can be determined by an increase in radiographic progression free survival (rPFS) if cancer is metastatic, or an increase metastasis-free survival (MFS) if cancer is non-metastatic, among others.

The invention encompasses methods of lowering serum prostate specific antigen (PSA) levels in a male subject suffering from prostate cancer, advanced prostate cancer, metastatic prostate cancer or castration resistant prostate cancer (CRPC) comprising administering a therapeutically effective amount of a SARD compound, wherein the compound is represented by the structure of formulas I-VII, IA, IB, IC, ID, IIA, IIB, VIIA, or VIIB.

The invention encompasses a method of secondary hormonal therapy that reduces serum PSA in a male subject suffering from castration resistant prostate cancer (CRPC) comprising administering a therapeutically effective amount of a compound of formulas I-VII, IA, IB, IC, ID, IIA, IIB, VIIA, or VIIB that reduces serum PSA in a male subject suffering from castration resistant prostate cancer.

The invention encompasses a method of reducing levels of AR, AR-full length (AR-FL), AR-FL with antiandrogen resistance-conferring AR-LBD mutations, AR-splice variant (AR-SV), and/or amplifications of the AR gene within the tumor in the subject in need thereof comprising administering a therapeutically effective amount of a compound of formulas I-VII, IA, IB, IC, ID, IIA, IIB, VIIA, or VIIB to reduce the level of AR, AR-full length (AR-FL), AR-FL with antiandrogen resistance-conferring AR-LBD or other AR mutations, AR-splice variant (AR-SV), and/or amplifications of the AR gene within the tumor.

The method may increase radiographic progression free survival (rPFS) or metastasis-free survival (MFS).

Subjects may have non-metastatic cancer; failed androgen deprivation therapy (ADT), undergone orchidectomy, or have high or increasing prostate specific antigen (PSA) levels; subjects may be a patient with prostate cancer, advanced prostate cancer, refractory prostate cancer, CRPC patient, metastatic castration resistant prostate cancer (mCRPC) patient, or non-metastatic castration resistant prostate cancer (nmCRPC) patient. In these subjects, the refractory may be enzalutamide resistant prostate cancer. In these subjects, the nmCRPC may be high-risk nmCRPC. Further the subject may be on androgen deprivation therapy (ADT) with or without castrate levels of total T.

As used herein, the phrase "a subject suffering from castration resistant prostate cancer" refers to a subject with at least one of the following characteristics: has been previously treated with androgen deprivation therapy (ADT); has responded to the ADT and currently has a serum PSA>2 ng/mL or >2 ng/mL and representing a 25% increase above the nadir achieved on the ADT; a subject which despite being maintained on androgen deprivation therapy is diagnosed to have serum PSA progression; a castrate level of serum total testosterone (<50 ng/dL) or a castrate level of serum total testosterone (<20 ng/dL). The subject may have rising serum PSA on two successive assessments at least 2 weeks apart; been effectively treated with ADT; or has a history of serum PSA response after initiation of ADT.

As used herein, the term "serum PSA progression" refers to a 25% or greater increase in serum PSA and an absolute increase of 2 ng/ml or more from the nadir; or to serum PSA>2 ng/mL, or >2 ng/mL and a 25% increase above the nadir after the initiation of androgen deprivation therapy (ADT). The term "nadir" refers to the lowest PSA level while a patient is undergoing ADT.

The term "serum PSA response" refers to at least one of the following: at least 90% reduction in serum PSA value prior to the initiation of ADT; to <10 ng/mL undetectable level of serum PSA (<0.2 ng/mL) at any time; at least 50% decline from baseline in serum PSA; at least 90% decline from baseline in serum PSA; at least 30% decline from baseline in serum PSA; or at least 10% decline from baseline in serum PSA.

The methods of this invention comprise administering a combination of forms of ADT and a compound of this invention. Forms of ADT include a LHRH agonist. LHRH agonist includes, but is not limited to, leuprolide acetate (Lupron®)(U.S. Pat. Nos. 5,480,656; 5,575,987; 5,631,020; 5,643,607; 5,716,640; 5,814,342; 6,036,976 hereby incorporated by reference) or goserelin acetate (Zoladex®) (U.S. Pat. Nos. 7,118,552; 7,220,247; 7,500,964 hereby incorporated by reference). Forms of ADT include, but are not limited to LHRH antagonists, reversible antiandrogens, or bilateral orchidectomy. LHRH antagonists include, but are not limited to, degarelix and abarelix. Antiandrogens include, but are not limited to, bicalutamide, flutamide, finasteride, dutasteride, enzalutamide, EPI-001, EPI-506, ARN-509, ODM-201, nilutamide, chlormadinone, abiraterone, or any combination thereof.

The methods of the invention encompass administering at least one compound of the invention and a lyase inhibitor (e.g., abiraterone).

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. Patients with significant risk of progressive disease and/or death from prostate cancer should be included in the definition and any patient with cancer outside the prostate capsule with disease stages as low as IIB clearly has "advanced" disease. "Advanced prostate cancer" can refer to locally advanced prostate cancer. Similarly, "advanced breast cancer" refers to metastatic cancer having originated in the breast, and having widely metastasized to beyond the breast to surrounding tissues or other parts of the body such as the liver, brain, lungs, or bone.

The term "refractory" may refer to cancers that do not respond to treatment. E.g., prostate or breast cancer may be resistant at the beginning of treatment or it may become resistant during treatment. "Refractory cancer" may also be referred to herein as "resistant cancer".

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant. CRPC may be the result of AR activation by intracrine androgen synthesis; expression of AR splice variants (AR-SV) that lack ligand binding domain (LBD); or expression of AR-LBD or other AR mutations with potential to resist antagonists. Castration resistant prostate cancer (CRPC) is an advanced prostate cancer which developed despite ongoing ADT and/or surgical castration. Castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix or abarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa®), cabozantinib (Cometriq™, also known as XL184)) or other prostate cancer therapies (e.g., vaccines (sipuleucel-T (Provenge®), GVAX, etc.), herbal (PC-SPES) and lyase inhibitor (abiraterone)) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

Castration resistant prostate cancer may be defined as hormone naïve prostate cancer. In men with castration resistant prostate cancer, the tumor cells may have the ability to grow in the absence of androgens (hormones that promote the development and maintenance of male sex characteristics).

Many early prostate cancers require androgens for growth, but advanced prostate cancers are androgen-independent, or hormone naïve.

The term "androgen deprivation therapy" (ADT) may include orchiectomy; administering luteinizing hormone-releasing hormone (LHRH) analogs; administering luteinizing hormone-releasing hormone (LHRH) antagonists; administering 5α-reductase inhibitors; administering antiandrogens; administering inhibitors of testosterone biosynthesis; administering estrogens; or administering 17α-hydroxylase/C17,20 lyase (CYP17A1) inhibitors. LHRH drugs lower the amount of testosterone made by the testicles. Examples of LHRH analogs available in the United States include leuprolide (Lupron®, Viadur®, Eligard®), goserelin (Zoladex®), triptorelin (Trelstar®), and histrelin (Vantas®). Antiandrogens block the body's ability to use any androgens. Examples of antiandrogens drugs include enzalutamide (Xtandi®), flutamide (Eulexin®), bicalutamide (Casodex®), and nilutamide (Nilandron®). Luteinizing hormone-releasing hormone (LHRH) antagonists include abarelix (Plenaxis®) or degarelix (Firmagon®) (approved for use by the FDA in 2008 to treat advanced prostate cancer). 5α-Reductase inhibitors block the body's ability to convert testosterone to the more active androgen, 5α-dihydrotestosterone (DHT) and include drugs such as finasteride (Proscar®) and dutasteride (Avodart®). Inhibitors of testosterone biosynthesis include drugs such as ketoconazole (Nizoral®).

Estrogens include diethylstilbestrol or 17β-estradiol. 17α-Hydroxylase/C17,20 lyase (CYP17A1) inhibitors include abiraterone (Zytiga®).

The invention encompasses a method of treating antiandrogen-resistant prostate cancer. The antiandrogen may include, but is not limited to, bicalutamide, hydroxyflutamide, flutamide, enzalutamide or abiraterone.

Treatment of Triple Negative Breast Cancer (TNBC)

Triple negative breast cancer (TNBC) is a type of breast cancer lacking the expression of the estrogen receptor (ER), progesterone receptor (PR), and HER2 receptor kinase. As such, TNBC lacks the hormone and kinase therapeutic targets used to treat other types of primary breast cancers. Correspondingly, chemotherapy is often the initial pharmacotherapy for TNBC. Interestingly, AR is often still expressed in TNBC and may offer a hormone targeted therapeutic alternative to chemotherapy. In ER-positive breast cancer, AR is a positive prognostic indicator as it is believed that activation of AR limits and/or opposes the effects of the ER in breast tissue and tumors. However, in the absence of ER, it is possible that AR actually supports the growth of breast cancer tumors. Though the role of AR is not fully understood in TNBC, we have evidence that certain TNBC's may be supported by androgen independent activation of AR-SVs lacking the LBD or androgen-dependent activation of AR full length. As such, enzalutamide and other LBD-directed traditional AR antagonists would not be able to antagonize AR-SVs in these TNBC's. However, SARDs of this invention which are capable of destroying AR-SVs (see Table 1 and Example 5) through a binding site in the NTD of AR (see Example 9) would be able to antagonize AR in these TNBC's and provide an anti-tumor effect, as shown in Example 8.

Treatment of Kennedy's Disease

Muscle atrophy (MA) is characterized by wasting away or diminution of muscle and a decrease in muscle mass. For example, post-polio MA is muscle wasting that occurs as part of the post-polio syndrome (PPS). The atrophy includes weakness, muscle fatigue, and pain. Another type of MA is X-linked spinal-bulbar muscular atrophy (SBMA—also known as Kennedy's Disease). This disease arises from a defect in the androgen receptor gene on the X chromosome, affects only males, and its onset is in late adolescence to adulthood. Proximal limb and bulbar muscle weakness results in physical limitations including dependence on a wheelchair in some cases. The mutation results in an extended polyglutamine tract at the N-terminal domain of the androgen receptor (polyQ AR).

Binding and activation of the polyQ AR by endogeneous androgens (testosterone and DHT) results in unfolding and nuclear translocation of the mutant androgen receptor. The androgen-induced toxicity and androgen-dependent nuclear accumulation of polyQ AR protein seems to be central to the pathogenesis. Therefore, the inhibition of the androgen-activated polyQ AR might be a therapeutic option (A. Baniahmad. Inhibition of the androgen receptor by antiandrogens in spinobulbar muscle atrophy. *J. Mol. Neurosci.* 2016 58(3), 343-347). These steps are required for pathogenesis and result in partial loss of transactivation function (i.e., an androgen insensitivity) and a poorly understood neuromuscular degeneration. Peripheral polyQ AR antisense therapy rescues disease in mouse models of SBMA (*Cell Reports* 7, 774-784, May 8, 2014). Further support of use antiandrogen comes in a report in which the antiandrogen flutamide protects male mice from androgen-dependent toxicity in three models of spinal bulbar muscular atrophy (Renier K J, Troxell-Smith S M, Johansen J A, Katsuno M, Adachi H, Sobue G, Chua J P, Sun Kim H, Lieberman A P, Breedlove S M, Jordan C L. *Endocrinology* 2014, 155(7), 2624-2634). These steps are required for pathogenesis and result in partial loss of transactivation function (i.e., an androgen insensitivity) and a poorly understood neuromuscular degeneration. Currently there are no disease-modifying treatments but rather only symptom directed treatments. Efforts to target the polyQ AR as the proximal mediator of toxicity by harnessing cellular machinery to promote its degradation hold promise for therapeutic intervention.

Selective androgen receptor degraders such as those reported herein bind to, inhibit transactivation, and degrade all androgen receptors tested to date (full length, splice variant, antiandrogen resistance mutants, etc.), indicating that they are promising leads for treatment diseases whose pathogenesis is androgen-dependent such as SBMA.

The invention encompasses methods of treating Kennedy's disease comprising administering a therapeutically effective amount of a compound of formulas I-VII, IA, IB, IC, ID, IIA, IIB, VIIA, or VIIB.

As used herein, the term "androgen receptor associated conditions" or "androgen sensitive diseases or disorders" or "androgen-dependent diseases or disorders" are conditions, diseases, or disorders that are modulated by or whose pathogenesis is dependent upon the activity of the androgen receptor. The androgen receptor is expressed in most tissues of the body however it is overexpressed in, inter alia, the prostate and skin. ADT has been the mainstay of prostate cancer treatment for many years, and SARDs may also be useful in treating various prostate cancers, benign prostatic hypertrophy, prostamegaly, and other maladies of the prostate.

The invention encompasses methods of treating benign prostatic hypertrophy comprising administering a therapeutically effective amount of at least one compound of formulas I-VII, IA, IB, IC, ID, IIA, IIB, VIIA, or VIIB.

The invention encompasses methods of treating prostamegaly comprising administering a therapeutically effective amount of at least one compound of formulas I-VII, IA, IB, IC, ID, IIA, IIB, VIIA, or VIIB.

The invention encompasses methods of treating hyperproliferative prostatic disorders and diseases comprising administering a therapeutically effective amount of a compound of formulas I-VII, IA, IB, IC, ID, IIA, IIB, VIIA, or VIIB.

The effect of the AR on the skin is apparent in the gender dimorphism and puberty related dermatological problems common to teens and early adults. The hyperandrogenism of puberty stimulates terminal hair growth, sebum production, and predisposes male teens to acne, acne vulgaris, seborrhea, excess sebum, hidradenitis suppurativa, hirsutism, hypertrichosis, hyperpilosity, androgenic alopecia, male pattern baldness, and other dermatological maladies. Although antiandrogens theoretically should prevent the hyperandrogenic dermatological diseases discussed, they are limited by toxicities, sexual side effects, and lack of efficacy when topically applied. The SARDs of this invention potently inhibit ligand-dependent and ligand-independent AR activation, and (in some cases) have short biological half-lives in the serum, suggesting that topically formulated SARDs of this invention could be applied to the areas affected by acne, seborrheic dermatitis, and/or hirsutism without risk of systemic side effects.

The invention encompasses methods of treating acne, acne vulgaris, seborrhea, seborrheic dermatitis, hidradenitis supporativa, hirsutism, hypertrichosis, hyperpilosity, or alopecia comprising administering a therapeutically effective amount of a compound of formulas I-VII, IA, IB, IC, ID, IIA, IIB, VIIA, or VIIB, or any of compounds 1001 to 1049.

The compounds and/or compositions described herein may be used for treating hair loss, alopecia, androgenic alopecia, alopecia areata, alopecia secondary to chemotherapy, alopecia secondary to radiation therapy, alopecia induced by scarring or alopecia induced by stress. Generally "hair loss" or "alopecia" refers to baldness as in the very common type of male-pattern baldness. Baldness typically begins with patch hair loss on the scalp and sometimes progresses to complete baldness and even loss of body hair. Hair loss affects both males and females.

The invention encompasses methods of treating androgenic alopecia comprising administering a therapeutically effective amount of a compound of formula I-VII, IA, IB, IC, ID, IIA, IIB, VIIA, or VIIB, or any of compounds 1001 to 1049.

SARDs of this invention may also be useful in the treatment of hormonal conditions in females which can have hyperandrogenic pathogenesis such as precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and/or vaginal dryness.

The invention encompasses methods of treating precocious puberty or early puberty, dysmenorrhea or amenorrhea, multilocular uterus syndrome, endometriosis, hysteromyoma, abnormal uterine bleeding, hyper-androgenic diseases (such as polycystic ovary syndrome (PCOS)), fibrocystic breast disease, fibroids of the uterus, ovarian cysts, polycystic ovary syndrome, pre-eclampsia, eclampsia of pregnancy, preterm labor, premenstrual syndrome, or vaginal dryness comprising administering a therapeutically effective amount of a compound of formulas I-VII, IA-ID, IIA, IIB, VIIA, or VIIB, or any of compounds 1001 to 1049.

SARDs of this invention may also find utility in treatment of sexual perversion, hypersexuality, paraphilias, androgen psychosis, virilization, androgen insensitivity syndromes (AIS) (such as complete AIS (CAIS) and partial AIS (PAIS)), and improving ovulation in an animal.

The invention encompasses methods of treating sexual perversion, hypersexuality, paraphilias, androgen psychosis, virilization androgen, insensitivity syndromes, increasing or modulating or improving ovulation comprising administering a therapeutically effective amount of a compound of formulas I-VII, IA, IB, IC, ID, IIA, IIB, VIIA, or VIIB, or any of compounds 1001 to 1049.

SARDs of this invention may also be useful for treating hormone-dependent cancers such as prostate cancer, breast cancer, testicular cancer, ovarian cancer, hepatocellular carcinoma, urogenital cancer, etc. In another embodiment, the breast cancer is triple negative breast cancer. Further, local or systemic SARD administration may be useful for treatment of precursors of hormone-dependent cancers such as prostatic intraepithelial neoplasia (PIN) and atypical small acinar proliferation (ASAP).

The invention encompasses methods of treating breast cancer, testicular cancer, uterine cancer, ovarian cancer, urogenital cancer, precursors of prostate cancer, or AR related or AR expressing solid tumors, comprising administering a therapeutically effective amount of a compound of formulas I-VII, IA, IB, IC, ID, IIA, IIB, VIIA, or VIIB. A precursor of prostate cancers may be prostatic intraepithelial neoplasia (PIN) or atypical small acinar proliferation (ASAP). The tumor may be hepatocellular carcinoma (HCC) or bladder cancer. Serum testosterone may be positively linked to the development of HCC. Based on epidemiologic, experimental observations, and notably the fact that men have a substantially higher risk of bladder cancer than women, androgens and/or the AR may also play a role in bladder cancer initiation.

Although traditional antiandrogens such as enzalutamide, bicalutamide and flutamide and androgen deprivation therapies (ADT) such as leuprolide were approved for use in prostate cancer, there is significant evidence that antiandrogens could also be used in a variety of other hormone-dependent and hormone-independent cancers. For example, antiandrogens have been successfully tested in breast cancer (enzalutamide; Breast Cancer Res (2014) 16(1): R7), non-small cell lung cancer (shRNAi AR), renal cell carcinoma (ASC-J9), partial androgen insensitivity associated malignancies such as gonadal tumors and seminoma, advanced pancreatic cancer (World J Gastroenterology 20(29):9229), cancer of the ovary, fallopian tubes, or peritoneum, cancer of the salivary gland (Head and Neck (2016) 38: 724-731; ADT was tested in AR-expressing recurrent/metastatic salivary gland cancers and was confirmed to have benefit on progression free survival and overall survival endpoints), bladder cancer (Oncotarget 6 (30): 29860-29876); Int J Endocrinol (2015), Article ID 384860), pancreatic cancer, lymphoma (including mantle cell), and hepatocellular carcinoma. Use of a more potent antiandrogen such as a SARD in these cancers may treat the progression of these and other cancers. Other cancers may also benefit from SARD treatment such as testicular cancer, uterine cancer, ovarian cancer, urogenital cancer, breast cancer, brain cancer, skin cancer, lymphoma, liver cancer, renal cancer, osteosarcoma, pancreatic cancer, endometrial cancer, lung cancer, non-small cell lung cancer (NSCLC), colon cancer, perianal adenoma, or central nervous system cancer.

SARDs of this invention may also be useful for treating other cancers containing AR such as breast, brain, skin, ovarian, bladder, lymphoma, liver, kidney, pancreas, endometrium, lung (e.g., NSCLC), colon, perianal adenoma, osteosarcoma, CNS, melanoma, hypercalcemia of malignancy and metastatic bone disease, etc.

Thus, the invention encompasses methods of treating hypercalcemia of malignancy, metastatic bone disease, brain cancer, skin cancer, bladder cancer, lymphoma, liver cancer, renal cancer, osteosarcoma, pancreatic cancer, endometrial cancer, lung cancer, central nervous system cancer, gastric cancer, colon cancer, melanoma, amyotrophic lateral sclerosis (ALS), and/or uterine fibroids comprising administering a therapeutically effective amount of a compound of formulas I-VII, IA, IB, IC, ID, IIA, IIB, VIIA, or VIIB, or any of compounds 1001 to 1049. The lung cancer may be non-small cell lung cancer (NSCLC).

SARDs of this invention may also be useful for the treating of non-hormone-dependent cancers. Non-hormone-dependent cancers include liver, salivary duct, etc.

In another embodiment, the SARDs of this invention are used for treating gastric cancer. In another embodiment, the SARDs of this invention are used for treating salivary duct carcinoma. In another embodiment, the SARDs of this invention are used for treating bladder cancer. In another embodiment, the SARDs of this invention are used for treating esophageal cancer. In another embodiment, the SARDs of this invention are used for treating pancreatic cancer. In another embodiment, the SARDs of this invention are used for treating colon cancer. In another embodiment, the SARDs of this invention are used for treating non-small cell lung cancer. In another embodiment, the SARDs of this invention are used for treating renal cell carcinoma.

AR plays a role in cancer initiation in hepatocellular carcinoma (HCC). Therefore, targeting AR may be an appropriate treatment for patients with early stage HCC. In late-stage HCC disease, there is evidence that metastasis is suppressed by androgens. In another embodiment, the SARDs of this invention are used for treating hepatocellular carcinoma (HCC).

Locati et al. in Head & Neck, 2016, 724-731 demonstrated the use of androgen deprivation therapy (ADT) in AR-expressing recurrent/metastatic salivary gland cancers and confirmed improved progression free survival and overall survival endpoints with ADT. In another embodiment, the SARDs of this invention are used for treating salivary gland cancer.

Kawahara et al. in Oncotarget, 2015, Vol 6 (30), 29860-29876 demonstrated that ELK1 inhibition, together with AR inactivation, has the potential of being a therapeutic approach for bladder cancer. McBeth et al. Int J Endocrinology, 2015, Vol 2015, Article ID 384860 suggested that the combination of antiandrogen therapy plus glucocorticoids as treatment of bladder cancer as this cancer is believed to have an inflammatory etiology. In another embodiment, the SARDs of this invention are used for treating bladder cancer, optionally in combination with glucocorticoids.

Abdominal Aortic Aneurysm (AAA)

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it is necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated AAA induced by porcine pancreatic elastase (0.35 U/mL) by 84.2% and 91.5% compared to vehicle (121%). Further AR −/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

Treatment of Wounds

Wounds and/or ulcers are normally found protruding from the skin or on a mucosal surface or as a result of an infarction in an organ. A wound may be a result of a soft tissue defect or a lesion or of an underlying condition. The term "wound" denotes a bodily injury with disruption of the normal integrity of tissue structures, sore, lesion, necrosis, and/or ulcer. The term "sore" refers to any lesion of the skin or mucous membranes and the term "ulcer" refers to a local defect, or excavation, of the surface of an organ or tissue, which is produced by the sloughing of necrotic tissue. "Lesion" generally includes any tissue defect. "Necrosis" refers to dead tissue resulting from infection, injury, inflammation, or infarctions. All of these are encompassed by the term "wound," which denotes any wound at any particular stage in the healing process including the stage before any healing has initiated or even before a specific wound like a surgical incision is made (prophylactic treatment).

Examples of wounds which can be treated in accordance with the present invention are aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores include, but are not limited to, bed sores, canker sores, chrome sores, cold sores, pressure sores, etc. Examples of ulcers include, but are not limited to, peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g., caused by gonorrhoea (including urethritis, endocervicitis and proctitis). Conditions related to wounds or sores which may be successfully treated according to the invention include, but are not limited to, burns, anthrax, tetanus, gas gangrene, scalatina, erysipelas, sycosis barbae, folliculitis, impetigo contagiosa, impetigo bullosa, etc. It is understood, that there may be an overlap between the use of the terms "wound" and "ulcer," or "wound" and "sore" and, furthermore, the terms are often used at random.

The kinds of wounds to be treated according to the invention include also: i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is by tissue loss, where: i) small tissue loss (due to surgical incisions, minor abrasions, and minor bites) or ii) significant tissue loss. The latter group includes ischemic ulcers, pressure sores, fistulae, lacerations, severe bites, thermal burns and donor site wounds (in soft and hard tissues) and infarctions. Other wounds include ischemic ulcers, pressure sores, fistulae, severe bites, thermal burns, or donor site wounds.

Ischemic ulcers and pressure sores are wounds, which normally only heal very slowly and especially in such cases an improved and more rapid healing is of great importance to the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

In one case, the wound to be treated is selected from the group consisting of aseptic wounds, infarctions, contused wounds, incised wounds, lacerated wounds, non-penetrating wounds, open wounds, penetrating wounds, perforating wounds, puncture wounds, septic wounds, and subcutaneous wounds.

The invention encompasses methods of treating a subject suffering from a wound comprising administering to the subject a therapeutically effective amount of a compound of formulas I-VII, IA, IB, IC, ID, IIA, IIB, VIIA, or VIIB, pharmaceutically acceptable salt thereof, or a pharmaceutical compostion thereof.

The invention encompasses methods of treating a subject suffering from a burn comprising administering to the subject a therapeutically effective amount of a compound of formulas I-VII, IA, IB, IC, ID, IIA, IIB, VIIA, or VIIB, pharmaceutically acceptable salt thereof, or a pharmaceutical composition thereof.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

Burns are associated with reduced testosterone levels, and hypogonadism is associated with delayed wound healing.

The invention encompasses methods for treating a subject suffering from a wound or a burn by administering at least one SARD compound according to this invention. The SARD may promote resolving of the burn or wound, participates in the healing process of a burn or a wound, or, treats a secondary complication of a burn or wound.

The treatment of burns or wounds may further use at least one growth factor such as epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof, which promote wound healing.

Wound healing may be measured by many procedures known in the art, including, but not limited to, wound tensile strength, hydroxyproline or collagen content, procollagen expression, or re-epithelialization. As an example, a SARD as described herein may be administered orally or topically at a dosage of about 0.1-100 mg per day. Therapeutic effectiveness is measured as effectiveness in enhancing wound healing as compared to the absence of the SARD compound. Enhanced wound healing may be measured by known techniques such as decrease in healing time, increase in collagen density, increase in hydroxyproline, reduction in complications, increase in tensile strength, and increased cellularity of scar tissue.

The term "reducing the pathogenesis" is to be understood to encompass reducing tissue damage, or organ damage associated with a particular disease, disorder or condition. The term may include reducing the incidence or severity of an associated disease, disorder or condition, with that in question or reducing the number of associated diseases, disorders or conditions with the indicated, or symptoms associated thereto.

Pharmaceutical Compositions

The compounds of the invention may be used in pharmaceutical compositions. As used herein, "pharmaceutical composition" means either the compound or pharmaceutically acceptable salt of the active ingredient with a pharmaceutically acceptable carrier or diluent. A "therapeutically effective amount" as used herein refers to that amount which provides a therapeutic effect for a given indication and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. The subjects may be a male or female subject or both.

Numerous standard references are available that describe procedures for preparing various compositions or formulations suitable for administration of the compounds of the invention. Examples of methods of making formulations and preparations can be found in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form are closely related to the therapeutic amounts of the compounds or compositions which are desirable and efficacious for the given treatment application.

The pharmaceutical compositions of the invention can be administered to a subject by any method known to a person skilled in the art. These methods include, but are not limited to, orally, parenterally, intravascularly, paracancerally, transmucosally, transdermally, intramuscularly, intranasally, intravenously, intradermally, subcutaneously, sublingually, intraperitoneally, intraventricularly, intracranially, intravaginally, by inhalation, rectally, or intratumorally. These methods include any means in which the composition can be delivered to tissue (e.g., needle or catheter). Alternatively, a topical administration may be desired for application to dermal, ocular, or mucosal surfaces. Another method of administration is via aspiration or aerosol formulation. The pharmaceutical compositions may be administered topically to body surfaces, and are thus formulated in a form suitable for topical administration. Suitable topical formulations include gels, ointments, creams, lotions, drops and the like. For topical administrations, the compositions are prepared and applied as solutions, suspensions, or emulsions in a physiologically acceptable diluent with or without a pharmaceutical carrier.

Suitable dosage forms include, but are not limited to, oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients. Depending on the indication, formulations suitable for oral or topical administration are preferred.

Topical Administration:

The compounds of formulas I-VII, IA, IB, IC, ID, IIA, IIB, VIIA, or VIIB may be administered topically. As used herein, "topical administration" refers to application of the compounds of formulas I-VII, IA-ID, IIA, IIB, VIIA, or VIIB (and optional carrier) directly to the skin and/or hair. The topical composition can be in the form of solutions, lotions, salves, creams, ointments, liposomes, sprays, gels, foams, roller sticks, and any other formulation routinely used in dermatology.

Topical administration is used for indications found on the skin, such as hirsutism, alopecia, acne, and excess sebum. The dose will vary, but as a general guideline, the compound will be present in a dermatologically acceptable carrier in an amount of from about 0.01 to 50 w/w %, and more typically from about 0.1 to 10 w/w %. Typically, the dermatological preparation will be applied to the affected area from 1 to 4 times daily. "Dermatologically acceptable" refers to a carrier which may be applied to the skin or hair, and which will allow the drug to diffuse to the site of action. More specifically "site of action", it refers to a site where inhibition of androgen receptor or degradation of the androgen receptor is desired.

The compounds of formulas I-VII, IA, IB, IC, ID, IIA, IIB, VIIA, or VIIB, may be used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for the balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds of formulas I-VII, IA, IB, IC, ID, IIA, IIB, VIIA, or VIIB will most typically be used to alleviate androgenic alopecia, the compounds may be used to alleviate any type of alopecia. Examples of non-androgenic alopecia include, but are not limited to, alopecia areata, alopecia due to radiotherapy or chemotherapy, scarring alopecia, or stress related alopecia.

The compounds of formulas I-VII, IA, IB, IC, ID, IIA, IIB, VIIA, or VIIB can be applied topically to the scalp and hair to prevent, or treat balding. Further, the compound of formulas I-VII, IA, IB, IC, ID, IIA, IIB, VIIA, or VIIB can be applied topically in order to induce or promote the growth or regrowth of hair on the scalp.

The invention also encompasses topically administering a compound of formula I-VII, IA, IB, IC, ID, IIA, IIB, VIIA, or VIIB to treat or prevent the growth of hair in areas where such hair growth in not desired. One such use will be to alleviate hirsutism. Hirsutism is excessive hair growth in areas that typically do not have hair (e.g., a female face). Such inappropriate hair growth occurs most commonly in women and is frequently seen at menopause. The topical administration of the compounds of formulas I-VII, IA, IB, IC, ID, IIA, IIB, VIIA, or VIIB will alleviate this condition leading to a reduction, or elimination of this inappropriate, or undesired, hair growth.

The compounds of formulas I-VII, IA, IB, IC, ID, IIA, IIB, VIIA, or VIIB may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the luminal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including androgens. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. The compounds of formulas I-VII, IA, IB, IC, ID, IIA, IIB, VIIA, or VIIB inhibit the secretion of sebum and thus reduce the amount of sebum on the surface of the skin. The compounds of formulas I-VII, IA, IB, IC, ID, IIA, IIB, VIIA, or VIIB can be used to treat a variety of dermal diseases such as acne or seborrheic dermatitis.

In addition to treating diseases associated with excess sebum production, the compounds of formulas I-VII, IA, IB, IC, ID, IIA, IIB, VIIA, or VIIB can also be used to achieve a cosmetic effect. Some consumers believe that they are afflicted with overactive sebaceous glands. They feel that their skin is oily and thus unattractive. These individuals may use the compounds of formulas I-VII, IA, IB, IC, ID, IIA, IIB, VIIA, or VIIB to decrease the amount of sebum on their skin. Decreasing the secretion of sebum will alleviate oily skin in individuals afflicted with such conditions.

To treat these topical indications, the invention encompasses cosmetic or pharmaceutical compositions (such as dermatological compositions), comprising at least one of the compounds of formulas I-VII, IA, IB, IC, ID, IIA, IIB, VIIA, or VIIB. Such dermatological compositions will contain from 0.001% to 10% w/w % of the compound(s) in admixture with a dermatologically acceptable carrier, and more typically, from 0.1 to 5 w/w % of the compounds. Such compositions will typically be applied from 1 to 4 times daily. The reader's attention is directed to Remington's Pharmaceutical Science, Edition 17, Mark Publishing Co., Easton, Pa. for a discussion of how to prepare such formulations.

The compositions of the invention may also include solid preparations such as cleansing soaps or bars. These compositions are prepared according to methods known in the art.

Formulations such as aqueous, alcoholic, or aqueous-alcoholic solutions, or creams, gels, emulsions or mousses, or aerosol compositions with a propellant may be used to treat indications that arise where hair is present. Thus, the composition can also be a hair care composition. Such hair care compositions include, but are not limited to, shampoo, a hair-setting lotion, a treating lotion, a styling cream or gel, a dye composition, or a lotion or gel for preventing hair loss. The amounts of the various constituents in the dermatological compositions are those conventionally used in the fields considered.

Medicinal and cosmetic agents containing the compounds of formulas I-VII, IA, IB, IC, ID, IIA, IIB, VIIA, or VIIB will typically be packaged for retail distribution (i.e., an article of manufacture). Such articles will be labeled and packaged in a manner to instruct the patient how to use the product. Such instructions will include the condition to be treated, duration of treatment, dosing schedule, etc.

Antiandrogens, such as finasteride or flutamide, have been shown to decrease androgen levels or block androgen action in the skin to some extent but suffer from undesirable systemic effects. An alternative approach is to topically apply a selective androgen receptor degrader (SARD) compound to the affected areas. Such SARD compound would exhibit potent but local inhibition of AR activity, and local degradation of the AR, would not penetrate to the systemic circulation of the subject, or would be rapidly metabolized upon entry into the blood, limiting systemic exposure.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

As used herein "pharmaceutically acceptable carriers or diluents" are well known to those skilled in the art. The carrier or diluent may be a solid carrier or diluent for solid formuations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Oral and Parenteral Administration:

In preparing the compositions in oral dosage form, any of the usual pharmaceutical media may be employed. Thus, for liquid oral preparations, such as, suspensions, elixirs, and solutions, suitable carriers and additives include water, glycols, oils, alcohols, flavoring agents, preservatives, coloring agents, and the like. For solid oral preparations such as, powders, capsules, and tablets, suitable carriers and additives include starches, sugars, diluents, granulating agents, lubricants, binders, disintegrating agents, and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients may be included, such as ingredients that aid solubility or for preservation. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Methods of treatment using formulations suitable for oral administration may be presented as discrete units such as capsules, cachets, tablets, or lozenges, each containing a predetermined amount of the active ingredient. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more ingredient selected from diluents, buffers, flavoring agents, binders, disintegrants, surface active agents, thickeners, lubricants, preservatives (including antioxidants), and the like.

The formulations may be of immediate release, sustained release, delayed-onset release or any other release profile known to one skilled in the art.

For administration to mammals, and particularly humans, it is expected that the physician will determine the actual dosage and duration of treatment, which will be most suitable for an individual and can vary with the age, weight, genetics and/or response of the particular individual.

The methods of the invention comprise administration of a compound at a therapeutically effective amount. The theraperutically effective amount may include various dosages.

In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day.

The methods may comprise administering a compound at various dosages. For example, the compound may be administered at a dosage of 3 mg, 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg.

Alternatively, the compound may be administered at a dosage of 0.1 mg/kg/day. The compound may administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day, 30 mg/kg/day, 50 mg/kg/day or 100 mg/kg/day.

The pharmaceutical composition may be a solid dosage form, a solution, or a transdermal patch. Solid dosage forms include, but are not limited to, tablets and capsules.

The following examples are presented in order to more fully illustrate the preferred embodiments of the invention. They should in no way, however, be construed as limiting the broad scope of the invention.

EXAMPLES

Example 1

Synthesis of SARDs

Synthesis of Intermediates 9-10

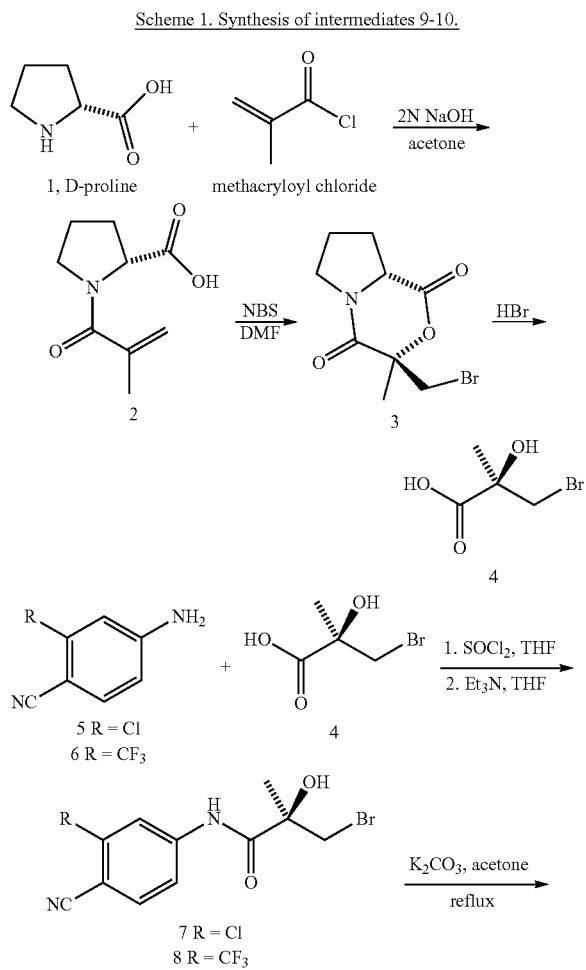

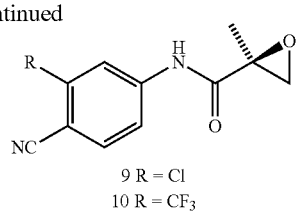

9 R = Cl
10 R = CF$_3$ (2R)-1-Methacryloylpyrrolidin-2-carboxylic acid (2)

D-Proline (1, 14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10-11° C. during the addition of the methacryloyl chloride. After stirring (3 hours (h), room temperature (RT)), the mixture was evaporated in vacuo at a temperature of 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na$_2$SO$_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (lit. mp 102.5-103.5° C.); the NMR spectrum of this compound demonstrated the existence of two rotamers of the title compound.

$^1$H NMR (300 MHz, DMSO-d$_6$) δ 5.28 (s) and 5.15 (s) for the first rotamer, 5.15 (s) and 5.03 (s) for the second rotamer (totally 2H for both rotamers, vinyl CH$_2$), 4.48-4.44 for the first rotamer, 4.24-4.20 (m) for the second rotamer (totally 1H for both rotamers, CH at the chiral center), 3.57-3.38 (m, 2H, CH$_2$), 2.27-2.12 (1H, CH), 1.97-1.72 (m, 6H, CH$_2$, CH, Me); $^{13}$C NMR (75 MHz, DMSO-d$_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; [α]$_D^{26}$+80.8° (c=1, MeOH); Anal. Calcd. for C$_9$H$_{13}$NO$_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione (3)

A solution of NBS (23.5 g, 0.132 mol) in 100 mL of DMF was added dropwise to a stirred solution of the (methylacryloyl)-pyrrolidine (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried ~34%) of the titled compound as a yellow solid: mp 158.1-160.3° C.;

$^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; [α]$_D^{26}$+124.5° (c=1.3, chloroform); Anal. Calcd. for C$_9$H$_{12}$BrNO$_3$: C, 41.24, H, 4.61, N, 5.34. Found: C, 41.46, H, 4.64, N, 5.32.

(2R)-3-Bromo-2-hydroxy-2-methylpropanoic acid (4)

A mixture of bromolactone (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.;

$^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^{-1}$; [α]$_D^{26}$+10.5° (c=2.6, MeOH); Anal. Calcd. for C$_4$H$_7$BrO$_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-hydroxy-2-methylpropanoic acid (4, 51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (6, 40.0 g, 0.21 mol), 400 mL of THF were added and then the mixture was allowed to stir overnight at RT. The solvent was removed under reduced pressure to give a solid which was treated with 300 mL of H$_2$O, and extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide as a light-yellow solid.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). MS (ESI) 349.0 [M–H]$^-$; mp 124-126° C.

(2R)-3-Bromo-N-(4-cyano-3-chlorophenyl)-2-hydroxy-2-methylpropanamide (7)

Under an argon atmosphere, thionyl chloride (15 mL, 0.20 mol) was added dropwise to a cooled solution (less than 4° C.) of (R)-3-bromo-2-hydroxy-2-methylpropanoic acid (4, 24.3 g, 0.133 mol) in 300 mL of THF at ice-water bath. The resulting mixture stirred for 3 h under the same condition. To this was added Et$_3$N (35 mL, 0.245 mol) and stirred for 20 min under the same condition. After 20 min, a solution of 4-amino-2-chlorobenzonitrile (5, 15.6 g, 0.10 mol) in 100 mL of THF were added and then the mixture was allowed to stir overnight at RT. The solvent removed under reduced pressure to give a solid, which treated with 300 mL of H$_2$O, and extracted with EtOAc (2×150 mL). The combined organic extracts washed with saturated NaHCO$_3$ solution (2×150 mL) and brine (300 mL). The organic layer was dried over MgSO$_4$ and concentrated under reduced pressure to give a solid, which purified by flash column chromatography using CH$_2$Cl$_2$/EtOAc (80:20) to give a solid. This solid was recrystallized from CH$_2$Cl$_2$/hexane to give 31.8 g (73%) of (2R)-3-bromo-N-(4-cyano-3-chlorophenyl)-2-hydroxy-2-methylpropanamide (7) as a light-yellow solid.

$^1$H NMR (CDCl$_3$, 400 MHz) δ 1.7 (s, 3H, CH$_3$), 3.0 (s, 1H, OH), 3.7 (d, 1H, CH), 4.0 (d, 1H, CH), 7.5 (d, 1H, ArH), 7.7 (d, 1H, ArH), 8.0 (s, 1H, ArH), 8.8 (s, 1H, NH). MS: 342 (M+23); mp 129° C.

(S)—N-(3-Chloro-4-cyanophenyl)-2-methyloxirane-2-carboxamide (9)

A mixture of 3-bromo-N-(4-cyano-3-chlorophenyl)-2-hydroxy-2-methylpropanamide (7, 0.84 mmol) and potassium carbonate (1.68 mmol) in 10 mL acetone was heated to reflux for 30 min. After complete conversion of starting bromide 7 to desired epoxide 9 as monitored by TLC, the solvent was evaporated under reduced pressure to give yellowish residue, which was poured into 10 mL of anhydrous EtOAc. The solution was filtered through Celite® pad to remove K$_2$CO$_3$ residue and condensed under reduced pressure to give epoxide 9 as a light yellowish solid.

$^1$H NMR (CDCl$_3$, 400 MHz) δ 8.41 (bs, NH), 8.02 (d, J=2.0 Hz, 1H, ArH), 7.91 (dd, J=2.0, 8.4 Hz, 1H, ArH), 7.79 (d, J=2.0 Hz, 1H, ArH), 3.01 (s, 2H), 1.69 (s, 3H). MS (ESI) m/z 235.0 [M–H]$^-$.

5-Membered Ring Compounds

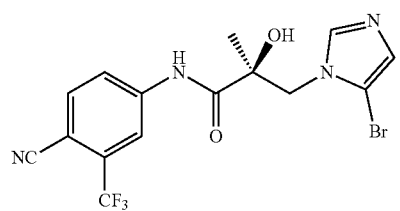

1005

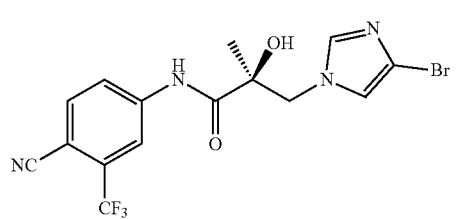

1006

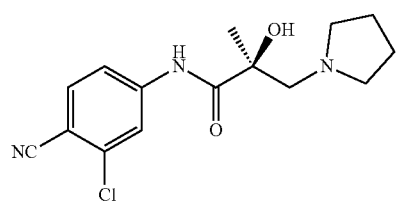

1009

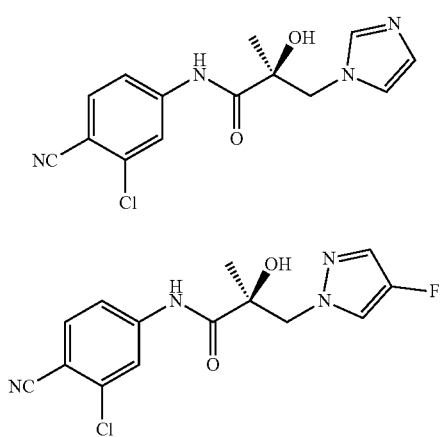

1008

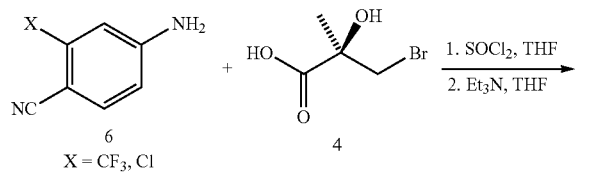

1007

Five membered ring compounds of the invention were made using the following general synthetic routes (Method A and Method B) where m=0. Variables X and Y are defined as necessary to obtain the desired compound.

Method A:

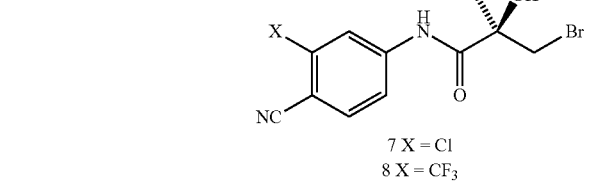

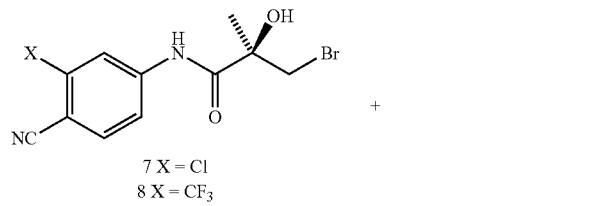

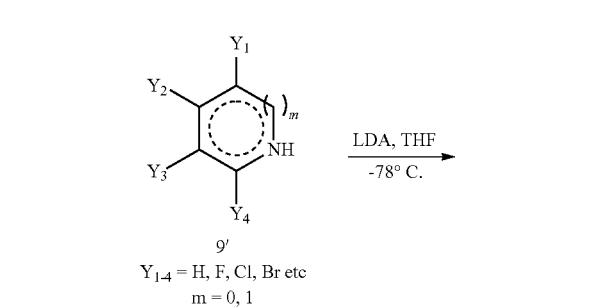

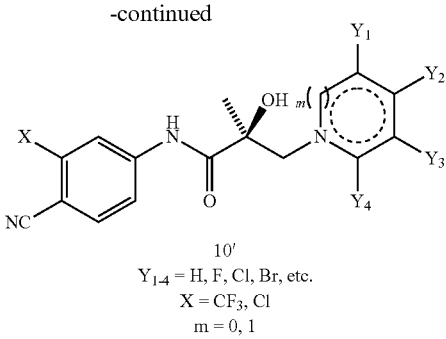

10'
$Y_{1-4}$ = H, F, Cl, Br, etc.
X = $CF_3$, Cl
m = 0, 1

Preparation of lithium diisopropylamide (LDA) solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or commercial 2.0 M LDA was slowly warmed to 0° C. and stirred for 10 min and cooled again to −78° C. To the LDA solution was added dropwise a solution of 9' (1.0 mmol) in 5 mL of THF for 20 min. Compound 7 or 8 in THF was added dropwise through dropping funnel under argon atmosphere at −78° C. The reaction mixture was stirred at the same temperature for 30 min and quenched by addition of sat. $NH_4Cl$. The solution was concentrated under reduced pressure and dispersed into excess EtOAc and dried over $Na_2SO_4$. The solution was concentrated and the resulting solid was recrystallized from EtOAc/hexane or DCM/hexane to give designed compound 10'. The mother liquor was concentrated and purified by flash column chromatography (EtOAc/hexane) to give a second crop of 10'.

Method B:

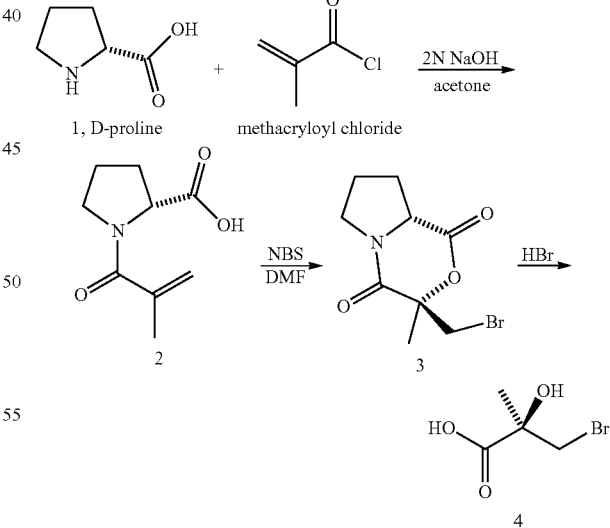

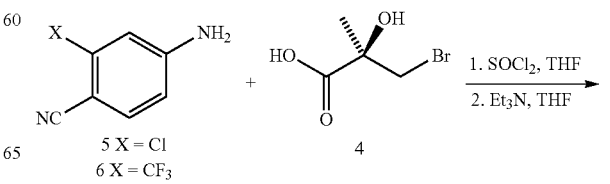

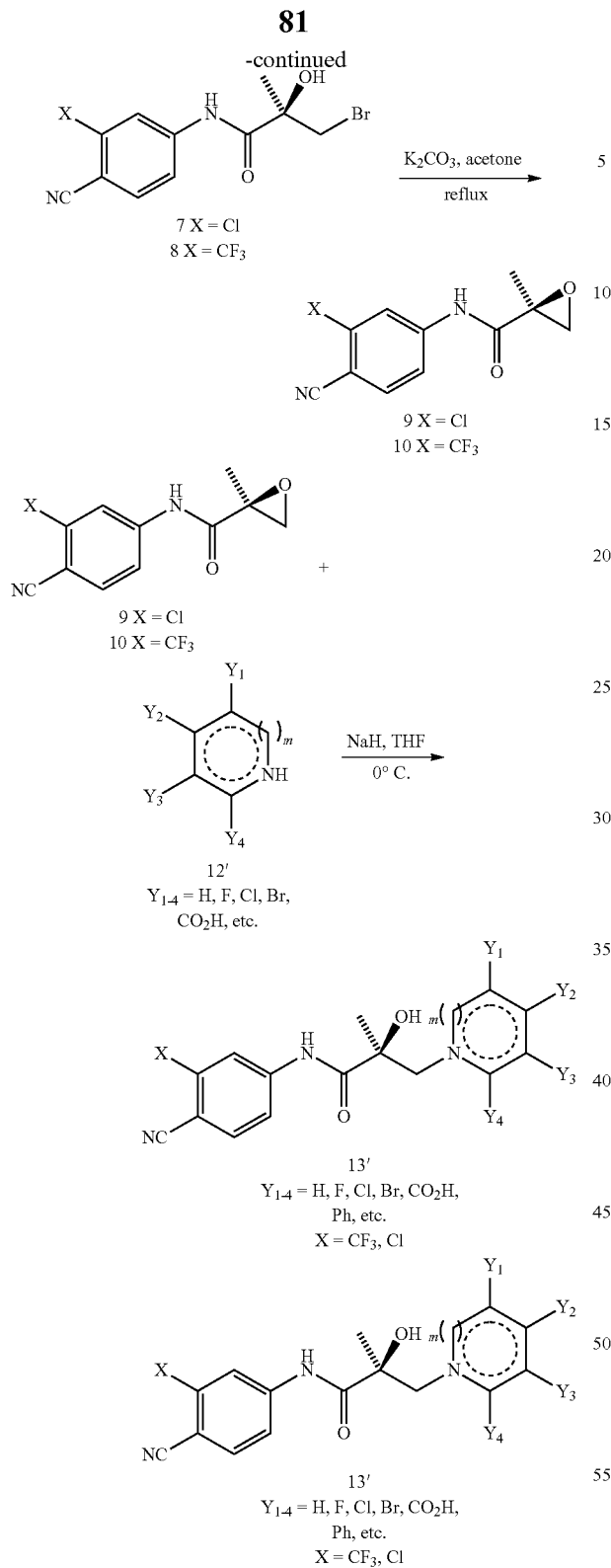

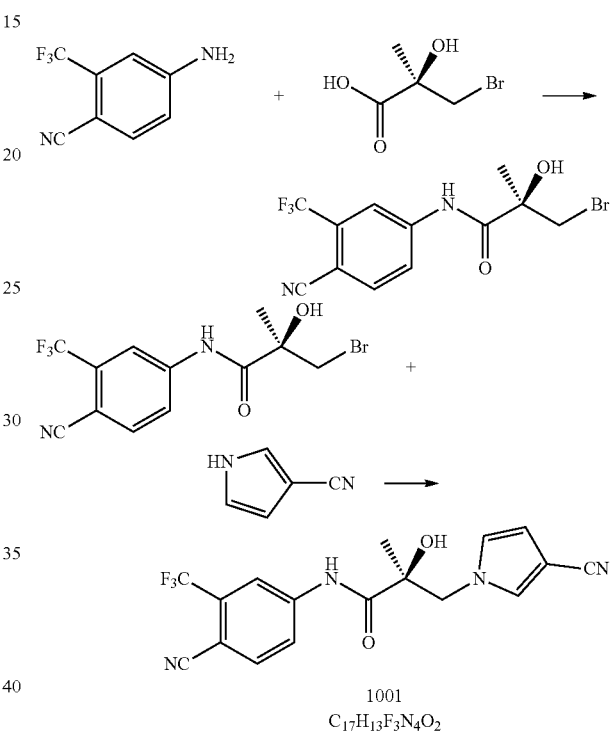

and the resulting solution was stirred for 30 min at the ice-water bath. Into the flask, epoxide 9 or 10 (2.84 mmol in THF) was added through dropping funnel under argon atmosphere at the ice-water bath and stirred overnight at RT. After adding 1 mL of H₂O, the reaction mixture was condensed under reduced pressure, and then dispersed into 50 mL of EtOAc, washed with 50 mL (×2) water, brine, dried over anhydrous MgSO₄, and evaporated to dryness. The mixture was purified with flash column chromatography with an eluent of EtOAc/hexane, and the condensed compounds were then recrystallized in EtOAc/hexane to give a product of general structure 13'.

The synthetic procedure for 1001 as an example:

(S)-3-(3-Cyano-1H-pyrrol-1-yl)-N-(4-cyano-3-(trifluoromethyl)phenyl)-2-hydroxy-2-methylpropanamide (C₁₇H₁₃F₃N₄O₂) (1001)

The steps through the synthesis of the oxiranes 9 and 10 are the same as above for Scheme 1. NaH of 60% dispersion in mineral oil (228 mg, 5.7 mmol) was added in 20 mL of anhydrous THF solvent into a 100 mL dried two necked round bottom flask equipped with a dropping funnel. A compound of general structure 12' (2.84 mmol) was added to the solution under argon atmosphere in ice-water bath, To a solution of 1H-pyrrole-3-carbonitrile (0.10 g, 0.00108 mol) in anhydrous THF (10 mL), which was cooled in an ice water bath under an argon atmosphere, was added sodium hydride (60% dispersion in oil, 0.090 g, 0.00217 mol). After addition, the resulting mixture was stirred for 3 h. (R)-3-Bromo-N-(4-cyano-3-(trifluoromethyl)phenyl)-2-hydroxy-2-methylpropanamide (8, 0.38 g, 0.00108 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:1) as eluent to afford 0.26 g of the titled compound as pinkish solid.

Compound 1001 was characterized as follows: $^1$H NMR (400 MHz, DMSO-d$_6$) δ 10.44 (s, 1H, NH), 8.44 (s, 1H, ArH), 8.24 (d, J=8.8 Hz, 1H, ArH), 8.10 (d, J=8.8 Hz, 1H, ArH), 7.49 (s, 1H, Pyrrole-H), 6.38 (t, J=2.0 Hz, 1H, Pyrrole-H), 6.41-6.40 (m, 2H, OH and Pyrrole-H), 4.30 (d, J=14.0 Hz, 1H, CH), 4.14 (d, J=14.0 Hz, 1H, CH), 1.34 (s, 3H, CH$_3$); (ESI, Positive): 363.1079[M+H]$^+$.

(S)—N-(4-Cyano-3-(trifluoromethyl)phenyl)-3-(4-fluoro-1H-pyrazol-1-yl)-2-hydroxy-2-methylpropanamide (C$_{15}$H$_{12}$F$_4$N$_4$O$_2$) (1002)

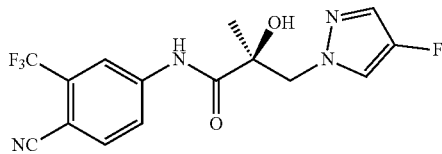 [SMILES: C[C@](O)(Cn1cc(F)cn1)C(=O)Nc1ccc(C#N)c(C(F)(F)F)c1]

To a solution of 4-fluoro-pyrazole (0.10 g, 0.00116 mol) in anhydrous THF (10 mL), which was cooled in an ice water bath under an argon atmosphere, was added sodium hydride (60% dispersion in oil, 0.12 g, 0.00291 mol). After addition, the resulting mixture was stirred for 3 h. (R)-3-Bromo-N-(4-cyano-3-(trifluoromethyl)phenyl)-2-hydroxy-2-methylpropanamide (8) (0.41 g, 0.00116 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:1) as eluent to afford 0.13 g of the titled compound as white solid.

Compound 1002 was characterized as follows: $^1$H NMR (400 MHz, DMSO-d$_6$) δ 10.39 (s, 1H, NH), 8.47 (d, J=1.6 Hz, 1H, ArH), 8.24 (dd, J=8.4 Hz, J=2.0 Hz, 1H, ArH), 8.10 (d, J=8.4 Hz, 1H, ArH), 7.73 (d, J=4.4 Hz, 1H, Pyrazole-H), 7.41 (d, J=4.4 Hz, 1H, Pyrazole-H), 6.31 (s, 1H, OH), 4.38 (d, J=14.0 Hz, 1H, CH), 4.21 (d, J=14.0 Hz, 1H, CH), 1.34 (s, 3H, CH$_3$); Mass (ESI, Positive): 357.0966[M+H]$^+$; mp 109-111° C.

(S)—N-(4-Cyano-3-(trifluoromethyl)phenyl)-3-(4-fluoro-1H-pyrazol-1-v)-2-hydroxy-2-methylpropanamide hydrochloride (C$_{15}$H$_{13}$ClF$_4$N$_4$O$_2$) (1002-HCl)

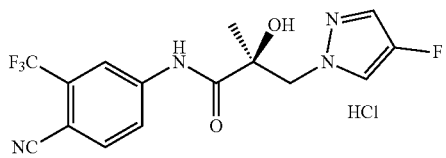 [SMILES: C[C@](O)(Cn1cc(F)cn1)C(=O)Nc1ccc(C#N)c(C(F)(F)F)c1 ; Cl]

To a solution of (S)—N-(4-cyano-3-(trifluoromethyl)phenyl)-3-(4-fluoro-1H-pyrazol-1-yl)-2-hydroxy-2-methylpropanamide (0.100 g, 0.2807 mmol) in 3 mL of methanol was added hydrochloride (2 M HCl in ether, 0.15 mL, 0.2947 mol). After addition, the resulting mixture was stirred for 1-2 h at RT. Solvent was removed under vacuum, and dried to afford 0.11 g (99%) of the titled compound as white foam.

(S)—N-(4-Cyano-3-(trifluoromethyl)phenyl)-3-(4-fluoro-H-pyrazol-1-yl)-2-hydroxy-2-methylpropanamide oxalate (C$_{17}$H$_{14}$F$_4$N$_4$O$_6$) (1002-oxalic acid salt)

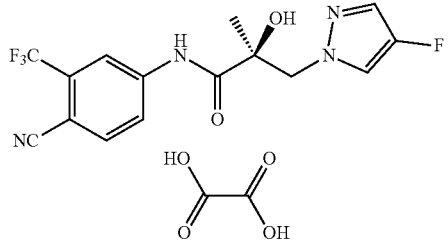

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added oxalic acid (0.0177 g, 0.14034 mol). After addition, the resulting mixture was stirred for 1-2 h at RT. Diethyl ether was added to above solution, and the solid was filtered, and dried under vacuum to afford 0.058 g (92%) of the titled compound as white solid.

Compound 1002-oxalate was characterized as follows: $^1$H NMR (400 MHz, DMSO-d$_6$) δ 14.02 (bs, 2H), 10.38 (s, 1H, NH), 8.46 (s, 1H, ArH), 8.24 (d, J=8.4 Hz, 1H, ArH), 8.10 (d, J=8.4 Hz, 1H, ArH), 7.73 (d, J=4.8 Hz, 1H, Pyrazole-H), 7.41 (d, J=4.0 Hz, 1H, Pyrazole-H), 6.30 (s, 1H, OH), 4.38 (d, J=14.0 Hz, 1H, CH), 4.31 (s, 2H), 4.21 (d, J=14.0 Hz, 1H, CH), 2.42 (s, 4H), 1.34 (s, 3H, CH$_3$).

(S)—N-(4-Cyano-3-(trifluoromethyl)phenyl)-3-(4-fluoro-1H-pyrazol-1-yl)-2-hydroxy-2-methylpropanamide 2,3-dihydroxysuccinate (C$_{19}$H$_{18}$F$_4$N$_4$O$_8$) (1002-tartaric acid salt)

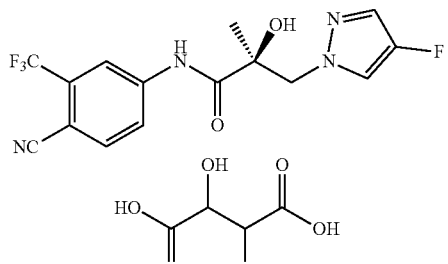

To a solution of (S)—N-(4-cyano-3-(trifluoromethyl)phenyl)-3-(4-fluoro-1H-pyrazol-1-yl)-2-hydroxy-2-methylpropanamide (0.050 g, 0.14034 mmol) in 2 mL of methanol was added L-(+)-tartaric acid (0.021 g, 0.14034 mol). After addition, the resulting mixture was stirred for 1-2 h at RT. Diethyl ether was added to above solution, and the solid was filtered and dried under vacuum to afford 0.067 g (94%) of the titled compound as white solid.

Compound 1002—tartaric acid salt was characterized as follows: ¹H NMR (400 MHz, DMSO-d₆) δ 12.69 (s, 2H), 10.38 (s, 1H, NH), 8.46 (s, 1H, ArH), 8.24 (d, J=8.4 Hz, 1H, ArH), 8.10 (d, J=8.4 Hz, 1H, ArH), 7.73 (d, J=4.4 Hz, 1H, Pyrazole-H), 7.41 (d, J=4.0 Hz, 1H, Pyrazole-H), 6.30 (s, 1H, OH), 5.08 (s, 2H, OH), 4.38 (d, J=14.0 Hz, 1H, CH), 4.31 (s, 2H), 4.21 (d, J=14.0 Hz, 1H, CH), 2.42 (s, 4H), 1.34 (s, 3H, CH₃).

(S)—N-(4-Cyano-3-(trifluoromethyl)phenyl)-3-(4-fluoro-1H-pyrazol-1-yl)-2-hydroxy-2-methylpropanamide hydrobromide (C₁₅H₁₃BrF₄N₄O₂) (1002-HBr)

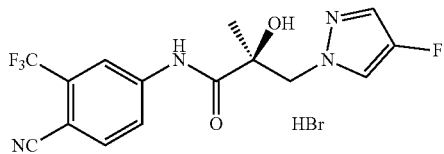 [SMILES: C[C@](O)(Cn1cc(F)cn1)C(=O)Nc1ccc(C#N)c(C(F)(F)F)c1 ; Br]

To a solution of (S)—N-(4-cyano-3-(trifluoromethyl)phenyl)-3-(4-fluoro-1H-pyrazol-1-yl)-2-hydroxy-2-methylpropanamide (0.050 g, 0.1403 mmol) in 2 mL of methanol was added hydrobromide (48% w/w aqueous solution, 0.0159 mL, 0.1403 mol). After addition, the resulting mixture was stirred for 1-2 h at RT. Solvent was removed under vacuum, and dried to afford 0.061 g (99%) of the titled compound as yellowish foam.

(S)—N-(4-Cyano-3-(trifluoromethyl)phenyl)-3-(4-fluoro-1H-pyrazol-1-yl)-2-hydroxy-2-methylpropanamide succinate (1002-succinic acid salt) (C₁₉H₁₈F₄N₄O₆)

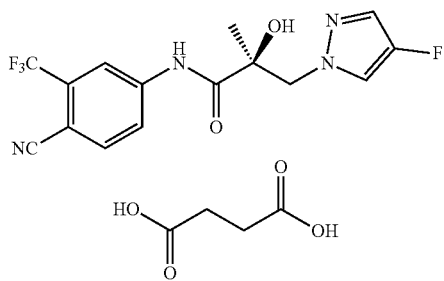

To a solution of (S)—N-(4-cyano-3-(trifluoromethyl)phenyl)-3-(4-fluoro-H-pyrazol-1-yl)-2-hydroxy-2-methylpropanamide (0.050 g, 0.14034 mmol) in 2 mL of methanol was added succinic acid (0.0166 g, 0.14034 mmol). After addition, the resulting mixture was stirred for 1-2 h at RT. Diethyl ether was added to above solution, and the solid was filtered and dried under vacuum to afford 0.063 g (95%) of the titled compound as white solid.

Compound 1002—tartaric acid salt was characterized as follows: ¹H NMR (400 MHz, DMSO-d₆) δ 12.14 (s, 2H), 10.39 (s, 1H, NH), 8.46 (s, 1H, ArH), 8.24 (d, J=8.8 Hz, 1H, ArH), 8.10 (d, J=8.8 Hz, 1H, ArH), 7.73 (d, J=4.4 Hz, 1H, Pyrazole-H), 7.41 (d, J=4.4 Hz, 1H, Pyrazole-H), 6.30 (s, 1H, OH), 4.39 (d, J=14.0 Hz, 1H, CH), 4.21 (d, J=14.0 Hz, 1H, CH), 2.42 (s, 4H), 1.34 (s, 3H, CH₃).

(S)—N-(4-Cyano-3-(trifluoromethyl)phenyl)-2-hydroxy-2-methyl-3-(4-phenyl-1H-pyrazol-1-yl)propanamide (C₂₁H₁₇F₃N₄O₂) (1003)

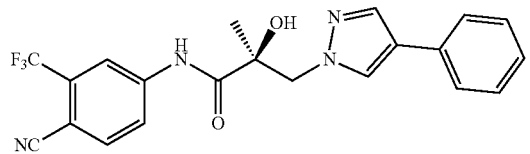 [SMILES: C[C@](O)(Cn1cc(-c2ccccc2)cn1)C(=O)Nc1ccc(C#N)c(C(F)(F)F)c1]

To a solution of 4-phenyl-pyrazole (0.50 g, 0.003468 mol) in anhydrous THF (10 mL), which was cooled in an ice water bath under an argon atmosphere, was added sodium hydride (60% dispersion in oil (0.35 g, 0.00867 mol). After addition, the resulting mixture was stirred for 3 h. (R)-3-Bromo-N-(4-cyano-3-(trifluoromethyl)phenyl)-2-hydroxy-2-methylpropanamide (8, 1.22 g, 0.003468 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:2) as eluent to afford 0.90 g of the titled compound as white needles.

Compound 1003 was characterized as follows: ¹H NMR (400 MHz, DMSO-d₆) δ 10.40 (s, 1H, NH), 8.46 (d, J=2.0 Hz, 1H, ArH), 8.24 (dd, J=8.4 Hz, J=2.0 Hz, 1H, ArH), 8.09 (d, J=8.4 Hz, 1H, ArH), 8.05 (s, 1H, Pyrazole-H), 7.82 (s, 1H, Pyrazole-H), 7.52-7.45 (m, 2H, ArH), 7.35-7.31 (m, 2H, ArH), 7.20-7.16 (m, 1H, ArH), 6.33 (s, 1H, OH), 4.50 (d, J=14.0 Hz, 1H, CH), 4.30 (d, J=14.0 Hz, 1H, CH), 1.40 (s, 3H, CH₃); Mass (ESI, Positive): 415.1455[M+H]⁺.

(S)—N-(4-Cyano-3-(trifluoromethyl)phenyl)-2-hydroxy-2-methyl-3-(3-phenyl-1H-pyrrol-1-yl)propanamide (C₂₂H₁₈F₃N₃O₂) (1004)

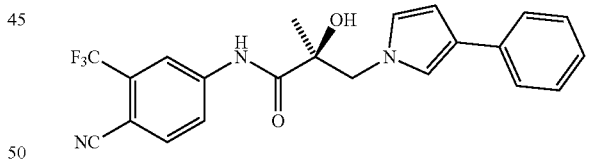

To a solution of 3-phenyl-pyrrole (0.50 g, 0.00349 mol) in anhydrous THF (10 mL), which was cooled in an ice water bath under an argon atmosphere, was added sodium hydride (60% dispersion in oil, 0.35 g, 0.00873 mol). After addition, the resulting mixture was stirred for 3 h. (R)-3-Bromo-N-(4-cyano-3-(trifluoromethyl)phenyl)-2-hydroxy-2-methylpropanamide (8, 1.23 g, 0.00349 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexanes (1:2) as eluent to afford 0.90 g of the titled compound as pink solid.

Compound 1004 was characterized as follows: ¹H NMR (400 MHz, DMSO-d₆) δ 10.41 (s, 1H, NH), 8.24 (d, J=1.6

Hz, 1H, ArH), 8.17 (dd, J=8.4 Hz, J=2.0 Hz, 1H, ArH), 8.07 (d, J=8.4 Hz, 1H, ArH), 7.38-7.33 (m, 4H, ArH), 7.28-7.24 (m, 1H, ArH), 6.96 (t, J=3.0 Hz, 1H, Pyrrole-H), 6.28 (s, 1H, OH), 6.07 (t, J=3.5 Hz, 1H, Pyrrole-H), 6.03 (m, 1H, Pyrrole-H), 4.30-4.22 (m, 2H, CH$_2$), 1.01 (s, 3H, CH$_3$); Mass (ESI, Positive): 414.1432[M+H]$^+$.

Bromo-1H-imidazol-1-yl)-N-(4-cyano-3-(trifluoromethyl)phenyl)-2-hydroxy-2-methylpropanamides (1005 and 1006)

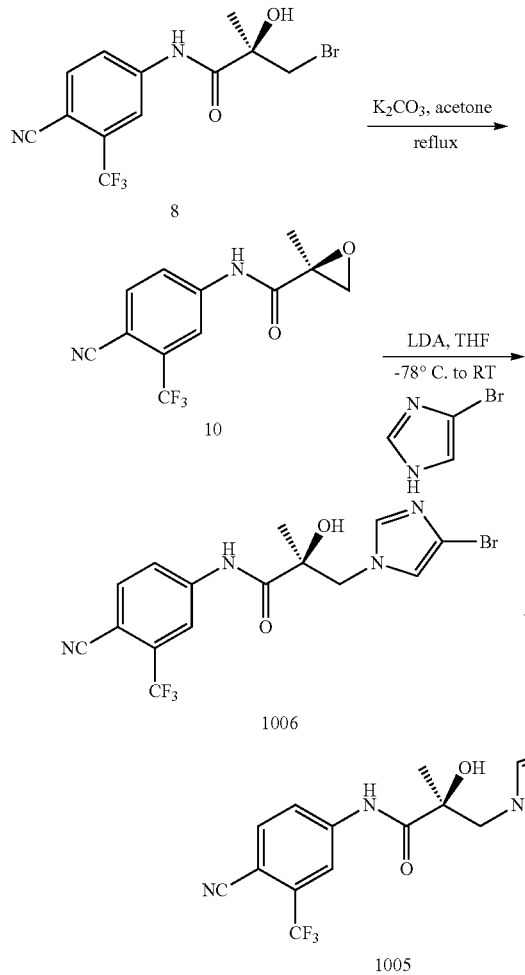

1005

Lithium diisopropylamide solution (2.0 M) in THF/heptane/ethylbenzene (1 mL) was slowly added to a solution of 4-bromo-1H-imidazole (1.0 mmol, 2 mmol) in 5 mL of anhydrous THF at −78° C. and warmed to 0° C. and stirred for 10 min and cooled again to −78° C. To the solution was added dropwise a solution of (S)—N-(4-cyano-3-(trifluoromethyl)phenyl)-2-methyloxirane-2-carboxamide (10, 1 mmol) prepared from 8 (1 mmol) and the reaction mixture was stirred for overnight. After quenching by addition of sat. NH$_4$Cl, the solution was concentrated under reduced pressure and dispersed into excess EtOAc and dried over Na$_2$SO$_4$. The solution was concentrated and purified by flash column chromatography (EtOAc/hexane) to give the desired products as total yield of 69% (37% for 1005 and 32% for 1006) as white solids.

The compounds were characterized as follows:

(S)-3-(5-Bromo-1H-imidazol-1-yl)-N-(4-cyano-3-(trifluoromethyl)phenyl)-2-hydroxy-2-methylpropanamide (C$_{15}$H$_{12}$BrF$_3$N$_4$O$_2$) (1005)

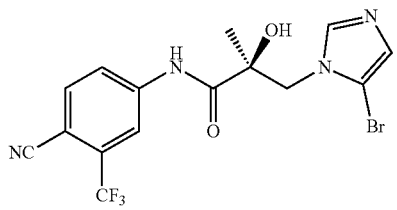 [SMILES: C[C@](O)(Cn1cncc1Br)C(=O)Nc1ccc(C#N)c(C(F)(F)F)c1]

Method A (using bromoamide 8 and 4-bromo-1H-imidazole instead of general structure 9') gave a white solid; $^1$H NMR (acetone-d$_6$, 400 MHz) δ 9.93 (bs, 1H, NH), 8.44 (d, J=2.0 Hz, 1H), 8.26 (dd, J=8.6, 2.0 Hz, 1H), 8.03 (d, J=8.6 Hz, 1H), 7.47 (s, 1H), 7.11 (s, 1H), 5.83 (s, 1H, OH), 4.50 (d, J=14.0 Hz, 1H), 4.23 (d, J=14.0 Hz, 1H), 1.55 (s, 3H); $^{19}$F NMR (acetone-d$_6$, 400 MHz) δ 114.69; MS (ESI): 415.0 [M−H]$^-$; LCMS (ESI) m/z calcd for C$_{15}$H$_{11}$N$_4$O$_2$F$_3$Br: 415.0088. Found: 415.0017 [M−H]$^-$.

(S)-3-(4-Bromo-1H-imidazol-1-yl)-N-(4-cyano-3-(trifluoromethyl)phenyl)-2-hydroxy-2-methylpropanamide (C$_{15}$H$_{12}$BrF$_3$N$_4$O$_2$) (1006)

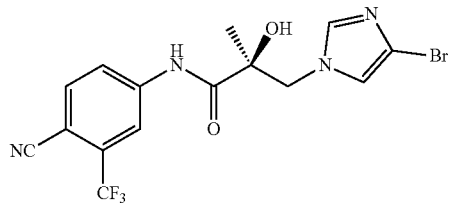 [SMILES: C[C@](O)(Cn1cnc(Br)c1)C(=O)Nc1ccc(C#N)c(C(F)(F)F)c1]

Method A (using bromoamide 8 and 4-bromo-1H-imidazole instead of general structure 9') gave a white solid; $^1$H NMR (CDCl$_3$, 400 MHz) δ 9.48 (bs, 1H, NH), 8.15 (s, 1H), 7.97 (d, J=8.6 Hz, 1H), 7.83 (d, J=8.6 Hz, 1H), 7.71 (s, 1H), 6.75 (s, 1H), 4.53 (d, J=14.4 Hz, 1H), 4.09 (d, J=14.4 Hz, 1H), 2.84 (s, 1H, OH), 1.45 (s, 3H); $^{19}$F NMR (CDCl$_3$, 400 MHz) δ −62.19; MS (ESI): 415.0 [M−H]$^-$.

(S)—N-(3-Chloro-4-cyanophenyl)-2-hydroxy-3-(1H-imidazol-1-yl)-2-methylpropanamide (C$_{14}$H$_{13}$ClN$_4$O$_2$) (1008)

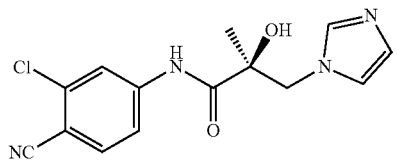

Method A (using bromoamide 7 and 1H-imidazole instead of general structure 9') gave a yellowish solid. Yield 53%; $^1$H NMR (DMSO-d$_6$, 400 MHz) δ 10.24 (bs, 1H, NH), 8.19 (s, 1H), 7.90 (m, 2H), 7.53 (s, 1H), 7.05 (s, 1H), 6.83 (s, 1H), 6.40 (bs, 1H, OH), 4.31 (d, J=14.4 Hz, 1H), 4.11 (d, J=14.4

Hz, 1H), 1.34 (s, 3H); LCMS (ESI) m/z calcd for $C_{14}H_{14}ClN_4O_2$: 305.0805. Found: 305.0809 $[M+H]^+$.

(S)—N-(3-Chloro-4-cyanophenyl)-2-hydroxy-2-methyl-3-(pyrrolidin-1-yl)propanamide ($C_{15}H_{18}ClN_3O_2$) (1009)

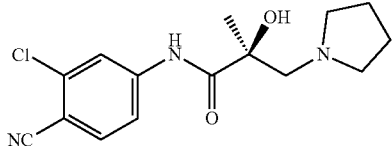 [SMILES: C[C@](O)(CN1CCCC1)C(=O)Nc1ccc(C#N)c(Cl)c1]

Method A (using bromoamide 7 and pyrrolidine instead of general structure 9') gave a yield of 89%; $^1$H NMR (CDCl$_3$, 400 MHz) δ 9.41 (bs, 1H, NH), 7.98 (d, J=2.0 Hz, 1H), 7.62 (d, J=8.8 Hz, 1H), 7.51 (dd, J=8.8, 2.0 Hz, 1H), 5.20 (s, 1H), 3.15 (d, J=12.4 Hz, 1H), 2.72 (d, J=12.4 Hz, 1H), 2.64-2.58 (m, 4H), 1.76 (m, 4H), 1.41 (s, 3H); $^{13}$C NMR (CDCl$_3$, 100 MHz) δ 175.6 (—NHCO—), 142.5, 137.9, 134.6, 119.9, 117.3, 116.1, 108.0, 72.9, 62.3, 54.6 (2C), 25.5, 24.0; LCMS (ESI) m/z calcd for $C_{15}H_{19}ClN_3O_2$: 308.1166. Found: 308.1173 $[M+H]^+$.

Preparation of HCl salt type of (S)—N-(3-chloro-4-cyanophenyl)-2-hydroxy-2-methyl-3-(pyrrolidin-1-yl)propanamide To a solution of 1009 in EtOH (20 mL) was added dropwise acetyl chloride (1 mL) at 0° C. and further stirred at RT overnight and removed the solvent to gain target salt of 1009.

(S)—N-(3-Chloro-4-cyanophenyl)-3-(4-fluoro-1H-pyrazol-1-yl)-2-hydroxy-2-methylpropanamide ($C_{14}H_{12}ClFN_4O_2$) (1007)

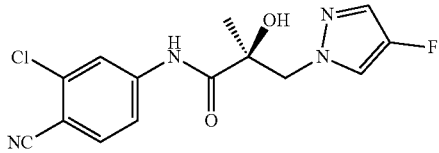

Method B (using oxirane 9 and 4-fluoro-1H-pyrazole instead of general structure 12') gave a yellowish solid; yield 72%; $^1$H NMR (CDCl$_3$, 400 MHz) δ 8.97 (bs, 1H, NH), 7.88 (d, J=2.0 Hz, 1H), 7.60 (d, J=8.4 Hz, 1H), 7.45 (dd, J=8.4, 2.0 Hz, 1H), 7.36 (d, J=4.0 Hz, 1H), 7.35 (d, J=4.4 Hz, 1H), 5.86 (bs, 1H, OH), 4.54 (d, J=14.0 Hz, 1H), 4.15 (d, J=14.0 Hz, 1H), 1.46 (s, 3H); $^{19}$F NMR (CDCl$_3$, 400 MHz) δ −176.47; LCMS (ESI) m/z calcd for $C_{14}H_{13}ClFN_4O_2$: 323.0711. Found: 323.0710 $[M+H]^+$.

(S)—N-(4-Cyano-3-(trifluoromethyl)phenyl)-3-(3-(4-fluorophenyl)-1H-pyrrol-1-yl)-2-hydroxy-2-methylpropanamide ($C_{22}H_{17}F_4N_3O_2$) (1010)

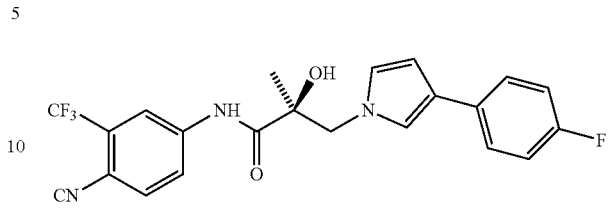

To a solution of 3-(4-fluorophenyl)-pyrrole (0.50 g, 0.003102 mol) in anhydrous THF (10 mL), which was cooled in an ice water bath under an argon atmosphere, was added sodium hydride (60% dispersion in oil, 0.37 g, 0.009306 mol). After addition, the resulting mixture was stirred for 3 h. (R)-3-Bromo-N-(4-cyano-3-(trifluoromethyl)phenyl)-2-hydroxy-2-methylpropanamide (8) (1.09 g, 0.003102 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:2 to 1:1) as eluent to afford 0.60 g (45%) of the compound as yellowish solid.

Compound 1010 was characterized as follows: $^1$H NMR (400 MHz, DMSO-d$_6$) δ 10.40 (s, 1H, NH), 8.42 (d, J=2.0 Hz, 1H, ArH), 8.24 (dd, J=8.8 Hz, J=2.0 Hz, 1H, ArH), 8.07 (d, J=8.8 Hz, 1H, ArH), 7.43-7.38 (m, 2H, ArH), 7.11-7.05 (m, 3H, ArH), 6.73 (t, J=2.0 Hz, 1H, Pyrrole-H), 6.33 (s, 1H, OH), 4.24 (d, J=14.0 Hz, 1H, CH), 4.05 (d, J=14.0 Hz, 1H, CH), 1.37 (s, 3H, CH$_3$); Mass (ESI, Positive): 432.1352[M+H]$^+$; mp 187-189° C.

(S)—N-(4-Cyano-3-(trifluoromethyl)phenyl)-2-hydroxy-2-methyl-3-(3-phenyl-1H-pyrazol-1-yl)propanamide ($C_{21}H_{17}F_3N_4O_2$) (1011)

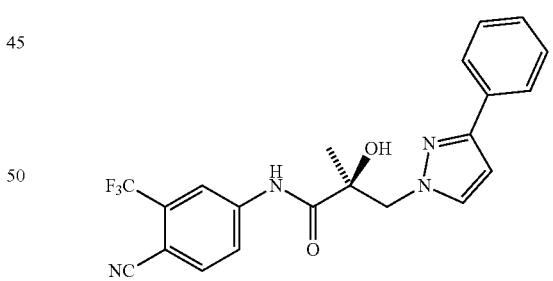

To a solution of 3-phenyl-pyrazole (0.50 g, 0.003468 mol) in anhydrous THF (10 mL), which was cooled in an ice water bath under an argon atmosphere, was added sodium hydride (60% dispersion in oil, 0.35 g, 0.00867 mol). After addition, the resulting mixture was stirred for 3 h. (R)-3-Bromo-N-(4-cyano-3-(trifluoromethyl)phenyl)-2-hydroxy-2-methylpropanamide (8, 1.22 g, 0.003468 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:3 to 1:2) as eluent to afford 0.60 g of the titled compound as white needles.

Compound 1011 was characterized as follows: $^1$H NMR (400 MHz, DMSO-d$_6$) δ 10.33 (s, 1H, NH), 8.48 (d, J=2.0 Hz, 1H, ArH), 8.22 (dd, J=8.2 Hz, J=2.0 Hz, 1H, ArH), 8.05 (d, J=8.2 Hz, 1H, ArH), 7.69 (d, J=2.0 Hz, 1H, ArH), 7.60-7.57 (m, 2H, ArH), 7.28-7.21 (m, 3H, ArH), 6.66 (d, J=3.0 Hz, 1H, ArH), 6.31 (s, 1H, OH), 4.52 (d, J=14.6 Hz, 1H, CH), 4.32 (d, J=14.6 Hz, 1H, CH), 1.43 (s, 3H, CH$_3$).

(S)—N-(4-Cyano-3-(trifluoromethyl)phenyl)-3-(3-fluoro-1H-pyrazol-1-yl)-2-hydroxy-2-methylpropanamide (C$_{15}$H$_{12}$F$_4$N$_4$O$_2$) (1012)

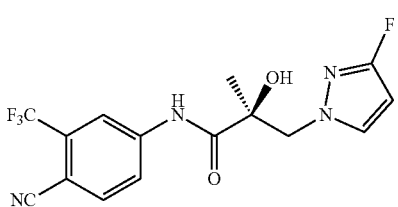 [SMILES: C[C@](O)(Cn1ccc(F)n1)C(=O)Nc1ccc(C#N)c(C(F)(F)F)c1]

To a solution of 3-fluoro-pyrazole (0.20 g, 0.00232 mol) in anhydrous THF (10 mL), which was cooled in an ice water bath under an argon atmosphere, was added sodium hydride (60% dispersion in oil, 0.24 g, 0.00582 mol). After addition, the resulting mixture was stirred for 3 h. (R)-3-Bromo-N-(4-cyano-3-(trifluoromethyl)phenyl)-2-hydroxy-2-methylpropanamide (8, 0.82 g, 0.00232 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.36 g of the compound as white needles.

Compound 1012 was characterized as follows: $^1$H NMR (400 MHz, DMSO-d$_6$) δ 10.39 (s, 1H, NH), 8.47 (d, J=2.0 Hz, 1H, ArH), 8.24 (dd, J=8.8 Hz, J=2.0 Hz, 1H, ArH), 8.11 (d, J=8.8 Hz, 1H, ArH), 7.55 (t, J=3.0 Hz, 1H, Pyrazole-H), 6.29 (s, 1H, OH), 5.93-5.91 (m, 1H, Pyrazole-H), 4.34 (d, J=13.6 Hz, 1H, CH), 4.15 (d, J=13.6 Hz, 1H, CH), 1.36 (s, 3H, CH$_3$); Mass (ESI, Positive): 357.0966 [M+H]$^+$.

(S)—N-(4-Cyano-3-(trifluoromethyl)phenyl)-2-hydroxy-2-methyl-3-(1H-pyrazol-1-yl)propanamide (C$_{15}$H$_{13}$F$_3$N$_4$O$_2$) (1013)

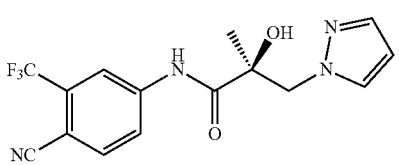 [SMILES: C[C@](O)(Cn1cccn1)C(=O)Nc1ccc(C#N)c(C(F)(F)F)c1]

To a solution of 1H-pyrazole (0.20 g, 0.002938 mol) in anhydrous THF (10 mL), which was cooled in an ice water bath under an argon atmosphere, was added sodium hydride (60% dispersion in oil, 0.29 g, 0.007344 mol). After addition, the resulting mixture was stirred for 3 h. (R)-3-Bromo-N-(4-cyano-3-(trifluoromethyl)phenyl)-2-hydroxy-2-methylpropanamide (8, 1.03 g, 0.002938 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.52 g of the compound as white solid.

Compound 1013 was characterized as follows: $^1$H NMR (400 MHz, DMSO-d$_6$) δ 10.39 (s, 1H, NH), 8.48 (d, J=2.0 Hz, 1H, ArH), 8.22 (dd, J=8.2 Hz, J=2.0 Hz, 1H, ArH), 8.08 (d, J=8.2 Hz, 1H, ArH), 7.66-7.65 (m, 1H, Pyrazole-H), 7.39-7.38 (m, 1H, Pyrazole-H), 6.28 (s, 1H, OH), 6.25-6.23 (m, 1H, Pyrazole-H), 4.50 (d, J=13.6 Hz, 1H, CH), 4.29 (d, J=13.6 Hz, 1H, CH), 1.35 (s, 3H, CH$_3$); Mass (ESI, Positive): 339.1105 [M+H]$^+$.

(S)—N-(4-Cyano-3-(trifluoromethyl)phenyl-2-hydroxy-2-methyl-3-(3-(trifluoromethyl)-1H-pyrazol-1-yl)propanamide (C$_{16}$H$_{12}$F$_6$N$_4$O$_2$) (1014)

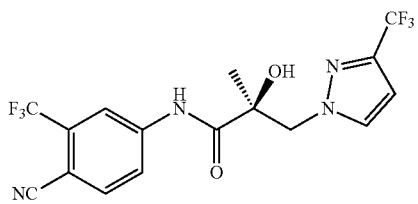 [SMILES: C[C@](O)(Cn1ccc(C(F)(F)F)n1)C(=O)Nc1ccc(C#N)c(C(F)(F)F)c1]

To a solution of 3-trifluoromethyl-pyrazole (0.20 g, 0.00147 mol) in anhydrous THF (10 mL), which was cooled in an ice water bath under an argon atmosphere, was added sodium hydride (60% dispersion in oil, 0.15 g, 0.003674 mol). After addition, the resulting mixture was stirred for 3 h. (R)-3-Bromo-N-(4-cyano-3-(trifluoromethyl)phenyl)-2-hydroxy-2-methylpropanamide (8) (0.516 g, 0.00147 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford the titled compound (103 mg, 70%) as a white solid.

Compound 1014 was characterized as follows: $^1$H NMR (400 MHz, DMSO-d$_6$) δ 10.31 (bs, 1H, NH), 8.42 (d, J=2.0 Hz, 1H, ArH), 8.19 (dd, J=8.8, 2.0 Hz, 1H, ArH), 8.09 (d, J=8.8 Hz, 1H, ArH), 7.83 (d, J=1.2 Hz, 1H, ArH), 6.67 (d, J=2.0 Hz, 1H, ArH), 6.41 (bs, OH), 4.56 (d, J=14.0 Hz, 1H, CHH), 4.37 (d, J=14.0 Hz, 1H, CHH), 1.41 (s, 3H, CH$_3$); $^{19}$F NMR (CDCl$_3$, decoupling) δ −60.44, −61.25; HRMS (ESI) m/z calcd for C$_{16}$H$_{12}$F$_6$N$_4$O$_2$: 407.0943 [M+H]$^+$; Found: 407.0943 [M+H]$^+$; mp 153-155° C.

(S)—N-(4-Cyano-3-(trifluoromethyl)phenyl)-3-(3-(4-fluorophenyl)-1H-pyrazol-1-yl)-2-hydroxy-2-methylpropanamide ($C_{21}H_{16}F_4N_4O_2$) (1015)

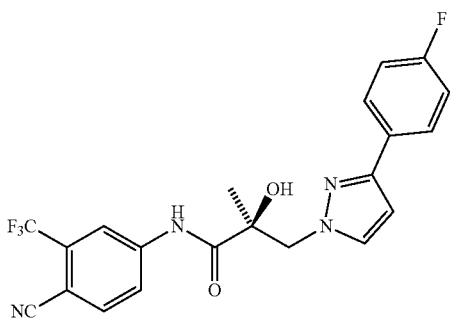 [SMILES: C[C@](O)(Cn1ccc(-c2ccc(F)cc2)n1)C(=O)Nc1ccc(C#N)c(C(F)(F)F)c1]

To a solution of 3-(4-fluorophenyl)-pyrazole (0.30 g, 0.00185 mol) in anhydrous THF (10 mL), which was cooled in an ice water bath under an argon atmosphere, was added sodium hydride (60% dispersion in oil, 0.22 g, 0.00555 mol). After addition, the resulting mixture was stirred for 3 h. (R)-3-Bromo-N-(4-cyano-3-(trifluoromethyl)phenyl)-2-hydroxy-2-methylpropanamide (8) (0.65 g, 0.00185 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (2:1) as eluent to afford 0.32 g (40%) of the titled compound as pinkish solid.

Compound 1015 was characterized as follows: $^1$H NMR (400 MHz, DMSO-d$_6$) δ 10.30 (s, 1H, NH), 8.41 (d, J=2.0 Hz, 1H, ArH), 8.21 (dd, J=8.2 Hz, J=2.0 Hz, 1H, ArH), 8.05 (d, J=8.2 Hz, 1H, ArH), 7.68 (d, J=2.0 Hz, 1H, ArH), 7.64-7.59 (m, 2H, ArH), 7.11-7.05 (m, 2H, ArH), 6.65 (d, J=3.0 Hz, 1H, ArH), 6.31 (s, 1H, OH), 4.50 (d, J=13.6 Hz, 1H, CH), 4.30 (d, J=13.6 Hz, 1H, CH), 1.42 (s, 3H, CH$_3$); Mass (ESI, Positive): 433.1312 [M+H]$^+$.

(S)—N-(4-Cyano-3-(trifluoromethyl)phenyl)-2-hydroxy-2-methyl-3-morpholinopropanamide ($C_{16}H_{18}F_3N_3O_3$) (1016)

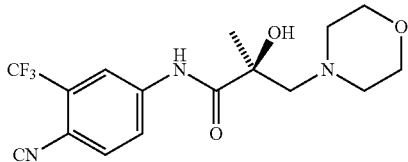

Under an argon atmosphere, 1.0 mL of lithium bis(trimethylsilyl)amide in THF (1 mmol, Aldrich, 1 M solution in THF) was slowly added to a solution of 0.09 mL of morpholine (0.67 mmol) in THF (10 mL) at −78° C. and stirred for 30 min at that temperature. A solution of 8 (234 mg, 0.67 mmol) in 5 mL of THF was added dropwise to the solution. The reaction mixture was stirred at the same temperature for 30 min, then stirred overnight at RT, and quenched by an addition of sat. NH$_4$Cl solution. The mixture was concentrated under reduced pressure, dispersed into excess EtOAc, dried over Na$_2$SO$_4$, concentrated and purified by flash column chromatography (EtOAc/hexane) to give the target compound (209 mg, yield 88%) as white solid.

Compound 1016 was characterized as follows: $^1$H NMR (CDCl$_3$, 400 MHz) δ 9.36 (bs, 1H, NH), 8.08 (d, J=1.6 Hz, 1H), 7.94 (dd, J=8.4, 1.6 Hz, 1H), 7.80 (d, J=8.4 Hz, 1H), 3.68 (m, 4H), 3.28 (d, J=13.2 Hz, 1H), 2.55 (m, 4H), 2.42 (d, J=13.2 Hz, 1H), 1.50 (bs, 1H, OH), 1.42 (s, 3H); $^{19}$F NMR (acetone-d$_6$, 400 MHz) δ −62.20; LCMS (ESI) m/z calcd for $C_{16}H_{19}F_3N_3O_3$: 358.1379. Found: 358.1383 [M+H]$^+$.

(S)—N-(4-Cyano-3-(trifluoromethyl)phenyl)-2-hydroxy-2-methyl-3-(4-(trifluoromethyl)-1H-pyrazol-1-yl)propanamide ($C_{16}H_{12}F_6N_4O_2$) (1017)

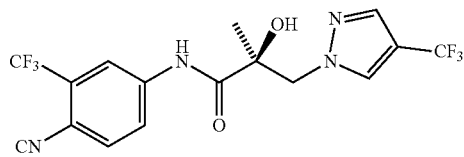

To a solution of 4-trifluoromethyl-pyrazole (0.20 g, 0.00147 mol) in anhydrous THF (10 mL), which was cooled in an ice water bath under an argon atmosphere, was added sodium hydride (60% dispersion in oil, 0.18 g, 0.004409 mol). After addition, the resulting mixture was stirred for 3 h. (R)-3-Bromo-N-(4-cyano-3-(trifluoromethyl)phenyl)-2-hydroxy-2-methylpropanamide (8) (0.516 g, 0.00147 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using DCM and ethyl acetate (19:1) as eluent to afford 0.30 g (50%) of the titled compound as white foam.

Compound 1017 was characterized as follows: $^1$H NMR (400 MHz, DMSO-d$_6$) δ 10.38 (s, 1H, NH), 8.45 (d, J=2.0 Hz, 1H, ArH), 8.25-8.22 (m, 2H, ArH & Pyrazole-H), 8.11 (d, J=8.2 Hz, 1H, ArH), 7.82 (s, 1H, Pyrazole-H), 6.39 (s, 1H, OH), 4.55 (d, J=14.0 Hz, 1H, CH), 4.37 (d, J=14.0 Hz, 1H, CH), 1.40 (s, 3H, CH$_3$); Mass (ESI, Positive): 407.0945 [M+H]$^+$.

Triazoles 1018 and 1019

(S)—N-(4-Cyano-3-(trifluoromethyl)phenyl)-2-hydroxy-2-methyl-3-(1H-1,2,4-triazol-1-yl)propanamide ($C_{14}H_{12}F_3N_5O_2$) (1018)

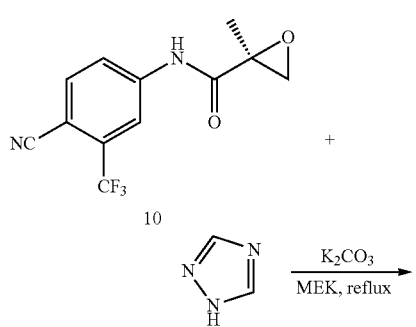

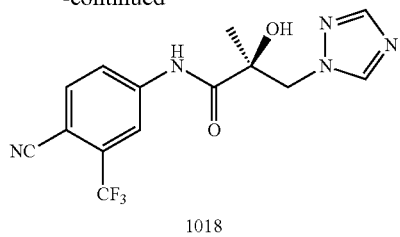

1018

To a dry, nitrogen-purged 50 mL round-bottom flask, epoxide (10, 270 mg, 1 mmol), 1,2,4-triazole (69 mg, 1 mmol) and K₂CO₃ (268 mg, 2 mmol) were dispersed into 10 mL of 2-butanone (methylethylketone (MEK)). The mixture was heated to reflux for 12 h. The resulting mixture was cooled down to RT. The volume of mixture was reduced under reduced pressure, poured into water, and extracted with ethyl acetate (3 times). The organic layer was dried over MgSO₄, concentrated and purified by flash column chromatography (ethyl acetate/hexane 2:3 v/v) on silica gel to produce target product (143 mg, 43% yield). Compound 1018 was characterized as follows: ¹H NMR (CDCl₃, 400 MHz) δ 9.10 (bs, 1H, NH), 8.15 (s, 1H), 8.02 (d, J=2.0 Hz, 1H), 7.88 (dd, J=8.4, 2.0 Hz, 1H), 7.78 (d, J=8.4 Hz, 1H), 5.70 (bs, 1H, OH), 4.79 (d, J=14.0 Hz, 1H), 4.35 (d, J=14.0 Hz, 1H), 1.53 (s, 3H); ¹⁹F NMR (CDCl₃, 400 MHz) δ −62.22; HRMS (ESI) m/z calcd for C₁₄H₁₂F₃N₅O₂ Exact Mass: 340.1021 [M+H]⁺. Found: 340.1067 [M+H]⁺.

(S)—N-(4-Cyano-3-(trifluoromethyl)phenyl)-2-hydroxy-2-methyl-3-(3-(trifluoromethyl)-1H-1,2,4-triazol-1-yl)propanamide (C₁₅H₁₁F₆N₅O₂) (1019)

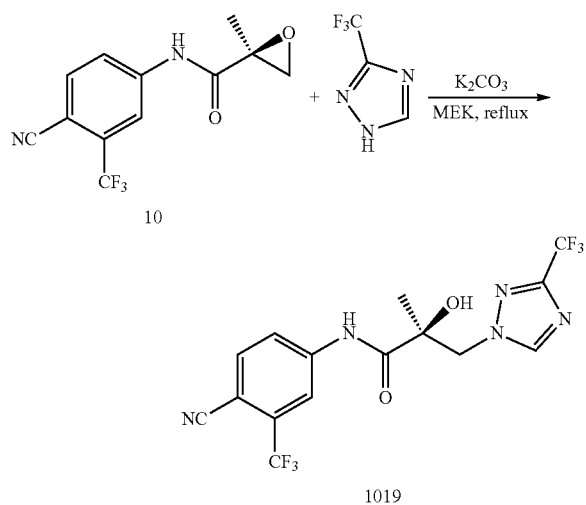

1019

To a dry, nitrogen-purged 50 mL round-bottom flask, epoxide (10, 270 mg, 1 mmol), 3-(trifluoromethyl)-1H-1,2,4-triazole (137 mg, 1 mmol) and K₂CO₃ (268 mg, 2 mmol) were dispersed into 10 mL of 2-butanone (methylethylketone or MEK). The mixture was heated to reflux for 12 h. The resulting mixture was cooled down to RT. The volume of mixture was reduced under reduced pressure, poured into water, and extracted with ethyl acetate (3 times). The organic layer was dried over MgSO₄, concentrated and purified by flash column chromatography (ethyl acetate/hexane 2:3 v/v) on silica gel to produce target product (213 mg, 53% yield).

Compound 1019 was characterized as follows: ¹H NMR (acetone-d₆, 400 MHz) δ 9.88 (bs, 1H, NH), 9.44 (s, 1H), 8.44 (s, 1H), 8.25 (d, J=8.4 Hz, 1H), 8.04 (d, J=8.4 Hz, 1H), 4.82 (d, J=14.4 Hz, 1H), 4.61 (d, J=14.4 Hz, 1H), 2.88 (bs, 1H, OH), 1.61 (s, 3H); ¹⁹F NMR (CDCl₃, 400 MHz) δ −62.26, −65.25; HRMS (ESI) m/z calcd for C₁₅H₁₁F₆N₅O₂ Exact Mass: 408.0895 [M+H]⁺. Found: 408.0898 [M+H]⁺.

(R)—N-(4-Cyano-3-(trifluoromethyl)phenyl)-3-(4-fluoro-1H-pyrazol-1-yl)-2-hydroxy-2-methylpropanamide (C₁₅H₁₂F₄N₄O₂) (1020)

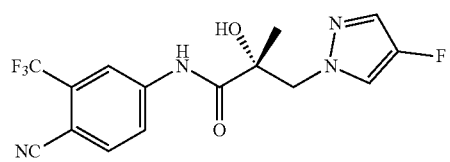 [SMILES: C[C@@](O)(Cn1cc(F)cn1)C(=O)Nc1ccc(C#N)c(C(F)(F)F)c1]

To a solution of 4-fluoro-1H-pyrazole (0.1 g, 1.16 mmol) in anhydrous THF (10 mL), which was cooled in an ice bath under an argon atmosphere, was added sodium hydride (60% dispersion in mineral oil, 0.12 g, 2.91 mmol). After addition, the resulting mixture was stirred for 3 h. (S)-3-Bromo-N-(4-cyano-3-(trifluoromethyl)phenyl)-2-hydroxy-2-methylpropanamide (S-isomer of 8 (8S)*; 0.41 g, 1.16 mmol) was added to the above solution, and the resulting reaction mixture was allowed to stir overnight at RT under argon atmosphere. The reaction was quenched by water and extracted with ethyl acetate. The organic layer was washed with brine, dried with anhydrous MgSO₄, filtered, and concentrated under reduced pressure. The mixture was purified by flash column chromatography using ethyl acetate and hexanes (2/3, v/v) as eluent to afford the titled compound (127 mg, 71%) as white solid.

Compound 1020 was characterized as follows: ¹H NMR (400 MHz, CDCl₃) δ 9.07 (bs, 1H, NH), 8.01 (d, J=2.0 Hz, 1H), 7.95 (dd, J=8.4, 2.0 Hz, 1H), 7.78 (d, J=8.4 Hz, 1H), 7.38 (d, J=4.0 Hz, 1H), 7.34 (d, J=4.4 Hz, 1H), 5.92 (s, OH), 4.54 (d, J=14.0 Hz, 1H), 4.16 (d, J=14.4 Hz, 1H), 1.47 (s, 3H); ¹⁹F NMR (CDCl₃, decoupling) δ −62.23, −176.47; HRMS (ESI) m/z calcd for C₁₅H₁₂F₄N₄O₂: 357.0975 [M+H]⁺; Found: 357.0984 [M+H]⁺; [α]_D²⁴ +126.7° (c=1.0, MeOH) (compared with S-isomer: [α]_D²⁴ −136.0° (c=0.5, MeOH)).

*: 8S was synthesized from L-proline using the same procedure as for 8 (i.e., the R-isomer), as outlined in Scheme 1.

(S)—N-(4-Cyano-3-(trifluoromethyl)phenyl)-3-(3-fluoro-1H-pyrrol-1-yl)-2-hydroxy-2-methylpropanamide (C₁₆H₁₃F₄N₃O₂) (1021)

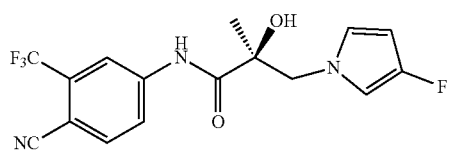

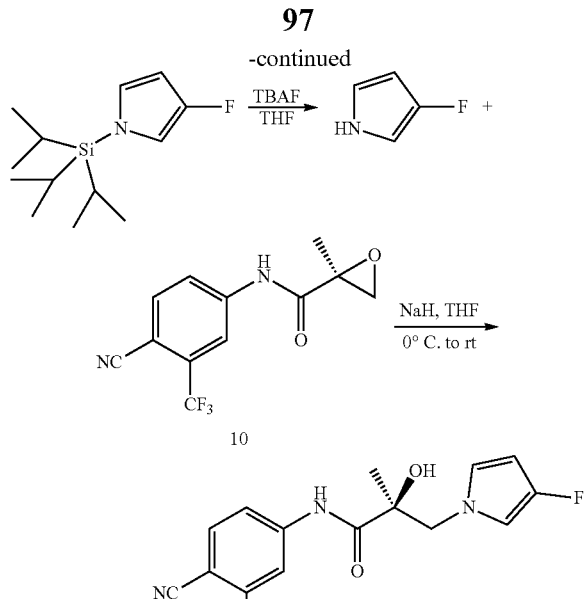

To a solution of 3-fluoro-1-(triisopropylsilyl)-1H-pyrrole (1.21 g, 5 mmol) in 20 mL of anhydrous THF, n-tetrabutylammonium fluoride trihydrate in tetrahydrofuran (7.5 mL, 7.5 mmol; 1M) was added at RT under argon atmosphere. The solution was stirred for 1 h. Without work-up procedure, the flask was cooled down to 0° C. at ice-water bath. To the solution, NaH of 60% in mineral oil (133 mg, 3.33 mmol) was added. The reaction mixture was stirred for 30 min and epoxide 10 (450 mg, 1.67 mmol) in anhydrous THF was added through dropping funnel under argon atmosphere at the ice-water bath and stirred overnight at RT. After quenching with 1 mL of $H_2O$, the reaction was condensed under reduced pressure, and then dispersed into 50 mL of EtOAc, washed with water, evaporated, dried over anhydrous $MgSO_4$, and evaporated to dryness. The mixture was purified with flash column chromatography by EtOAc/hexane=1/1 as eluent, and then the condensed compounds were recrystallized with EtOAc/hexane to give a target product 1021 (181 mg, 31%) as white solid.

Compound 1021 was characterized as follows: $^1H$ NMR (400 MHz, $CDCl_3$) δ 8.91 (bs, 1H, NH), 8.03 (d, J=2.0 Hz, 1H), 7.90 (dd, J=8.4, 2.0 Hz, 1H), 7.81 (d, J=8.4 Hz, 1H), 6.47 (m, 1H), 6.41 (m, 1H), 5.91 (dd, J=2.8, 2.0 Hz, 1H), 4.36 (d, J=14.4 Hz, 1H), 3.98 (d, J=14.4 Hz, 1H), 1.54 (s, 3H); $^{19}F$ NMR ($CDCl_3$, decoupling) δ −62.18, −164.26; HRMS (ESI) m/z calcd for $C_{16}H_{14}F_4N_3O_2$: 356.1022 [M+H]$^+$, Found: 356.1021 [M+H]$^+$; 378.0839 [H+Na]$^+$.

(S)—N-(6-Cyano-5-(trifluoromethyl)pyridin-3-yl)-3-(4-fluoro-1H-pyrazol-1-yl)-2-hydroxy-2-methylpropanamide ($C_{14}H_{11}F_4N_5O_2$) (1022)

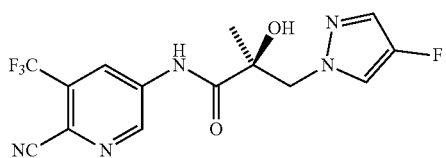 [SMILES: C[C@](O)(Cn1cc(F)cn1)C(=O)Nc1cnc(C#N)c(C(F)(F)F)c1]

(R)-3-Bromo-N-(6-cyano-5-(trifluoromethyl)pyridin-3-yl)-2-hydroxy-2-methylpropanamide

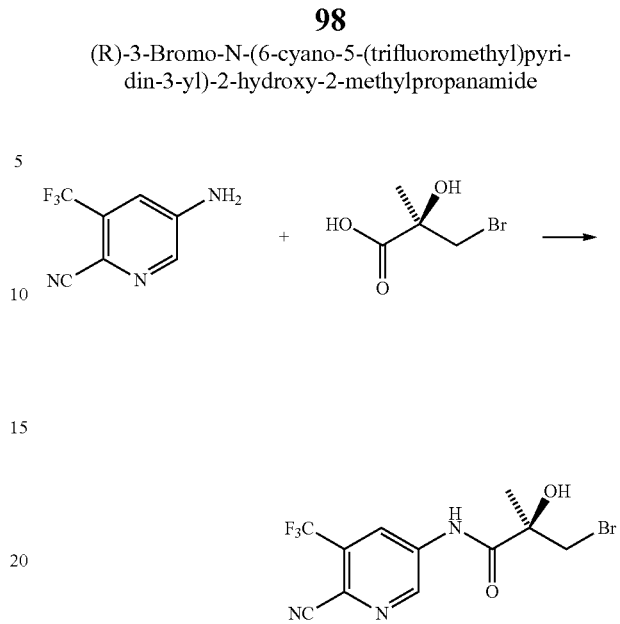

(R)-3-Bromo-2-hydroxy-2-methylpropanoic acid (4, 1.03 g, 0.005625 mol) reacted with thionyl chloride (0.80 g, 0.006751 mol), trimethylamine (0.74 g, 0.007313 mol), and 5-amino-3-(trifluoromethyl)picolinonitrile (1.00 g, 0.005344 mol) to afford the titled compound. The product was purified by a silica gel column using hexanes and ethyl acetate (2:1) as eluent to afford 1.70 g (90%) of the titled compound as a yellowish solid.

$^1H$ NMR (400 MHz, DMSO-$d_6$) δ 10.82 (s, 1H, NH), 9.41 (d, J=2.0 Hz, 1H, ArH), 8.90 (d, J=2.0 Hz, 1H, ArH), 6.51 (s, 1H, OH), 3.84 (d, J=10.4 Hz, 1H, CH), 3.61 (d, J=10.4 Hz, 1H, CH), 1.50 (s, 3H, $CH_3$); Mass (ESI, Positive): 351.9915 [M+H]$^+$.

(S)—N-(6-Cyano-5-(trifluoromethyl)pyridin-3-yl)-3-(4-fluoro-1H-pyrazol-1-yl)-2-hydroxy-2-methylpropanamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. (R)-3-Bromo-N-(6-cyano-5-(trifluoromethyl)pyridin-3-yl)-2-hydroxy-2-methylpropanamide (0.82 g, 0.0023237 mol) was added to above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using hexanes and ethyl acetate (1:1) as eluent to afford 0.50 g (60.2%) of the titled compound as white solid.

Compound 1022 was characterized as follows: $^1H$ NMR (400 MHz, DMSO-$d_6$) δ 10.64 (s, 1H, NH), 9.32 (d, J=2.0 Hz, 1H, ArH), 8.82 (d, J=2.0 Hz, 1H, ArH), 7.75 (d, J=4.8 Hz, 1H, Pyrazole-H), 7.40 (d, J=4.0 Hz, 1H, Pyrazole-H), 6.41 (s, 1H, OH), 4.39 (d, J=14.0 Hz, 1H, CH), 4.22 (d, J=14.0 Hz, 1H, CH), 1.36 (s, 3H, $CH_3$); (ESI, Positive): 358.0939 [M+H]$^+$, 380.0749 [M+Na]$^+$.

(S)-5-(3-(4-Fluoro-1H-pyrazol-1-yl)-2-hydroxy-2-methylpropanamido)picolinamide (C₁₃H₁₄FN₅O₃) (1023)

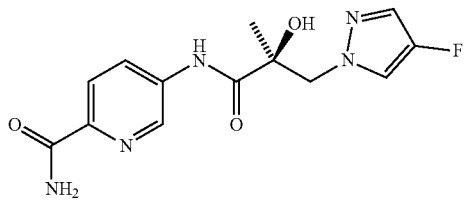 [SMILES: C[C@](O)(Cn1cc(F)cn1)C(=O)Nc1ccc(C(N)=O)nc1]

(R)-3-Bromo-N-(6-cyanopyridin-3-yl)-2-hydroxy-2-methylpropanamide

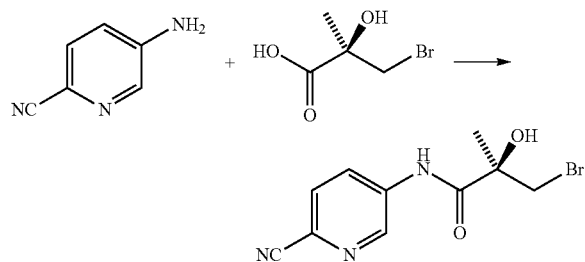

(R)-3-Bromo-2-hydroxy-2-methylpropanoic acid (4, 3.24 g, 0.017674 mol) reacted with thionyl chloride (2.53 g, 0.021208 mol), trimethylamine (2.33 g, 0.022976 mol), and 5-aminopicolinonitrile (2.00 g, 0.01679 mol) to afford the titled compound. The product was purified by a silica gel column using dichloromethane (DCM) and methanol (19:1) as eluent to afford 4.40 g (92%) of the titled compound as yellowish solid.

¹H NMR (400 MHz, DMSO-d₆) δ 10.42 (s, 1H, NH), 9.12 (d, J=2.4 Hz, 1H, ArH), 8.44 (dd, J=8.8 Hz, J=2.4 Hz, 1H, ArH), 8.00 (d, J=8.8 Hz, 1H, ArH), 6.40 (s, 1H, OH), 3.83 (d, J=10.4 Hz, 1H, CH), 3.59 (d, J=10.4 Hz, 1H, CH), 1.49 (s, 3H, CH₃); Mass (ESI, Positive): 284.0042 [M+H]⁺.

(S)-5-(3-(4-Fluoro-1H-pyrazol-1-yl)-2-hydroxy-2-methylpropanamido)picolinamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. (R)-3-Bromo-N-(6-cyanopyridin-3-yl)-2-hydroxy-2-methylpropanamide (0.66 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and methanol (9:1) as eluent to afford 0.10 g (15%) of the titled compound as white solid.

Compound 1023 was characterized as follows: ¹H NMR (400 MHz, DMSO-d₆) δ 10.08 (s, 1H, NH), 8.89 (d, J=2.4 Hz, 1H, ArH), 8.30 (dd, J=8.2 Hz, J=2.4 Hz, 1H, ArH), 8.01 (s, 1H, NH), 7.98 (d, J=8.2 Hz, 1H, ArH), 7.73 (d, J=4.4 Hz, 1H, Pyrazole-H), 7.51 (s, 1H, NH), 7.42 (d, J=4.0 Hz, 1H, Pyrazole-H), 6.24 (s, 1H, OH), 4.38 (d, J=14.0 Hz, 1H, CH), 4.42 (d, J=14.0 Hz, 1H, CH), 1.34 (s, 3H, CH₃); Mass (ESI, Positive): 308.1177 [M+H]⁺, 330.0987 [M+Na]⁺.

N-(4-Cyano-3-(trifluoromethyl)phenyl)-3-(4-fluoro-1H-pyrazol-1-yl)-2-methylpropanamide (C₁₅H₁₂F₄N₄O) (1024)

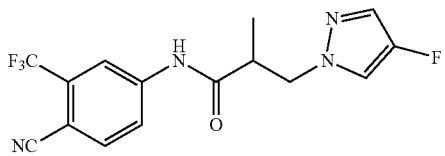 [SMILES: CC(Cn1cc(F)cn1)C(=O)Nc1ccc(C#N)c(C(F)(F)F)c1]

3-Bromo-N-(4-cyano-3-(trifluoromethyl)phenyl)-2-methylpropanamide

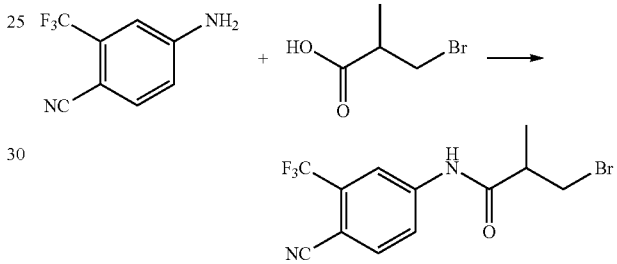

3-Bromo-2-methylpropanoic acid (2.00 g, 0.011976 mol) reacted with thionyl chloride (1.71 g, 0.014371 mol), trimethylamine (1.58 g, 0.015569 mol), and 4-amino-2-(trifluoromethyl)benzonitrile (2.12 g, 0.011377 mol) to afford the titled compound. The product was purified by a silica gel column using hexanes and ethyl acetate (2:1) as eluent to afford 3.50 g (91%) of the titled compound as a yellow to light brown solid.

¹H NMR (400 MHz, DMSO-d₆) δ 10.85 (s, 1H, NH), 8.30 (s, 1H, ArH), 8.12 (d, J=8.2 Hz, 1H, ArH), 8.03 (d, J=8.2 Hz, 1H, ArH), 3.72-3.67 (m, 1H, CH), 3.63-3.59 (m, 1H, CH), 3.03-2.97 (m, 1H, CH), 1.24 (d, J=6.8 Hz, 3H, CH₃); Mass (ESI, Negative): 334.85[M−H]⁻.

N-(4-Cyano-3-(trifluoromethyl)phenyl)-3-(4-fluoro-1H-pyrazol-1-yl)-2-methylpropanamide To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. 3-Bromo-N-(4-cyano-3-(trifluoromethyl)phenyl)-2-methylpropanamide (0.78 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (1:1) as eluent to afford 0.050 g of the titled compound as yellowish solid.

Compound 1024 was characterized as follows: ¹H NMR (400 MHz, DMSO-d₆) δ 10.77 (s, 1H, NH), 8.25 (s, 1H, ArH), 8.10 (d, J=8.2 Hz, 1H, ArH), 7.96 (d, J=8.2 Hz, 1H, ArH), 7.85 (d, J=4.4 Hz, 1H, Pyrazole-H), 7.47 (d, J=4.4 Hz, 1H, Pyrazole-H), 4.35-4.30 (m, 1H, CH), 4.12-4.07 (m, 1H, CH), 3.12-3.10 (m, 1H, CH), 1.22 (d, J=6.8 Hz, 3H, CH₃).

(S)—N-(4-Cyano-3-(trifluoromethyl)phenyl)-3-(4-(4-fluorophenyl)-H-pyrazol-1-yl)-2-hydroxy-2-methylpropanamide (C₂₁H₁₆F₄N₄O₂) (1025)

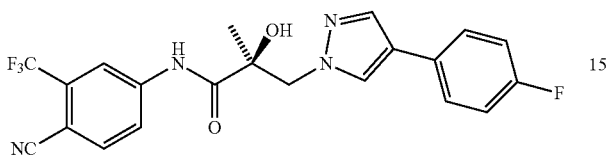

To a solution of 4-(4-fluorophenyl)-1H-pyrazole (0.20 g, 0.0012334 mol) in anhydrous THF (10 mL), which was cooled in an ice water bath under an argon atmosphere, was added sodium hydride (60% dispersion in oil, 0.15 g, 0.0037001 mol). After addition, the resulting mixture was stirred for 3 h. (R)-3-Bromo-N-(4-cyano-3-(trifluoromethyl)phenyl)-2-hydroxy-2-methylpropanamide (0.43 g, 0.0012334 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 0.33 g (62%) of the titled compound as white solid.

Compound 1025 was characterized as follows: ¹H NMR (400 MHz, DMSO-d₆) δ 10.29 (s, 1H, NH), 8.41 (s, 1H, ArH), 8.21 (d, J=8.8 Hz, 1H, ArH), 8.05 (d, J=8.8 Hz, 1H, ArH), 7.68 (s, 1H, Pyrazole-H), 7.61 (t, J=6.4 Hz, 2H, ArH), 7.08 (t, J=8.4 Hz, 2H, ArH), 6.65 (s, 1H, Pyrazole-H), 6.30 (s, 1H, OH), 4.51 (d, J=14.0 Hz, 1H, CH), 4.31 (d, J=14.0 Hz, 1H, CH), 1.42 (s, 3H, CH₃); Mass (ESI, Negative): 431.12 [M−H]⁻.

(S)-3-((1H-1,2,4-Triazol-3-yl)amino)-N-(4-cyano-3-(trifluoromethyl)phenyl)-2-hydroxy-2-methylpropanamide (C₁₄H₁₃F₃N₆O₂) (1026)

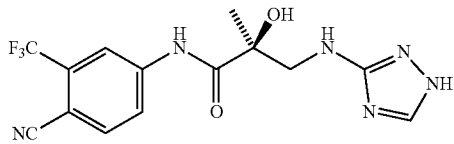 [SMILES: C[C@](O)(CNc1nc[nH]n1)C(=O)Nc1ccc(C#N)c(C(F)(F)F)c1]

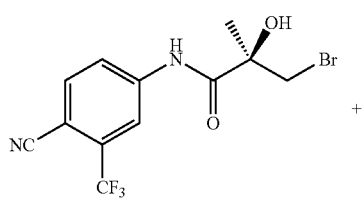

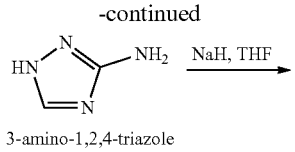

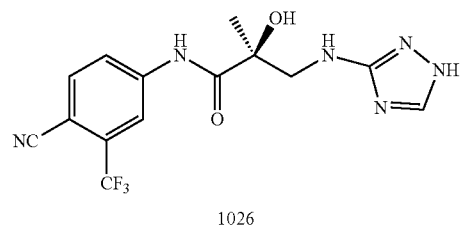

Under argon atmosphere, 100 mL round bottom flask was cooled down to 0° C. at ice-water bath. NaH of 60% in mineral oil (265 mg, 6.6 mmol) was added to the flask at the ice-water bath and anhydrous THF (20 mL) was poured into the flask at that temperature. Into the flask, 3-amino-1,2,4-triazole (164 mg, 2 mmol) was added into the flask at that temperature and the reaction mixture was stirred for 30 min. Then, a prepared solution of (R)-3-bromo-N-(4-cyano-3-(trifluoromethyl)phenyl)-2-hydroxy-2-methylpropanamide (8, 702 mg, 2 mmol) in anhydrous THF (10 mL) was added through dropping funnel under argon atmosphere at the ice-water bath and stirred overnight at RT. After quenching with 1 mL of H₂O, the reaction mixture was condensed under reduced pressure, and then dispersed into 50 mL of EtOAc, washed with water, evaporated, dried over anhydrous MgSO₄, and evaporated to dryness. The mixture was purified with flash column chromatography with an eluent of EtOAc/hexane (2:1 v/v) to give a target product as brown solid.

Compound 1026 was characterized as follows: ¹H NMR (CDCl₃, 400 MHz) δ 9.10 (bs, 1H, C(O)NH), 8.01 (m, 1H, ArH), 7.87 and 7.81 (dd, J=8.4, 2.0 Hz, 1H, ArH), 7.78 (d, J=8.4 Hz, 1H, ArH), 7.72 and 7.51 (s, 1H, ArH), 5.90 and 5.65 (bs, 1H, NH), 4.74 (bs, 1H, NH), 4.56 and 4.55 (d, J=14.4 and 13.6 Hz, 1H, CH₂), 4.24 (bs, 1H, OH), 4.07 and 3.97 (d, J=13.6 and 14.4 Hz, 1H, CH₂), 1.56 and 1.48 (s, 3H, CH₃); ¹⁹F NMR (acetone-d₆, 400 MHz) δ −62.24; MS (ESI) m/z 353.03 [M−H]⁻; 355.10 [M+H]⁺; HRMS (ESI) m/z calcd for C₁₄H₁₃F₃N₆O₂: 355.1130 [M+H]⁺, Found: 355.1128 [M+H]⁺.

tert-Butyl (S)-(1-(3-((4-cyano-3-(trifluoromethyl)phenyl)amino)-2-hydroxy-2-methyl-3-oxopropyl)-1H-pyrazol-4-yl)carbamate (C₂₀H₂₂F₃N₅O₄) (1027)

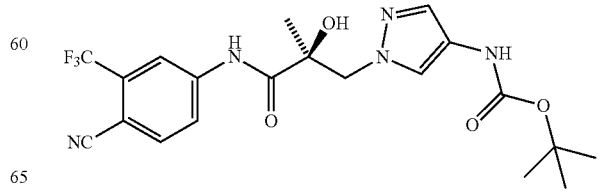

tert-Butyl-1H-pyrazol-4-ylcarbamate (1027a)

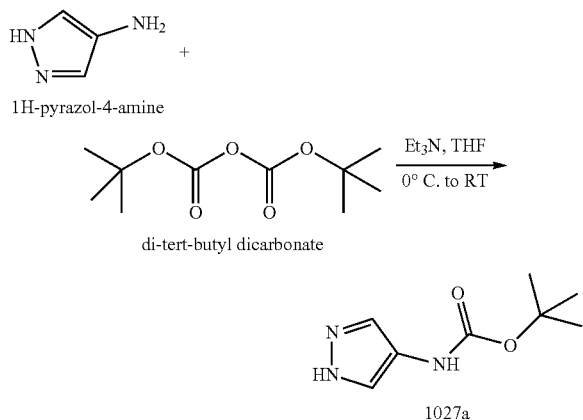

Under argon atmosphere, to a solution of 1H-pyrazol-4-amine (2 g, 28.9 mmol) and di-tert-butyl dicarbonate (6.3 g, 28.9 mmol) in 100 mL of anhydrous THF was added triethylamine (1.68 mL, 12 mmol) at 0° C. After stirring for 30 min, the temperature was raised to RT and the mixture was stirred for 2 h. The reaction mixture was condensed under reduced pressure, and then dispersed into 50 mL of EtOAc, washed with water, evaporated, dried over anhydrous MgSO$_4$, and evaporated to dryness. The mixture was purified with flash column chromatography with an eluent of EtOAc/hexane in a 1:1 v/v ratio, and then the condensed compounds were then recrystallized using EtOAc/hexane (1:1 v/v) to give a target product. $^1$H NMR (CDCl$_3$, 400 MHz) δ 7.63 (s, 2H, ArH), 6.29 (bs, 1H, NH), 1.51 (s, 9H, C(CH$_3$)$_3$); MS (ESI) m/z 182.1 [M–H]$^-$.

(S)-tert-Butyl (1-(3-((4-cyano-3-(trifluoromethyl)phenyl)amino)-2-hydroxy-2-methyl-3-oxopropyl)-1H-pyrazol-4-yl)carbamate

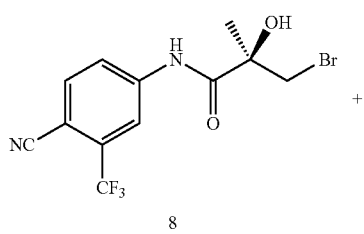

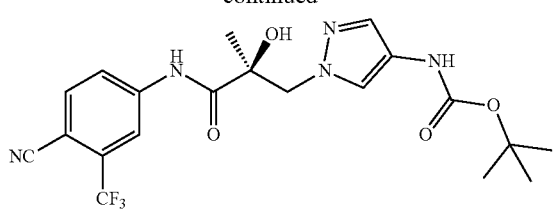

Under argon atmosphere, a 100 mL round bottom flask was cooled down to 0° C. at ice-water bath. NaH of 60% in mineral oil (160 mg, 4 mmol) was added to the flask at the ice-water bath and anhydrous THF (20 mL) was poured into the flask at that temperature. Into the flask, tert-butyl-1H-pyrazol-4-ylcarbamate (1027a, 366 mg, 2 mmol) was added at that temperature and the reaction mixture was stirred for 30 min, then a prepared solution of (R)-3-bromo-N-(4-cyano-3-(trifluoromethyl)phenyl)-2-hydroxy-2-methylpropanamide (8, 702 mg, 2 mmol) in anhydrous THF was added through a dropping funnel under argon atmosphere at the ice-water bath and stirred overnight at RT. After quenching with 1 mL of H$_2$O, the reaction was condensed under reduced pressure, and then dispersed into 50 mL of EtOAc, washed with water, evaporated, dried over anhydrous MgSO$_4$, and evaporated to dryness. The mixture was purified with flash column chromatography using EtOAc/hexane (2:1 v/v) as an eluent to give a target product (563 mg, 62%) as yellowish solid.

Compound 1027 was characterized as follows: $^1$H NMR (CDCl$_3$, 400 MHz) δ 9.13 (bs, 1H, C(O)NH), 8.01 (d, 1H, J=8.4 Hz, ArH), 7.85 (dd, J=8.4, 1.6 Hz, 1H, ArH), 7.76 (d, J=8.4 Hz, 1H, ArH), 7.63 (s, 1H, ArH), 7.43 (s, 1H, ArH), 6.21 (bs, 1H, C(O)NH), 6.17 (bs, 1H, OH), 4.54 (d, J=14.0 Hz, 1H, CH$_2$), 4.17 (d, J=14.0 Hz, 1H, CH$_2$), 1.47 (s, 9H, C(CH$_3$)$_3$), 1.45 (s, 3H, CH$_3$); $^{19}$F NMR (acetone-d$_6$, 400 MHz) δ −62.10; MS (ESI) m/z 452.11 [M–H]$^-$; 454.06 [M+H]$^+$.

(S)-3-(4-Amino-1H-pyrazol-1-yl)-N-(4-cyano-3-(trifluoromethyl)phenyl)-2-hydroxy-2-methylpropanamide (C$_{15}$H$_{14}$F$_3$N$_5$O$_2$) (1028)

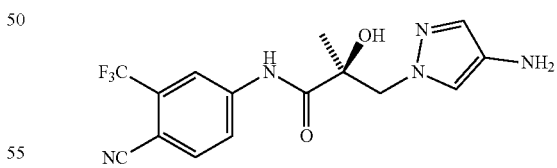

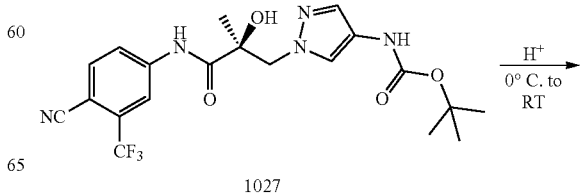

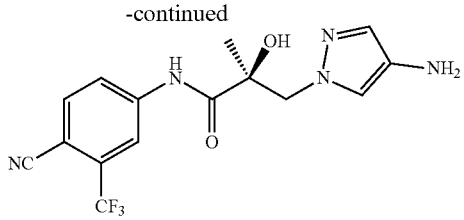

1028

Under argon atmosphere, a 100 mL round bottom flask was cooled down to 0° C. at ice-water bath. 5 mL of acetyl chloride was added dropwise to the solution of 1027 (815 mg, 1.80 mmol) of anhydrous EtOH (20 mL) at the ice-water bath. The reaction mixture was stirred for 30 min at that temperature. The solvent was concentrated under reduced pressure, and then dispersed into 50 mL of EtOAc, washed with water, evaporated, dried over anhydrous MgSO₄, and evaporated to dryness. The mixture was purified with flash column chromatography EtOAc/hexane (using 3:1 to 6:1 v/v ratios) as an eluent to give the target product (583 mg, 92%) as brown solid.

Compound 1028 was characterized as follows: $^1$H NMR (acetone-d$_6$, 400 MHz) δ 10.07 (bs, 1H, C(O)NH), 8.50 (s, 1H, ArH), 8.46 (s, 1H, ArH), 8.26 (d, J=8.0 Hz, 1H, ArH), 8.01 (d, J=8.0 Hz, 1H, ArH), 7.83 (s, 1H, ArH), 4.73 (d, J=14.0 Hz, 1H, CH$_2$), 4.53 (d, J=14.0 Hz, 1H, CH$_2$), 2.95 (bs, 1H, OH), 1.51 (s, 3H, CH$_3$); $^{19}$F NMR (acetone-d$_6$, 400 MHz) δ 114.77; MS (ESI) m/z 351.98 [M−H]⁻; 354.08 [M+H]⁺.

N-(4-Cyano-3-(trifluoromethyl)phenyl)-3-(4-fluoro-1H-pyrazol-1-yl)propanamide (C$_{14}$H$_{10}$F$_4$N$_4$O) (1029)

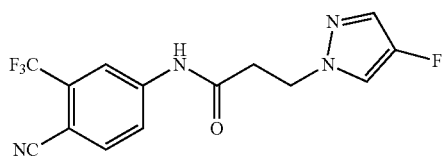

3-Bromo-N-(4-cyano-3-(trifluoromethyl)phenyl) propanamide (C$_{11}$H$_8$BrF$_3$N$_2$O)

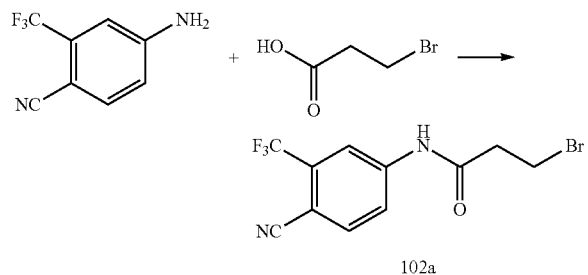

102a

3-Bromopropanoic acid (2.00 g, 0.0130745 mol) reacted with thionyl chloride (1.87 g, 0.0156894 mol), trimethylamine (1.72 g, 0.0169968 mol), and 4-amino-2-(trifluoromethyl)benzonitrile (2.31 g, 0.0124207 mol) to afford the titled compound. The product was purified by a silica gel column using DCM and methanol (19:1) as eluent to afford 2.31 g (55%) of the titled compound as yellowish solid. $^1$H NMR (400 MHz, DMSO-d$_6$) δ 10.85 (s, 1H, NH), 8.28 (d, J=2.4 Hz, 1H, ArH), 8.12 (dd, J=8.8 Hz, J=2.4 Hz, 1H, ArH), 7.99 (d, J=8.8 Hz, 1H, ArH), 3.76 (t, J=6.0 Hz, 2H, CH$_2$), 3.06 (t, J=6.0 Hz, 2H, CH$_2$).

N-(4-Cyano-3-(trifluoromethyl)phenyl)-3-(4-fluoro-1H-pyrazol-1-yl)propanamide (C$_{14}$H$_{10}$F$_4$N$_4$O)

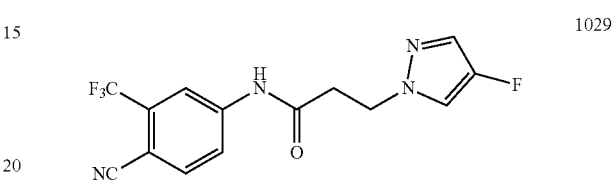

1029

To a solution of 4-fluoro-pyrazole (0.20 g, 0.0023237 mol) in anhydrous THF (5 mL), which was cooled in an ice water bath under an argon atmosphere, was added sodium hydride (60% dispersion in oil, 0.28 g, 0.0069711 mol). After addition, the resulting mixture was stirred for 3 h. 3-Bromo-N-(4-cyano-3-(trifluoromethyl)phenyl)propanamide (1029a, 0.75 g, 0.0023237 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and methanol (19:1) as eluent to afford 0.75 mg (10%) of the titled compound as white solid.

Compound 1029 was characterized as follows: $^1$H NMR (400 MHz, DMSO-d$_6$) δ 10.81 (s, 1H, NH), 8.25 (d, J=2.4 Hz, 1H, ArH), 8.10 (dd, J=8.8 Hz, J=2.4 Hz, 1H, ArH), 7.95 (d, J=8.8 Hz, 1H, ArH), 7.88 (s, 1H, Pyrazole-H), 7.46 (s, 1H, Pyrazole-H), 4.35 (t, J=6.0 Hz, 2H, CH$_2$), 2.79 (t, J=6.0 Hz, 2H, CH$_2$); Mass (ESI, Negative): 325.03 [M−H]⁻.

(S)-tert-Butyl (1-(3-((6-cyano-5-(trifluoromethyl) pyridin-3-yl)amino)-2-hydroxy-2-methyl-3-oxopropyl)-1H-pyrazol-4-yl)carbamate (C$_{19}$H$_{21}$F$_3$N$_6$O$_4$) (1030)

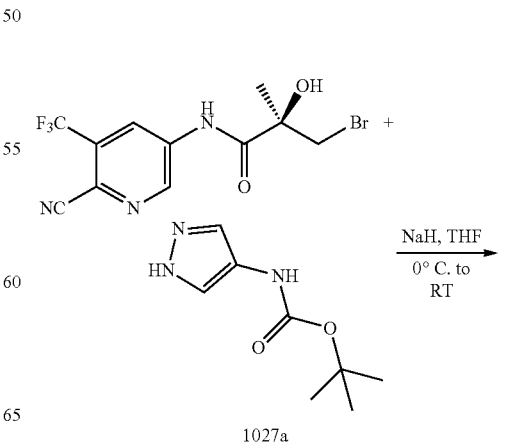

1027a

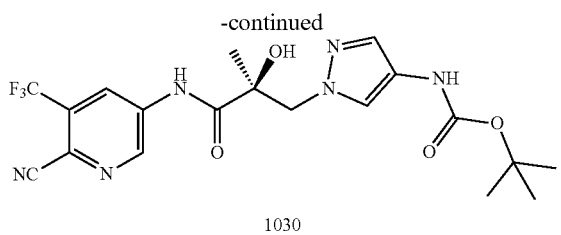

Under argon atmosphere, a 50 mL round bottom flask was cooled down to 0° C. at an ice-water bath. NaH of 60% in mineral oil (160 mg, 4 mmol) was added to the flask at the ice-water bath and anhydrous THF (10 mL) was poured into the flask at that temperature. Tert-butyl-1H-pyrazol-4-ylcarbamate (1027a, 183 mg, 1 mmol) was added into the flask at that temperature and the reaction mixture was stirred for 30 min. Then a prepared solution of (R)-3-bromo-N-(6-cyano-5-(trifluoromethyl)pyridin-3-yl)-2-hydroxy-2-methylpropanamide (352 mg, 1 mmol) in anhydrous THF was added through dropping funnel under argon atmosphere at the ice-water bath and stirred overnight at RT. After quenching with 1 mL of H$_2$O, the reaction was condensed under reduced pressure, and then dispersed into 30 mL of EtOAc, washed with water, evaporated, dried over anhydrous MgSO$_4$, and evaporated to dryness. The mixture was purified with flash column chromatography as an eluent EtOAc/hexane to give the target product (273 mg, 60%) as yellowish solid.

Compound 1030 was characterized as follows: $^1$H NMR (CDCl$_3$, 400 MHz) δ 9.28 (bs, 1H, C(O)NH), 8.80 (s, 1H, ArH), 8.67 (s, 1H, ArH), 7.63 (bs, 1H, C(O)NH), 7.43 (s, 1H, ArH), 6.29 (bs, 1H, OH), 6.21 (s, 1H, ArH), 4.55 (d, J=14.0 Hz, 1H, CH$_2$), 4.18 (d, J=14.0 Hz, 1H, CH$_2$), 1.51 (s, 3H, CH$_3$) 1.47 (s, 9H, C(CH$_3$)$_3$); $^{19}$F NMR (CDCl$_3$, 400 MHz) δ −62.11; MS (ESI) m/z 453.16 [M−H]$^−$; 477.16 [M+Na]$^+$.

(S)-3-(4-Acetamido-1H-pyrazol-1-yl)-N-(4-cyano-3-(trifluoromethyl)phenvy)-2-hydroxy-2-methylpropanamide (C$_{17}$H$_{16}$F$_3$N$_5$O$_3$) (1031)

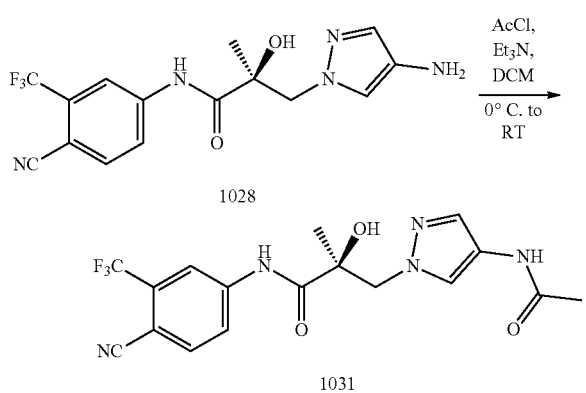

Under argon atmosphere, to a solution of 1028 (150 mg, 0.43 mmol) and triethyl amine (0.09 mL, 0.64 mmol) in 10 mL of anhydrous DCM was added acetyl chloride (AcCl, 0.038 mL, 0.53 mmol) at an ice-water bath. After stirring for 30 min, the temperature was raised to RT and the mixture was stirred for 2 h. The reaction mixture was condensed under reduced pressure, and then dispersed into 10 mL of EtOAc, washed with water, evaporated, dried over anhydrous MgSO$_4$, and evaporated to dryness. The mixture was purified with flash column chromatography as an eluent acetone/hexane (1/2, v/v) to produce 1031 (150 mg, 89%) as white solids.

Compound 1031 was characterized as follows: $^1$H NMR (CDCl$_3$, 400 MHz) δ 9.08 (bs, 1H, C(O)NH), 7.92 (bs, 1H, C(O)NH), 7.82-7.80 (m, 2H, ArH), 7.69 (d, J=8.4 Hz, 1H, ArH), 7.44 (s, 1H, ArH), 7.15 (s, 1H, ArH), 6.10 (bs, 1H, OH), 4.49 (d, J=13.6 Hz, 1H, CH$_2$), 4.13 (d, J=13.6 Hz, 1H, CH$_2$), 2.04 (s, 3H, NH(CO)CH$_3$), 1.39 (s, 3H, CH$_3$); $^{19}$F NMR (CDCl$_3$, 400 MHz) δ −62.20; MS (ESI) m/z 394.06 [M−H]$^−$; 396.11 [M+H]$^+$.

(S)-3-(4-Amino-1H-pyrazol-1-yl)-1-((4-cyano-3-(trifluoromethyl)phenyl)amino)-2-methyl-1-oxopropan-2-yl 2-chloroacetate (C$_{17}$H$_{15}$ClF$_3$N$_5$O$_3$) (1032); and (S)-3-(4-(2-Chloroacetamido)-1H-pyrazol-1-yl)-N-(4-cyano-3-(trifluoromethyl)phenyl)-2-hydroxy-2-methylpropanamide (C$_{17}$H$_{15}$ClF$_3$N$_5$O$_3$) (1033)

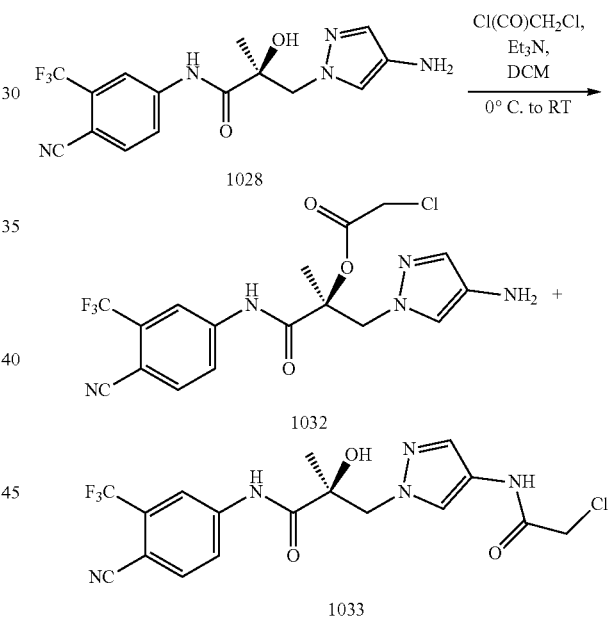

Under argon atmosphere, to a solution of 1028 (263 mg, 0.75 mmol) and triethyl amine (0.16 mL, 1.12 mmol) in 50 mL of anhydrous DCM was added chloroacetyl chloride (0.074 mL, 0.94 mmol) at an ice-water bath. After stirring for 30 min, the temperature was raised to RT and the mixture was stirred for 2 h. The reaction mixture was condensed under reduced pressure, and then dispersed into 30 mL of EtOAc, washed with water, evaporated, dried over anhydrous MgSO$_4$, and evaporated to dryness. The mixture was purified with flash column chromatography as an eluent EtOAc/hexane (3/1, v/v) to produce 1032 (105 mg, 33%) and 1033 (117 mg, 36%) as yellowish solids. Total yield 70%.

Compound 1032 was characterized as follows: $^1$H NMR (CDCl$_3$, 400 MHz) δ 9.22 (bs, NH$_2$), 8.10 (bs, 1H, C(O)NH), 7.93 (d, J=1.8 Hz, 1H, ArH), 7.86 (d, J=1.8 Hz, 1H, ArH), 7.79 (d, J=8.4 Hz, 1H, ArH), 5.16 (d, J=14.8 Hz, 1H, CH₂), 4.62 (d, J=14.8 Hz, 1H, CH₂), 4.11 (s, 2H, CH₂Cl), 1.77 (s, 3H, CH₃); ¹⁹F NMR (CDCl₃, 400 MHz) δ 114.77; MS (ESI) m/z 428.03 [M−H]⁻; 452.02 [M+Na]⁺.

Compound 1033 was characterized as follows: ¹H NMR (CDCl₃, 400 MHz) δ 9.12 (bs, 1H, C(O)NH), 8.12 (bs, 1H, C(O)NH), 7.99 (d, J=1.6 Hz, 1H, ArH), 7.92 (s, 1H, ArH), 7.87 (dd, J=8.8, 1.6 Hz, 1H, ArH), 7.76 (d, J=8.8 Hz, 1H, ArH), 7.61 (s, 1H, ArH), 6.11 (bs, 1H, OH), 4.60 (d, J=13.6 Hz, 1H, CH₂), 4.22 (d, J=13.6 Hz, 1H, CH₂), 4.17 (s, 2H, CH₂Cl), 1.47 (s, 3H, CH₃); ¹⁹F NMR (CDCl₃, 400 MHz) δ −62.19; MS (ESI) m/z 428.00 [M−H]⁻; 452.01 [M+Na]⁺.

(S)-Methyl (1-(3-((4-cyano-3-(trifluoromethyl)phenyl)amino)-2-hydroxy-2-methyl-3-oxopropyl)-1H-pyrazol-4-yl)carbamate (C₁₇H₁₆F₃N₅O₄) (1034)

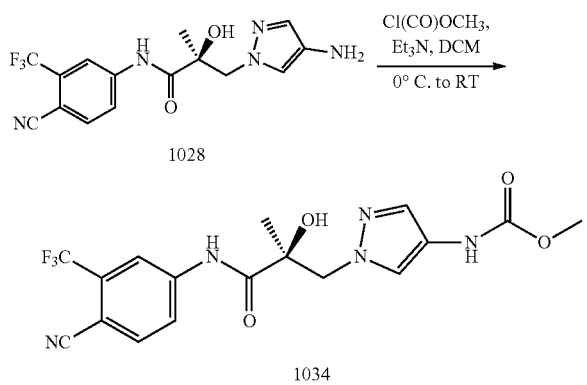

Under argon atmosphere, to a solution of 1028 (170 mg, 0.48 mmol) and triethyl amine (0.16 mL, 1.15 mmol) in 10 mL of anhydrous DCM was added methyl carbonochloridate (0.04 mL, 0.58 mmol) at ice-water bath. After stirring for 30 min, the temperature was raised to RT and the mixture stirred for 2 h. The reaction mixture was condensed under reduced pressure, and then dispersed into 10 mL of EtOAc, washed with water, evaporated, dried over anhydrous MgSO₄, and evaporated to dryness. The mixture was purified with flash column chromatography as an eluent EtOAc/hexane (2/1, v/v) to produce 1034 (141 mg, 71%) as white solids.

Compound 1034 was characterized as follows: ¹H NMR (CDCl₃, 400 MHz) δ 9.07 (bs, 1H, C(O)NH), 7.91 (s, 1H, ArH), 7.79 (d, J=7.2 Hz, 1H, ArH), 7.69 (d, J=7.2 Hz, 1H, ArH), 7.57 (s, 1H, ArH), 7.40 (s, 1H, ArH), 6.33 (bs, 1H, NH), 6.08 (bs, 1H, OH), 4.50 (d, J=13.6 Hz, 1H, CH₂), 4.12 (d, J=13.6 Hz, 1H, CH₂), 3.67 (s, 3H, NH(CO)OCH₃), 1.39 (s, 3H, CH₃); ¹⁹F NMR (CDCl₃, 400 MHz) δ −62.21; MS (ESI) m/z 410.30 [M−H]⁻; 413.21 [M+H]⁺.

(S)-3-(4-Acetyl-1H-pyrazol-1-yl)-N-(4-cyano-3-(trifluoromethyl)phenyl)-2-hydroxy-2-methylpropanamide (C₁₇H₁₅F₃N₄O₃) (1035)

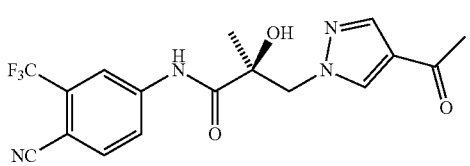 [SMILES: CC(=O)c1cnn(C[C@](C)(O)C(=O)Nc2ccc(C#N)c(C(F)(F)F)c2)c1]

To a solution of 1-(1H-pyrazol-4-yl)ethanone (0.10 g, 0.000908 mol) in anhydrous THF (5 mL), which was cooled in an ice water bath under an argon atmosphere, was added sodium hydride (60% dispersion in oil, 0.11 g, 0.002725 mol). After addition, the resulting mixture was stirred for 3 h. (R)-3-Bromo-N-(4-cyano-3-(trifluoromethyl)phenyl)-2-hydroxy-2-methylpropanamide (8, 0.32 g, 0.000908 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using DCM and ethyl acetate (19:1) as eluent to afford 70 mg (20%) of the titled compound as yellowish solid.

Compound 1035 was characterized as follows: ¹H NMR (400 MHz, DMSO-d₆) δ 10.37 (s, 1H, NH), 8.45 (d, J=1.2 Hz, 1H, ArH), 8.25 (s, 1H, Pyrazole-H), 8.23 (d, J=8.2 Hz, J=1.2 Hz, 1H, ArH), 8.10 (d, J=8.2 Hz, 1H, ArH), 7.86 (s, 1H, Pyrazole-H), 6.37 (s, 1H, OH), 4.50 (d, J=14.0 Hz, 1H, CH), 4.33 (d, J=14.0 Hz, 1H, CH), 2.34 (s, 3H, CH₃), 1.39 (s, 3H, CH₃); mass (ESI, Negative): 379.14 [M−H]⁻; (ESI, Positive): 413.18 [M+Na]⁺.

(S)—N-(4-Cyano-3-(trifluoromethyl)phenyl)-2-hydroxy-2-methyl-3-(4-nitro-1H-pyrazol-1-yl)propanamide (C₁₅H₁₂F₃N₅O₄) (1036)

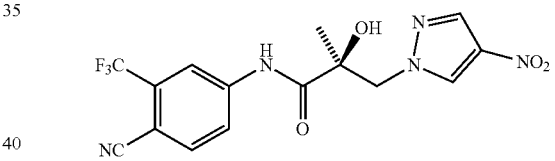

To a solution of 4-nitro-1H-pyrazole (0.10 g, 0.0008844 mol) in anhydrous THF (5 mL), which was cooled in an ice water bath under an argon atmosphere, was added sodium hydride (60% dispersion in oil, 0.106 g, 0.002653 mol). After addition, the resulting mixture was stirred for 3 h. (R)-3-Bromo-N-(4-cyano-3-(trifluoromethyl)phenyl)-2-hydroxy-2-methylpropanamide (8, 0.31 g, 0.0008844 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (1:1) as eluent to afford 0.15 g (44%) of the titled compound as off-white solid.

Compound 1036 was characterized as follows: ¹H NMR (400 MHz, DMSO-d₆) δ 10.36 (s, 1H, NH), 8.69 (s, 1H, Pyrazole-H), 8.45 (d, J=1.2 Hz, 1H, ArH), 8.23 (d, J=8.8 Hz, J=1.2 Hz, 1H, ArH), 8.19 (s, 1H, Pyrazole-H), 8.11 (d, J=8.8 Hz, 1H, ArH), 6.47 (s, 1H, OH), 4.56 (d, J=14.0 Hz, 1H, CH), 4.38 (d, J=14.0 Hz, 1H, CH), 1.41 (s, 3H, CH₃); mass (ESI, Negative): 382.13 [M−H]⁻.

111

(R)-3-Bromo-N-(6-cyanopyridin-3-)-2-hydroxy-2-methylpropanamide ($C_{10}H_{10}BrN_3O_2$) (1037)

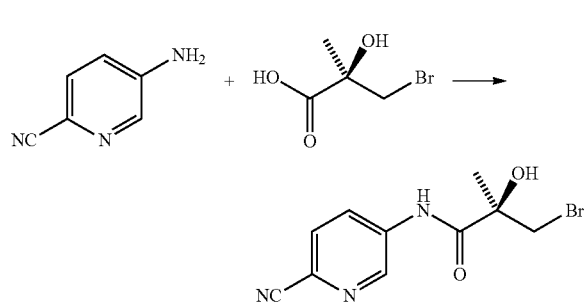

(R)-3-Bromo-2-hydroxy-2-methylpropanoic acid (4, 3.24 g, 0.017674 mol) reacted with thionyl chloride (2.53 g, 0.021208 mol), trimethylamine (2.33 g, 0.022976 mol), and 5-aminopicolinonitrile (2.00 g, 0.01679 mol) to afford the titled compound. The product was purified by a silica gel column using DCM and methanol (19:1) as eluent to afford 4.40 g (92%) of the titled compound as yellowish solid.

Compound 1037 was characterized as follows: $^1$H NMR (400 MHz, DMSO-$d_6$) δ 10.42 (s, 1H, NH), 9.12 (d, J=2.4 Hz, 1H, ArH), 8.44 (dd, J=8.8 Hz, J=2.4 Hz, 1H, ArH), 8.00 (d, J=8.8 Hz, 1H, ArH), 6.40 (s, 1H, OH), 3.83 (d, J=10.4 Hz, 1H, CH), 3.59 (d, J=10.4 Hz, 1H, CH), 1.49 (s, 3H, $CH_3$); mass (ESI, Positive): 284.0042 [M+H]$^+$.

(R)-3-Bromo-N-(6-cyano-5-(trifluoromethyl)pyridin-3-yl)-2-hydroxy-2-methylpropanamide ($C_{11}H_9BrF_3N_3O_2$) (1038)

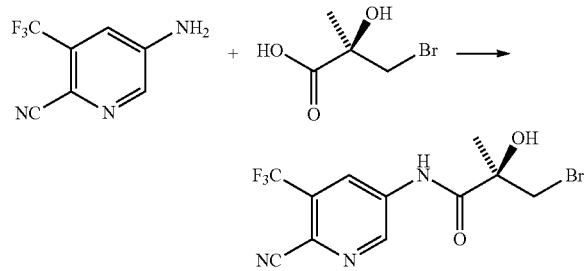

(R)-3-Bromo-2-hydroxy-2-methylpropanoic acid (4, 1.03 g, 0.005625 mol) reacted with thionyl chloride (0.80 g, 0.006751 mol), trimethylamine (0.74 g, 0.007313 mol), and 5-amino-3-(trifluoromethyl)picolinonitrile (1.00 g, 0.005344 mol) to afford the titled compound. The product was purified by a silica gel column using hexanes and ethyl acetate (2:1) as eluent to afford 1.70 g (90%) of the titled compound as yellowish solid.

Compound 1038 was characterized as follows: $^1$H NMR (400 MHz, DMSO-$d_6$) δ 10.82 (s, 1H, NH), 9.41 (d, J=2.0 Hz, 1H, ArH), 8.90 (d, J=2.0 Hz, 1H, ArH), 6.51 (s, 1H, OH), 3.84 (d, J=10.4 Hz, 1H, CH), 3.61 (d, J=10.4 Hz, 1H, CH), 1.50 (s, 3H, $CH_3$); mass (ESI, Positive): 351.9915 [M+H]$^+$.

112

(R)-3-Bromo-2-hydroxy-2-methyl-N-(quinazolin-6-yl)propanamide ($C_{12}H_{12}BrN_3O_2$) (1039)

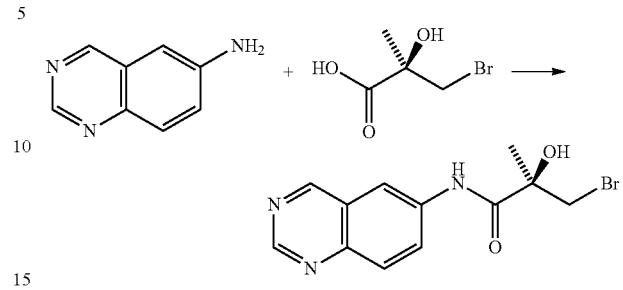

(R)-3-Bromo-2-hydroxy-2-methylpropanoic acid (2.65 g, 0.014503 mol) was reacted with thionyl chloride (2.07 g, 0.017404 mol), trimethylamine (1.91 g, 0.018854 mol), and quinazolin-6-amine (2.00 g, 0.013778 mol) to afford the titled compound. The product was purified by a silica gel column using hexanes and ethyl acetate (3:1 to 2:1) as eluent to afford 0.71 g of the titled compound as yellowish solid.

Compound 1039 was characterized as follows: Mass (ESI, Positive) 309.98 [M+H]$^+$.

3-Bromo-N-(4-cyano-3-(trifluoromethyl)phenyl)propanamide ($C_{11}H_8BrF_3N_2O$) (1040)

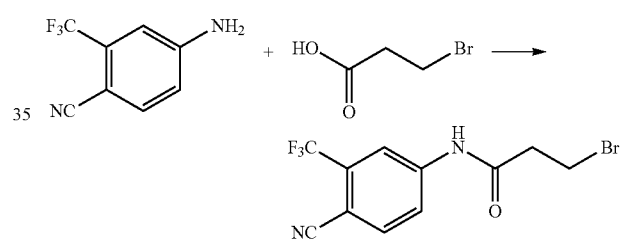

3-Bromopropanoic acid (2.00 g, 0.0130745 mol) reacted with thionyl chloride (1.87 g, 0.0156894 mol), trimethylamine (1.72 g, 0.0169968 mol), and 4-amino-2-(trifluoromethyl)benzonitrile (2.31 g, 0.0124207 mol) to afford the titled compound. The product was purified by a silica gel column using DCM and methanol (19:1) as eluent to afford 2.31 g (55%) of the titled compound as yellowish solid.

Compound 1040 was characterized as follows: $^1$H NMR (400 MHz, DMSO-$d_6$) δ 10.85 (s, 1H, NH), 8.28 (d, J=2.4 Hz, 1H, ArH), 8.12 (dd, J=8.8 Hz, J=2.4 Hz, 1H, ArH), 7.99 (d, J=8.8 Hz, 1H, ArH), 3.76 (t, J=6.0 Hz, 2H, $CH_2$), 3.06 (t, J=6.0 Hz, 2H, $CH_2$).

(S)—N-(2-Chloropyridin-4-yl)-3-(4-fluoro-1H-pyrazol-1-yl)-2-hydroxy-2-methylpropanamide ($C_{12}H_{12}ClFN_4O_2$) (1041)

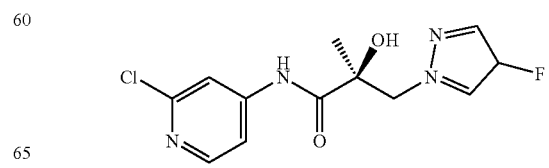

(R)-3-Bromo-N-(2-chloropyridin-4-yl)-2-hydroxy-2-methylpropanamide

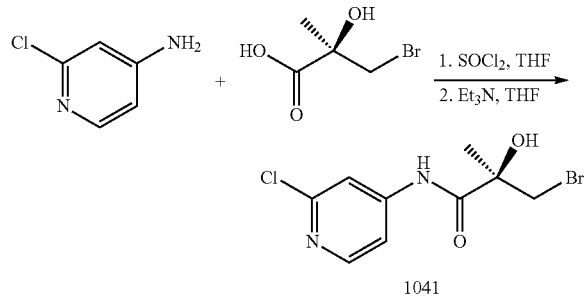

1041

Thionyl chloride (11.2 mL, 0.154 mol) was added dropwise to a cooled solution (less than 4° C.) of (R)-3-bromo-2-hydroxy-2-methylpropanoic acid (4, 18.3 g, 0.100 mol) in 100 mL of THF under an argon atmosphere. The resulting mixture stirred for 3 h under the same condition. To this was added Et$_3$N (25.7 mL, 0.185 mol) and then stirred for 20 min under the same condition. After 20 min, 2-chloropyridin-4-amine (9.89 g, 0.077 mol), 100 mL of THF were added and then the mixture was allowed to stir overnight at RT. The solvent was removed under reduced pressure to give a solid, which was treated with 100 mL of H$_2$O, and extracted with EtOAc (2×50 mL). The combined organic extracts were washed with saturated NaHCO$_3$ solution (2×100 mL) and brine (100 mL). The organic layer was dried over MgSO$_4$ and concentrated under reduced pressure to give a solid, which was dissolved and purified by column chromatography using CH$_2$Cl$_2$/EtOAc (80:20) to give a solid. This solid recrystallized from CH$_2$Cl$_2$/hexane to give 12.6 g (43%) of (R)-3-bromo-N-(2-chloropyridin-4-yl)-2-hydroxy-2-methylpropanamide as a light-yellow solid. $^1$H NMR (400 MHz, CDCl$_3$) δ 9.06 (bs, 1H, NH), 8.31 (d, J=5.6 Hz, 1H), 7.77 (d, J=0.8 Hz, 1H), 7.45 (dd, J=5.6, 0.8 Hz, 1H), 4.81 (bs, 1H, OH), 3.97 (d, J=10.6 Hz, 1H), 3.60 (d, J=10.6 Hz, 1H), 1.64 (s, 3H); MS (ESI) m/z 295.28 [M+H]$^+$.

(S)—N-(2-Chloropyridin-4-yl)-3-(4-fluoro-1H-pyrazol-1-yl)-2-hydroxy-2-methylpropanamide (C$_{12}$H$_{12}$ClFN$_4$O$_2$)

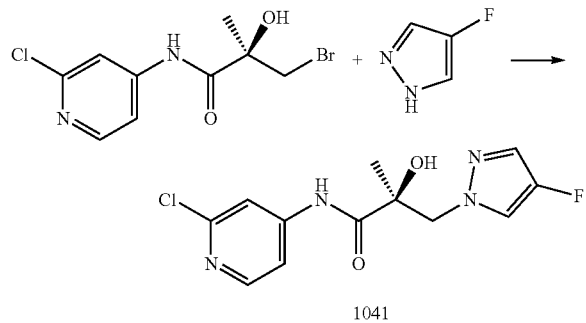

1041

To a dry, nitrogen-purged 100 mL round-bottom flask equipped with a dropping funnel under argon atmosphere, NaH of 60% dispersion in mineral oil (96 mg, 2.4 mmol) was added in 10 mL of anhydrous THF solvent at ice-water bath. 4-Fluoro-1H-pyrazole (103 mg, 1.2 mmol) was added and the solution stirred 30 min at the ice-water bath. Into the flask, the solution of (R)-3-bromo-N-(2-chloropyridin-4-yl)-2-hydroxy-2-methylpropanamide (293 mg, 1.0 mmol) in 5 mL of anhydrous THF was added through dropping funnel under argon atmosphere at the ice-water bath and stirred overnight at RT. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography using as an eluent EtOAc/hexane as a 1:2 ratio to produce compounds to produce the titled compound (55%) as a white solid.

Compound 1041 was characterized as follows: $^1$H NMR (400 MHz, CDCl$_3$) δ 8.90 (bs, 1H, NH), 8.26 (d, J=5.6 Hz, 1H), 7.63 (s, 1H), 7.75 (d, J=4.2 Hz, 1H), 7.33 (d, J=4.2 Hz, 1H), 7.31 (dd, J=5.6, 1.2 Hz, 1H), 5.88 (s, 1H, OH), 4.53 (d, J=13.6 Hz, 1H), 4.14 (d, J=13.6 Hz, 1H), 1.45 (s, 3H); $^{19}$F NMR (CDCl$_3$, decoupled) δ −176.47; MS (ESI) m/z 298.98 [M+H]$^+$; 296.96 [M−H]$^−$.

(S)-3-Azido-N-(4-cyano-3-(trifluoromethyl)phenyl)-2-hydroxy-2-methylpropanamide (C$_{12}$H$_{10}$F$_3$N$_5$O$_2$) (1042)

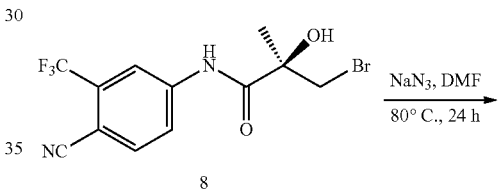

8

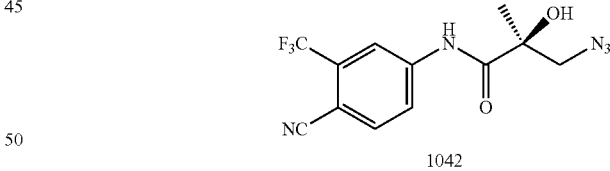

1042

A solution of 8 (351 mg, 1 mmol) in DMF (10 mL) was treated with NaN$_3$ (325 mg, 5 mmol) under argon at 80° C. for 24 h. The reaction mixture was then, cooled and extracted with CH$_2$Cl$_2$ (3×20 mL). The combined organic layers were washed with H$_2$O (3×20 mL) and brine, dried and evaporated to give a crude oil, which was purified by silica gel chromatography (EtOAc/n-hexane=1:2, v/v) to afford the titled compound as a yellow solid (224 mg, 72%).

Compound 1042 was characterized as follows: $^1$H NMR (400 MHz, CDCl$_3$) δ 9.00 (bs, 1H, NH), 8.08 (s, 1H), 7.95 (d, J=8.4 Hz, 1H), 7.81 (d, J=8.4 Hz, 1H), 3.92 (d, J=12.4 Hz, 1H), 3.50 (d, J=12.4 Hz, 1H), 2.96 (s, 1H, OH), 1.54 (s, 3H); $^{19}$F NMR (CDCl$_3$, decoupled) δ −62.21; MS (ESI) m/z 314.03 [M+H]$^+$; 312.18 [M−H]$^−$.

(S)—N-(6-Cyano-5-(trifluoromethyl)pyridin-3-yl)-2-hydroxy-2-methyl-3-(4-(trifluoromethyl)-1H-pyrazol-1-yl)propanamide ($C_{15}H_{11}F_6N_5O_2$) (1043)

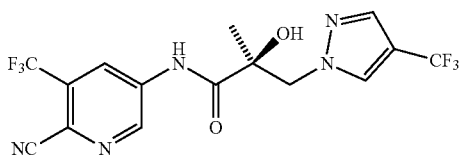 [SMILES: C[C@](O)(Cn1cc(C(F)(F)F)cn1)C(=O)Nc1cnc(C#N)c(C(F)(F)F)c1]

To a solution of 4-trifluoromethyl-pyrazole (0.10 g, 0.0007349 mol) in anhydrous THF (5 mL), which was cooled in an ice water bath under an argon atmosphere, was added sodium hydride (60% dispersion in oil, 0.09 g, 0.002025 mol). After addition, the resulting mixture was stirred for 3 h. (R)-3-Bromo-N-(6-cyano-5-(trifluoromethyl)pyridin-3-yl)-2-hydroxy-2-methylpropanamide (0.26 g, 0.0007349 mol) was added to the above solution, and the resulting reaction mixture was allowed to stir overnight at RT under argon. The reaction was quenched by water, and extracted with ethyl acetate. The organic layer was washed with brine, dried with $MgSO_4$, filtered, and concentrated under vacuum. The product was purified by a silica gel column using DCM and ethyl acetate (19:1) as eluent to afford 0.18 g (60%) of the titled compound as white solid.

Compound 1043 was characterized as follows: $^1$H NMR (400 MHz, DMSO-$d_6$) δ 10.63 (s, 1H, NH), 9.31 (s, 1H, ArH), 8.80 (s, 1H, ArH), 8.32 (s, 1H, Pyrazole-H), 7.81 (s, 1H, Pyrazole-H), 6.48 (s, 1H, OH), 4.55 (d, J=14.0 Hz, 1H, CH), 4.37 (d, J=14.0 Hz, 1H, CH), 1.42 (s, 3H, $CH_3$); mass (ESI, Negative): 406.08 [M−H]$^−$; (ESI, Positive): [M+H]$^+$, 430.13 [M+Na]$^+$.

(S)—N-(4-Cyano-3-(trifluoromethyl)phenyl)-3-(5-(4-fluorophenyl)-1H-1,2,3-triazol-1-yl)-2-hydroxy-2-methylpropanamide ($C_{20}H_{15}F_4N_5O_2$) (1044)

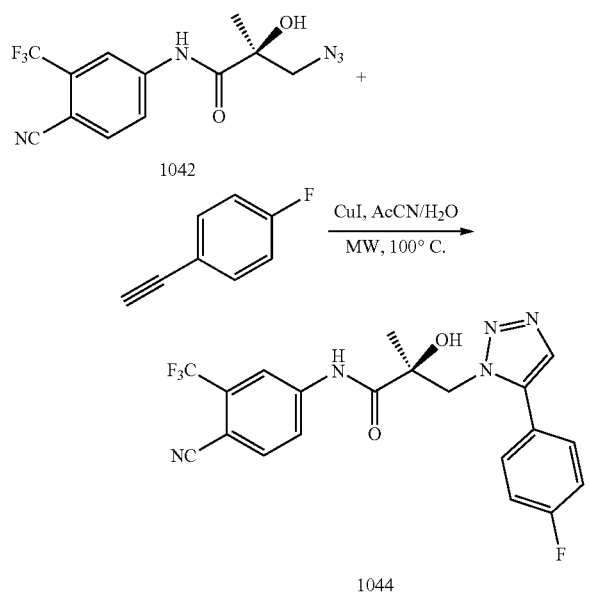

A mixture of 1042 (57 mg, 0.18 mmol), 1-ethylnyl-4-fluorobenzene (0.015 mL, 0.18 mmol), and copper iodide (11 mg, 0.055 mmol) in AcCN/$H_2O$ (1/0.5 mL) were loaded into a vessel with a cap. The reaction vessels were placed in a reactor block in the microwave reactor. A programmable microwave (MW) irradiation cycle of 30 min on (300 W) at 100° C. and 25 min off (fan-cooled) was executed twice because starting materials were shown on TLC after the first cycle (total irradiation time, 60 min). The mixture was transferred to a round bottom flask to be concentrated under reduced pressure and poured into EtOAc, which was washed with water and dried over $MgSO_4$, concentrated, and purified by silica gel chromatography (EtOAc/hexane=2:1) to afford the titled compound as yellow solid (69.8 mg, 90%).

Compound 1044 was characterized as follows: $^1$H NMR (400 MHz, acetone-$d_6$) δ 9.00 (bs, 1H, NH), 8.44 (s, 1H), 8.30 (s, 1H), 8.25 (d, J=8.4 Hz, 1H), 8.02 (d, J=8.4 Hz, 1H), 7.89 (dd, J=8.0, 2.4 Hz, 2H), 7.20 (d, J=8.8 Hz, 2H), 5.67 (s, 1H, OH), 4.92 (d, J=14.0 Hz, 1H), 4.72 (d, J=14.0 Hz, 1H), 1.60 (s, 3H); $^{19}$F NMR (acetone-$d_6$, decoupled) δ 114.68, 61.64; MS (ESI) m/z 432.11 [M−H]-434.08 [M+H]$^+$. The structure of 1044 was distinguished from its isomer 1045 (see below) by the 2D NMR techniques of NOESY and COSY.

(S)—N-(4-Cyano-3-(trifluoromethyl)phenyl)-3-(4-(4-fluorophenyl)-1H-1,2,3-triazol-1-yl)-2-hydroxy-2-methylpropanamide ($C_{20}H_{15}F_4N_5O_2$) (1045)

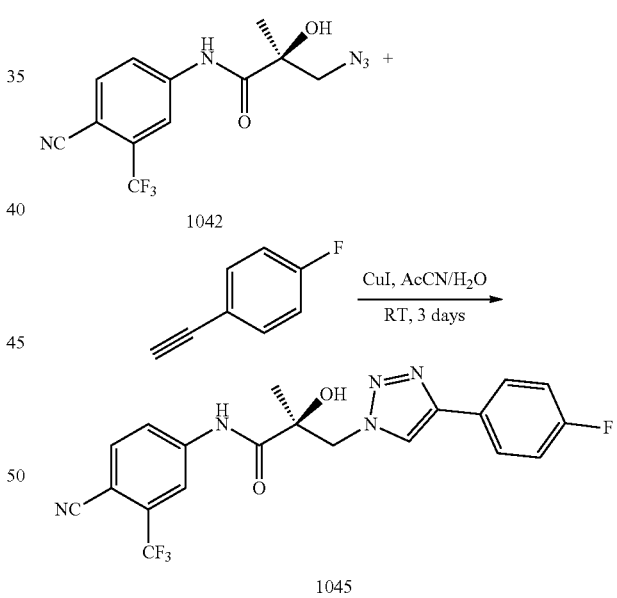

To a suspension of copper(I)iodide (11 mg, 0.055 mmoL) in acetonitrile (7 mL)/water (3 mL) was added 1042 (57 mg, 0.182 mmol) at RT and then 1-ethynyl-4-fluorobenzene (0.015 mL, 0.182 mmol) was added. The resulting reaction mixture was stirred at RT for 3 days. The mixture was evaporated under reduced pressure, poured into water:brine (1:1, v/v) and then extracted with ethyl acetate. The combined organic extracts were then washed with brine, dried over sodium sulfate, filtered and evaporated. Purification was by chromatography (silica, 60% ethyl acetate in hexane) to afford a yellow solid (51.3 mg, 65%).

Compound 1045 was characterized as follows: $^1$H NMR (400 MHz, CDCl$_3$) δ 9.07 (bs, 1H, NH), 7.82-7.80 (m, 1H), 7.79 (s, 1H), 7.76-7.74 (m, 2H), 7.72 (dd, J=8.2, 2.8 Hz, 2H), 7.10 (t, J=8.8 Hz, 2H), 5.15 (bs, 1H, OH), 4.96 (d, J=14.0 Hz, 1H), 4.61 (d, J=14.0 Hz, 1H), 1.62 (s, 3H); $^{19}$F NMR (CDCl$_3$, decoupled) δ −62.24, −112.36; MS (ESI) m/z 432.17 [M−H]-434.09 [M+H]$^+$. The structure of 1045 was distinguished from its isomer 1044 (see above) by the 2D NMR techniques of NOESY and COSY. E.g, 1045 showed an NOE cross-peak between the methylene proton and the triazole proton indicating that these protons are within ~4.5 Å of each other as would be the case for 1045 but not 1044. This cross-peak was not seen for 1044.

(S)-3-(4-Fluoro-1H-pyrazol-1-yl)-2-hydroxy-2-methyl-N-(4-nitro-3-(trifluoromethyl)phenyl)-propanamide (C$_{14}$H$_{12}$F$_4$N$_4$O$_4$) (1046)

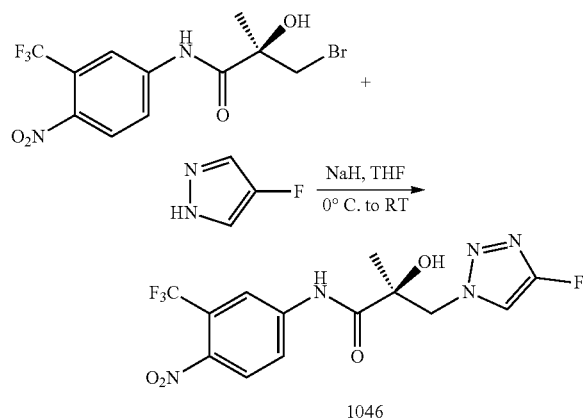

1046

To a dry, nitrogen-purged 100 mL round-bottom flask equipped with a dropping funnel under argon atmosphere containing 4-fluoro-1H-pyrazole (691 mg, 8.03 mmol), NaH of 60% dispersion in mineral oil (674 mg, 16.9 mmol) was added in 60 mL of anhydrous THF solvent at ice-water bath. The mixture was stirred 30 min at the ice-water bath. Into the flask through dropping funnel, a solution of (R)-3-bromo-2-hydroxy-2-methyl-N-(4-nitro-3-(trifluoromethyl)phenyl) propanamide (2.98 g, 8.03 mmol) in 10 mL of anhydrous THF was added under argon atmosphere at the ice-water bath, and stirred overnight at RT. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography using as an eluent EtOAc/hexane in a 1:2 ratio to produce the titled compound (2.01 g, 67%) as yellow solid.

Compound 1046 was characterized as follows: $^1$H NMR (400 MHz, CDCl$_3$) δ 9.14 (bs, 1H, NH), 8.01 (s, 1H), 7.97-7.91 (m, 2H), 7.38 (d, J=3.6 Hz, 1H), 7.35 (d, J=4.4 Hz, 1H), 5.95 (s, 1H, OH), 4.56 (d, J=14.0 Hz, 1H), 4.17 (d, J=14.0 Hz, 1H), 1.48 (s, 3H); $^{19}$F NMR (CDCl$_3$, decoupled) 6-60.13, −176.47; MS (ESI) m/z 375.08 [M−H]; 377.22 [M+H]$^+$; 399.04 [M+Na]$^+$.

(S)—N-(4-Cyano-3-(trifluoromethyl)phenyl)-2-hydroxy-3-(4-iodo-1H-pyrazol-1-yl)-2-methylpropanamide (C$_{15}$H$_{12}$F$_3$IN$_4$O$_2$) (1047)

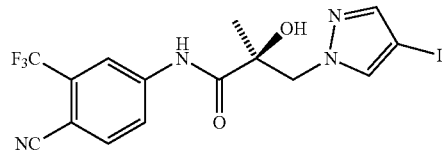

To a solution of 4-iodo-1H-pyrazole (0.20 g, 0.001031 mol) in anhydrous THF (5 mL), which was cooled in an ice water bath under an argon atmosphere, was added sodium hydride (60% dispersion in oil, 0.124 g, 0.003093 mol). After addition, the resulting mixture was stirred for 3 h. (R)-3-Bromo-N-(4-cyano-3-(trifluoromethyl)phenyl)-2-hydroxy-2-methylpropanamide (8, 0.36 g, 0.001031 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using DCM and ethyl acetate (19:1) as eluent to afford 0.25 g (52%) of the titled compound as off-white solid.

Compound 1047 was characterized as follows: $^1$H NMR (400 MHz, DMSO-d$_6$) δ 10.36 (s, 1H, NH), 8.45 (s, 1H, ArH), 8.23 (d, J=8.8 Hz, J=1.2 Hz, 1H, ArH), 8.10 (d, J=8.8 Hz, 1H, ArH), 7.78 (s, 1H, Pyrazole-H), 7.46 (s, 1H, Pyrazole-H), 6.31 (s, 1H, OH), 4.48 (d, J=14.0 Hz, 1H, CH), 4.31 (d, J=14.0 Hz, 1H, CH), 1.35 (s, 3H, CH$_3$); mass (ESI, Negative): 463.18 [M−H]$^-$; (ESI, Positive): 486.96 [M+Na]$^+$.

(S)-3-(4-Cyano-1H-pyrazol-1-yl)-N-(4-cyano-3-(trifluoromethyl)phenyl)-2-hydroxy-2-methylpropanamide (C$_{16}$H$_{12}$F$_3$N$_5$O$_2$) (1048)

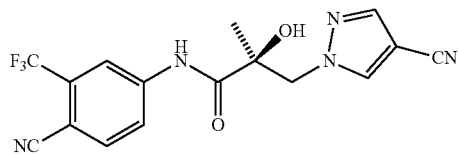 [SMILES: C[C@](O)(Cn1cc(C#N)cn1)C(=O)Nc1ccc(C#N)c(C(F)(F)F)c1]

To a solution of 1H-pyrazole-4-carbonitrile (0.10 g, 0.001074 mol) in anhydrous THF (5 mL), which was cooled in an ice water bath under an argon atmosphere, was added sodium hydride (60% dispersion in oil, 0.11 g, 0.003223 mol). After addition, the resulting mixture was stirred for 3 h. (R)-3-Bromo-N-(4-cyano-3-(trifluoromethyl)phenyl)-2-hydroxy-2-methylpropanamide (8, 0.377 g, 0.001074 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using hexane and ethyl acetate (1:1 to 1:2) as eluent to afford 0.18 g (46%) of the titled compound as white solid.

Compound 1048 was characterized as follows: $^1$H NMR (400 MHz, DMSO-d$_6$) δ 10.35 (s, 1H, NH), 8.45 (d, J=1.2 Hz, 1H, ArH), 8.43 (s, 1H, Pyrazole-H), 8.22 (d, J=8.8 Hz, J=1.2 Hz, 1H, ArH), 8.10 (d, J=8.8 Hz, 1H, ArH), 7.98 (s, 1H, Pyrazole-H), 6.41 (s, 1H, OH), 4.45 (d, J=14.0 Hz, 1H, CH), 4.36 (d, J=14.0 Hz, 1H, CH), 1.38 (s, 3H, CH$_3$); mass (ESI, Negative): 362.11 [M−H]$^-$; (ESI, Positive): 386.07 [M+Na]$^+$.

(S)-3-(4-Chloro-1H-pyrazol-1-yl)-N-(4-cyano-3-(trifluoromethyl)phenyl)-2-hydroxy-2-methylpropanamide (C$_{15}$H$_{12}$ClF$_3$N$_4$O$_2$) (1049)

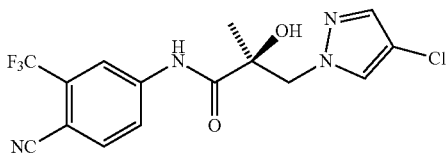 [SMILES: C[C@](O)(Cn1cc(Cl)cn1)C(=O)Nc1ccc(C#N)c(C(F)(F)F)c1]

To a solution of 4-chloro-1H-pyrazole (0.15 g, 0.001463 mol) in anhydrous THF (5 mL), which was cooled in an ice water bath under an argon atmosphere, was added sodium hydride (60% dispersion in oil, 0.18 g, 0.004389 mol). After addition, the resulting mixture was stirred for 3 h. (R)-3-Bromo-N-(4-cyano-3-(trifluoromethyl)phenyl)-2-hydroxy-2-methylpropanamide (8, 0.51 g, 0.001463 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using dichloromethane and ethyl acetate (19:1) as eluent to afford 0.30 g (55%) of the titled compound as white solid.

Compound 1049 was characterized as follows: $^1$H NMR (400 MHz, DMSO-d$_6$) δ 10.38 (s, 1H, NH), 8.46 (s, 1H, ArH), 8.23 (d, J=8.6 Hz, J=1.2 Hz, 1H, ArH), 8.10 (d, J=8.6 Hz, 1H, ArH), 7.83 (s, 1H, Pyrazole-H), 7.47 (s, 1H, Pyrazole-H), 6.34 (s, 1H, OH), 4.45 (d, J=14.0 Hz, 1H, CH), 4.27 (d, J=14.0 Hz, 1H, CH), 1.36 (s, 3H, CH$_3$); mass (ESI, Negative): 371.68 [M−H]$^-$.

Example 2

Octanol-Water Partition Coefficient (Log P)

Log P is the log of the octanol-water partition coefficient, commonly used early in drug discovery efforts as a rough estimate of whether a particular molecule is likely to cross biological membranes. Log P was calculated using ChemDraw Ultra version is 12.0.2.1016 (Perkin-Elmer, Waltham, Mass. 02451). Calculated Log P values are reported in Table 1 in the column labeled 'Log P (−0.4 to +5.6)'. Lipinski's rule of five is a set of criteria intended to predict oral bioavailability. One of these criteria for oral bioavailability is that the Log P is between the values shown in the column heading (−0.4 (relatively hydrophilic) to +5.6 (relatively lipophilic) range), or more generally stated <5. One of the goals of SARD design was to improve water solubility. The monocyclic templates of this invention such as the pyrazoles, pyrroles, etc. were more water soluble than earlier analogs. For instance, one may compare the Log P values of SARDs from other templates, e.g., alkyl-amine 17, indoline 100 and indole 11, to the monocyclics of the invention (1001-1049).

TABLE 1

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (µL/min/mg) |
|---|---|---|---|---|---|---|---|---|
| | | | | K$_i$ (nM) (DHT = 1 nM) | IC$_{50}$ (nM) | Full Length % inhibition at 1,10 µM | S.V. % inhibition at 10 µM | |
| Enobosarm (agonist) | 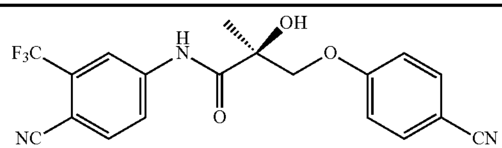 | 3.44 | 389.89 | 20.21 | ~20 (EC$_{50}$) | Not applicable | Not applicable | |
| R-Bicalutamide | 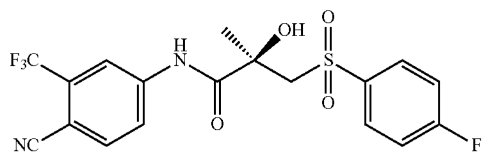 [SMILES: C[C@](O)(CS(=O)(=O)c1ccc(F)cc1)C(=O)Nc1ccc(C#N)c(C(F)(F)F)c1] | 2.57 | 430.37 | 508.84 | 248.2 | 0 | 0 | |
| Enzalutamide | 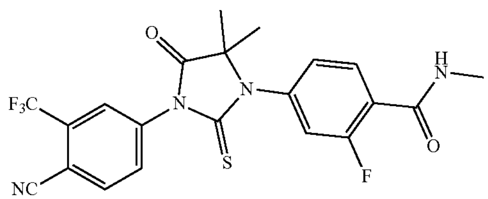 [SMILES: CNC(=O)c1ccc(N2C(=S)N(c3ccc(C#N)c(C(F)(F)F)c3)C(=O)C2(C)C)cc1F] | 4.56 | 464.44 | 3641.29 | 216.3 | 0 | 0 | |
| ARN-509 | 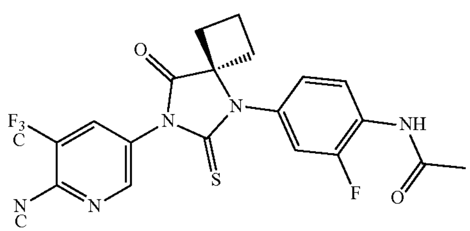 | 3.47 | 477.43 | 1452.29 | | 0 | 0 | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding ($K_i$ (left)) & Transactivation ($IC_{50}$ (right)) (nM) | | SARD Activity (% inh): Full Length (left) and S.V. (right) | | DMPK (MLM) |
|---|---|---|---|---|---|---|---|---|
| | | | | $K_i$ (nM) (DHT = 1 nM) | $IC_{50}$ (nM) | Full Length % inhibition at 1, 10 μM | S.V. % inhibition at 10 μM | $T_{1/2}$ (min) & $CL_{int}$ (μL/min/mg) |
| 17 | 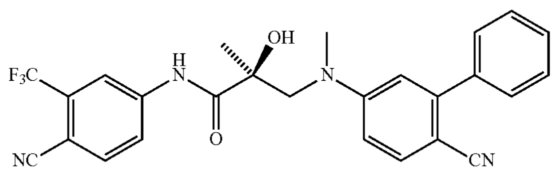 [SMILES: CN(C[C@](C)(O)C(=O)Nc1ccc(C#N)c(C(F)(F)F)c1)c1ccc(C#N)c(-c2ccccc2)c1] | 5.69 | 478.48 | 28.4 | 95 | | | |
| 100 | 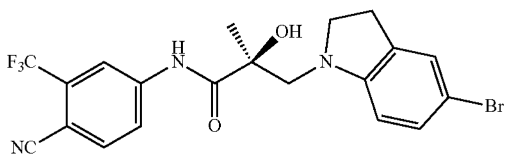 [SMILES: C[C@](O)(CN1CCc2cc(Br)ccc21)C(=O)Nc1ccc(C#N)c(C(F)(F)F)c1] | 4.62 | 468.27 | 197.67 | 530.95 | 60 | 41 | 66.87 10.38 |
| 11 | 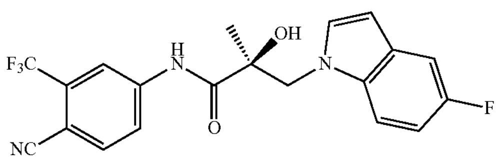 [SMILES: C[C@](O)(Cn1ccc2cc(F)ccc21)C(=O)Nc1ccc(C#N)c(C(F)(F)F)c1] | 3.47 | 405.35 | 267.39 | 85.10 | 65-83 | 60-100 | 12.35 56.14 |
| 1001 | 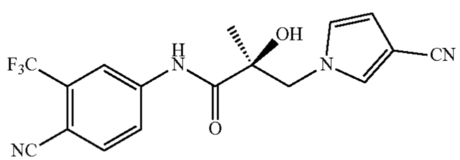 [SMILES: C[C@](O)(Cn1ccc(C#N)c1)C(=O)Nc1ccc(C#N)c(C(F)(F)F)c1] | 2.29 | 362.31 | 327.97 | partial agonist | 0 | 0 | 23.5 29.5 |
| 1002 | 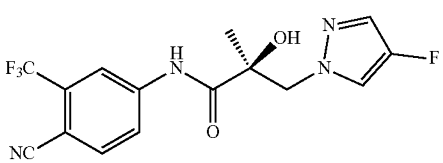 [SMILES: C[C@](O)(Cn1cc(F)cn1)C(=O)Nc1ccc(C#N)c(C(F)(F)F)c1] | 2.03 | 356.27 | No binding | 199.36 | 100 | 100 | 77.96 0.89 |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1,10 μM | S.V. % inhibition at 10 μM | T$_{1/2}$ (min) & CL$_{int}$ (μL/min/mg) |
| 1003 | 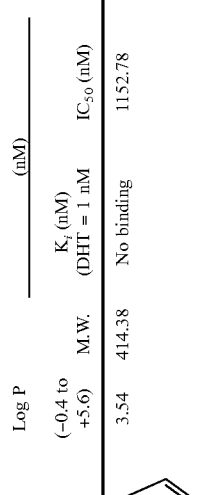 | 3.54 | 414.38 | No binding | 1152.78 | 0 | 0 | 48.45 / 14.31 |
| 1004 | 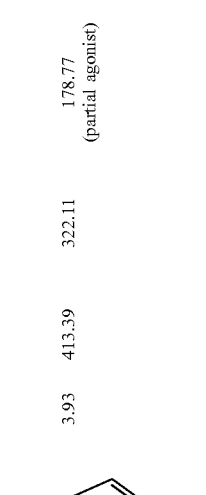 | 3.93 | 413.39 | 322.11 | 178.77 (partial agonist) | 0%, 40% @ 10 μM | 0 | 3.96 / 175.2 |
| 1005 | 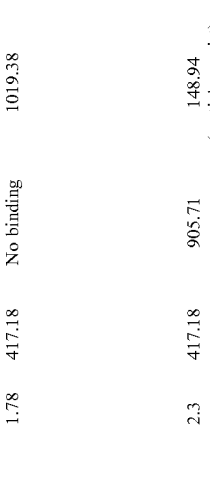 | 1.78 | 417.18 | No binding | 1019.38 | 50 | 70 | 16.51 / 41.58 |
| 1006 | 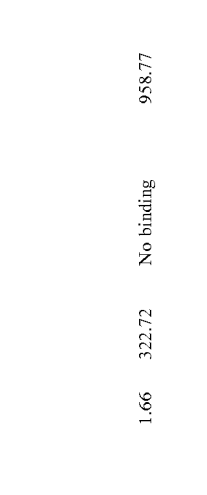 | 2.3 | 417.18 | 905.71 | 148.94 (partial agonist) | 0 | 0 | |
| 1007 | 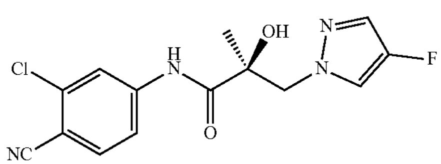 [SMILES: C[C@](O)(Cn1cc(F)cn1)C(=O)Nc1ccc(C#N)c(Cl)c1] | 1.66 | 322.72 | No binding | 958.77 | 0 | 0 | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1008 | 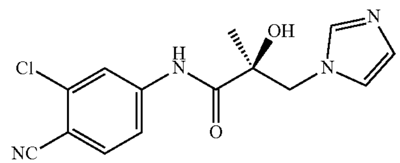 [SMILES: C[C@](O)(Cn1ccnc1)C(=O)Nc1ccc(C#N)c(Cl)c1] | 0.71 | 304.73 | No binding | 1856.8 | 0 | 30 | 24.61 / 28.16 |
| 1009 | 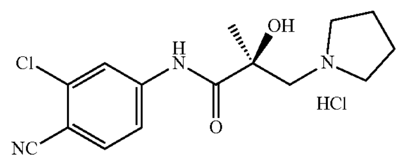 [SMILES: C[C@](O)(CN1CCCC1)C(=O)Nc1ccc(C#N)c(Cl)c1 ; Cl] | 1.69 (for free amine) | 307.78 (for free amine) | No binding | No inhibition | | | |
| 1010 | 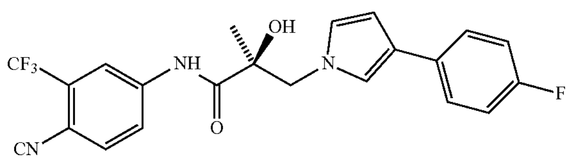 | 4.09 | 431.38 | 259.29 | 225.91 | 0 | 0 | |
| 1011 | 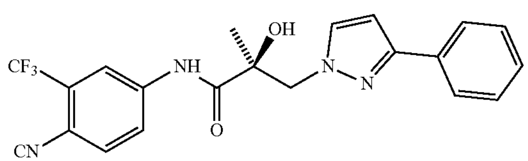 | 3.97 | 414.38 | 3660 | 4770 | 100 | 60 | 17.93 / 38.66 |
| 1012 | 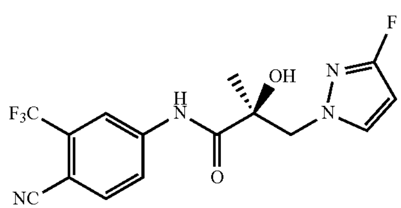 [SMILES: C[C@](O)(Cn1ccc(F)n1)C(=O)Nc1ccc(C#N)c(C(F)(F)F)c1] | 2.49 | 356.27 | 820.97 | 219.48 | 82 | 73 | 64.07 / 1.02 |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) T$_{1/2}$ (min) & CL$_{int}$ (µL/min/mg) |
|---|---|---|---|---|---|---|---|---|
| | | | | K$_i$ (nM) (DHT = 1 nM) | IC$_{50}$ (nM) | Full Length % inhibition at 1,10 µM | S.V. % inhibition at 10 µM | |
| 1013 | 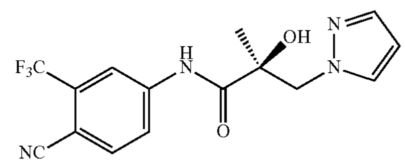 [SMILES: C[C@](O)(Cn1cccn1)C(=O)Nc1ccc(C#N)c(C(F)(F)F)c1] | 1.87 | 338.28 | 7398 | 1441.58 | 0 | | |
| 1014 | 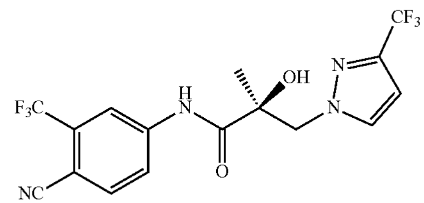 [SMILES: C[C@](O)(Cn1ccc(C(F)(F)F)n1)C(=O)Nc1ccc(C#N)c(C(F)(F)F)c1] | 3.21 | 406.28 | 512.3 | 204.59 | 67 (comparable to 11 in the same exp) | 54 (comparable to 11 in the same exp) | 3300 |
| 1015 | 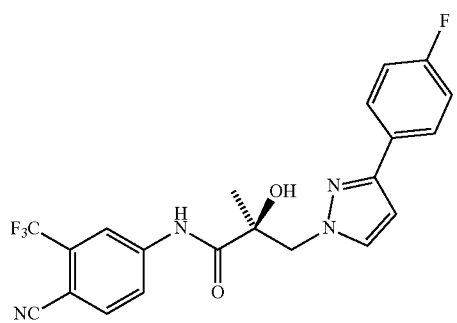 [SMILES: C[C@](O)(Cn1ccc(-c2ccc(F)cc2)n1)C(=O)Nc1ccc(C#N)c(C(F)(F)F)c1] | 4.13 | 432.37 | >10000 | 1742 | 72 | 0 | |
| 1016 | 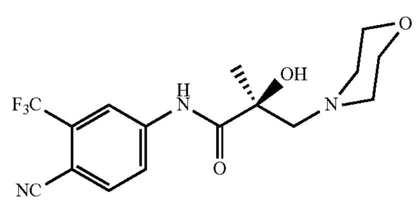 [SMILES: C[C@](O)(CN1CCOCC1)C(=O)Nc1ccc(C#N)c(C(F)(F)F)c1] | 1.34 | 357.33 | 1874.68 | 1018.68 | 52 | 80 | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
|---|---|---|---|---|---|---|---|---|
| | | | | K$_i$ (nM) (DHT = 1 nM) | IC$_{50}$ (nM) | Full Length % inhibition at 1,10 μM | S.V. % inhibition at 10 μM | T$_{1/2}$ (min) & CL$_{int}$ (μL/min/mg) |
| 1017 | 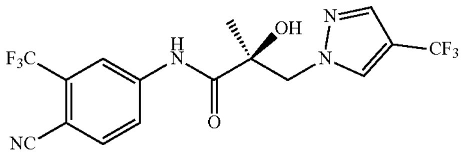 [SMILES: C[C@](O)(Cn1cc(C(F)(F)F)cn1)C(=O)Nc1ccc(C#N)c(C(F)(F)F)c1] | 2.79 | 406.28 | 898.23 | 404.39 | 80 | 100 | Infinity 0 |
| 1018 | 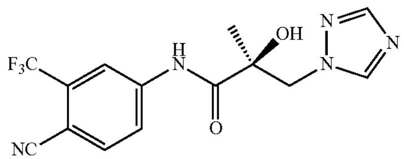 [SMILES: C[C@](O)(Cn1cncn1)C(=O)Nc1ccc(C#N)c(C(F)(F)F)c1] | 1.42 | 339.27 | No binding | 1091.56 | 0 | 0 | |
| 1019 | 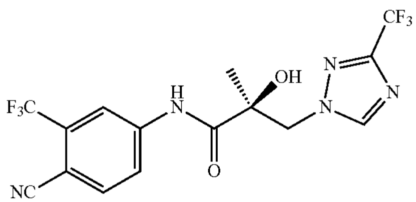 [SMILES: C[C@](O)(Cn1cnc(C(F)(F)F)n1)C(=O)Nc1ccc(C#N)c(C(F)(F)F)c1] | 3.23 | 407.23 | No binding | 1012.75 | 68 | 100 | |
| 1020 | 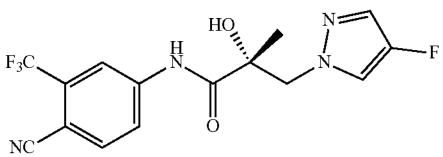 [SMILES: C[C@@](O)(Cn1cc(F)cn1)C(=O)Nc1ccc(C#N)c(C(F)(F)F)c1] | 2.03 | 356.27 | No binding | 192 | 84 | | |
| 1021 | 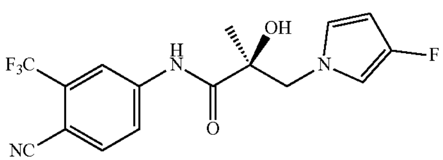 [SMILES: C[C@](O)(Cn1ccc(F)c1)C(=O)Nc1ccc(C#N)c(C(F)(F)F)c1] | 2.41 | 355.39 | 633.23 | partial | 0 | 0 | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
|---|---|---|---|---|---|---|---|---|
| | | | | K$_i$ (nM) (DHT = 1 nM) | IC$_{50}$ (nM) | Full Length % inhibition at 1,10 μM | S.V. % inhibition at 10 μM | T$_{1/2}$ (min) & CL$_{int}$ (μL/min/mg) |
| 1022 | 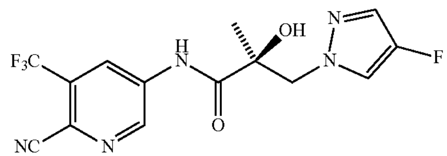 [SMILES: C[C@](O)(Cn1cc(F)cn1)C(=O)Nc1cnc(C#N)c(C(F)(F)F)c1] | 1.11 | 357.26 | No binding | 92.17 | 54 | 81 | |
| 1023 | 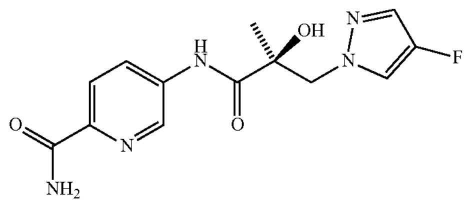 [SMILES: C[C@](O)(Cn1cc(F)cn1)C(=O)Nc1ccc(C(N)=O)nc1] | −0.93 | 307.28 | No binding | No effect | 0 | | Infinity 0 |
| 1024 | 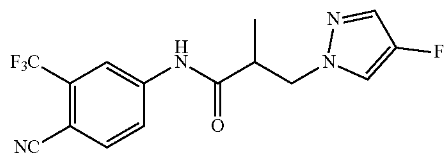 [SMILES: CC(Cn1cc(F)cn1)C(=O)Nc1ccc(C#N)c(C(F)(F)F)c1] | 2.86 | 340.28 | No binding | 463.9 | 60 | 70 | |
| 1025 | 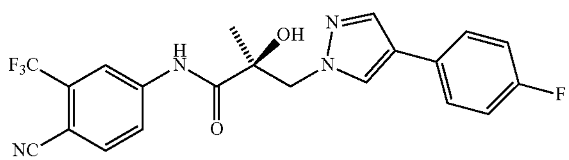 [SMILES: C[C@](O)(Cn1cc(-c2ccc(F)cc2)cn1)C(=O)Nc1ccc(C#N)c(C(F)(F)F)c1] | 3.7 | 432.37 | 612.4 | 969 | 60 | 0 | Infinity 0 |
| 1026 | 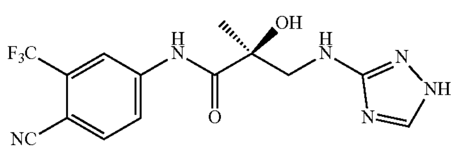 [SMILES: C[C@](O)(CNc1nc[nH]n1)C(=O)Nc1ccc(C#N)c(C(F)(F)F)c1] | 1.19 | 354.29 | — | — | 0 | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
|---|---|---|---|---|---|---|---|---|
| | | | | K$_i$ (nM) (DHT = 1 nM) | IC$_{50}$ (nM) | Full Length % inhibition at 1,10 μM | S.V. % inhibition at 10 μM | T$_{1/2}$ (min) & CL$_{int}$ (μL/min/mg) |
| 1027 | 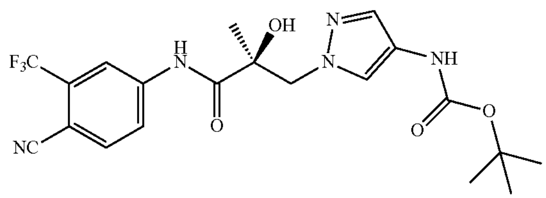 [SMILES: CC(C)(C)OC(=O)Nc1cnn(C[C@](C)(O)C(=O)Nc2ccc(C#N)c(C(F)(F)F)c2)c1] | 2.24 | 453.41 | 1382.06 | 1153 | 20 | | |
| 1028 | 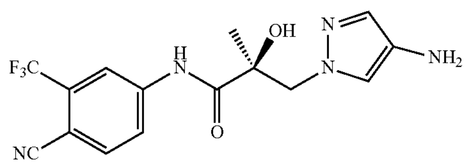 [SMILES: C[C@](O)(Cn1cc(N)cn1)C(=O)Nc1ccc(C#N)c(C(F)(F)F)c1] | 1.07 | 353.30 | 227.48 | Agonist | | | |
| 1029 | 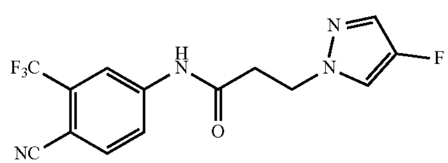 [SMILES: N#Cc1ccc(NC(=O)CCn2cc(F)cn2)cc1C(F)(F)F] | 2.29 | 326.25 | No Binding | 2124 | 35 | 40 | |
| 1030 | 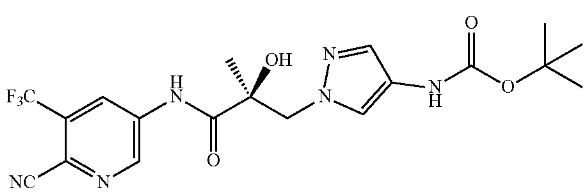 [SMILES: CC(C)(C)OC(=O)Nc1cnn(C[C@](C)(O)C(=O)Nc2cnc(C#N)c(C(F)(F)F)c2)c1] | 1.32 | 454.40 | No binding | 6108 | — | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1,10 μM | S.V. % inhibition at 10 μM | T$_{1/2}$ (min) & CL$_{int}$ (μL/min/mg) |
| 1031 | | 0.78 | 395.34 | No binding | No effect | — | | |
| 1032 | | 1.82 | 429.78 | No binding | 900.86 | | | |
| 1033 | | 1.3 | 411.34 | No binding | No effect | | | |
| 1034 | | 1.3 | 411.34 | | 827 | | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
|---|---|---|---|---|---|---|---|---|
| | | | | K$_i$ (nM) (DHT = 1 nM) | IC$_{50}$ (nM) | Full Length % inhibition at 1,10 μM | S.V. % inhibition at 10 μM | T$_{1/2}$ (min) & CL$_{int}$ (μL/min/mg) |
| 1035 | 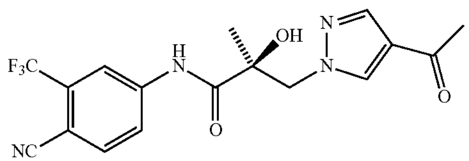 [SMILES: CC(=O)c1cnn(C[C@](C)(O)C(=O)Nc2ccc(C#N)c(C(F)(F)F)c2)c1] | 1.2 | 380.32 | | 757.7 | | | |
| 1036 | 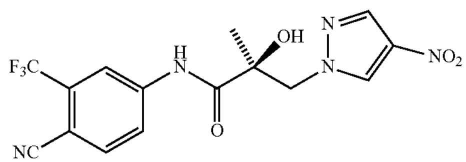 [SMILES: C[C@](O)(Cn1cc([N+](=O)[O-])cn1)C(=O)Nc1ccc(C#N)c(C(F)(F)F)c1] | 1.9 | 383.28 | 2225 | 36.22 | 20 | | |
| 1037 | 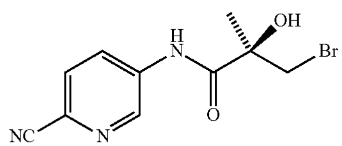 [SMILES: C[C@](O)(CBr)C(=O)Nc1ccc(C#N)nc1] | 0.7 | 284.11 | 4547 | 350.5 | >50 | | |
| 1038 | 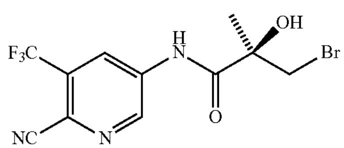 [SMILES: C[C@](O)(CBr)C(=O)Nc1cnc(C#N)c(C(F)(F)F)c1] | 1.6 | 352.11 | | 2490 | | | |
| 1039 | 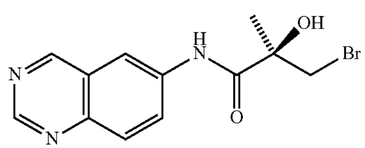 [SMILES: C[C@](O)(CBr)C(=O)Nc1ccc2ncncc2c1] | 1.1 | 310.15 | | 1750 | | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1040 | 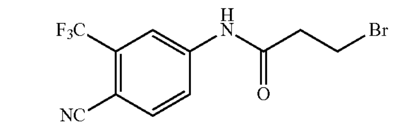 [SMILES: N#Cc1ccc(NC(=O)CCBr)cc1C(F)(F)F] | 2.8 | 321.09 | | — | | | |
| 1041 | 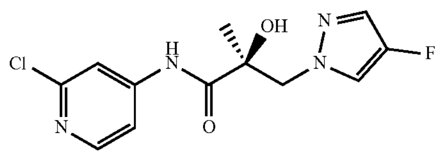 [SMILES: C[C@](O)(Cn1cc(F)cn1)C(=O)Nc1ccnc(Cl)c1] | 0.6 | 298.70 | | 2470 | >75 | | |
| 1042 | 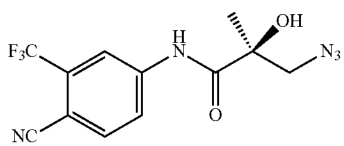 [SMILES: C[C@](O)(CN=[N+]=[N-])C(=O)Nc1ccc(C#N)c(C(F)(F)F)c1] | 0.8 | 313.24 | | — | | | |
| 1043 | 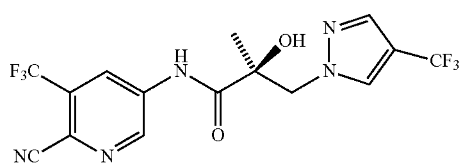 [SMILES: C[C@](O)(Cn1cc(C(F)(F)F)cn1)C(=O)Nc1cnc(C#N)c(C(F)(F)F)c1] | 1.8 | 407.27 | | 57.91 | 10 | | |
| 1044 | 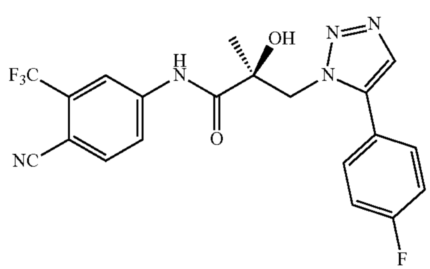 [SMILES: C[C@](O)(Cn1nncc1-c1ccc(F)cc1)C(=O)Nc1ccc(C#N)c(C(F)(F)F)c1] | 3.4 | 433.36 | | 316.7 | 73 | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1, 10 μM | S.V. % inhibition at 10 μM | T$_{1/2}$ (min) & CL$_{int}$ (μL/min/mg) |
| 1045 | 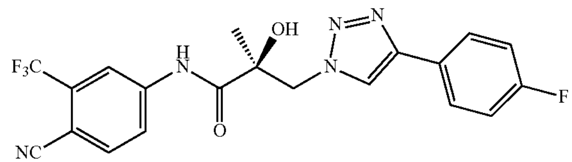 [SMILES: C[C@](O)(Cn1cc(-c2ccc(F)cc2)nn1)C(=O)Nc1ccc(C#N)c(C(F)(F)F)c1] | 3.7 | 433.36 | | 250.9 | 84 | | |
| 1046 | 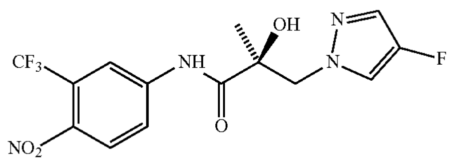 [SMILES: C[C@](O)(Cn1cc(F)cn1)C(=O)Nc1ccc([N+](=O)[O-])c(C(F)(F)F)c1] | 2.0 | 376.24 | | Partial | | | |
| 1047 | 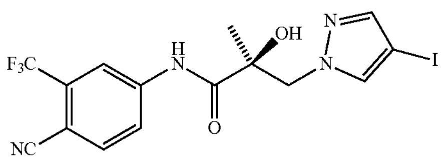 | 3.2 | 464.19 | | | | | |
| 1048 | 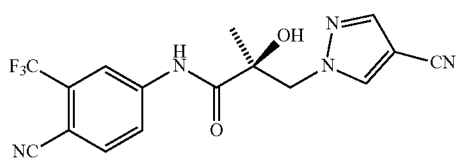 [SMILES: C[C@](O)(Cn1cc(C#N)cn1)C(=O)Nc1ccc(C#N)c(C(F)(F)F)c1] | 1.9 | 363.30 | | | | | |
| 1049 | 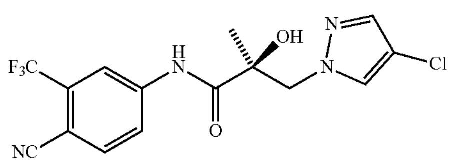 [SMILES: C[C@](O)(Cn1cc(Cl)cn1)C(=O)Nc1ccc(C#N)c(C(F)(F)F)c1] | 2.4 | 372.73 | | | | | |

TABLE 1-continued

In vitro screening of LBD binding (Ki), AR antagonism (IC50), SARD activity, and metabolic stability

| Compound # | Structure | Log P (−0.4 to +5.6) | M.W. | wtAR Binding (K$_i$ (left)) & Transactivation (IC$_{50}$ (right)) (nM) | | SARD Activity (% inh): Full Length (left) and S.V. (right) | | DMPK (MLM) |
| --- | --- | --- | --- | --- | --- | --- | --- | --- |
| | | | | K$_i$ (nM) (DHT = 1 nM) | IC$_{50}$ (nM) | Full Length % inhibition at 1,10 μM | S.V. % inhibition at 10 μM | T$_{1/2}$ (min) & CL$_{int}$ (μL/min/mg) |
| 1002-oxalic acid salt | | | | | 57.99 | | | |
| 1002-succinic acid salt | | | | | 83.06 | | | |
| 1002-HBr | | | | | 77.2 | | | |
| 1002-tartaric acid salt | | | | | 259.1 (similar to 1002 in this experiment) | | | |
| 1002-HCl | | | | | 123.5 | | | |

TABLE 2

| Compd ID | Structure | MLM T$_{1/2}$ (min) | MLM CL$_{Int}$ (μL/min/mg) | HLM T$_{1/2}$ (min) | HLM CL$_{Int}$ (μL/min/mg) |
|---|---|---|---|---|---|
| 11 | *(structure)* | 14.35 | 48.30 | 14.62 | 47.40 |
| 1001 | *(structure)* | 23.5 | 29.5 | | |
| 1002 | *(structure)* | 77.96 | 0.89 | 73.36 | 0.949 |
| 1004 | *(structure)* | 3.96 | 175.2 | 2.261 | 306.5 |
| 1012 | *(structure)* | 64.07 | 1.02 | | |

Example 3

Transactivation Assay

Methods:

HEK-293 cells were transfected with the indicated receptors and GRE-LUC and CMV-*renilla* luc. Cells were treated 24 h after transfection and luciferase assay performed 48 h after transfection. The SARD compounds did not inhibit transactivation of receptors other than AR until 10 μM. The experimental method is described below.

Human AR was cloned into a CMV vector backbone and was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 μg GRE-LUC, 0.01 μg CMV-LUC (*renilla* luciferase) and 25 ng of the AR. The cells were treated 24 h after transfection and the luciferase assay performed 48 h after transfection. Transactivation results were based on measured luciferase light emissions and reported as relative light unit intensity (RLU). The assay was run in antagonist mode (IC$_{50}$) using known agonist R1881 at its EC$_{50}$ concentration of 0.1 nM and increasing concentrations of SARDs of this invention. Agonist mode data was reported qualitatively, e.g., partial agonist or an approximate EC$_{50}$ for enobosarm, for some compounds in Table 1. Antagonist data are represented as IC$_{50}$ (nM) obtained from four parameter logistics curve and are reported in Table 1 in the column labeled 'IC$_{50}$'.

Results:

Representative example graphs are shown in FIGS. 1A (1002), 2A (11 vs. 1002), 3A (1003), 4A (1004), 5A (1005), 6A (1006), 8-12 (1007-1011), and 13A (1001) with results plotted as RLU reported on the y-axis and SARD concentration on the x-axis (nM). In these Figures, antagonist mode data was shown as curve fitted data, whereas agonist mode data (if present) is reported without curve fitting. Only weak and partial agonism was seen. In vivo pharmacodynamics demonstrate potent and highly efficacious antagonism of androgen dependent tissues (see Examples 7 and 10 herein). FIG. 2 is a direct comparison of antagonism between 11 (closed dots) and 1002 (open dots). Other IC$_{50}$ values reported in Table 1 were calculated by the same method.

1002 was a potent antagonist (199.36 nM; Table 1 and FIG. 1A) with comparable inhibition as 11 (85.1 nM; FIG. 2) which is an extremely potent indole SARD lacking oral bioavailability. Despite the 2-fold increased IC$_{50}$ (Table 1) and lack of AR-LBD binding (see Example 4 and Table 1), 1002 was a more potent AR degrader in vitro (see Example 5 and Table 1). Further and unlike 11, 1002 was very stable in vitro in mouse (Table 1) and human liver microsomes (Table 2) which translated into improved in vivo pharmacodynamics (see Example 7 herein) in mice and rats. Based on the structural differences alone, the increased SARD activity in vitro and metabolic stability were each unexpected results. Likewise, the greatly improved in vivo efficacy could not have been predicted (i.e., was unexpected) based on structural differences alone. 1012, 1014, and 1017 also demonstrated improved metabolic stability in vitro suggesting that the pyrazole moiety may be responsible for the unexpected stability of 1002.

As discussed below, 1002 and 1014 also demonstrated significant anti-tumor activity in in vivo xenograft studies (see Examples 8 and 10), suggesting that the bioavailability of these compounds is sufficient for their intended uses.

Figure 4A:
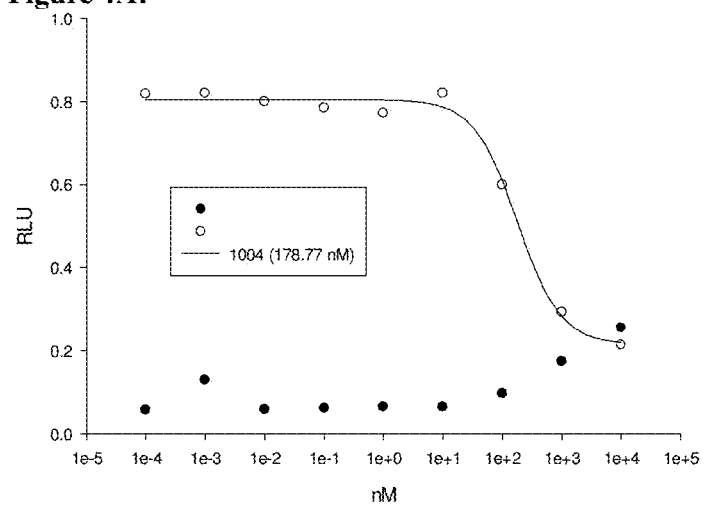
FIG. 4A and FIG. 4B: The transactivation result of 1004 was reported based on measured luciferase light emissions and reported as relative light unit intensity (RLU).
Figure 4B:
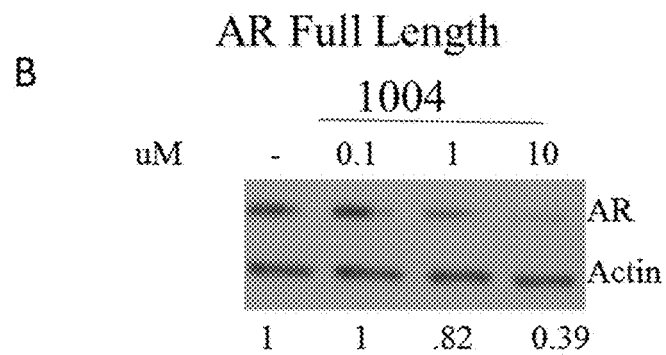
Figure 5A:
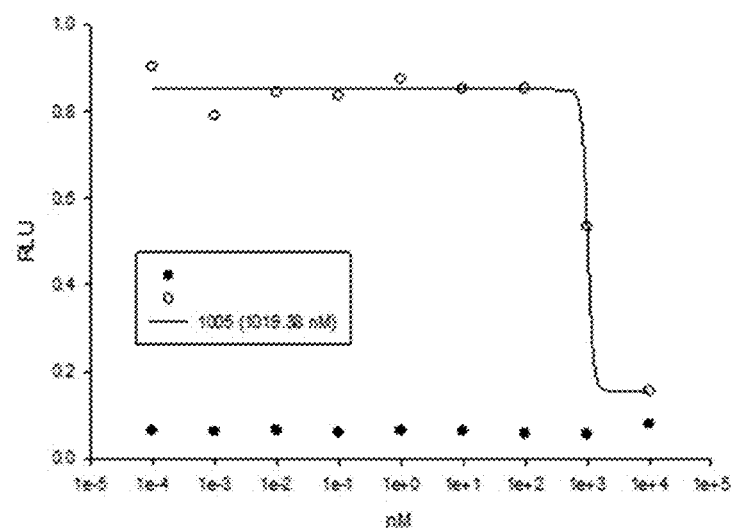
FIG. 5A and FIG. 5B: The transactivation results of 1005 were reported based on measured luciferase light emissions and reported as relative light unit intensity (RLU).
Figure 5B:
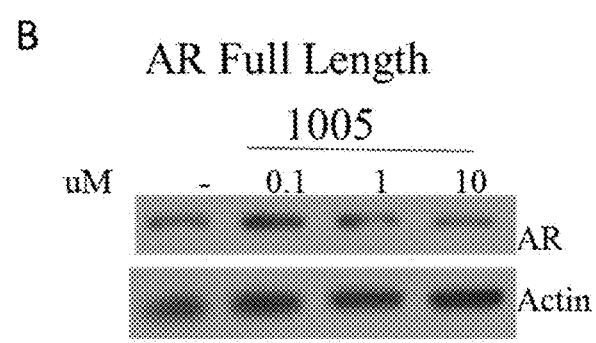
Figure 7:
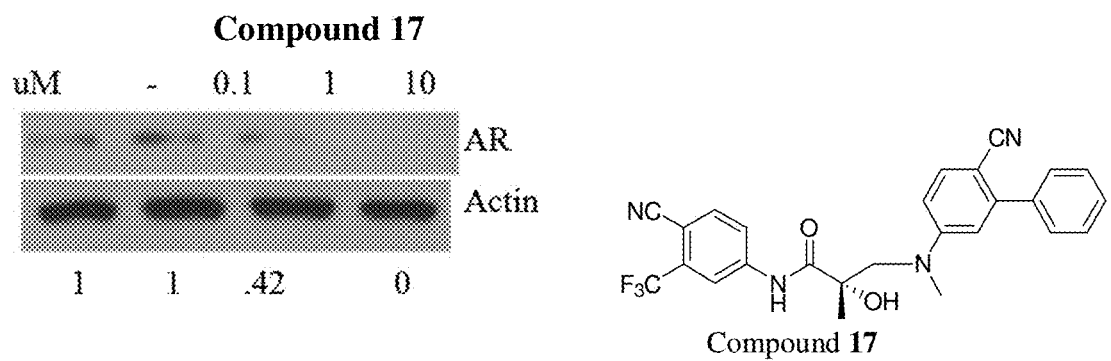
FIG. 7: The Western blot of the full length androgen receptor degradation assay is shown for compound 17 and the results are reported in Table 1, under SARD Activity: Full Length % Inhibition.
Figure 8:
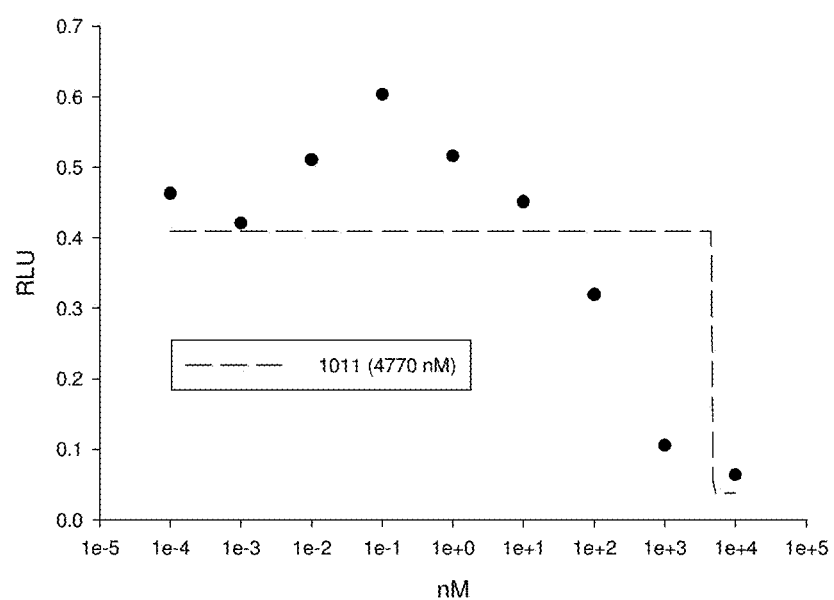
FIG. 8: The transactivation result of 1011 was reported based on measured luciferase light emissions and reported as relative light unit intensity (RLU).
Figure 9:
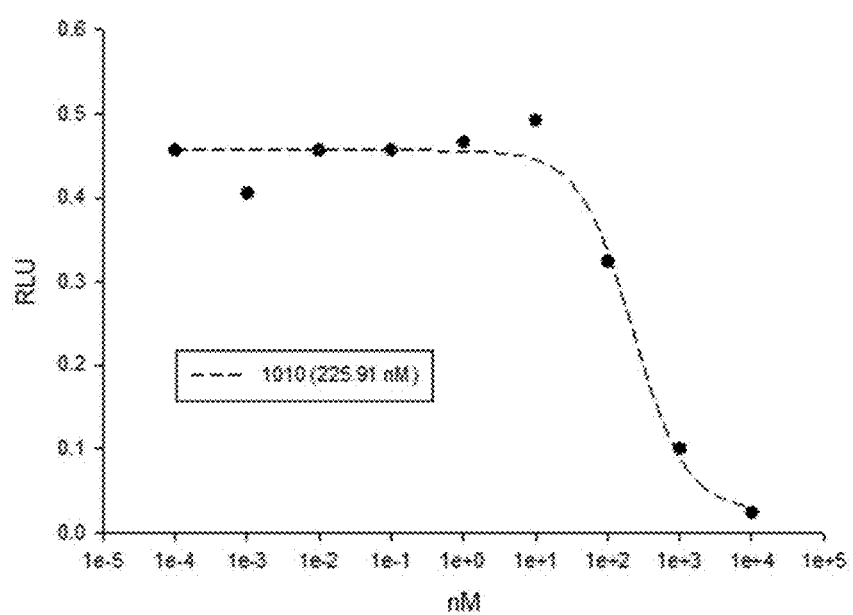
FIG. 9: The transactivation result of 1010 was reported based on measured luciferase light emissions and reported as relative light unit intensity (RLU).
Figure 10:
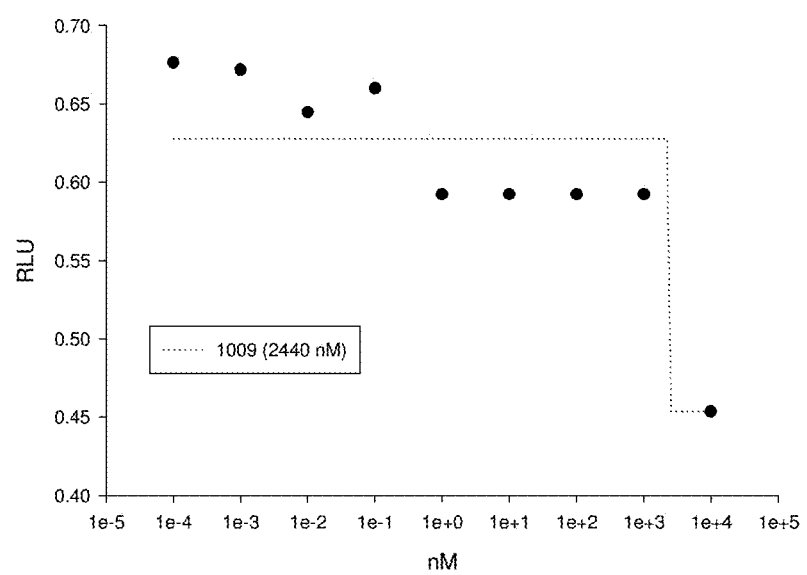
FIG. 10: The transactivation result of 1009 was reported based on measured luciferase light emissions and reported as relative light unit intensity (RLU).
Figure 11:
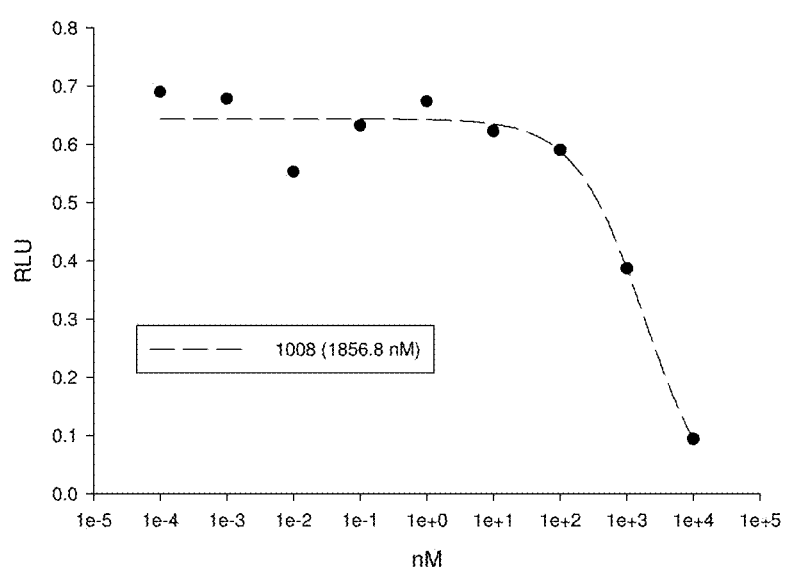
FIG. 11: The transactivation result of 1008 was reported based on measured luciferase light emissions and reported as relative light unit intensity (RLU).
Figure 12:
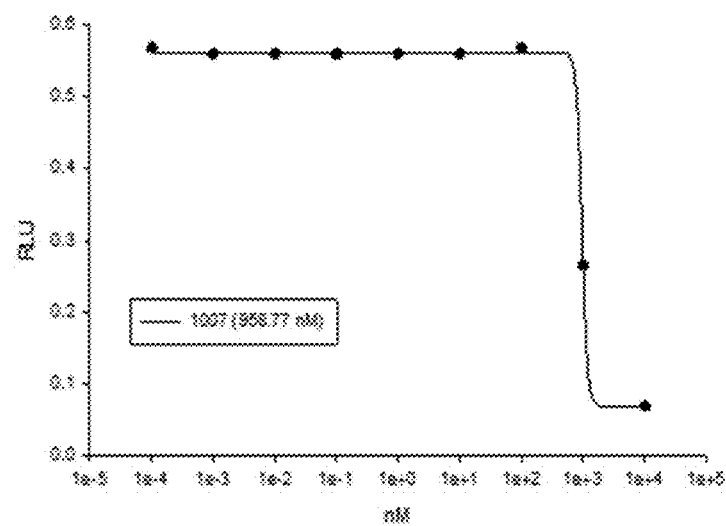
FIG. 12: The transactivation result of 1007 was reported based on measured luciferase light emissions and reported as relative light unit intensity (RLU).
Figure 13A:
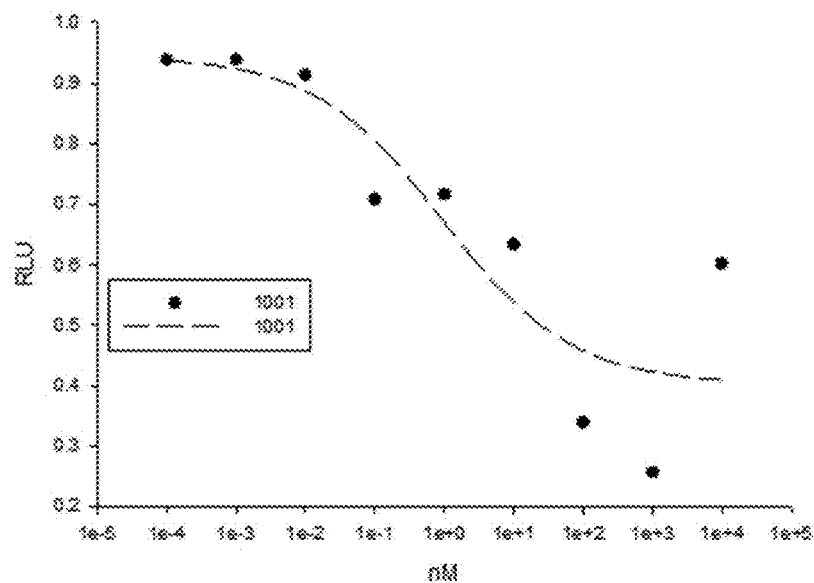
FIGS. 13A-13C: The transactivation result of 1001 was reported based on measured luciferase light emissions and reported as relative light unit intensity (RLU).
Figure 13B:
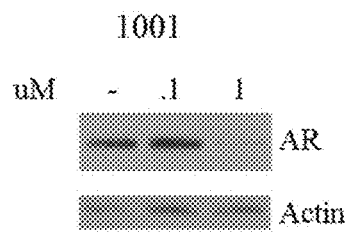
Figure 13C:
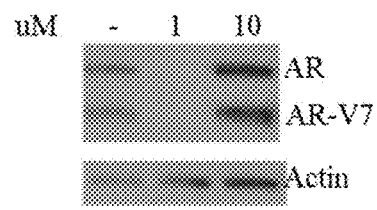

1004 (pyrrole) and 1006 (imidazole) demonstrated potent inhibition (178.77 nM and 148.94 nM; Table 1; FIGS. 4A and 6A) but weak SARD activity, whereas 1005 and 1016 demonstrated weak inhibition but strong SARD activity, suggesting that in vitro inhibition is not well correlated with SARD activity. However, 1010 (pyrrole), 1012 (pyrazole), and 1014 (pyrazole) were potent inhibitors and degraders. In general, LBD binding or LBD-dependent inhibition and in vitro SARD activity seem to be separate but highly tolerant structure activity relationships. Values for other compounds of the invention are reported in Tables 1 and 2.

Potent inhibition of transactivation was also seen for 1020 (192 nM), 1022 (92 nM), and 1024 (464 nM). 1020 is an R-isomer of pyrazole 1002, and like 1002, does not bind to the LBD yet has strong SARD activity. Similarly, the indole SARD 11 and the R-isomer of 11 have comparable SARD activities (Table 1 and FIG. 2B) for AR-FL (LNCaP) and AR-SV (22RV1). This is in sharp contrast to propanamide SARMs such as enobosarm which typically have 100-fold lower LBD binding and agonist activity for R-isomers (data not shown). This is further evidence that SARD activity is not mediated through the LBD, as will be discussed in more detail in Example 9 below. Example 9 demonstrates a novel binding site in the N-terminal domain (NTD), providing a basis for the distinct structure activity relationships from traditional AR antagonists that bind to the LBD and SARD of this invention which act through the NTD. The retention of SARD activity in opposite isomers (unlike SARMs) suggests that the NTD binding site does not require stereo-specificity in its ligands. Further, the NTD binding site does not seem to require the chiral hydroxyl group which is conserved for LBD-binding (agonists and) antagonists. E.g., 1024 is a non-chiral propanamide racemate which lacks the hydroxyl but retains SARD activity (Table 1: 60% degradation of AR-FL) and the ability to inhibit the AR (Table 1: $IC_{50}$=464 nM) despite not binding the LBD (Table 1: $K_i$: no binding). Also, 1029 replaces the chiral center with a methylene group and yets retains some SARD activity (Table 1: 35% degradation of AR-FL) and AR antagonism (Table 1: $IC_{50}$=2124 nM). 1032 has its hydroxyl group protected by acylation and and does not bind the LBD yet is an antagonist of AR. Another possible divergence in SAR's is the A-ring which is conserved for LBD binders as 4-cyano or nitro and 3-trifluoromethyl or 3-chloro. However, changing the $CF_3$ of 1002 to the Cl of 1007 ablated SARD activity. Further, 1022 has a novel pyridine A-ring and does not bind to the LBD yet retains potent inhibition of transactivation (92 nM) and SARD activity (Table 1). Similarly, SARD activity is shown for 1037 and 1041 that contain pyridine A-rings (Table 1 and FIG. 28C), and 1043 is a highly potent pyridine antagonist but weak SARD activity (Table 1). Further, 1037 is a 3-bromopropanamide (i.e., lacks a heterocyclic B-ring) which binds weakly to the LBD (4547 nM) but is a potent antagonist (350.5 nM) and retains SARD activity, demonstrating that the B-ring may not be necessary (Table 1) for SARDs of this invention. Such observations confirm that SARD activity can be optimized in the absence of LBD binding data and provide a rationale for the degradation of AR splice variants lacking the LBD.

Example 4

Human Androgen Receptor (hAR) Ligand Binding Domain (LBD) Affinity Assay

Methods:

hAR-LBD (633-919) was cloned into pGex4t.1. Large scale GST-tagged AR-LBD was prepared and purified using a GST column. Recombinant AR-LBD was combined with [³H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [³H] mibolerone. Protein was incubated with increasing concentrations of [³H]mibolerone with and without a high concentration of unlabeled mibolerone at 4° C. for 18 h in order to determine total and non-specific binding. Non-specific binding was then subtracted from total binding to determine specific binding and non-linear regression for the ligand binding curve with one site saturation was used to determine the $K_d$ of mibolerone.

Increasing concentrations of SARDs or DHT (range: $10^{-12}$ to $10^{-4}$ M) were incubated with [³H]mibolerone and AR-LBD using the conditions described above. Following incubation, the ligand bound AR-LBD complex was isolated using BiogelHT hydroxyapatite, washed and counted in a scintillation counter after adding scintillation cocktail.

Results:

The results of this assay are reported as $K_i$ values (nM) in Table 1 in the column labeled 'wt AR Binding ($K_i$(left))'. As discussed above and is apparent from Table 1, there is a poor correlation between AR-LBD affinity and SARD activity. E.g., see in vitro SARD activity for 1002, 1005, 1015, 1019, 1020, and 1022 despite no binding affinity for the LBD (Table 1).

Example 5

In Vitro Assays to Determine SARD Activity

LNCaP or AD1 Androgen Receptor Degradation (Full Length AR):

The compounds of the invention were tested for their effect on full length AR protein expression. Methods: LNCaP or AD1 cells expressing full length AR were plated at 750,000-1,000,000 cells/well of a 6 well plate in growth medium (RPMI+10% FBS). Twenty four hours after plating, the medium was changed to RPMI+1% csFBS without phenol red and maintained in this medium for 2 days. The medium again was changed to RPMI+1% csFBS without phenol red and cells were treated with SARDs (1 nM to 10 mM) in combination with 0.1 nM R1881. After 24 h of treatment, cells were washed with cold PBS and harvested. Protein was extracted using salt-containing lysis buffer with three freeze-thaw cycles. The protein concentration was estimated and five microgram of total protein was loaded on a SDS-PAGE, fractionated, and transferred to a PVDF membrane. The membrane was probed with AR N-20 antibody (SantaCruz Biotechnology, Inc., Dallas, Tex. 75220) and actin antibody (Sigma-Aldrich, St. Louis, Mo.).

Figure 1B:
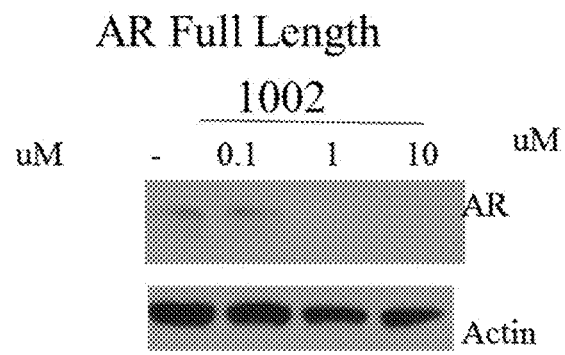

Results:

Degradation in LNCaP or AD1 cells are reported in Table 1 in the column labeled 'Full Length % Inhibition at 1, 10 μM'. The results of this assay were reported in FIGS. 1B (1002), 2B (11, 11R, 1002, 1020), 3B-6B (1003-1006), 7 (17), 13B (1001), 20A (1010, 1012, 1014, 1015, 1017, 1019 and 1022), 28A (1024 and 1029), 28C (1037 and 1041), 28D (1044 and 1045) as images of Western blot films (chemiluminescence exposed films).

22RV1 or D567es Androgen Receptor Degradation (Splice Variant (S.V.) AR):

The effect of SARD treatment on the AR levels was measured in androgen-refractory 22RV-1 or D567es prostate cancer cells. Methods: 22RV1 or D567es cells expressing AR splice variants (AR-SV) were plated at 750,000-1,000,000 cells/well of a 6 well plate in growth medium (RPMI+ 10% FBS). Twenty four hours after plating, medium was changed and treated. After 24-30 h of treatment, cells were washed with cold PBS and harvested. Protein was extracted using salt-containing lysis buffer with three freeze-thaw cycles. Protein concentration was estimated and five microgram of total protein was loaded on a SDS-PAGE, fractionated, and transferred to a PVDF membrane. The membrane was probed with AR N-20 antibody (Santa Cruz Biotechnology, Inc., Dallas, Tex. 75220) and actin antibody (Sigma-Aldrich, St. Louis, Mo.).

Figure 1C:
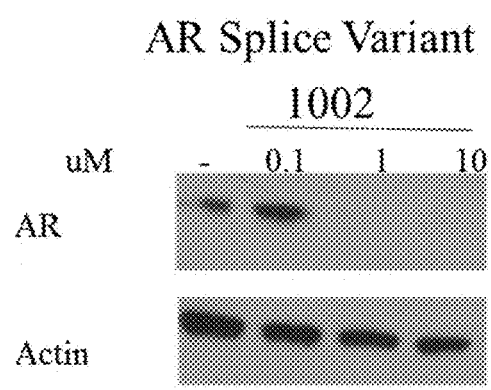
Figures 3A, 3B:
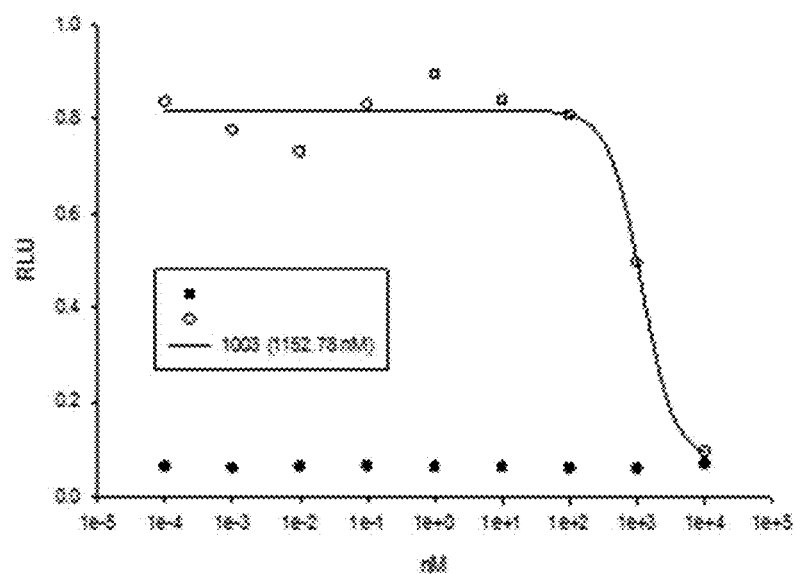
FIG. 3A and FIG. 3B: The transactivation result of 1003 was reported based on measured luciferase light emissions and reported as relative light unit intensity (RLU).

Results:

Degradation in 22RV1 or D567es cells are reported in Table 1 in the column labeled "S.V. % inhibition at 10 µM." The results of this assay in D567es cells were reported in FIGS. 1C (1002) and 20B (1010, 1012, 1014-1017, 1019 and 1022), and in 22RV1 cells in FIGS. 2B (11, 11R), 13C (1001), and 28B (1024 and 1029) as images of Western blot films (chemiluminescence exposed films).

Example 6

Metabolism Studies with Mouse Liver Microsomes (DMPK (MLM))

Determination of Metabolic Stability (In Vitro $CL_{int}$) of Test Compounds:

Phase I metabolism: The assay was done in a final volume of 0.5 mL in duplicates (n=2). The test compound (1 mM) was pre-incubated for 10 minutes at 37° C. in 100 mM Tris-HCl, pH 7.5 containing 0.5 mg/mL liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes). 100 mL aliquots were removed and quenched with 100 mL of acetonitrile containing internal standard. Samples were vortex mixed and centrifuged at 4000 rpm for 10 min. The supernatants were transferred to 96 well plates and submitted for LC-MS/MS analysis. As a control, sample incubations done in the absence of NADPH were included. From % PCR (% Parent Compound Remaining), rate of compound disappearance was determined (slope) and in vitro $CL_{int}$(l/min/mg protein) was calculated.

Results:

FIG. 14 reported phase I data as a raw data table for one experiment in MLM for compound 1002 and the $T_{1/2}$ (half-life) and $CL_{int}$ (clearance) values calculated therefrom. FIGS. 15A and 16A report phase I data as a raw data table and graphed data for one experiment for 1002 in mouse liver microsomes (MLM) and human liver microsomes (HLM), respectively. Similarly, FIG. 17 reported MLM data for 1001 and the $T_{1/2}$ (half-life) and $CL_{int}$ (clearance) values in Tables 1 and 2 were calculated therefrom.

Metabolic Stability in Phase I & Phase II Pathways

In this assay, the test compound was incubated with liver microsomes and disappearance of drug was determined using discovery grade LC-MS/MS. To simulate Phase II metabolic pathway (glucuronidation), UDPGA and alamethicin were included in the assay. From % PCR (% Parent Compound Remaining), rate of compound disappearance is determined (slope of concentration vs. time plot) and in vitro $CL_{int}$ (µl/min/mg protein) was calculated. The results of this assay utilizing mouse liver microsomes (MLM) are reported in Table 1 in the column labeled "DMPK (MLM) $T_{1/2}$ (min) & $CL_{int}$ (µL/min/mg)". The first value is the calculated half-life ($T_{1/2}$) of the test article in MLM expressed in minutes and the $2^{nd}$ value is the intrinsic CL ($CL_{int}$) of the test article in MLM expressed as mL/min/mg protein.

Results:

FIG. 14 reported phase I & II data as a raw data table for one experiment and the $T_{1/2}$ (half-life) and $CL_{int}$ (clearance) values calculated therefrom. FIGS. 15B (using mouse liver microsomes (MLM)) and 16B (using human liver microsomes (HLM)) reported phase I & II data for 1002 as a raw data table for separate single experiments and graphed data. This data demonstrated that 1002 is stable in MLM and very stable in HLM. The LC-MS/MS analysis was performed as described below.

The metabolic stability of 1002 and other pyrazoles of this invention was unexpected in view of previous SARDs (100, 17, & 11; see Table 1). See also Examples 8 and 10 for comparisons of pyrazoles to previous SARD templates and their unexpected results in terms of metabolic stabilities, in vivo pharmacodynamics, in vivo serum and tumor concentrations, and in vivo anti-tumor efficacies in advanced prostate cancer (Example 10) and triple negative breast cancer (Example 8). Further, MLM data for 1024 (Table 1), a non-hydroxy variant, and 1023, a pyridine A-ring compound (non-carbonitrile), both revealed a lack of metabolism after incubation with MLM for 60 minutes. This demonstrates metabolic stability of SARDs of this invention including those with pyrazole B-rings, that lack the hydroxyl group, and/or include alternative A-rings.

Lc-Ms/Ms Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 am) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

Example 7

In Vivo Antagonism Demonstrated by SARD Compound 1002

Hershberger Method:

Male mice (20-25 grams body weight; n=5-7/group) were either left intact or castrated and treated as indicated in the figures for 13 days. Treatment of castrated mice was initiated 3 days after castration. Mice were sacrificed on day 14 of treatment and seminal vesicles were removed and weighed. Seminal vesicles weights were either represented as is or were normalized to body weight and represented.

Results:

1002 significantly reduced the weight of seminal vesicles at 40 mg/kg oral daily dose in intact (FIG. 18A) and 100 mg/kg in castrated (FIG. 18B). The reduction in seminal vesicles weight, which is representative of androgen receptor (AR) antagonism, was more pronounced than that of the 20 mg/kg/day enzalutamide dose. 1002 was effective even in castrated mice, indicating that even any residual AR activity in castrated AR-target tissues was further inhibited by the potent activity of 1002 which bodes well for the abilities of SARDs of this invention to treat ADT-treated prostate cancer patients. This suggests that even though some weak partial AR agonism is observed in in vitro transactivation experiments, the predominant tone in vivo is AR antagonism. Further, in vivo activity at 40 mg/kg (40 mpk) for 1002 was a dramatic improvement over previously tested SARDs from our laboratory which typically only produced in vivo effects at 100 mg/kg or more despite comparable in vitro transcriptional inhibition potencies. This suggests the unexpected metabolic stability of 1002 translated into clinically significant oral bioavailability.

Figure 19A:
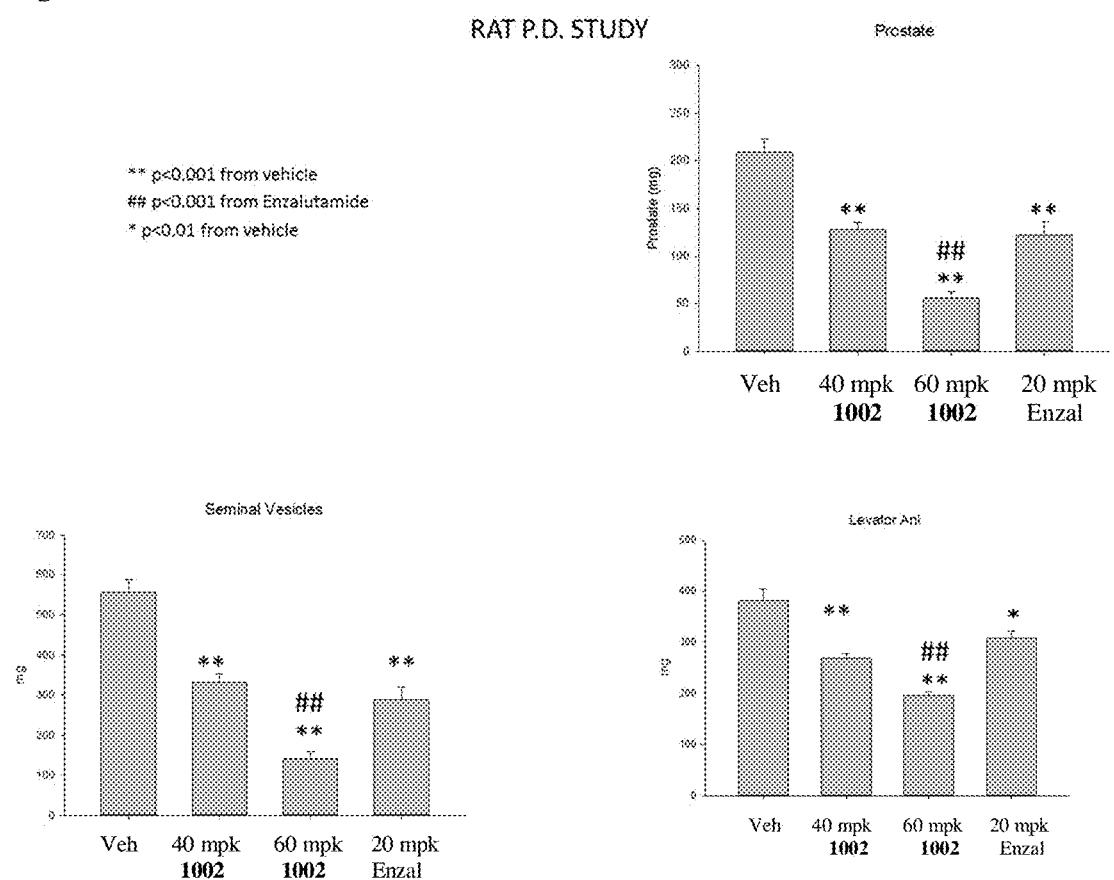
FIG. 19A and FIG. 19B: Hershberger method (rat)
Figure 19B:
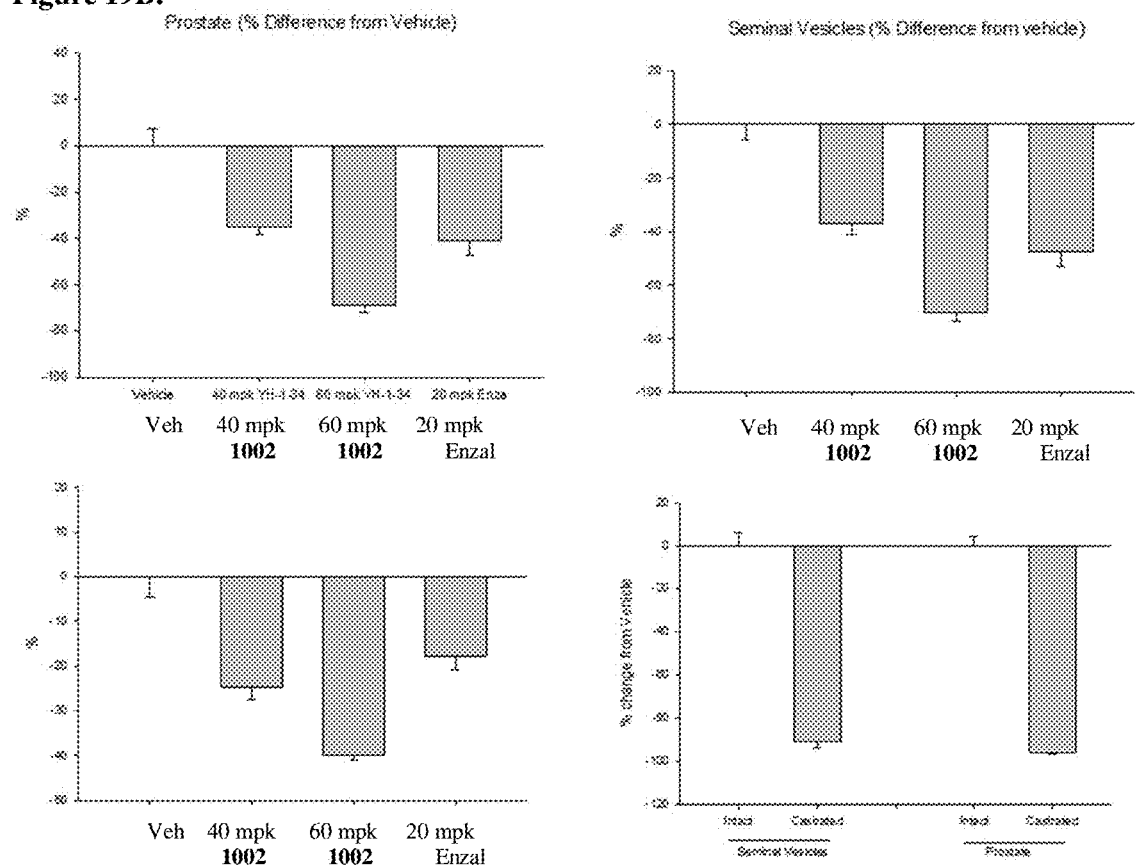

The Hershberger experiments were repeated in rats since rats are known to be more sensitive models of androgenic and anabolic activities of AR agonists and antagonists. Sprague Dawley rats (165-180 gms) body weight were treated with vehicle, 40 mpk 1002, 60 mpk 1002, or 20 mpk enzalutamide orally. After 13 days of treatment, the rats were sacrificed and the weights of prostate, seminal vesicles, and levator ani were measured. 1002 at 40 mg/kg antagonized the weights of seminal vesicles, prostate and levator ani muscle to approximately the same extent as 20 mg/kg enzalutamide and 60 mg/kg 1002 further suppressed the weights of each of these tissues to near castration levels (FIG. 19A). FIG. 19A shows the reductions in absolute organ weights in intact rats and FIG. 19B represents the same data of % inhibition relative to vehicle treated control. The bottom right panel of FIG. 19B presents the effect of castration on the weights of seminal vesicles and prostate. 1002 at 60 mg/kg reduced prostate and seminal vesicles weights by ~70% each compared to 90% and 85% reductions, respectively, produced by castration (not shown). 1002 is the first SARD with sufficient bioavailability to produce in vivo AR antagonism in excess of enzalutamide despite inferior in vitro potencies in transactivation ($IC_{50}$) and a lack of binding to LBD ($K_i$). 1002 possesses potent SARD degradation activities in vitro. Correspondingly, the unexpectedly superior in vivo antagonism of 1002 compared to enzalutamide (the IND of enzalutamide indicated that 100 mpk and 30 mpk had comparable in vivo efficacy, so the 20 mpk dose presumably was near $E_{max}$ and was barely soluble) is not explainable in terms of conventional inhibition of the AR through the LBD but rather suggests that the AR antagonism is attributable to the potent degradation of the AR which is a unique property to compounds of this invention.

See also Example 9 for multiple biophysical lines of evidence supporting NTD binding of 1002 and other SARDs of this invention. See also Example 10 for unexpected results for 1014 in a Hershberger assay, and other in vivo assays.

Example 8

In Vivo Anti-Tumor Activity Demonstrated by SARD Compound 1002 in Triple Negative Breast Cancer (TNBC) Patient Derived Xenografts (PDX)

Patient Specimen Collection and PDX Creation:

Specimens from breast cancer patients were collected with patient consent under a protocol approved by the University of Tennessee Health Science Center (UTHSC) Institutional Review Board (IRB). Briefly, specimens were collected immediately after surgery in RPMI medium containing penicillin:streptomycin and Fungizone (Thermo Fischer Scientific) and transported to the laboratory on ice. The tissues were minced finely and treated with collagenase for 2 h. The digested tissues were washed with serum-free medium and implanted as 1 $mm^3$ fragments subcutaneously in female Nod Scid Gamma (NSG) mice. Two such PDX from triple-negative patients (TNBC), HBrT-1071 and HBrT-1361, characterized as TNBC at the time of collection, were implanted in ovariectomized mice. All animal studies were conducted under the UTHSC Animal Care and Use Committee (ACUC) approved protocols. Female NSG mice (6-8 weeks old) purchased from JAX labs (Bar Harbor, Me.) were housed as five animals per cage and were allowed free access to water and commercial rodent chow (Harlan Teklad 22/5 rodent diet –8640). HBrT-1071 and HBrT-1361 were implanted (1 $mm^3$) under the mammary fat pad surgically under isofluorane anesthesia. Once tumor sizes reached 100-200 $mm^3$, the animals were randomized and treated with vehicle (polyethylene glycol-300: DMSO 85:15 ratio) or 1002 (60 mg/kg/day p.o.). Tumors were measured thrice weekly using caliper and the tumor volume was calculated using the formula length*width*width*0.5236. At the end of the experiments, animals were sacrificed, tumors were weighed and collected for further processing. Blood was collected, serum was separated, and stored in –80° C.

Results:

The SARD compound 1002 was able to inhibit tumor growth in two different TNBC PDX models (FIGS. 21A and 21B) whereas enzalutamide failed to inhibit tumor growth (FIG. 21A). 1002 significantly inhibited the growth of HBrt 1071 TNBC PDX with a percent tumor growth inhibition of 65%. Similarly, 1002 inhibited the tumor weight by over 50% (FIG. 21A). In contrast, tumors from enzalutamide treated animals were indistinguishable in size from vehicle treated animals, or possibled trended toward promoting tumor growth. 1002 significantly inhibited the growth of HBrt-1361 TNBC PDX with a percent tumor growth inhibition of ~50% and inhibited the tumor weight by over 40% (FIG. 21B). Further, analyses of the AR which was present in these tumors revealed high levels of AR splice variants (FIG. 21A, lane labeled 1071). This observation helps to rationalize why 1002, an NTD-binding SARD (see Example 9 below for biophysical evidence of NTD binding), was able to inhibit tumor growth whereas the LBD-dependent AR antagonist enzalutamide failed. This suggests that SARDs are able to inhibit AR splice variant dependent cancers such as TNBC and advanced prostate cancers (see Example 10), e.g. those expressing AR-V7 or other AR's lacking the LBD. Further, this is confirmation that the unexpected oral bioavailability of 1002 and other SARDs of this invention, e.g. 1014 and 1010, allowed serum and tumor (see also Example 10) levels following oral administration to be sufficient for treatment of advanced and refractory AR-dependent cancers.

Example 9

SARDs Bind to AF-1 Region of the N-Terminal Domain (NTD) of the Androgen Receptor Nuclear Magnetic Resonance (NMR):

AF-1 and various fragments of AF-1 were cloned in pGex4t.1 and pGex6p.1 vectors. To purify proteins, large scale Luria broth cultures were induced with 1 Mm isopropyl β-D-1-thiogalactopyranoside (IPTG) when the O.D. reached 0.6 and incubated at 25° C. for 6 h. Cells were harvested and lysed in a lysis buffer (50 mM Tris pH 7.5, 25-250 mM NaCl, DNase, protease inhibitors, glycerol, EGTA, DTT, and sucrose). Protein lysates were purified using glutathione sepharose beads by incubating overnight at 4° C. with gentle rocking and the purified protein was eluted with elution buffer (lysis buffer without DNase) containing 50 mM reduced glutathione. Purified proteins were concentrated using Amicon or GE protein concentrators. In cases where GST needed to be cleaved, PreScission Protease (GE Life Sciences) was used to cleave the GST. The proteins were further purified using FPLC (GE AKTA FPLC) with gel filtration (Superdex75 10/300 GL) and ion exchange (HiPrep Q FF 16/10) columns. Compounds alone or in combination with purified protein were run in $^1$H NMR (Bruker 400) in a total volume of 500 µL with 5 mM protein and 200-500 mM small molecule (made in deuterated DMSO (DMSO-$d_6$)) in 20 mM phosphate buffer made in 100% deuterated water.

NMR data were collected using a Bruker AVANCEIII 400 MHz NMR spectrometer (Bruker BioSpin Co. Billerica, Mass. USA) equipped with a BBO 5 mm NMR probe, and TopSpin 3.0 software. $^1$H proton NMR and Saturation-Transfer Difference (STD) experiments were acquired using standard pulse sequences in the TopSpin library. Spectral width was set to 16 ppm with $H_2O$ peak at center. 32K time domain (TD) complex data points and 256 scans were used for $^1$H proton NMR and 1024 scans for STD acquisition. For STD, on- and off-resonance [signals] were collected using interleaved method. Irradiation frequencies for on- and off-resonance were set at 0.8 ppm and −20 ppm, respectively. STD was acquired on a sample with ligand compound alone using identical settings to make sure the STD signals originated from protein in the protein-compound complex sample. Data were collected at room temperature. Chemical shift was referenced according to $H_2O$ peak at 4.70 ppm.

Results:

$^1$H NMR has been used in high-throughput screens to detect the binding of small molecules less than 500 Da to large proteins greater than 5 Kda. As opposed to other biophysical methods, it is easier to use one dimension NMR to observe changes in line-width or line broadening as a high-throughput method to identify the binding of the molecules to proteins and then use Water ligand-observed spectroscopy (WaterLOGSY) or Saturation-Transfer Difference (STD) NMR as confirmatory methodologies. These experiments are based on the fact that NMR observables such as linewidths and NOEs vary dramatically between small molecules and large molecules. The decreased rotational correlation times upon binding of a small molecule ligand to a heavy target molecule produces an atypical heavy molecule NMR result characterized by broadening and weakening of ligand peaks in $^1$H NMR and negative NOE peaks in the waterLOGSY as compared to the free state. In the absence of any affinity, the small molecule NMR result is obtained (sharp peaks in $^1$H NMR and positive NOEs) even in the presence of target protein. This distinction provides the basis for NMR screening experiments.

Using these principles, $^1$H NMR was utilized to confirm the binding of 1002 to the AF-1 region. 1002 (500 mM) was dissolved in deuterated DMSO (DMSO-$d_6$) and was incubated alone or mixed with 5 mM AF-1 and the binding of the molecules to the protein was determined by NMR. While 1002 alone exhibited sharp peaks revealing the ligand present in the free state, 1002 in combination with AF-1 provided broad, diffused, and shorter ligand peaks revealing that 1002 has affinity for AF-1 (FIG. 22). To further confirm the 1D NMR results, we performed WaterLOGSY with 1002 alone or in combination with AF-1. While the 1002 alone gave a flattened positive signal, 1002 in combination with AF-1 provided a negative signal, characteristic of binding to the protein (FIG. 22). These results provide evidence that 1002 binds to AF-1 in the NTD of AR, explaining how a molecule that does not bind the LBD of AR (Table 1) can inhibit the AR in vitro and in vivo.

Steady State Fluorescence:

Recombinant histidine tagged AR-NTD (amino acids 1-559) and AR-AF1 (amino acids 141-486) were purified as previously described. The steady-fluorescence spectrum for the proteins (1 µM) alone or after titration with increasing concentrations of 1002 (1 µM, 2 µM, 5 µM, 10 µM, 25 µM, & 50 µM) was measured after excitation at 278 nm on a Shimadzu Fluorescence spectrophotometer. Proteins were preincubated on ice for 30 minutes with 1002. The results represent three independent experiments (n-3) measured in duplicate.

Results:

The pyrazole SARD 1002 showed a dramatic increase in the fluorescence signal in the region seen for tyrosine emission (FIG. 27B, 307 nm). Normally, the tyrosine signal is not seen due to energy transfer to tryptophan residues in folded/partially folded polypeptides. The increase in the tyrosine signal is similar to what is seen in unfolded/denatured AR-NTD or AR-AF1, e.g., upon addition of urea (FIG. 27A). However, there is no corresponding 'red shift' (increase in wavelength) in the tryptophan signal (compare FIGS. 27A and 27B, in urea $\lambda_{max}$ 344 nm to 347 nm). 1002 may unfold the receptor polypeptides (resulting in tyrosine emission), but shield the tryptophan residues.

For the pyrrole SARD 1010, some evidence for quenching was observed, but the concentration dependence was poor. However, more strikingly there was a consistent and dramatic 'blue shift' (toward smaller wavelengths), which was consistent with the folded form of AR-NTD/AF (i.e. TMAO spectrum in FIG. 27C, $\lambda_{max}$ 344 nm to 340 nm). On the basis of data so far it seems 1010 may stabilize the structure of the AR polypeptides. The data with the indole SARD 36 (FIG. 27D) was similar to what was seen with 1002, but the changes in fluorescence were weaker. In each case, an interaction was observed between the SARD and the AR-1 or NTD. Though the perturbation of fluorescence polarization (FP) was not identical, these similar results across multiple templates of SARDs suggest that the interaction with the N-terminus of the androgen receptor is a conserved feature for the SARDs of this invention. Further, 1002 lacks an interaction with the LBD yet retains potent AR antagonism and SARD activity.

Example 10

Metabolic Stability of Pyrazoles Such as 1014 and 1002 Reveals the Therapeutic Potential of SARDs In Vivo In Vitro Characteristics:

Transactivation ($IC_{50}$):

As reported in Table 1 using the method of Example 3, 1014 is a potent inhibitor of the AR with an $IC_{50}$ value of 205 nM which is similar to 1002 (199 nM).

LBD Binding ($K_i$):

As reported in Table 1 using the method of Example 4, 1014 binds to the LBD of the AR with a $K_i$ value of 512 nM, whereas 1002 does not bind to the LBD.

Sard Activity:

As reported in Table 1 using the methods of Example 5, 1014 and 1002 are capable of potently degrading full length and splice variant androgen receptors.

LNCaP-Enzalutamide Resistant (LNCaP-EnzR) Cells MR49F Growth Assay:

Cells were plated at 10,000 cells/well in RPMI+1% csFBS without phenol red medium in 96 well plates. Cells were treated in the indicated medium with a dose response of the SARDs. At the end of three days, medium was changed and the cells were re-treated. At the end of 6 days, the live cells were measured by Cell-Titer-Glo (Promega) assay.

Results:

1002 and 1014 demonstrated comparable growth inhibition of an enzalutamide resistant variation of the LNCaP (LNCaP-EnzR) cell line which bears the double mutant F876L/T877A, conferring resistance to enzalutamide. 1002 and 1014 both had $IC_{50}$ values of ~3 µM and almost complete inhibition at 10 µM (FIG. 23), suggesting that either SARD could be beneficial for enzalutamide resistant prostate cancer patients if these levels could be achieved in the tumor. (see Table 4 below)

Liver Microsome Metabolism Study:

Materials:

Microsomes were purchased from Xenotech, LLC. Solution 'A' and 'B' (Cat #451220, and 451200, respectively) for NADPH regenerating system (NRS) solution were obtained from Corning Life Sciences. Verapamil, genistein, UDPGA, alamethicin and magnesium chloride were purchased from Sigma-Aldrich. Saccharolactone was obtained from Santa Cruz Biotechnology.

Method: Phase I

Test compound stock solutions were prepared at 10 mM in DMSO. They were diluted to a concentration of 50 µM in 50% acetonitrile (ACN)/$H_2O$ resulting in a working stock solution of 100×. Liver microsomes were utilized at a final concentration of 1.0 mg/mL of protein. Duplicate wells were used for each time point (0, 5, 10, 30, and 60 minutes). Reactions were carried out at 37° C. in a shaking water bath, and the final concentration of solvent was kept constant at 0.5%. At each time point, 100 µL of reaction was removed and added to a sample well containing 100 µL of ice-cold, 100% ACN (plus internal standard), to stop the reaction. The final volume for each reaction was 200 µL, composed of: 66 µL of 0.2 M $KPO_4$ buffer, (pH 7.4); 50 µL of NRS solution; and 10 µL of microsomes (20 mg/mL stock).

The NRS is a solution of glucose-6-phosphate dehydrogenase, $NADP^+$, $MgCl_2$, and glucose-6-phosphate, prepared per manufacturer's instructions. Each 5.0 mL stock of NRS solution contains 3.8 mL $H_2O$, 1.0 mL solution "A", and 0.2 mL solution "B". The reaction from the positive control wells (verapamil, 0.5 µM) were stopped with ice cold acetonitrile containing internal standard.

Phase I and II

Reaction conditions were followed similarly as described above. Additional cofactors were also included in each reaction. UDPGA was added at a final concentration of 5.0 mM. Saccharolactone (β-glucuronidase inhibitor) and alamethicin (pore forming peptide) were added to each reaction at a final concentration of 5.0 mM and 50 µg/mL, respectively. Each 200 µL of microsomal reaction was comprised of 65 µL of 0.2 M $KPO_4$ (pH 7.4), 50 µL of NRS mixture, 66 µL of UDPGA (15 Mm stock); 5.0 µL of saccharolactone (200 mM stock); 0.5 µL of alamethicin (20 mg/mL); 0.6 µL of $MgCl_2$ (1 M stock), and 10 µL of microsomes (20 mg/mL stock). The reaction from the positive control wells (genistein, 2.0 aM) was stopped with ice cold acetonitrile containing internal standard.

Samples were centrifuged at 3,000 rpm for 10 minutes to remove debris and precipitated protein. Approximately 150 µL of supernatant was subsequently transferred to a new sample block for analysis.

Data Analysis

For half-life determination and clearance, data was fitted using GraphPad Prism with a non-linear regression equation, and one phase exponential decay.

Results:

1014 was compared to other compounds, including 1002 in liver microsome metabolism studies. Interestingly, while 1002 showed a half-life around 1 h in vitro, 1014 had a half-life of infinity in the same test, i.e., after 120 min of incubation over 50% of the compound still remained in the reaction (Table 3). As seen in Table 3, the pyrazoles 1002, 1014, and 1022 (see also Table 1 for 1023 and 1024) demonstrated much improved in vitro metabolic stabilities compared to indole (11, 34, 36) and indoline (103) based compounds (and the pyrrole 1010) (Table 3) while retaining SARD activity (Table 1). This suggested that significant in vivo bioavailabilities may be possible for 1002 and 1014.

TABLE 3

| | Liver microsomes MLM/RLM | |
|---|---|---|
| | $t_{1/2}$ (min) | $CL_{int}$ (µL/min/mg) |
| 1002 | 77.96 | 0.89 |
| 1014 | infinity | ~0 |
| 96 | 54.44 | 12.73 |
| (S)-N-(4-Cyano-3-(trifluoromethyl)phenyl)-2-hydroxy-2-methyl-3-(4-(trifluoromethyl)-1H-indazol-1-yl)propanamide | | |
| 1010 | 17.93 | 38.66 |
| 36 | 11.77 | 58.8 |
| (S)-N-(3-Chloro-4-cyanophenyl)-3-(4-fluoro-1H-indol-1-yl)-2-hydroxy-2-methylpropanamide | | |
| 34 | 15.50 | 58.87 |
| (S)-N-(3-Chloro-4-cyanophenyl)-3-(5-fluoro-6-phenyl-1H-indol-1-yl)-2-hydroxy-2-methylpropanamide | | |
| 11 | 14.35 | 48.30 |
| (S)-N-4-Cyano-3-trifluoromethyl)phenyl)-3-(5-fluoro-1H-indol-1-yl)-2-hydroxy-2-methylpropanamide | | |
| 103 | 15 | 46.22 |
| (S)-N-(3-Chloro-4-cyanophenyl)-3-(4-fluoroindolin-1-yl)-2-hydroxy-2-methylpropanamide | | |
| 1022 | 58.06 | 11.94 |

In Vivo Characteristics:

1014 Drug Concentrations in Serum and Tumor in a Xenograft Experiment:

Nude mice implanted with 22RV1 cells subcutaneously were randomized when the tumors reached between 100 and 200 mm³. The mice were treated with vehicle (20:80 water: PEG-400) or 60 mg/kg/day 1014 (or indicated doses of other SARDs) in vehicle for 21 days. At the end of 21 days, the mice were sacrificed and blood and tumors were collected for further analysis. Measurement of drug concentration in animals treated with 1014 demonstrated a significant accumulation of the drug in serum (20.1 µM) and tumor (35.6 µM) (Table 4 and FIG. 24) compared to other molecules tested in parallel in the same experiment. These in vivo levels for 1014, even in view of structurally similar pyrazoles 1002 and 1012, was unexpected. Further, these levels help to explain the efficacy in LNCaP-EnzR xenografts (see FIG. 26 and its description below). Although 22RV1 tumors were not susceptible to SARDs in this particular experiment, likely due to androgen independent growth, this result suggests that androgen-dependent tumors, e.g., LNCaP-EnzR, would be susceptible. Another observation from these data is that tumor concentrations were in excess of serum concentrations, suggesting accumulation of drug in the tumor. The results are shown in Table 4 and FIG. 24.

TABLE 4

| Xenograft dose | Tumor concentration (nM) | Xenograft PK Serum concentration (nM) | |
|---|---|---|---|
| (mg/kg) | At sacrifice (8 hrs) | 2 hrs | 8 hrs |
| 1002 | 60 | 15,725 | 3,560 | 3,620 |
| 11 | 100 | 854 | 365 | 338 |
| 1012 | 60 | 6,655 | 2,114 | 1,914 |
| 1014 | 60 | 35,638 | 4,469 | 20,119 |
| 96 | 100 | 4,458 | 1,207 | 2,563 |
| 1010 | 100 | 17,683 | 862 | 4,173 |
| 103 | 100 | 1,748 | 380 | 1,776 |
| 36 | 100 | 7,128 | 570 | 4,142 |
| 34 | 100 | 2,948 | 261 | 965 |

Hershberger Assay:

Intact C57BL/6 male mice (6-8 weeks old) were randomized based on body weight and treated with various compounds indicated in FIG. 25 for 14 days. At the end of 14 days, the mice were sacrificed and seminal vesicles were weighed. 1014 demonstrated the best inhibition of seminal vesicles weight compared to other compounds, following by 1002, suggesting that these orally administered SARDs were present in levels sufficient to antagonize the AR in androgen-dependent tissues of intact animals. The indoles 34 and 36, pyrrole 1010, and the pyrazole 1012 did not exhibit strong AR antagonism in vivo in this assay.

LNCaP-Enzalutamide-Resistant (LNCaP-EnzR) Xenograft:

LNCaP-EnzR cells MR49F in RPMI+10% FBS were mixed with Matrigel (BD Biosciences) (1:1) and injected subcutaneously in NOD SCID Gamma (NSG) mice (100 µL). Once the tumors reached 100-200 mm³, the animals were randomized and were treated with vehicle (20:80 water:PEG-300) or 1014 (60 mg/kg/day) in vehicle. Tumor volume was measured twice weekly. At the end of the study, animals were sacrificed, tumors isolated, weighed, and stored for further analysis. The experiment was performed twice with two different batches of cells and the results are shown in FIG. 26. Results: In two separate experiments, 1014 was able attain high efficacy tumor growth inhibition, reducing tumor volumes by approximately 60-70% compared to vehicle treated animals. These results suggest that 1014 and other SARDs of this invention administered orally were capable of therapeutic efficacy in enzalutamide resistant (i.e., advanced and refractory) prostate cancers.

Conclusion:

All these results indicate that 1014 has unexpected properties due to its slow metabolism and tumor accumulation. Although, 1014 structurally is comparable to 1002, only differing slightly in the substitution with a $CF_3$ in the third position of the pyrazole ring (vs. 4-fluoro for 1002), it is extremely resistant to metabolism by liver microsomes and thereby has significant accumulation in serum, androgen dependent organs, and in tumors which is unexpected in view of other SARDs tested and in the prior art. This allowed for unexpected in vivo efficacies following oral administration, such as pharmacodynamics (Hershberger assay demonstrated most efficacious seminal vesicles weight effect seen with a SARD) and xenograft tumor growth inhibition (LNCaP-EnzR xenograft), that would not have been possible with our earlier reported SARD templates such as 11, 100, and 17, or other SARDs known in the prior art.

Example 11

SARDs Antagonize F876L

Figure 29A:
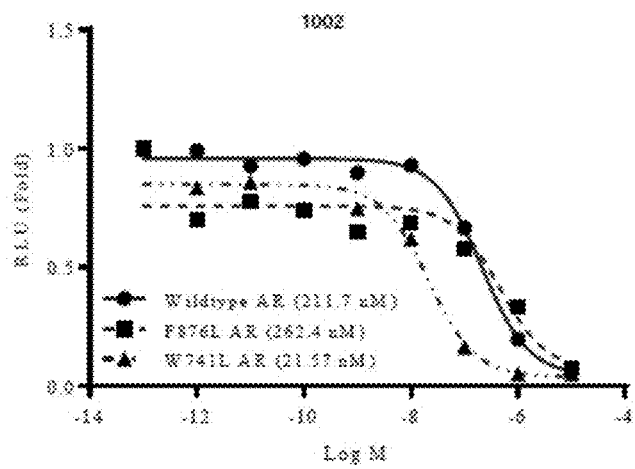
FIGS. 29A-29C: depict that SARDs such as 1002 can antagonize F876L AR at doses comparable to the wildtype AR and W741L AR at more potent doses than wildtype AR.
Figure 29B:
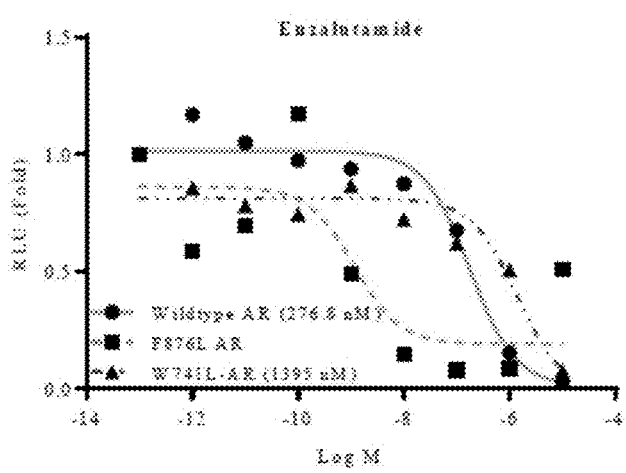
Figure 29C:
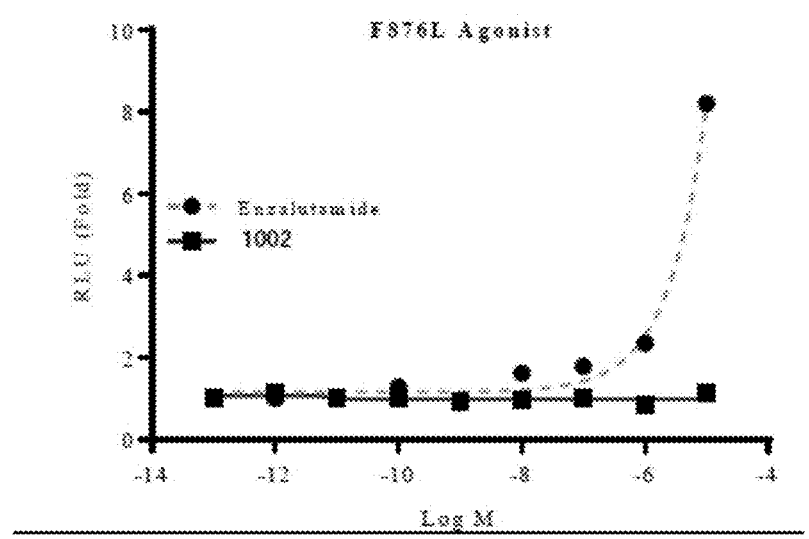
Figure 30A:
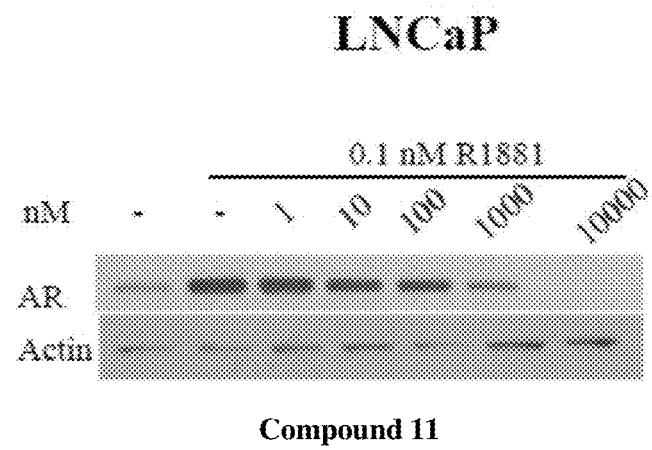
Figure 30B:
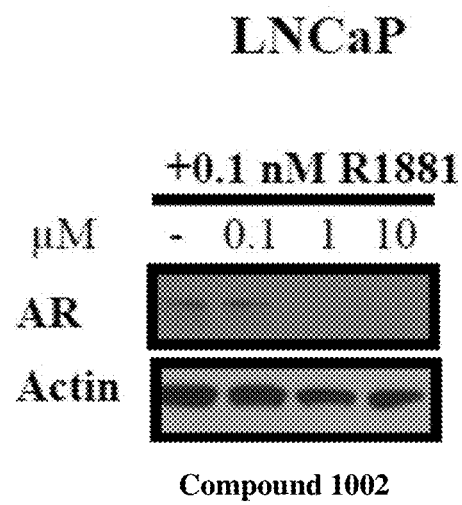
Figure 30C:
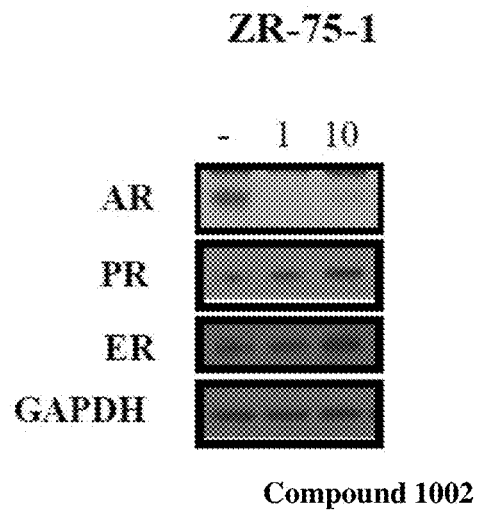
Figure 30D:
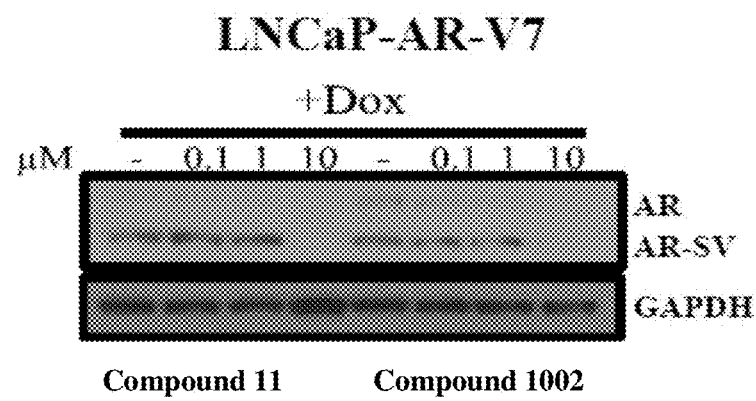
Figure 30E:
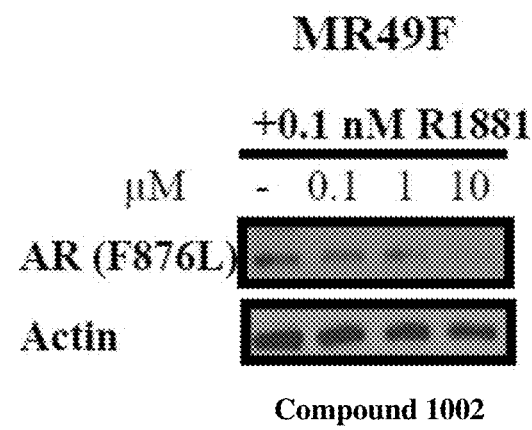
FIG. 30E demonstrates that SARDs of this invention can degrade F876L AR.
Figure 31A:
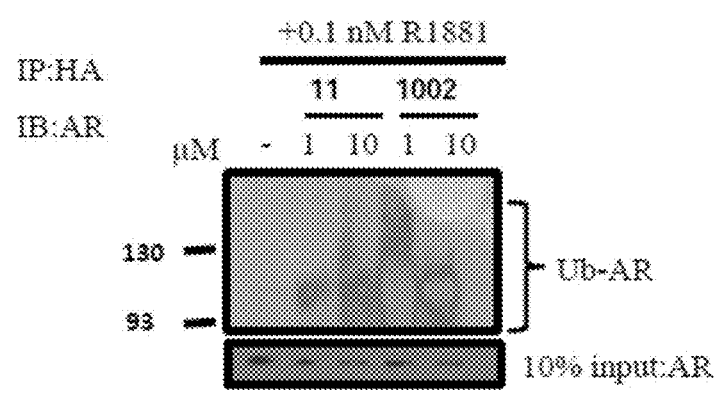
FIGS. 31A and 31B: SARDs promote ubiquitination and require the proteasome to degrade the AR.
Figure 31B:
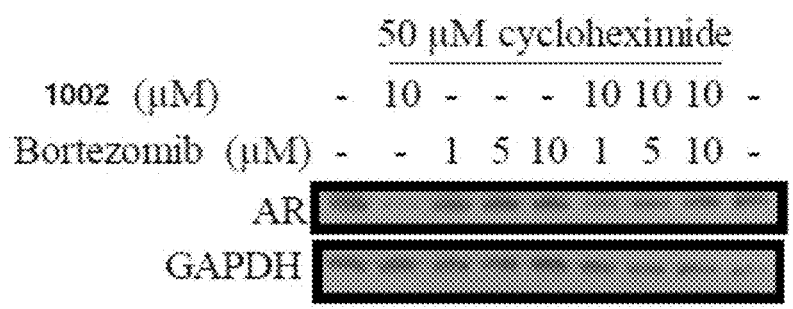
Figure 33:
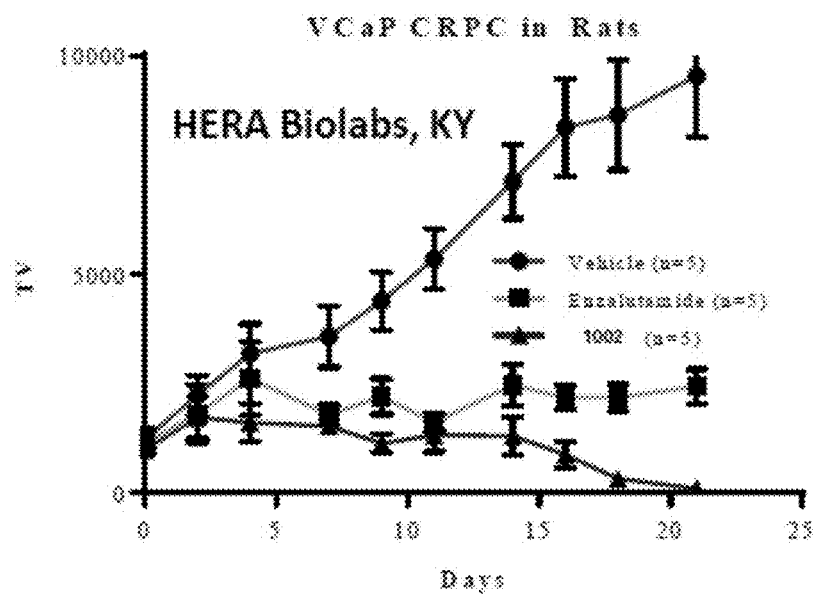
FIG. 33: SARDs inhibit the growth of enzalutamide-resistant VCaP CPRC xenografts in rats. The graph of tumor volume (TV) over time of VCaP CRPC in rats showed the ability of compound 1002 in rats (there is less metabolism of compound 1002 in rats than mice) to completely resolve VCaP xenografts (tumor volumes plotted as triangles) within 21 days, whereas enzalutamide only caused partial regression (tumor volumes plotted as squares). VCaP is an androgen-dependent CRPC cell line that is partially sensitive to enzalutamide, but fully sensitive to SARDs of this invention. This model demonstrated that in the absence of pharmacokinetic barriers (i.e., high levels of metabolism and/or poor absorption and distribution in mice tumor xenograft models), that SARDs can lead to the complete resolution of castration resistant prostate cancers.
Figure 34A:
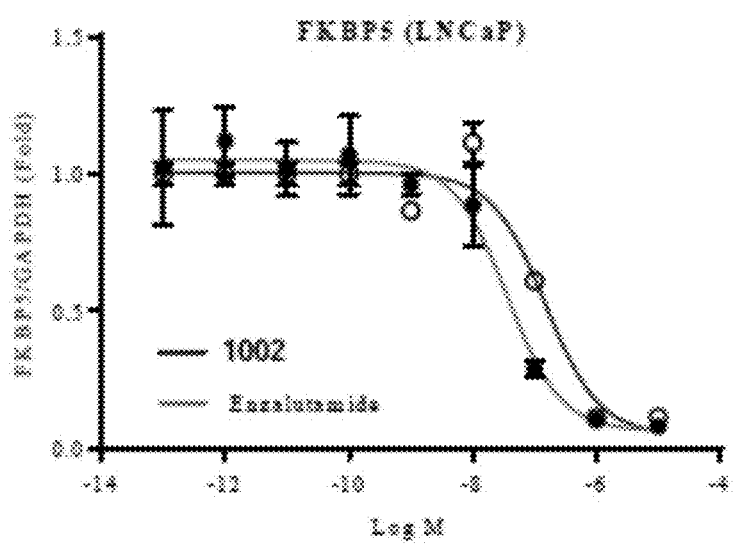
FIGS. 34A-34D: SARDs inhibit AR and Enz-R-AR function and cell growth.
Figure 34B:
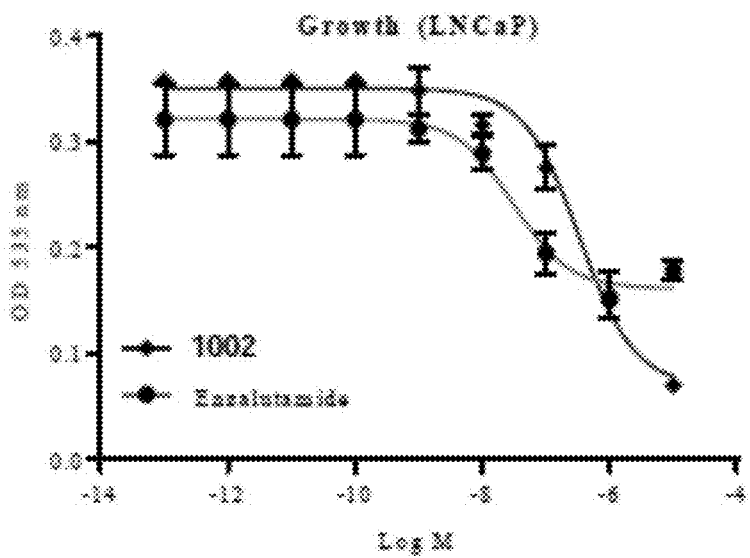
Figure 34C:
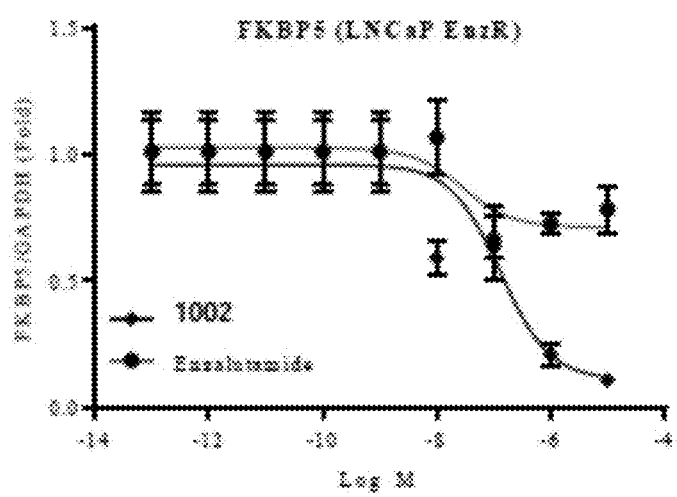
Figure 34D:
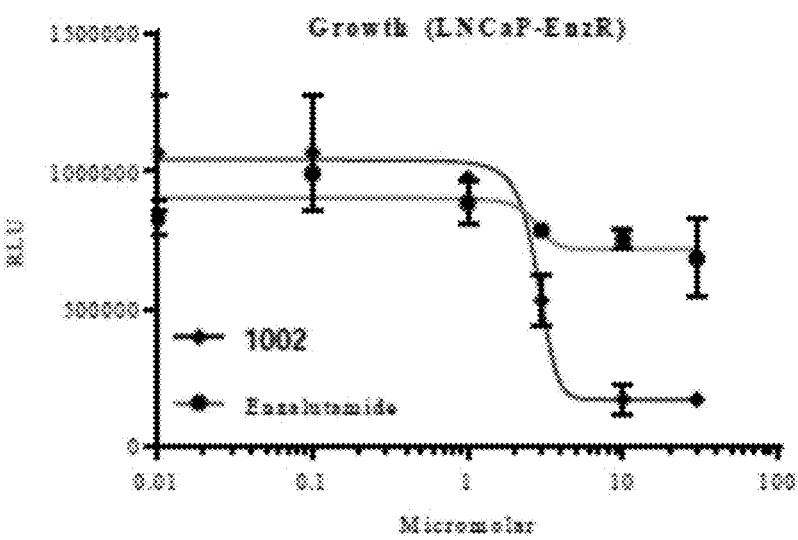

FIGS. 29A-29C illustrate that SARDs antagonized F876L AR at doses comparable to the wildtype AR and do not have any intrinsic agonist activity in F876L, showing their ability to overcome enzalutamide resistance. In FIGS. 29A-29C, compound 1002 was able to inhibit the transcriptional activation of wtAR and F876L (enzalutamide resistance) and W741L (bicalutamide resistance). Enzalutamide behaved similarly, however enzalutamide acted as an agonist at higher levels of treatment of F876L. This demonstrated the ability of SARDs to overcome antagonist switch mechanisms of resistance which are prevalent in CPRC. Further, Example 10 shows the ability of SARDs to overcome enzalutamide resistance with regard to cellular growth and with regard to xenograft growth.

Example 12

Binding to AR-NTD to Degrade

FIG. 32 shows that AR NTD binding of 1002 for required for degradation. Chimeric constructs were created in which the AR and GR were cloned such that the entire sequence was AR or GR, or the N-terminal domain was derived from AR but the DNA binding and ligand binding domains were derived from GR (AGG) or vice versa (GAA). Several lines of evidence summarized below suggested either NTD binding and/or dependence upon NTD for SARD activity. Further to that line of reasoning, the SARD 1002 was tested for its ability to degrade the AR, GR, AGG or GAA constructs as a way to demonstrate that AR NTD was required in order for the SARD to degrade the protein (i.e., demonstrate NTD-dependence). Other lines of evidence suggesting NTD-dependent SARD activity included: FIGS. 22 (NMR) and 27 (fluorescent polarization) demonstrated 1002 binding to NTD and their ability to degrade SV's which lack any LBD further suggested NTD binding. Example 3 discusses potent transcriptional activity in the absence of demonstrable LBD binding and structure-activity relationships of NTD binding that differ from known LBD SAR patterns. Example 8 discusses the ability of 1002 to inhibit SV-driven growth (i.e., FL AR is not expressed) of TNBC xenografts with SARD 1002, suggesting NTD binding. Consistent with this interpretation, the LBD-dependent AR antagonist enzalutamide failed to inhibit TNBC xenograft growth in these same TNBC xenografts.

The chimeric receptor data as provided in FIG. 32 is a strong evidence for NTD-dependence of SARD activity. From the Western blots of FIG. 32, it is apparent that SARDs degraded AR and/or AGG (NTD is AR and rest is GR) but not GR or GAA (NTD is GR and rest is AR). This suggests that AR NTD is required for SARD activity.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention

What is claimed is:

1. A method of treating prostate cancer (PCa) or increasing the survival of a male subject suffering from prostate cancer comprising administering to the subject a therapeutically effective amount of a selective androgen receptor degrader (SARD) compound represented by the structure of formula I:

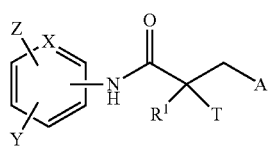

I wherein
T is OH, OR, OCOR, CH$_3$, —NHCOCH$_3$, or NHCOR;
R$^1$ is CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a five-membered saturated or five or six-membered unsaturated ring having at least one nitrogen atom and 0, 1, or 2 double bonds, optionally substituted with at least one of Q$^1$, Q$^2$, Q$^3$ or Q$^4$, each independently selected from hydrogen, keto, substituted or unsubstituted linear or branched alkyl, substituted or unsubstituted cycloalkyl, substituted or unsubstituted heterocloalkyl, haloalkyl, CF$_3$, substituted or unsubstituted aryl, substituted or unsubstituted phenyl, F, Cl, Br, I, CN, NO$_2$, hydroxyl, alkoxy, OR, benzyl, NCS, maleimide, NHCOOR, N(R)$_2$, NHCOR, CONHR, COOR or COR;
R$^3$ is halide, N$_3$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SO$_3$H, SO$_2$NH$_2$, SO2NH(R$^4$), SO$_2$N(R$^4$)$_2$, NH$_2$, CO(N-heterocycle), NO$_2$, cyanate, isocyanate, thiocyanate, isothiocyanate, mesylate, tosylate, triflate, PO(OH)$_2$ or OPO(OH)$_2$; and
R$^4$ is H, alkyl, haloalkyl, cycloalkyl, aryl or heteroaryl, wherein said alkyl, haloalkyl, cycloalkyl, aryl or heteroaryl groups are optionally substituted;
wherein if A is Br or I, R$^1$ is CH$_3$, and T is OH, then X is N or the aniline ring forms a fused heterocyclic ring,
or its isomer, pharmaceutically acceptable salt, pharmaceutical product, hydrate or any combination thereof.

2. The method according to claim 1, wherein the prostate cancer is at least one of advanced prostate cancer, refractory prostate cancer, castration resistant prostate cancer (CRPC), metastatic CRPC (mCRPC), non-metastatic CRPC (nmCRPC), or high-risk nmCRPC.

3. The method according to claim 1 further comprising administering androgen deprivation therapy (ADT).

4. The method according to claim 1, wherein the prostate cancer is resistant to treatment with an androgen receptor antagonist(s).

5. The method according to claim 4, wherein the androgen receptor antagonist is at least one of enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, or spironolactone.

6. A method of treating enzalutamide resistant prostate cancer in a subject comprising administering to the subject a therapeutically effective amount of a selective androgen receptor degrader (SARD) compound represented by the structure of formula I:

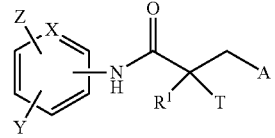

I wherein
T is OH, OR, OCOR, CH$_3$, —NHCOCH$_3$, or NHCOR;
R$^1$ is CH$_3$, CH$_2$F, CHF$_2$, CF$_3$, CH$_2$CH$_3$, or CF$_2$CF$_3$;
or T and R$^1$ form a 3-8 carbocyclic or heterocyclic ring;
Y is H, CF$_3$, F, I, Br, Cl, CN, or C(R)$_3$;
Z is H, NO$_2$, CN, halide, COOH, COR, NHCOR, CONHR,
or Y and Z form a 5 to 8 membered fused ring;
X is CH or N;
R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;
A is R$^2$ or R$^3$;
R$^2$ is a five-membered saturated or five or six-membered unsaturated ring having at least one nitrogen atom and 0, 1, or 2 double bonds, optionally substituted with at least one of Q$^1$, Q$^2$, Q$^3$ or Q$^4$, each independently selected from hydrogen, keto, substituted or unsubstituted linear or branched alkyl, substituted or unsubstituted cycloalkyl, substituted or unsubstituted heterocloalkyl, haloalkyl, CF$_3$, substituted or unsubstituted aryl, substituted or unsubstituted phenyl, F, Cl, Br, I, CN, NO$_2$, hydroxyl, alkoxy, OR, benzyl, NCS, maleimide, NHCOOR, N(R)$_2$, NHCOR, CONHR, COOR or COR;
R$^3$ is halide, N$_3$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SO$_3$H, SO$_2$NH$_2$, SO$_2$NH(R$^4$), SO$_2$N(R$^4$)$_2$, NH$_2$, CO(N-heterocycle), NO$_2$, cyanate, isocyanate, thiocyanate, isothiocyanate, mesylate, tosylate, triflate, PO(OH)$_2$ or OPO(OH)$_2$; and R$^4$ is H, alkyl, haloalkyl, cycloalkyl, aryl or heteroaryl, wherein said alkyl, haloalkyl, cycloalkyl, aryl or heteroaryl groups are optionally substituted;

wherein if A is Br or I, R$^1$ is CH$_3$, and T is OH, then X is N or the aniline ring forms a fused heterocyclic ring, or its isomer, pharmaceutically acceptable salt, pharmaceutical product, hydrate or any combination thereof.

7. A method of treating abiraterone resistant prostate cancer comprising administering to the subject a therapeutically effective amount of a selective androgen receptor degrader (SARD) compound represented by the structure of formula I:

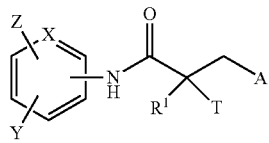

I wherein

T is OH, OR, OCOR, CH$_3$, —NHCOCH$_3$, or NHCOR;

R$^1$ is CH$_3$, CH$_2$F, CHF$_2$, CF$_3$, CH$_2$CH$_3$, or CF$_2$CF$_3$; or T and R$^1$ form a 3-8 carbocyclic or heterocyclic ring;

Y is H, CF$_3$, F, I, Br, Cl, CN, or C(R)$_3$;

Z is H, NO$_2$, CN, halide, COOH, COR, NHCOR, CONHR, or Y and Z form a 5 to 8 membered fused ring;

X is CH or N;

R is H, alkyl, alkenyl, haloalkyl, alcohol, CH$_2$CH$_2$OH, CF$_3$, CH$_2$Cl, CH$_2$CH$_2$Cl, aryl, F, Cl, Br, I, or OH;

A is R$^2$ or R$^3$;

R$^2$ is a five-membered saturated or five or six-membered unsaturated ring having at least one nitrogen atom and 0, 1, or 2 double bonds, optionally substituted with at least one of Q$^1$, Q$^2$, Q$^3$ or Q$^4$, each independently selected from hydrogen, keto, substituted or unsubstituted linear or branched alkyl, substituted or unsubstituted cycloalkyl, substituted or unsubstituted heterocycloalkyl, haloalkyl, CF$_3$, substituted or unsubstituted aryl, substituted or unsubstituted phenyl, F, Cl, Br, I, CN, NO$_2$, hydroxyl, alkoxy, OR, benzyl, NCS, maleimide, NHCOOR, N(R)$_2$, NHCOR, CONHR, COOR or COR;

R$^3$ is halide, N$_3$, CF$_3$, COR$^4$, COCl, COOCOR$^4$, COOR$^4$, OCOR$^4$, OCONHR$^4$, NHCOOR$^4$, NHCONHR$^4$, OCOOR$^4$, CN, CONH$_2$, CONH(R$^4$), CON(R$^4$)$_2$, SO$_3$H, SO$_2$NH$_2$, SO$_2$NH(R$^4$), SO$_2$N(R$^4$)$_2$, NH$_2$, CO(N-heterocycle), NO$_2$, cyanate, isocyanate, thiocyanate, isothiocyanate, mesylate, tosylate, triflate, PO(OH)$_2$ or OPO(OH)$_2$; and R$^4$ is H, alkyl, haloalkyl, cycloalkyl, aryl or heteroaryl, wherein said alkyl, haloalkyl, cycloalkyl, aryl or heteroaryl groups are optionally substituted;

wherein if A is Br or I, R$^1$ is CH$_3$, and T is OH, then X is N or the aniline ring forms a fused heterocyclic ring, or its isomer, pharmaceutically acceptable salt, pharmaceutical product, hydrate or any combination thereof.

8. The method of claim 1, wherein the SARD compound is represented by the structure of formula IA:

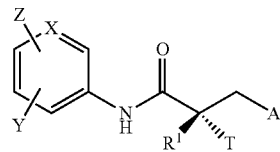

IA or its isomer, pharmaceutically acceptable salt, pharmaceutical product, hydrate or any combination thereof.

9. The method of claim 6, wherein the SARD compound is represented by the structure of formula IA:

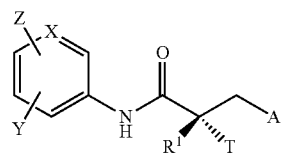

IA or its isomer, pharmaceutically acceptable salt, pharmaceutical product, hydrate or any combination thereof.

10. The method of claim 7, wherein the SARD compound is represented by the structure of formula IA:

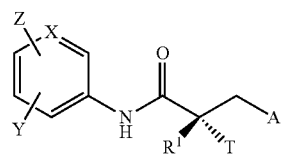

IA or its isomer, pharmaceutically acceptable salt, pharmaceutical product, hydrate or any combination thereof.

11. The method of claim 1, wherein the SARD compound is represented by the structure of formula IB:

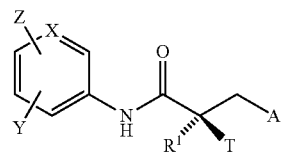

IB or its isomer, pharmaceutically acceptable salt, pharmaceutical product, hydrate or any combination thereof.

12. The method of claim 6, wherein the SARD compound is represented by the structure of formula IB:

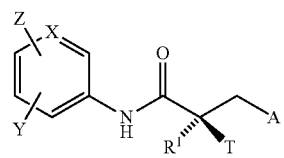

IB or its isomer, pharmaceutically acceptable salt, pharmaceutical product, hydrate or any combination thereof.

13. The method of claim 7, wherein the SARD compound is represented by the structure of formula IB:

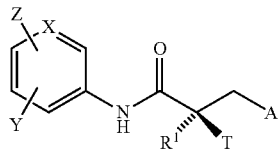

IB or its isomer, pharmaceutically acceptable salt, pharmaceutical product, hydrate or any combination thereof.

14. The method of claim 1, wherein the SARD compound is represented by the structure of formula II:

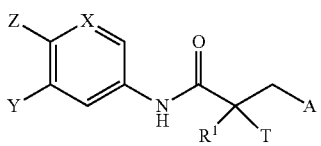

II or its optical isomer, isomer, pharmaceutically acceptable salt, pharmaceutical product, hydrate or any combination thereof.

15. The method of claim 14, wherein the SARD compound is represented by the structure of formula IIA:

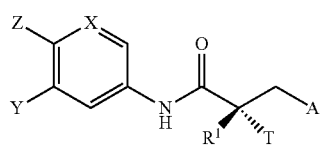

IIA or its isomer, pharmaceutically acceptable salt, pharmaceutical product, hydrate or any combination thereof;
or by the structure of formula IIB:

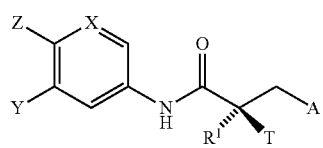

IIB or its isomer, pharmaceutically acceptable salt, pharmaceutical product, hydrate or any combination thereof.

16. The method of claim 6, wherein the SARD compound is represented by the structure of formula II:

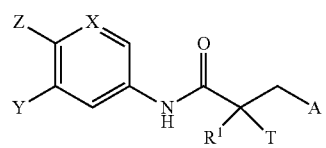

II or its optical isomer, isomer, pharmaceutically acceptable salt, pharmaceutical product, hydrate or any combination thereof.

17. The method of claim 16, wherein the SARD compound is represented by the structure of formula IIA:

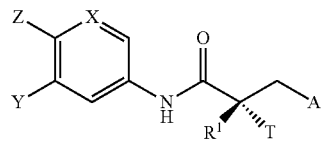

IIA or its isomer, pharmaceutically acceptable salt, pharmaceutical product, hydrate or any combination thereof;
or by the structure of formula IIB:

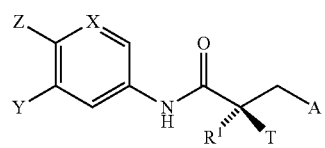

IIB or its isomer, pharmaceutically acceptable salt, pharmaceutical product, hydrate or any combination thereof.

18. The method of claim 7, wherein the SARD compound is represented by the structure of formula II:

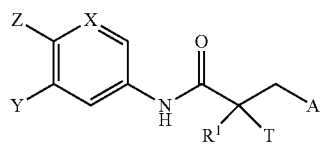

II or its optical isomer, isomer, pharmaceutically acceptable salt, pharmaceutical product, hydrate or any combination thereof.

19. The method of claim 18, wherein the SARD compound is represented by the structure of formula IIA:

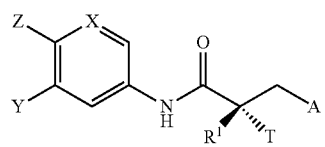

IIA or its isomer, pharmaceutically acceptable salt, pharmaceutical product, hydrate or any combination thereof;
or by the structure of formula IIB:

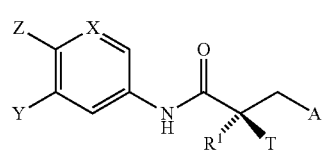

IIB or its isomer, pharmaceutically acceptable salt, pharmaceutical product, hydrate or any combination thereof.

20. The method of claim 1, wherein the SARD compound is represented by the structure of formula VII:

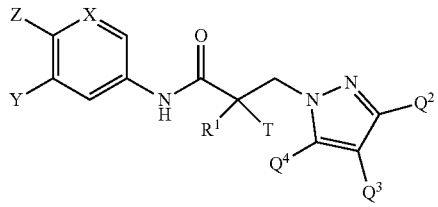

VII or its optical isomer, isomer, pharmaceutically acceptable salt, pharmaceutical product, hydrate or any combination thereof.

21. The method of claim 20, wherein the SARD compound is represented by the structure of formula VIIA:

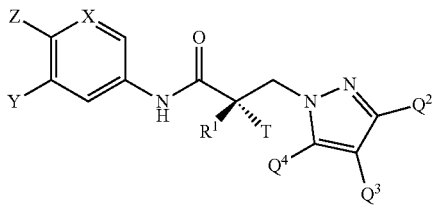

VIIA or its isomer, pharmaceutically acceptable salt, pharmaceutical product, hydrate or any combination thereof; or by the structure of formula VIIB:

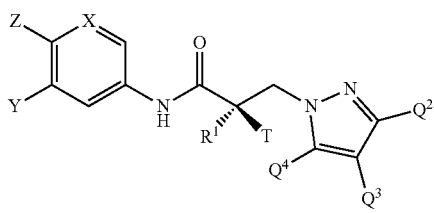

VIIB or its isomer, pharmaceutically acceptable salt, pharmaceutical product, hydrate or any combination thereof.

22. The method of claim 6, wherein the SARD compound is represented by the structure of formula VII:

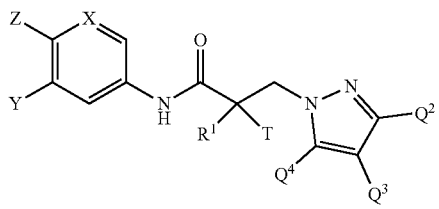

VII or its optical isomer, isomer, pharmaceutically acceptable salt, pharmaceutical product, hydrate or any combination thereof.

23. The method of claim 22, wherein the SARD compound is represented by the structure of formula VIIA:

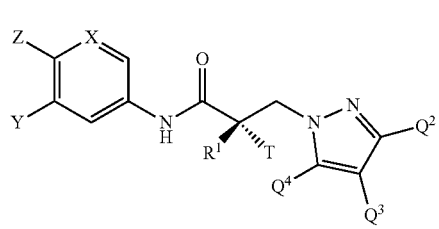

VIIA or its isomer, pharmaceutically acceptable salt, pharmaceutical product, hydrate or any combination thereof; or by the structure of formula VIIB:

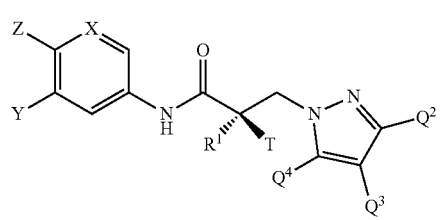

VIIB or its isomer, pharmaceutically acceptable salt, pharmaceutical product, hydrate or any combination thereof.

24. The method of claim 7, wherein the SARD compound is represented by the structure of formula VII:

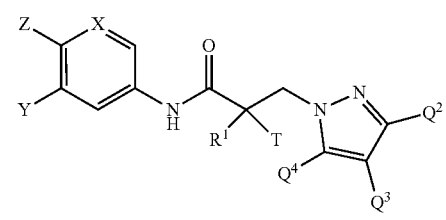

VII or its optical isomer, isomer, pharmaceutically acceptable salt, pharmaceutical product, hydrate or any combination thereof.

25. The method of claim 24, wherein the SARD compound is represented by the structure of formula VIIA:

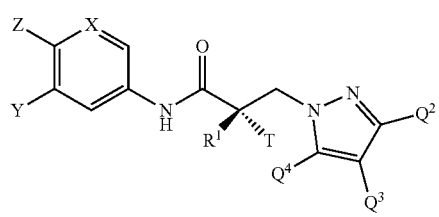

VIIA or its isomer, pharmaceutically acceptable salt, pharmaceutical product, hydrate or any combination thereof;

or by the structure of formula VIIB:

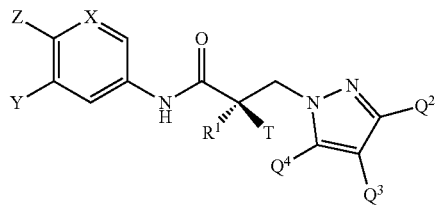

or its isomer, pharmaceutically acceptable salt, pharmaceutical product, hydrate or any combination thereof.

26. The method of claim 1, wherein $Q^1$, $Q^2$, $Q^3$ or $Q^4$ is hydrogen, CN, $NO_2$, $CF_3$, F, Cl, Br, I, NHCOOR, $N(R)_2$, NHCOR, COR, or substituted or unsubstituted phenyl.

27. The method of claim 6, wherein $Q^1$, $Q^2$, $Q^3$ or $Q^4$ is hydrogen, CN, $NO_2$, $CF_3$, F, Cl, Br, I, NHCOOR, $N(R)_2$, NHCOR, COR, or substituted or unsubstituted phenyl.

28. The method of claim 7, wherein $Q^1$, $Q^2$, $Q^3$ or $Q^4$ is hydrogen, CN, $NO_2$, $CF_3$, F, Cl, Br, I, NHCOOR, $N(R)_2$, NHCOR, COR, or substituted or unsubstituted phenyl.

29. The method of claim 1, wherein the SARD compound is represented by the structure of any one of the following compounds:

1001

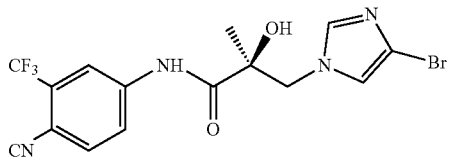

1002

1003

1004

1005

1006

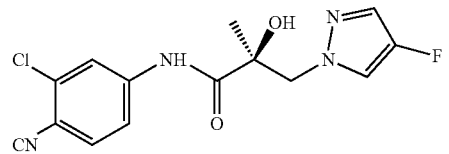

1007

1008

1009

1010

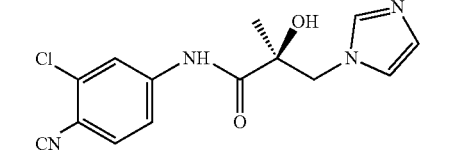

1011

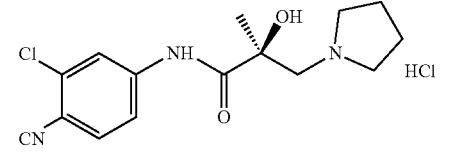

1012

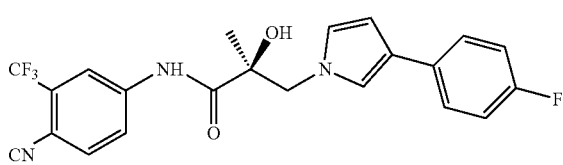

1013

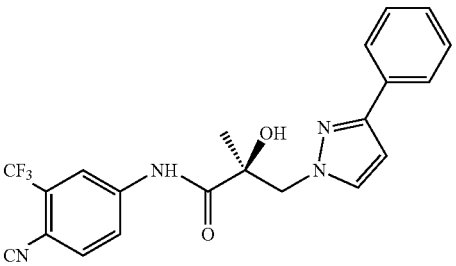
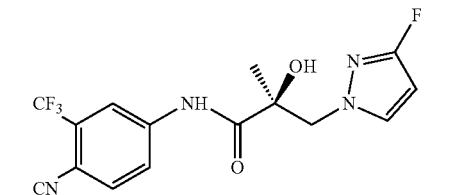
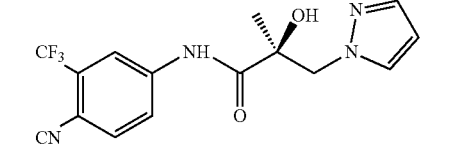

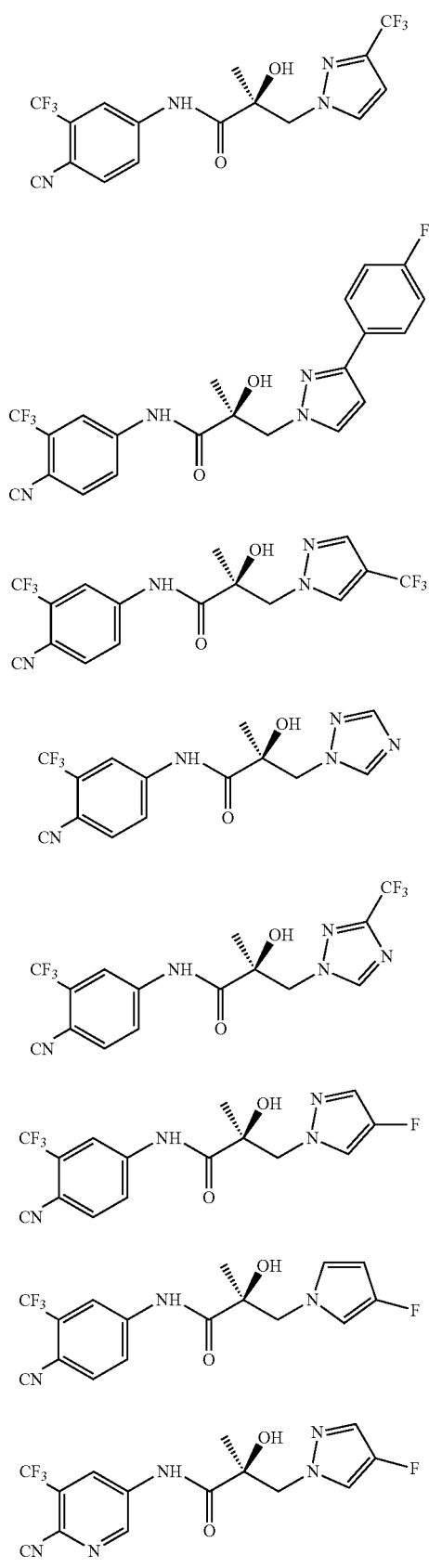
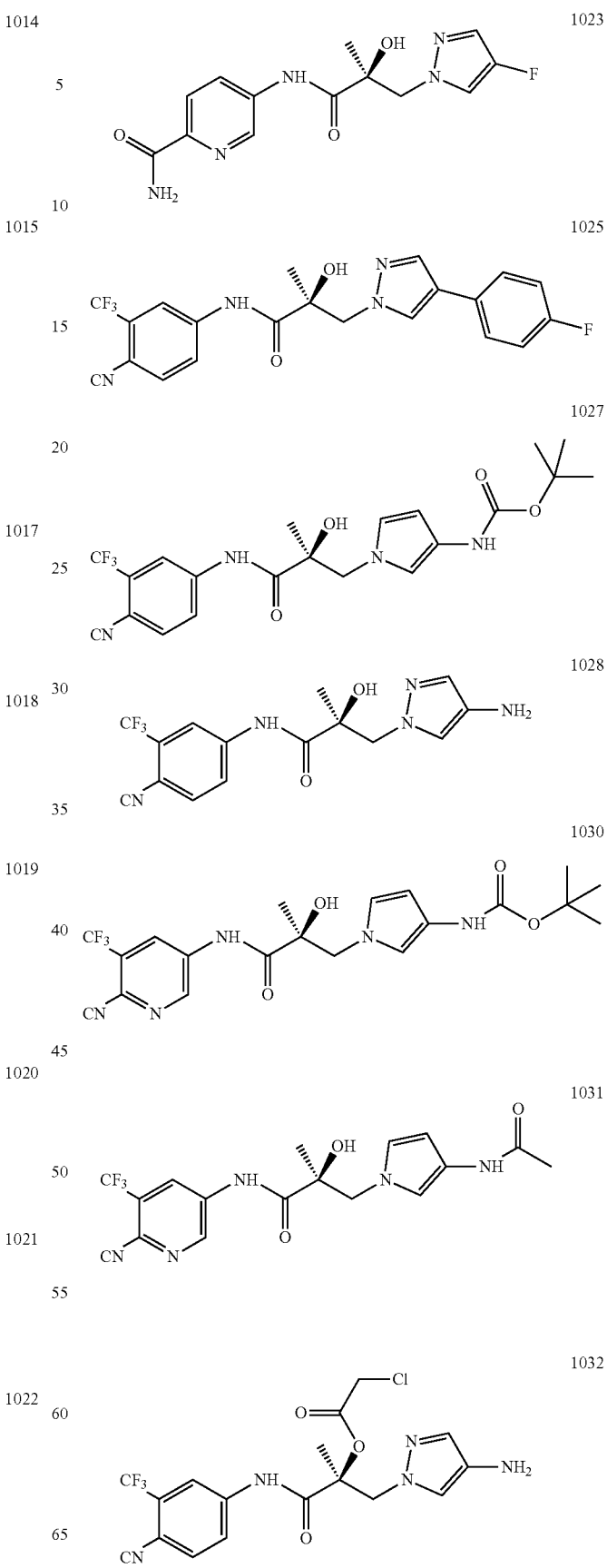

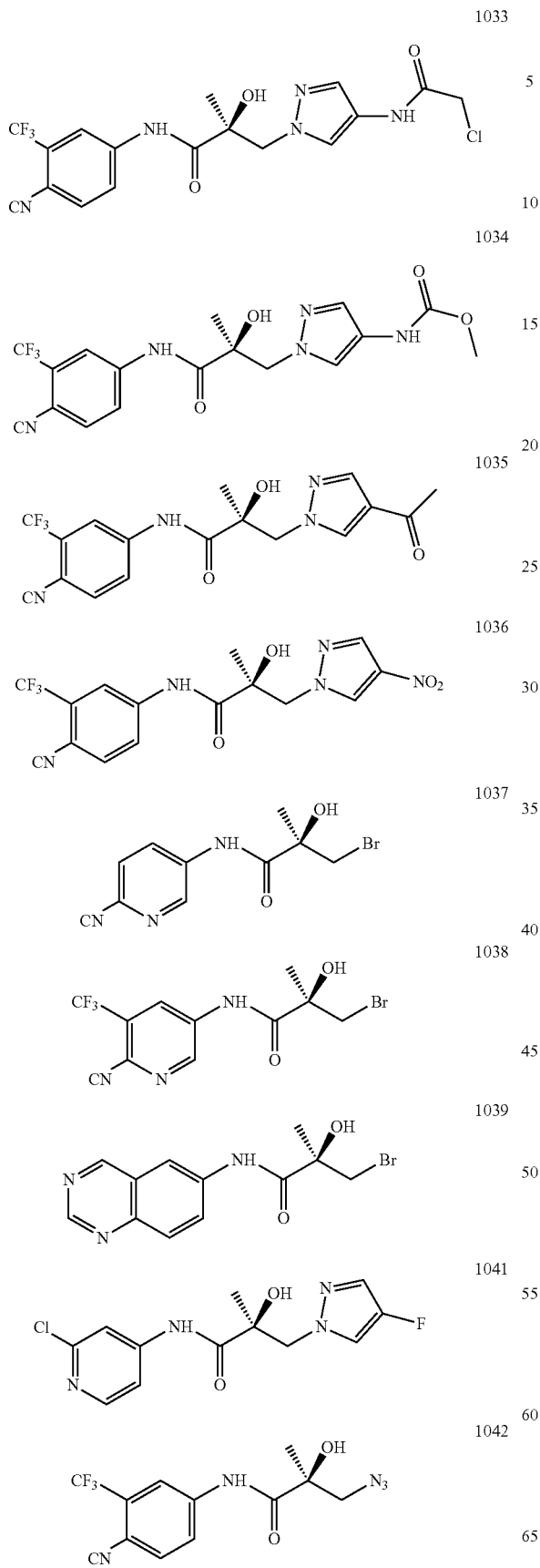
30. The method of claim 6, wherein the SARD compound is represented by the structure of any one of the following compounds:

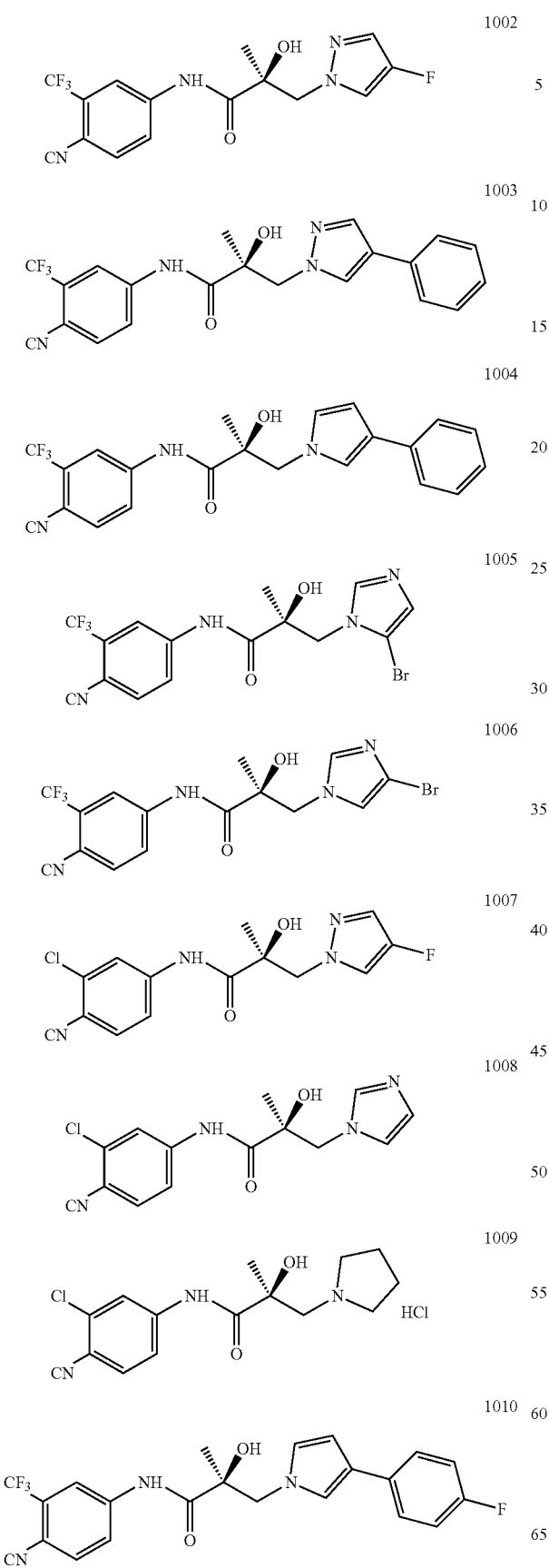
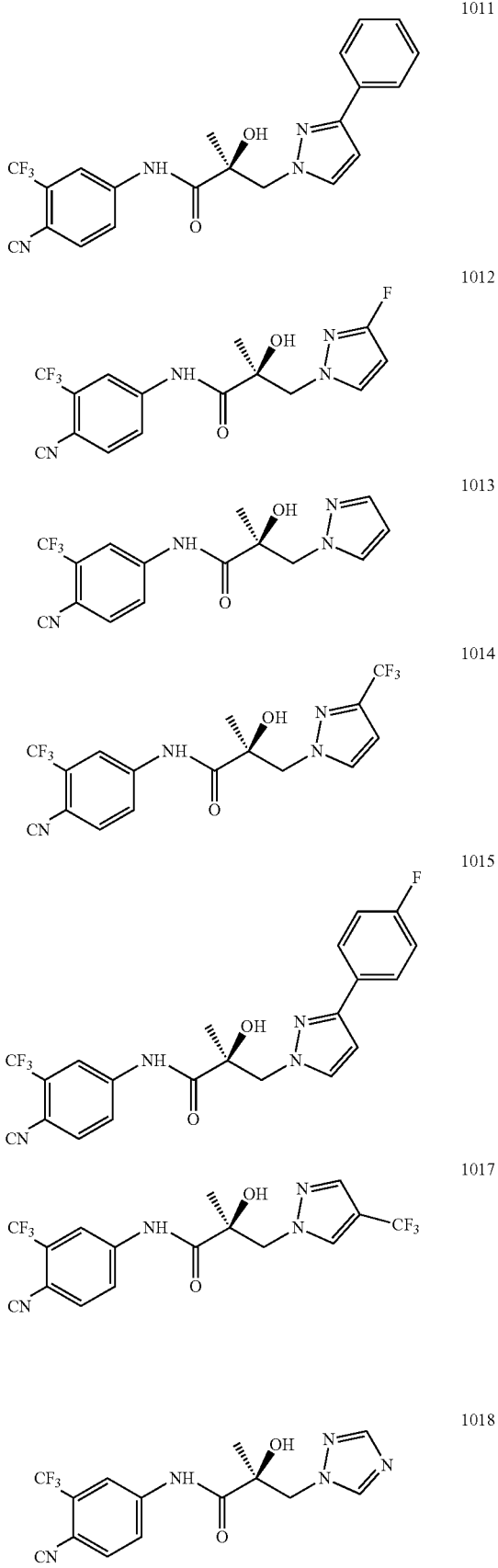

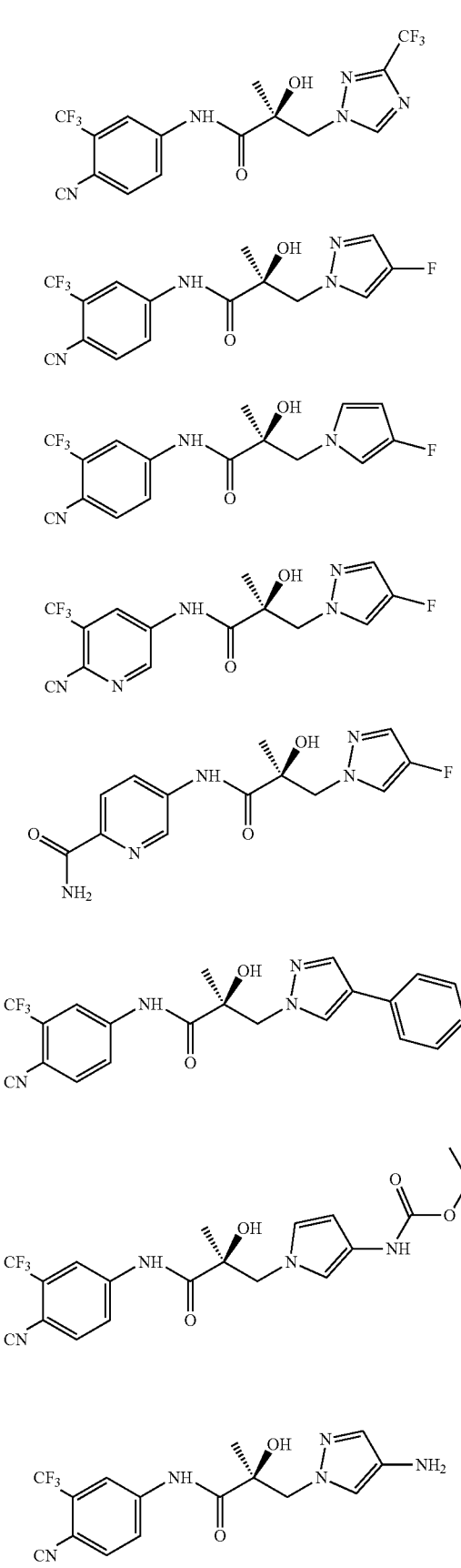
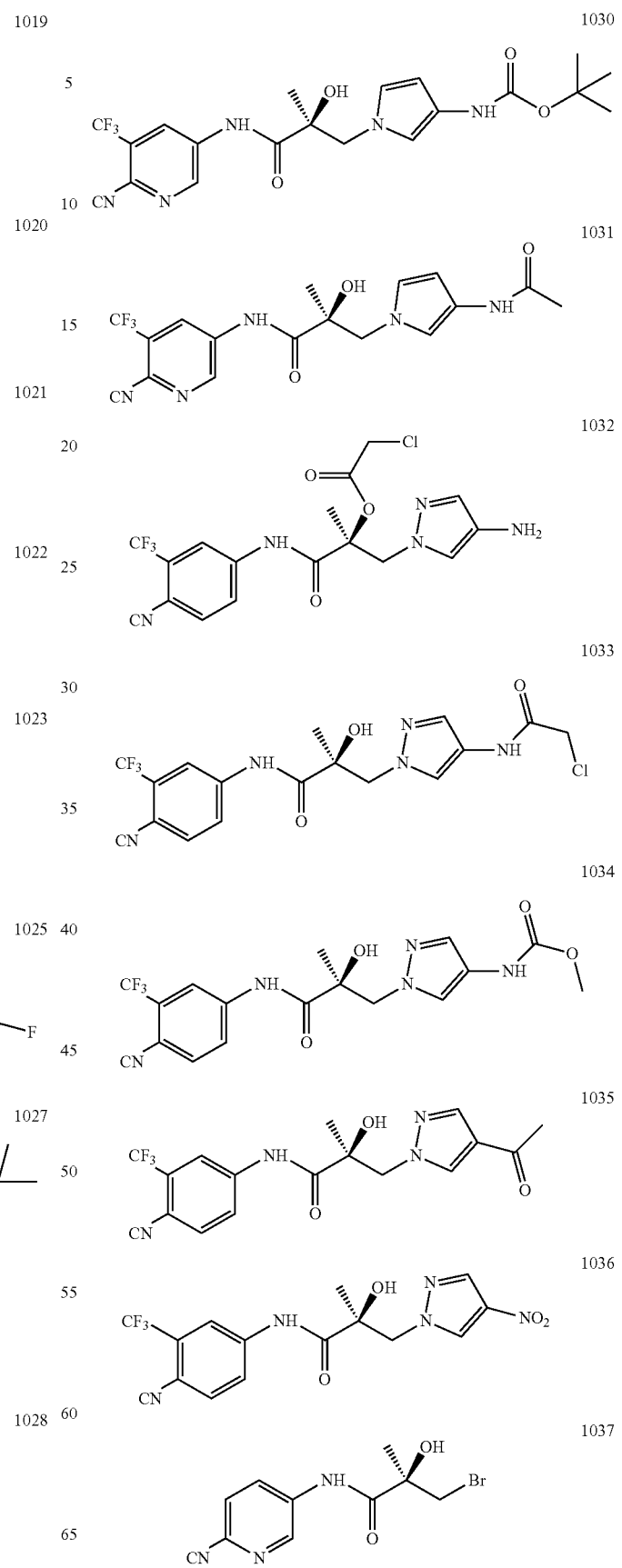

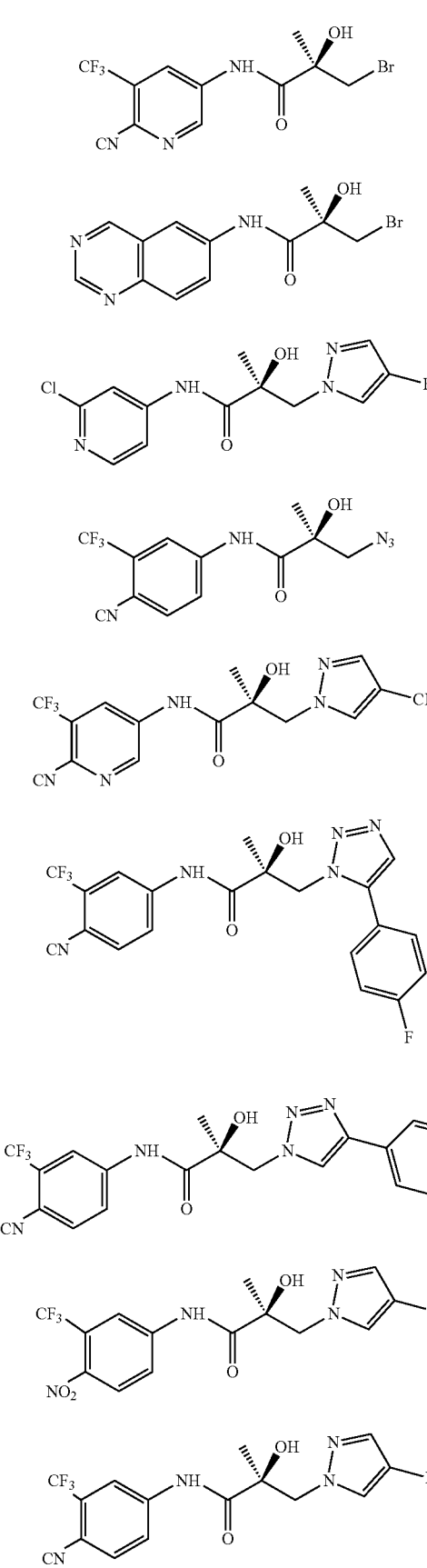
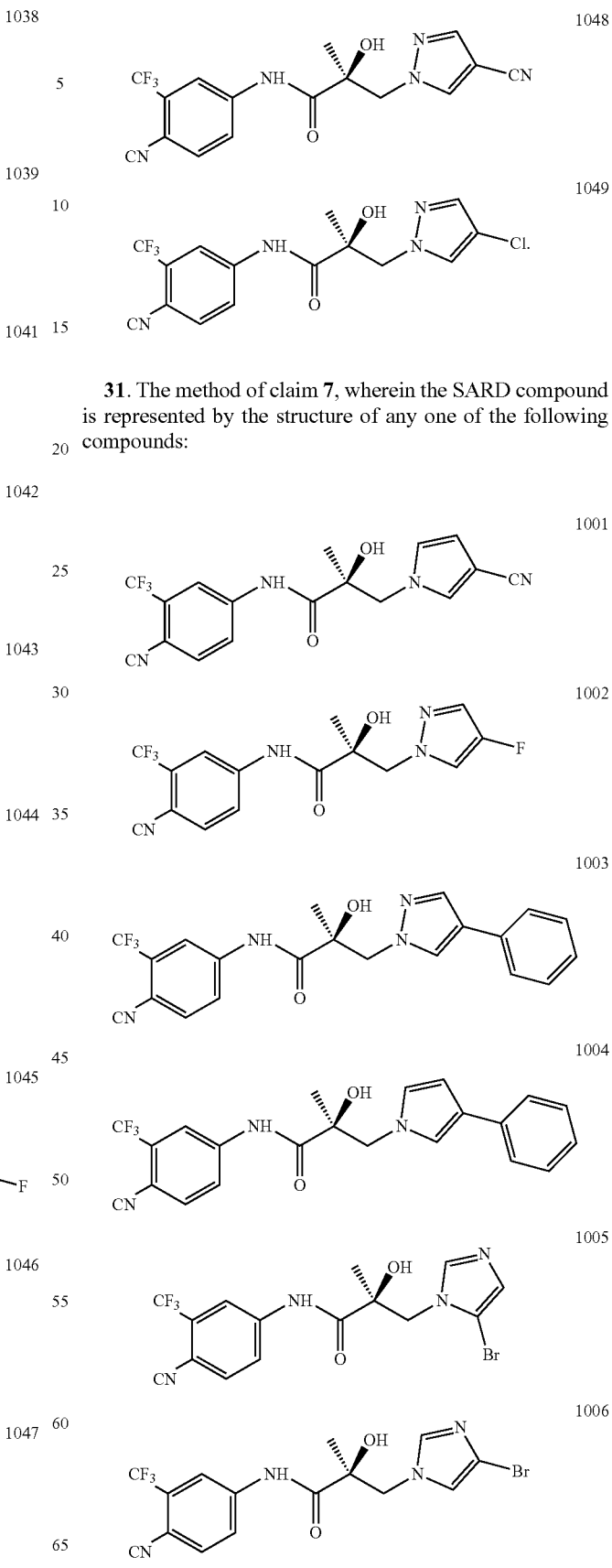
31. The method of claim 7, wherein the SARD compound is represented by the structure of any one of the following compounds:

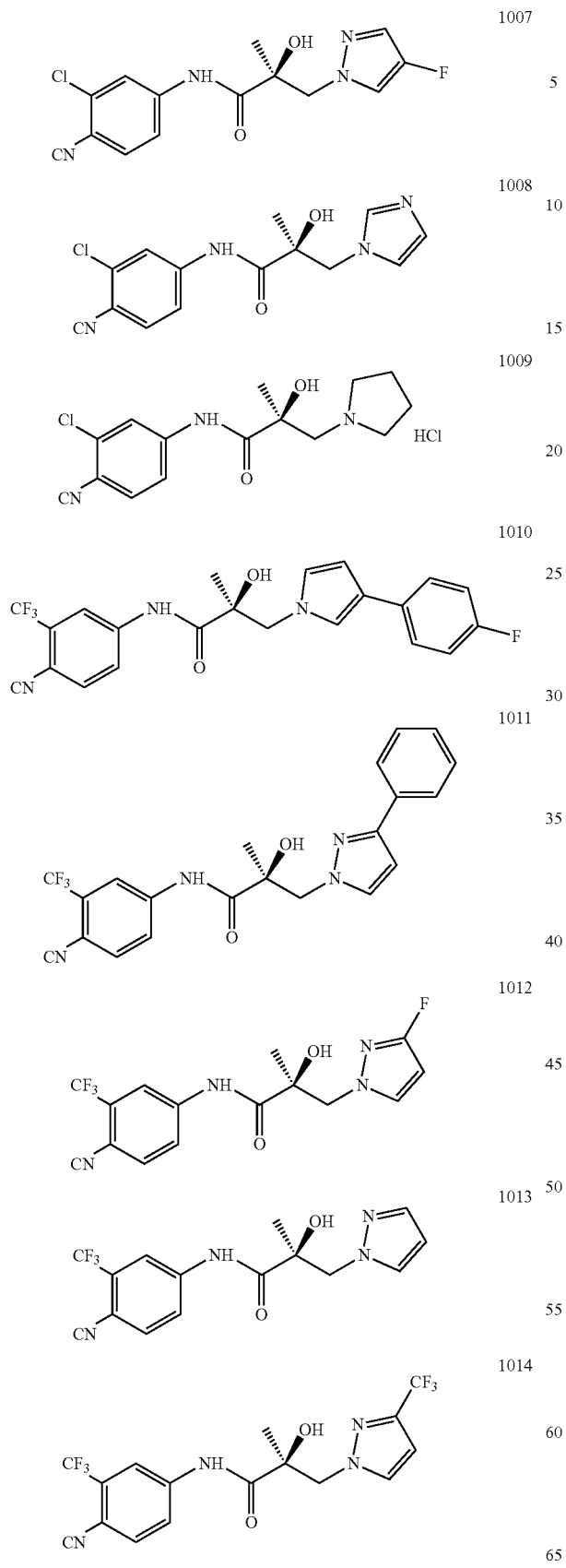
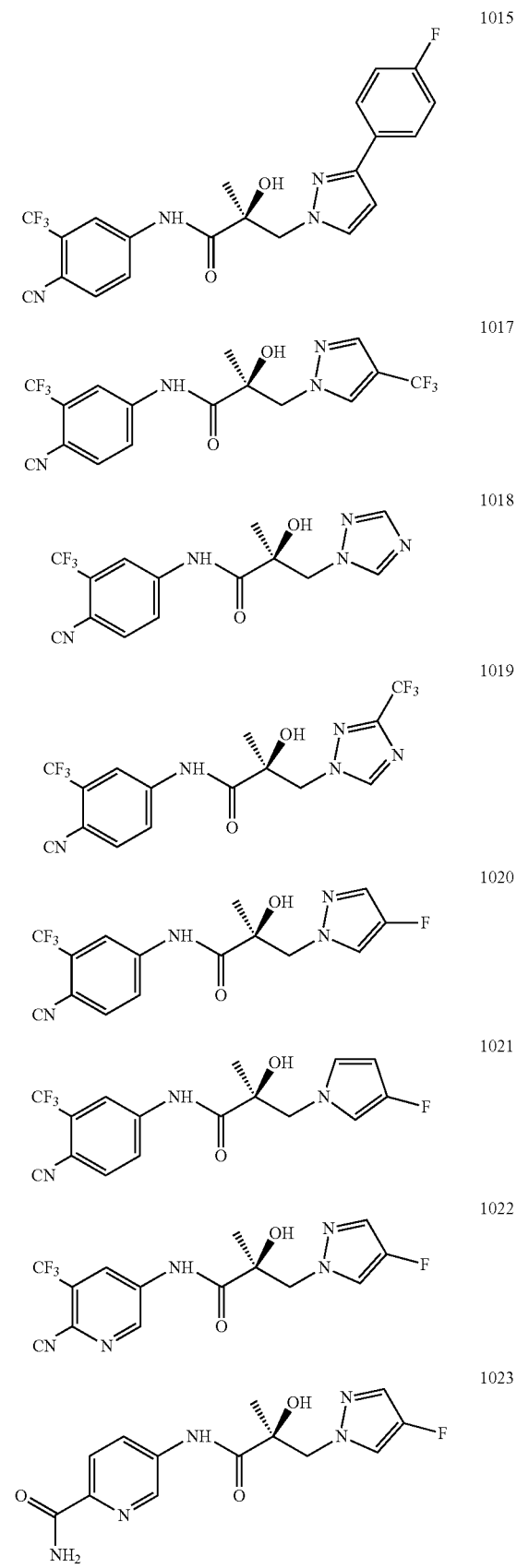

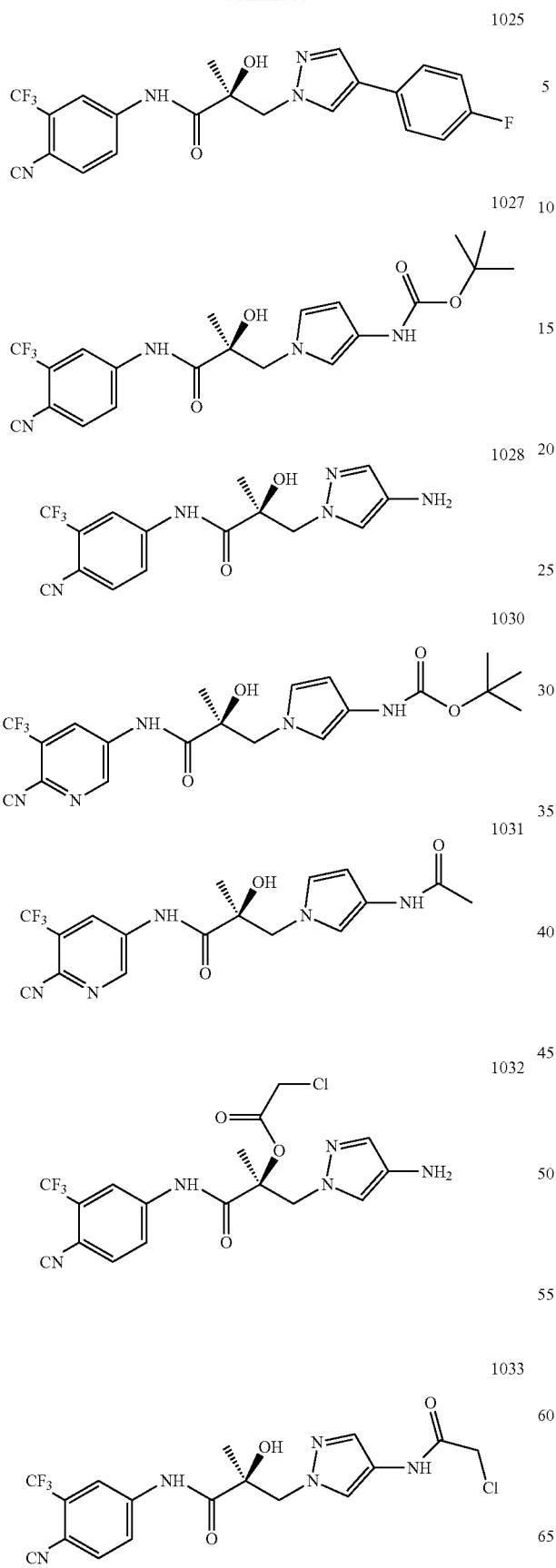
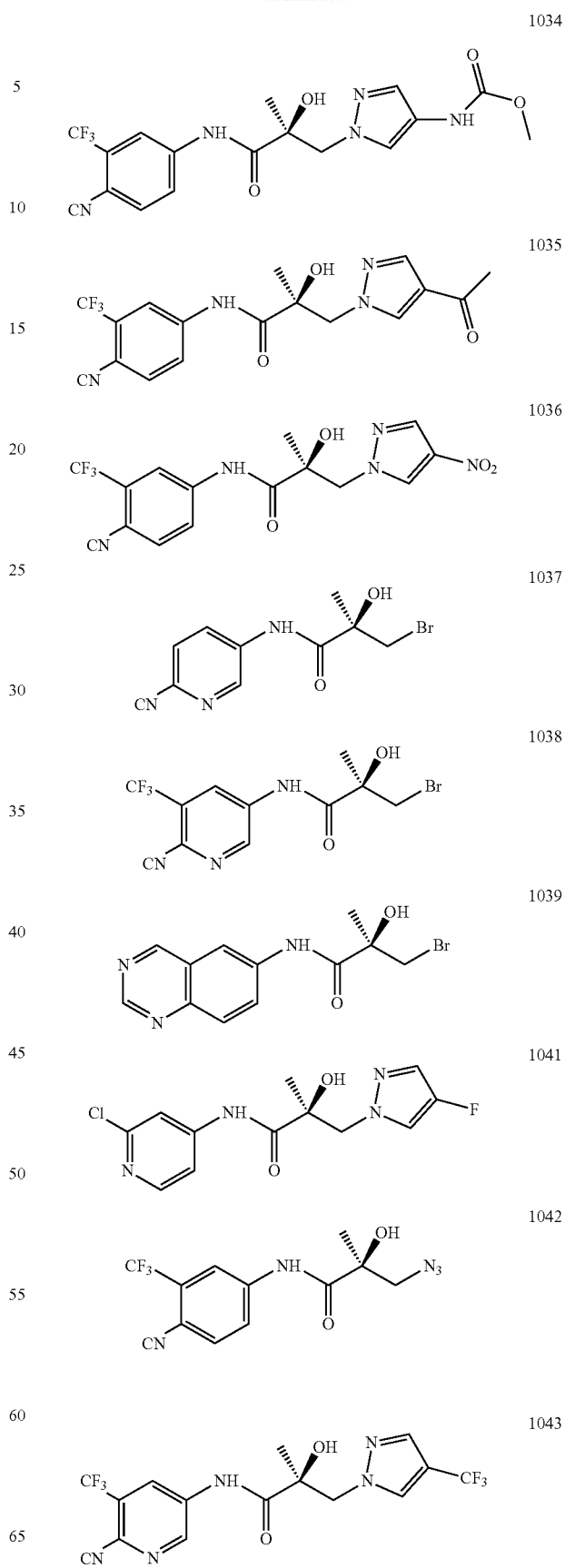

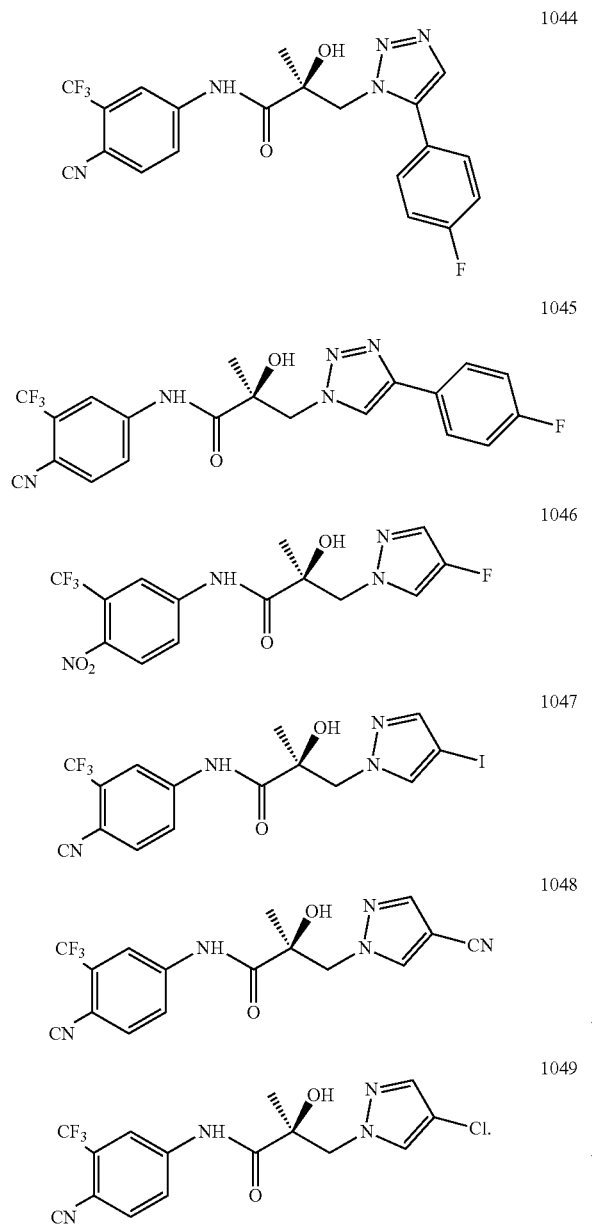

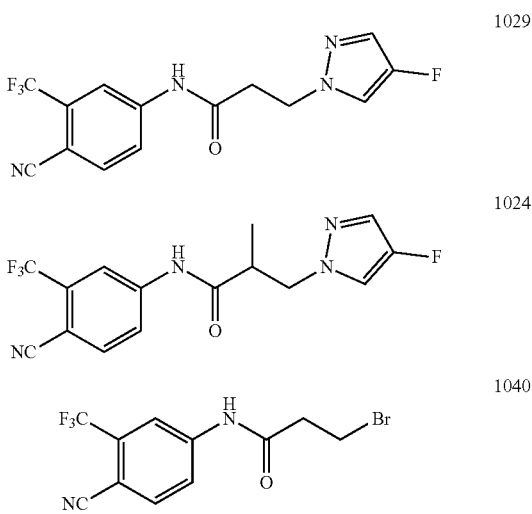

32. A method of treating prostate cancer (PCa) or increasing the survival of a male subject suffering from prostate cancer comprising administering to the subject a therapeutically effective amount of a selective androgen receptor degrader (SARD) compound represented by the structure of any one of compounds 1026, 1029, 1024, and 1040 or its isomer, pharmaceutically acceptable salt, pharmaceutical product, hydrate or any combination thereof.

33. The method according to claim 32, wherein the prostate cancer is at least one of advanced prostate cancer, refractory prostate cancer, castration resistant prostate cancer (CRPC), metastatic CRPC (mCRPC), non-metastatic CRPC (nmCRPC), or high-risk nmCRPC.

34. The method according to claim 32 further comprising administering androgen deprivation therapy (ADT).

35. The method according to claim 32, wherein the prostate cancer is resistant to treatment with an androgen receptor antagonist(s).

36. The method according to claim 35, wherein the androgen receptor antagonist is at least one of enzalutamide, bicalutamide, abiraterone, ARN-509, ODM-201, EPI-001, EPI-506, AZD-3514, galeterone, ASC-J9, flutamide, hydroxyflutamide, nilutamide, cyproterone acetate, ketoconazole, or spironolactone.

37. A method of treating enzalutamide resistant prostate cancer in a subject comprising administering to the subject a therapeutically effective amount of a selective androgen receptor degrader (SARD) compound represented by the structure of any one of compounds 1026, 1029, 1024, and 1040

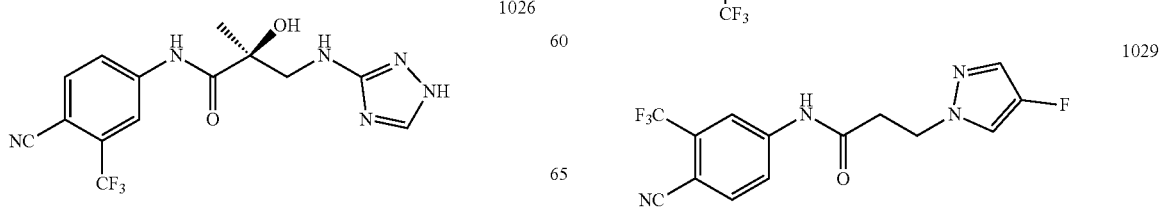

-continued

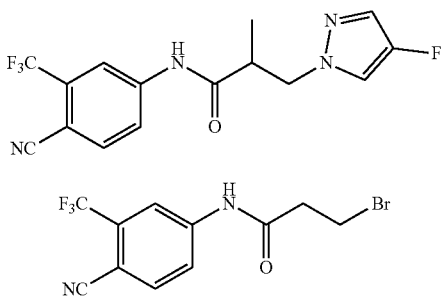

1024

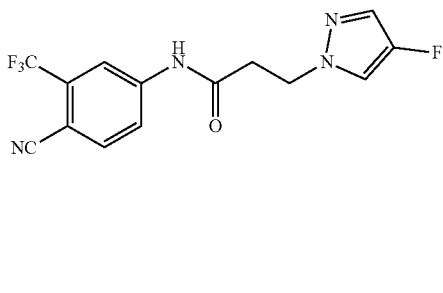

1029

1040 or its isomer, pharmaceutically acceptable salt, pharmaceutical product, hydrate or any combination thereof.

38. A method of treating abiraterone resistant prostate cancer comprising administering to the subject a therapeutically effective amount of a selective androgen receptor degrader (SARD) compound represented by the structure of any one of compounds 1026, 1029, 1024, and 1040

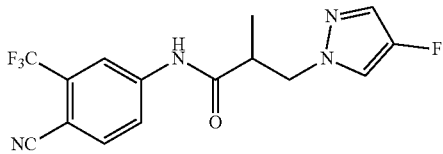

1024

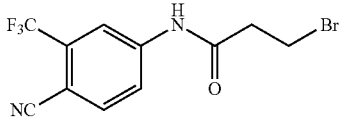

1040

1026 or its isomer, pharmaceutically acceptable salt, pharmaceutical product, hydrate or any combination thereof.

* * * * *

UNITED STATES PATENT AND TRADEMARK OFFICE
CERTIFICATE OF CORRECTION

| | |
|---|---|
| PATENT NO. | : 10,654,809 B2 |
| APPLICATION NO. | : 15/923668 |
| DATED | : May 19, 2020 |
| INVENTOR(S) | : Ramesh Narayanan |

It is certified that error appears in the above-identified patent and that said Letters Patent is hereby corrected as shown below:

In the Specification

Column 1, Line 15, insert:
--STATEMENT REGARDING FEDERALLY SPONSORED R&D
This invention was made with Government support under CA229164 awarded by the National Institutes of Health. The Government has certain rights in the invention.--

Signed and Sealed this
Seventh Day of May, 2024

Katherine Kelly Vidal
*Director of the United States Patent and Trademark Office*